US009550783B2

(12) United States Patent
Zhou et al.

(10) Patent No.: US 9,550,783 B2
(45) Date of Patent: *Jan. 24, 2017

(54) BIARYL HETEROCYCLIC COMPOUNDS AND METHODS OF MAKING AND USING THE SAME

(71) Applicant: Melinta Therapeutics, Inc., New Haven, CT (US)

(72) Inventors: Jiacheng Zhou, Newark, DE (US); Ashoke Bhattacharjee, Cheshire, CT (US); Shili Chen, Cheshire, CT (US); Yi Chen, West Roxbury, MA (US); Jay J. Farmer, Ithaca, NY (US); Joel A. Goldberg, New Orleans, LA (US); Roger Hanselmann, Branford, CT (US); Rongliang Lou, Cheshire, CT (US); Alia Orbin, Macungie, PA (US); Adegboyega K. Oyelere, Marietta, GA (US); Joseph M. Salvino, Chester Springs, PA (US); Dane M. Springer, Yardley, PA (US); Jennifer Tran, Guilford, CT (US); Deping Wang, Furlong, PA (US); Yusheng Wu, New Haven, CT (US)

(73) Assignee: MELINTA THERAPEUTICS, INC., New Haven, CT (US)

( * ) Notice: Subject to any disclaimer, the term of this patent is extended or adjusted under 35 U.S.C. 154(b) by 9 days.

This patent is subject to a terminal disclaimer.

(21) Appl. No.: 14/280,972

(22) Filed: May 19, 2014

(65) Prior Publication Data
US 2015/0072970 A1    Mar. 12, 2015

Related U.S. Application Data

(63) Continuation of application No. 13/770,407, filed on Feb. 19, 2013, now abandoned, which is a continuation of application No. 13/240,297, filed on Sep. 22, 2011, now abandoned, which is a continuation of application No. 12/767,380, filed on Apr. 26, 2010, now abandoned, which is a continuation of application No. 12/275,941, filed on Nov. 21, 2008, now Pat. No. 7,705,026, which is a continuation of application No. 11/486,769, filed on Jul. 14, 2006, now Pat. No. 7,456,206, which is a continuation of application No. 11/118,808, filed on Apr. 29, 2005, now Pat. No. 7,148,219, which is a continuation of application No. 10/859,476, filed on Jun. 2, 2004, now Pat. No. 6,969,726.

(60) Provisional application No. 60/475,430, filed on Jun. 3, 2003, provisional application No. 60/475,453, filed on Jun. 3, 2003, provisional application No.
(Continued)

(51) Int. Cl.
A01N 43/80 (2006.01)
C07D 261/04 (2006.01)
C07D 487/04 (2006.01)
C07D 263/20 (2006.01)
C07D 263/32 (2006.01)
C07D 413/10 (2006.01)
C07D 413/12 (2006.01)
C07D 413/14 (2006.01)
C07D 417/10 (2006.01)
C07D 417/12 (2006.01)
C07D 417/14 (2006.01)
C07D 453/02 (2006.01)
C07D 473/00 (2006.01)
C07D 263/24 (2006.01)
C07D 473/34 (2006.01)
C07D 263/26 (2006.01)
C07D 471/04 (2006.01)

(52) U.S. Cl.
CPC ........... *C07D 487/04* (2013.01); *C07D 263/20* (2013.01); *C07D 263/24* (2013.01); *C07D 263/26* (2013.01); *C07D 263/32* (2013.01); *C07D 413/10* (2013.01); *C07D 413/12* (2013.01); *C07D 413/14* (2013.01); *C07D 417/10* (2013.01); *C07D 417/12* (2013.01); *C07D 417/14* (2013.01); *C07D 453/02* (2013.01); *C07D 471/04* (2013.01); *C07D 473/00* (2013.01); *C07D 473/34* (2013.01)

(58) Field of Classification Search
None
See application file for complete search history.

(56) References Cited

U.S. PATENT DOCUMENTS 4,348,393 A    9/1982   Bourgery et al.
4,948,801 A    8/1990   Carlson et al.
(Continued)

FOREIGN PATENT DOCUMENTS

DE    10034627 A1    1/2002
EP    0352781 A2    1/1990
(Continued)

OTHER PUBLICATIONS

Barbachyn et al. "Oxazolidinone Structure-Activity Relationships Leading to Linezolid." *Angew Chem. Int. Ed. Engl.* 42.18(2003):2010-2023.

(Continued)

*Primary Examiner* — Kamal Saeed
(74) *Attorney, Agent, or Firm* — Wilmer Cutler Pickering Hale and Dorr

(57) ABSTRACT

The present invention relates generally to the field of anti-infective, anti-proliferative, anti-inflammatory, and prokinetic agents. More particularly, the invention relates to a family of compounds having both a biaryl moiety and at least one heterocylic moiety that are useful as such agents.

17 Claims, No Drawings

Related U.S. Application Data

60/490,855, filed on Jul. 29, 2003, provisional application No. 60/529,731, filed on Dec. 15, 2003, provisional application No. 60/531,584, filed on Dec. 19, 2003.

(56) References Cited

U.S. PATENT DOCUMENTS

| | | |
|---|---|---|
| 5,043,443 A | 8/1991 | Carlson et al. |
| 5,130,316 A | 7/1992 | Carlson et al. |
| 5,254,577 A | 10/1993 | Carlson et al. |
| 5,523,403 A | 6/1996 | Barbachyn |
| 5,565,571 A | 10/1996 | Barbachyn et al. |
| 5,627,181 A | 5/1997 | Riedl et al. |
| 5,654,428 A | 8/1997 | Barbachyn et al. |
| 5,654,435 A | 8/1997 | Barbachyn et al. |
| 5,684,023 A | 11/1997 | Riedl et al. |
| 5,756,732 A | 5/1998 | Barbachyn et al. |
| 5,801,246 A | 9/1998 | Barbachyn et al. |
| 5,843,967 A | 12/1998 | Riedl et al. |
| 5,922,708 A | 7/1999 | Riedl et al. |
| 5,929,248 A | 7/1999 | Barbachyn et al. |
| 5,981,528 A | 11/1999 | Gravestock |
| 6,239,152 B1 | 5/2001 | Gordeev et al. |
| 6,271,383 B1 | 8/2001 | Gravestock |
| 6,365,751 B1 | 4/2002 | Gravestock |
| 6,441,005 B1 | 8/2002 | Gordeev et al. |
| 6,495,551 B1 | 12/2002 | Betts et al. |
| 6,531,470 B1 | 3/2003 | Gordeev et al. |
| 6,562,844 B2 | 5/2003 | Gordeev et al. |
| 6,605,630 B1 | 8/2003 | Gravestock |
| 6,617,339 B1 | 9/2003 | Gravestock |
| 6,638,955 B2 | 10/2003 | Gravestock |
| 6,689,779 B2 | 2/2004 | Lee et al. |
| 6,821,980 B1 | 11/2004 | Guerry et al. |
| 6,969,726 B2 | 11/2005 | Lou et al. |
| 7,148,219 B2 | 12/2006 | Lou et al. |
| 2002/0169191 A1 | 11/2002 | Gordeev et al. |
| 2002/0183371 A1 | 12/2002 | Gordeev et al. |
| 2003/0144263 A1 | 7/2003 | Gravestock |
| 2003/0166620 A1 | 9/2003 | Lee et al. |
| 2004/0132764 A1 | 7/2004 | Locher |
| 2005/0038092 A1 | 2/2005 | Fukuda |
| 2005/0043317 A1 | 2/2005 | Zhou et al. |
| 2006/0270637 A1 | 11/2006 | Gravestock et al. |
| 2007/0197541 A1 | 8/2007 | Oyelere et al. |

FOREIGN PATENT DOCUMENTS

| | | |
|---|---|---|
| EP | 0694543 A1 | 1/1996 |
| EP | 1286998 A1 | 3/2003 |
| JP | 8151577 A | 6/1996 |
| JP | 8151578 A | 6/1996 |
| JP | A-2-124877 | 4/2002 |
| JP | 2006-515034 | 5/2006 |
| JP | 2006-213727 | 8/2006 |
| JP | 2011-15470 | 1/2011 |
| WO | WO-9309103 A1 | 5/1993 |
| WO | WO-9413649 A1 | 6/1994 |
| WO | WO-9730995 A1 | 8/1997 |
| WO | WO-9854161 A1 | 12/1998 |
| WO | WO-9910342 A1 | 3/1999 |
| WO | WO-9928317 A1 | 6/1999 |
| WO | WO-9933839 A1 | 7/1999 |
| WO | WO-9937630 A1 | 7/1999 |
| WO | WO-9964416 A2 | 12/1999 |
| WO | WO-9964417 A2 | 12/1999 |
| WO | WO-0010566 A1 | 3/2000 |
| WO | WO-0021960 A1 | 4/2000 |
| WO | WO-0029396 A1 | 5/2000 |
| WO | WO-0109107 A1 | 2/2001 |
| WO | WO-0132633 A1 | 5/2001 |
| WO | WO-0140236 A2 | 6/2001 |
| WO | WO-0142229 A1 | 6/2001 |
| WO | WO-0181350 A1 | 11/2001 |
| WO | WO-0194342 A1 | 12/2001 |
| WO | WO-02053560 A1 | 7/2002 |
| WO | WO-02080841 A2 | 10/2002 |
| WO | WO-02081468 A1 | 10/2002 |
| WO | WO-02081469 A1 | 10/2002 |
| WO | WO-02081470 A1 | 10/2002 |
| WO | WO-02096890 A2 | 12/2002 |
| WO | WO-02096916 A1 | 12/2002 |
| WO | WO-03022824 A1 | 3/2003 |
| WO | WO-03035648 A1 | 5/2003 |
| WO | WO-03072553 A1 | 9/2003 |
| WO | WO-03072575 A1 | 9/2003 |
| WO | WO-03084534 A1 | 10/2003 |
| WO | WO-2004029066 A2 | 4/2004 |
| WO | WO-2004048392 A1 | 6/2004 |
| WO | WO-2004056817 A1 | 7/2004 |
| WO | WO-2004056818 A1 | 7/2004 |
| WO | WO-2004056819 A1 | 7/2004 |
| WO | WO-2004078753 A1 | 9/2004 |
| WO | WO-2004089943 A1 | 10/2004 |
| WO | WO-2005003087 A2 | 1/2005 |
| WO | WO-2005012270 A2 | 2/2005 |
| WO | WO-2005012271 A2 | 2/2005 |
| WO | WO-2005019211 A2 | 3/2005 |
| WO | WO-2005058886 A1 | 6/2005 |
| WO | WO-2005061468 A1 | 7/2005 |
| WO | WO-2005070904 A2 | 8/2005 |
| WO | WO-2006083761 | 8/2006 |
| WO | WO-2008021133 | 2/2008 |

OTHER PUBLICATIONS

Brickner, Steven J., "Oxazolidione Antibacterial Agents", Current Pharmaceutical Design, vol. 2, 1996, pp. 175-194.

Gleave et al., "Synthesis and Antibacterial Activity of [6,5,5] and [6,6,5] Tricylcic Fused Oxazolidoinones", Bioorganic & Medicinal Chemistry Letters, vol. 8, 1998, pp. 1231-1236.

Gregory et al. "Antibacterials. Synthesis and Structure-Activity Studies of 3-Aryl-2-Oxazolidinones. 1. The 'B' Group." J. Med. Chem. 32.8(1989):1673-1681.

Molander et al. "Palladium-Catalyzed Suzuki-Miyaura Cross-Coupling Reactions of Potassium Aryl- and Heteroaryltrifluoroborates." J. Org. Chem. 68(2003):4302-4314.

Park et al. "Antibacterials. Synthesis and Structure-Activity Studies of 3-Aryl-2-Oxazolidinones. 4. Multiply-Substituted Aryl Derivatives." J. Med. Chem. 35.6(1992):1156-1165.

Reck et al. "Novel Substituted (Pyridin-3-yl)Phenyloxazolidinones: Antibacterial Agents with Reduced Activity against Monoamine Oxidase A and Increased Solubilit." J. Med. Chem. 50(2007):4868-4881.

Zurenko et al. "Oxazolidinone Antibacterial Agents: Development of the Clinical Candidates Eperezolid and Linezolid." Exp. Opin. Invest. Drugs. 6.2(1997):151-158.

BIARYL HETEROCYCLIC COMPOUNDS AND METHODS OF MAKING AND USING THE SAME

RELATED APPLICATIONS

This application is a continuation of U.S. patent application Ser. No. 13/770,407, filed Feb. 19, 2013, which is a continuation of U.S. patent application Ser. No. 13/240,297, filed Sep. 22, 2011, which is a continuation of U.S. patent application Ser. No. 12/767,380, filed Apr. 26, 2010, which is a continuation of U.S. patent application Ser. No. 12/275,941, filed Nov. 21, 2008, which issued as U.S. Pat. No. 7,705,026 on Apr. 27, 2010, which is a continuation of U.S. patent application Ser. No. 11/486,769, filed Jul. 14, 2006, which issued as U.S. Pat. No. 7,456,206 on Nov. 25, 2008, which is a continuation of U.S. patent application Ser. No. 11/118,808, filed Apr. 29, 2005, which issued as U.S. Pat. No. 7,148,219 on Dec. 12, 2006, which is a continuation of U.S. patent application Ser. No. 10/859,476, filed Jun. 2, 2004, which issued as U.S. Pat. No. 6,969,726 on Nov. 29, 2005, which claims the benefit of and priority to U.S. Patent Application Nos. 60/475,430, filed Jun. 3, 2003; 60/475,453, filed Jun. 3, 2003; 60/490,855, filed Jul. 29, 2003; 60/529,731, filed Dec. 15, 2003; and 60/531,584, filed Dec. 19, 2003, the contents of each of which are incorporated herein by reference in their entireties.

FIELD OF THE INVENTION

The present invention relates generally to the field of anti-infective, anti-proliferative, anti-inflammatory, and pro-kinetic agents. More particularly, the invention relates to a family of biaryl heterocyclic compounds, comprising both a biaryl moiety and at least one heterocyclic moiety, that are useful as therapeutic agents.

BACKGROUND

Since the discovery of penicillin in the 1920s and streptomycin in the 1940s, many new compounds have been discovered or specifically designed for use as antibiotic agents. It was once believed that infectious diseases could be completely controlled or eradicated with the use of such therapeutic agents. However, such beliefs have been shaken by the fact that strains of cells or microorganisms resistant to currently effective therapeutic agents continue to evolve. In fact, virtually every antibiotic agent developed for clinical use has ultimately encountered problems with the emergence of resistant bacteria. For example, resistant strains of Gram-positive bacteria such as methicillin-resistant staphylococci, penicillin-resistant streptococci, and vancomycin-resistant enterococci have developed, which can cause serious and even fatal results for patients infected with such resistant bacteria. Bacteria that are resistant to macrolide antibiotics, i.e., antibiotics based on a 14- to 16-membered lactone ring, have developed. Also, resistant strains of Gram-negative bacteria such as *H. influenzae* and *M. catarrhalis* have been identified. See, e.g., F. D. Lowry, "Antimicrobial Resistance: The Example of *Staphylococcus aureus*," *J. Clin. Invest.*, 2003, 111(9), 1265-1273; and Gold, H. S. and Moellering, R. C., Jr., "Antimicrobial-Drug Resistance," *N. Engl. J. Med.*, 1996, 335, 1445-53.

The problem of resistance is not limited to the area of anti-infective agents, because resistance has also been encountered with anti-proliferative agents used in cancer chemotherapy. Therefore, there exists a need for new anti-infective and anti-proliferative agents that are both effective against resistant bacteria and resistant strains of cancer cells.

In the antibiotic area, despite the problem of increasing antibiotic resistance, no new major classes of antibiotics have been developed for clinical use since the approval in the United States in 2000 of the oxazolidinone ring-containing antibiotic, N-[[(5S)-3-[3-fluoro-4-(4-morpholinyl)phenyl]-2-oxo-5-oxazolidinyl]methyl acetamide, which is known as linezolid and is sold under the tradename Zyvox® (see compound A). See, R. C. Moellering, Jr., "Linezolid: The First Oxazolidinone Antimicrobial," *Annals of Internal Medicine*, 2003, 138(2), 135-142.

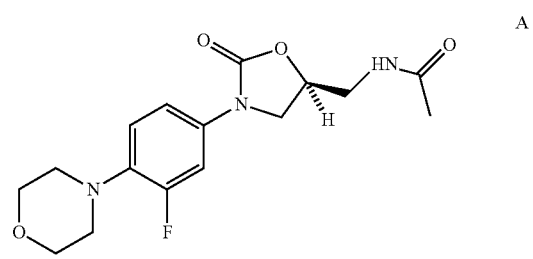 [SMILES: CC(=O)NC[C@H]1CN(c2ccc(N3CCOCC3)c(F)c2)C(=O)O1]

Linezolid was approved for use as an anti-bacterial agent active against Gram-positive organisms. Unfortunately, linezolid-resistant strains of organisms are already being reported. See, Tsiodras et al., *Lancet*, 2001, 358, 207; Gonzales et al., *Lancet*, 2001, 357, 1179; Zurenko et al., *Proceedings Of The 39th Annual Interscience Conference On Antibacterial Agents And Chemotherapy (ICAAC)*; San Francisco, Calif., USA, (Sep. 26-29, 1999). Because linezolid is both a clinically effective and commercially significant anti-microbial agent, investigators have been working to develop other effective linezolid derivatives.

Notwithstanding the foregoing, there is an ongoing need for new anti-infective and anti-proliferative agents. Furthermore, because many anti-infective and anti-proliferative agents have utility as anti-inflammatory agents and prokinetic agents, there is also an ongoing need for new compounds useful as anti-inflammatory and prokinetic agents.

SUMMARY OF THE INVENTION

The invention provides a family of compounds useful as anti-infective agents and/or anti-proliferative agents, for example, chemotherapeutic agents, anti-microbial agents, anti-bacterial agents, anti-fungal agents, anti-parasitic agents, anti-viral agents, anti-inflammatory agents, and/or prokinetic (gastrointestinal modulatory) agents. The compounds have the formula:

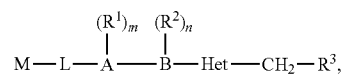

or a pharmaceutically acceptable salt, ester or prodrug thereof, wherein Het-CH$_2$—R$^4$ is selected from the group consisting of:

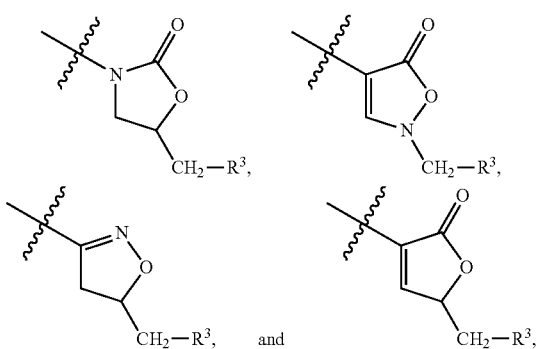

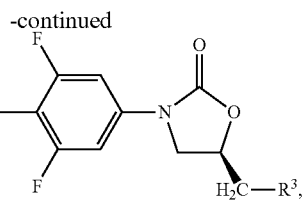

A and B independently are selected from the group consisting of phenyl, pyridyl, pyrazinyl, pyrimidinyl, and pyridazinyl; M-L is selected from the group consisting of M-X, M-$L^1$, M-$L^1$-X, M-X-$L^2$, M-$L^1$-X-$L^2$, M-X-$L^1$-X-$L^2$, M-$L^1$-X-$L^2$-X, M-X—X—, M-$L^1$-X—X—, M-X—X-$L^2$, and M-$L^1$-X—X-$L^2$; M is an optionally substituted saturated, unsaturated, or aromatic $C_{3-14}$ carbocycle, or an optionally substituted saturated, unsaturated, or aromatic 3-14 membered heterocycle containing one or more heteroatoms selected from the group consisting of nitrogen, oxygen, and sulfur; and the variables $L^1$, $L^2$, M, $R^1$, $R^2$, $R^3$, X, m, and n are selected from the respective groups of chemical moieties or integers later defined in the detailed description.

Particular embodiments of compounds of the invention include those having the formula:

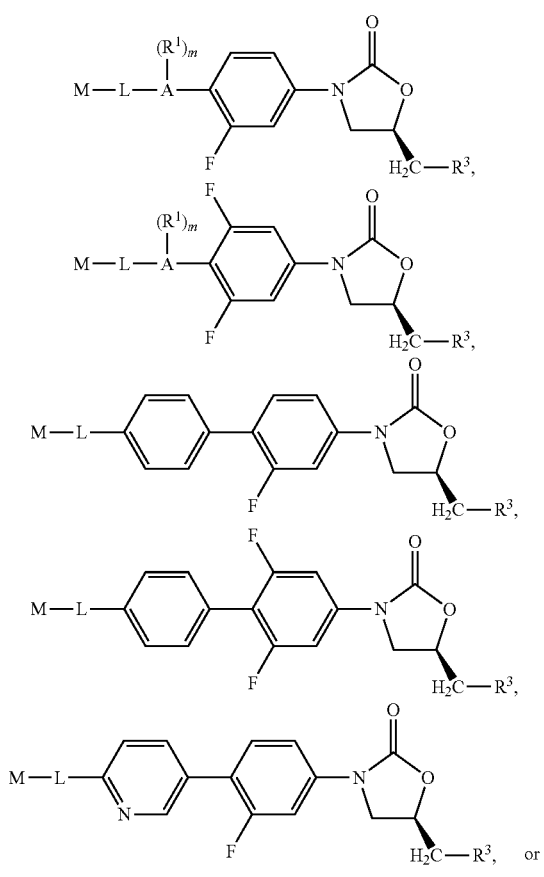

wherein the variables A, L, M, $R^1$, $R^3$, and m are selected from the respective groups of chemical moieties or integers later defined in the detailed description.

In addition, the invention provides methods of synthesizing the foregoing compounds. Following synthesis, an effective amount of one or more of the compounds may be formulated with a pharmaceutically acceptable carrier for administration to a mammal for use as an anti-cancer, anti-microbial, anti-biotic, anti-fungal, anti-parasitic or anti-viral agent, or to treat a proliferative disease, an inflammatory disease or a gastrointestinal motility disorder. The compounds or formulations may be administered, for example, via oral, parenteral, or topical routes, to provide an effective amount of the compound to the mammal.

The foregoing and other aspects and embodiments of the invention may be more fully understood by reference to the following detailed description and claims.

DETAILED DESCRIPTION OF THE INVENTION

The present invention provides a family of compounds that can be used as anti-proliferative agents and/or anti-infective agents. The compounds may be used without limitation, for example, as anti-cancer, anti-microbial, anti-bacterial, anti-fungal, anti-parasitic and/or anti-viral agents. Further, the present invention provides a family of compounds that can be used without limitation as anti-inflammatory agents, for example, for use in treating chronic inflammatory airway diseases, and/or as prokinetic agents, for example, for use in treating gastrointestinal motility disorders such as gastroesophageal reflux disease, gastroparesis (diabetic and post surgical), irritable bowel syndrome, and constipation.

1. Definitions

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N).

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

The compounds described herein may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic, and geometric isomeric forms of a structure are intended, unless the specific stereochemistry or isomeric form is specifically indicated. All processes used to prepare compounds of the present invention and intermediates made therein are considered to be part of the present invention. All tautomers of shown or described compounds are also considered to be part of the present invention.

When any variable (e.g., $R^1$) occurs more than one time in any constituent or formula for a compound, its definition at each occurrence is independent of its definition at every other occurrence. Thus, for example, if a group is shown to be substituted with 0-2 $R^1$ moieties, then the group may optionally be substituted with up to two $R^1$ moieties and $R^1$ at each occurrence is selected independently from the definition of $R^1$. Also, combinations of substituents and/or variables are permissible, but only if such combinations result in stable compounds.

When a bond to a substituent is shown to cross a bond connecting two atoms in a ring, then such substituent may be bonded to any atom in the ring. When a substituent is listed without indicating the atom via which such substituent is bonded to the rest of the compound of a given formula, then such substituent may be bonded via any atom in such substituent. Combinations of substituents and/or variables are permissible, but only if such combinations result in stable compounds.

Compounds of the present invention that contain nitrogens can be converted to N-oxides by treatment with an oxidizing agent (e.g., MCPBA and/or hydrogen peroxides) to afford other compounds of the present invention. Thus, all shown and claimed nitrogen-containing compounds are considered, when allowed by valency and structure, to include both the compound as shown and its N-oxide derivative (which can be designated as N→O or $N^+$—$O^-$). Furthermore, in other instances, the nitrogens in the compounds of the present invention can be converted to N-hydroxy or N-alkoxy compounds. For example, N-hydroxy compounds can be prepared by oxidation of the parent amine by an oxidizing agent such as MCPBA. All shown and claimed nitrogen-containing compounds are also considered, when allowed by valency and structure, to cover both the compound as shown and its N-hydroxy (i.e., N—OH) and N-alkoxy (i.e., N—OR, wherein R is substituted or unsubstituted $C_{1-6}$ alkyl, alkenyl, alkynyl, $C_{3-14}$ carbocycle, or 3-14-membered heterocycle) derivatives.

When an atom or chemical moiety is followed by a subscripted numeric range (e.g., $C_{1-6}$), the invention is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

As used herein, "alkyl" is intended to include both branched and straight-chain saturated aliphatic hydrocarbon groups having the specified number of carbon atoms. For example, $C_{1-6}$ alkyl is intended to include $C_1$, $C_2$, $C_3$, $C_4$, $C_5$, and $C_6$ alkyl groups. Examples of alkyl include, but are not limited to, methyl, ethyl, n-propyl, i-propyl, n-butyl, s-butyl, t-butyl, n-pentyl, s-pentyl, and n-hexyl.

As used herein, "alkenyl" is intended to include hydrocarbon chains of either straight or branched configuration having one or more carbon-carbon double bonds occurring at any stable point along the chain. For example, $C_{2-6}$ alkenyl is intended to include $C_2$, $C_3$, $C_4$, $C_5$, and $C_6$ alkenyl groups. Examples of alkenyl include, but are not limited to, ethenyl and propenyl.

As used herein, "alkynyl" is intended to include hydrocarbon chains of either straight or branched configuration having one or more carbon-carbon triple bonds occurring at any stable point along the chain. For example, $C_{2-6}$ alkynyl is intended to include $C_2$, $C_3$, $C_4$, $C_5$, and $C_6$ alkynyl groups. Examples of alkynyl include, but are not limited to, ethynyl and propynyl.

As used herein, "halo" or "halogen" refers to fluoro, chloro, bromo, and iodo. "Counterion" is used to represent a small, negatively charged species such as chloride, bromide, hydroxide, acetate, and sulfate.

As used herein, "carbocycle" or "carbocyclic ring" is intended to mean any stable monocyclic, bicyclic, or tricyclic ring having the specified number of carbons, any of which may be saturated, unsaturated, or aromatic. For example a $C_{3-14}$ carbocycle is intended to mean a mono-, bi-, or tricyclic ring having 3, 4, 5, 6, 7, 8, 9, 10, 11, 12, 13, or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, fluorenyl, phenyl, naphthyl, indanyl, adamantyl, and tetrahydronaphthyl. Bridged rings are also included in the definition of carbocycle, including, for example, [3.3.0]bicyclooctane, [4.3.0]bicyclononane, [4.4.0]bicyclodecane, and [2.2.2]bicyclooctane. A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge. Fused (e.g., naphthyl and tetrahydronaphthyl) and spiro rings are also included.

As used herein, the term "heterocycle" or "heterocyclic" is intended to mean any stable monocyclic, bicyclic, or tricyclic ring which is saturated, unsaturated, or aromatic and comprises carbon atoms and one or more ring heteroatoms, e.g., 1 or 1-2 or 1-3 or 1-4 or 1-5 or 1-6 heteroatoms, independently selected from the group consisting of nitrogen, oxygen, and sulfur. A bicyclic or tricyclic heterocycle may have one or more heteroatoms located in one ring, or the heteroatoms may be located in more than one ring. The nitrogen and sulfur heteroatoms may optionally be oxidized (i.e., N→O and $S(O)_p$, where p=1 or 2). When a nitrogen atom is included in the ring it is either N or NH, depending on whether or not it is attached to a double bond in the ring (i.e., a hydrogen is present if needed to maintain the trivalency of the nitrogen atom). The nitrogen atom may be substituted or unsubstituted (i.e., N or NR wherein R is H or another substituent, as defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge. Spiro and fused rings are also included.

As used herein, the term "aromatic heterocycle" or "heteroaryl" is intended to mean a stable 5, 6, or 7-membered monocyclic or bicyclic aromatic heterocyclic ring or 7, 8, 9, 10, 11, or 12-membered bicyclic aromatic heterocyclic ring which consists of carbon atoms and one or more heteroatoms, e.g., 1 or 1-2 or 1-3 or 1-4 or 1-5 or 1-6 heteroatoms, independently selected from the group consisting of nitrogen, oxygen, and sulfur. In the case of bicyclic heterocyclic aromatic rings, only one of the two rings needs to be aromatic (e.g., 2,3-dihydroindole), though both may be (e.g., quinoline). The second ring can also be fused or bridged as defined above for heterocycles. The nitrogen atom may be substituted or unsubstituted (i.e., N or NR wherein R is H or another substituent, as defined). The nitrogen and sulfur heteroatoms may optionally be oxidized (i.e., N→O and $S(O)_p$, where p=1 or 2). It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluene sulfonic.

The pharmaceutically acceptable salts of the present invention can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 18th ed. (Mack Publishing Company, 1990).

Since prodrugs are known to enhance numerous desirable qualities of pharmaceuticals (e.g., solubility, bioavailability, manufacturing, etc.) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent.

As used herein, "treating" or "treatment" means the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

As used herein, "mammal" refers to human and non-human patients.

As used herein, the term "effective amount" refers to an amount of a compound, or a combination of compounds, of the present invention effective when administered alone or in combination as an anti-proliferative and/or anti-infective agent. The combination of compounds is preferably a synergistic combination. Synergy, as described, for example, by Chou and Talalay, *Adv. Enzyme Regul.* 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased anti-proliferative and/or anti-infective effect, or some other beneficial effect of the combination compared with the individual components.

All percentages and ratios used herein, unless otherwise indicated, are by weight.

Throughout the description, where compositions are described as having, including, or comprising specific components, it is contemplated that compositions also consist essentially of, or consist of, the recited components. Similarly, where processes are described as having, including, or comprising specific process steps, the processes also consist essentially of, or consist of, the recited processing steps. Further, it should be understood that the order of steps or order for performing certain actions are immaterial so long as the invention remains operable. Moreover, two or more steps or actions may be conducted simultaneously.

2. Compounds of the Invention

In one aspect, the invention provides compounds having the formula:

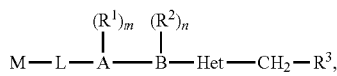

or a pharmaceutically acceptable salt, ester or prodrug thereof, wherein:

A is selected from the group consisting of:
phenyl, pyridyl, pyrazinyl, pyrimidinyl, and pyridazinyl;

B is selected from the group consisting of:
phenyl, pyridyl, pyrazinyl, pyrimidinyl, and pyridazinyl;

Het—CH$_2$—R$^3$ is selected from the group consisting of:

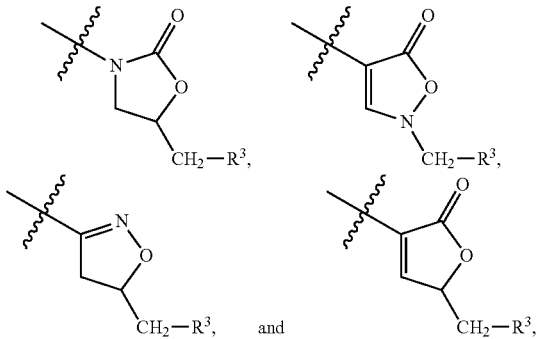

M is selected from the group consisting of:
a) saturated, unsaturated, or aromatic C$_{3-14}$ carbocycle, and b) saturated, unsaturated, or aromatic 3-14 membered heterocycle containing one or more heteroatoms selected from the group consisting of nitrogen, oxygen, and sulfur, wherein a) or b) optionally is substituted with one or more R$^5$ groups;

M-L is selected from the group consisting of:
a) M-X, b) M-L$^1$, c) M-L$^1$-X, d) M-X-L$^2$, e) M-L$^1$-X-L$^2$, f) M-X-L$^1$-X-L$^2$, g) M-L$^1$-X-L$^2$-X, h) M-X—X—, i) M-L$^1$-X—X—, j) M-X—X-L$^2$, and k) M-L$^1$-X—X-L$^2$, wherein X, at each occurrence, independently is selected from the group consisting of:
a) —O—, b) —NR$^4$—, c) —N(O)—, d) —N(OR$^4$)—, e) —S(O)$_p$—, f) —SO$_2$NR$^4$—, g) —NR$^4$SO$_2$—, h) —NR$^4$—N═, i) ═N—NR$^4$—, j) —O—N═, k) ═N—O—, l) —N═, m) ═N—, n) —NR$^4$—NR$^4$—, o) —NR$^4$C(O)O—, p) —OC(O)NR$^4$—, q) —NR$^4$C(O)NR$^4$— r) —NR$^4$C(NR$^4$)NR$^4$—, and s) 

L$^1$ is selected from the group consisting of:
a) C$_{1-6}$ alkyl, b) C$_{2-6}$ alkenyl, and c) C$_{2-6}$ alkynyl,
wherein any of a)-c) optionally is substituted with one or more R$^5$ groups; and L$^2$ is selected from the group consisting of:
a) C$_{1-6}$ alkyl, b) C$_{2-6}$ alkenyl, and c) C$_{2-6}$ alkynyl,
wherein any of a)-c) optionally is substituted with one or more R$^5$ groups;

R$^1$, at each occurrence, independently is selected from the group consisting of:
a) F, b) Cl, c) Br, d) I, e) —CF$_3$, f) —OR$^4$, g) —CN, h) —NO$_2$, i) —NR$^4$R$^4$, j) —C(O)R$^4$, k) —C(O)OR$^4$, l) —OC(O)R$^4$, m) —C(O)NR$^4$R$^4$, n) —NR$^4$C(O)R$^4$, o) —OC(O)NR$^4$R$^4$, p) —NR$^4$C(O)OR$^4$, q) —NR$^4$C(O)NR$^4$R$^4$, r) —C(S)R$^4$, s) —C(S)OR$^4$, t) —OC(S)R$^4$, u) —C(S)NR$^4$R$^4$, v) —NR$^4$C(S)R$^4$, w) —OC(S)NR$^4$R$^4$, x) —NR$^4$C(S)OR$^4$, y) —NR$^4$C(S)NR$^4$R$^4$, z) —NR$^4$C(NR$^4$)NR$^4$R$^4$, aa) —S(O)$_p$R$^4$, bb) —SO$_2$NR$^4$R$^4$, and cc) R$^4$;

R$^2$, at each occurrence, independently is selected from the group consisting of:
a) F, b) Cl, c) Br, d) I, e) —CF$_3$, f) —OR$^4$, g) —CN, h) —NO$_2$, i) —NR$^4$R$^4$, j) —C(O)R$^4$, k) —C(O)OR$^4$, l) —OC(O)R$^4$, m) —C(O)NR$^4$R$^4$, n) —NR$^4$C(O)R$^4$, o) —OC(O)NR$^4$R$^4$, p) —NR$^4$C(O)OR$^4$, q) —NR$^4$C(O)NR$^4$R$^4$, r) —C(S)R$^4$, s) —C(S)OR$^4$, t) —OC(S)R$^4$, u) —C(S)NR$^4$R$^4$, v) —NR$^4$C(S)R$^4$, w) —OC(S)NR$^4$R$^4$, x) —NR$^4$C(S)OR$^4$, y) —NR$^4$C(S)NR$^4$R$^4$, z) —NR$^4$C(NR$^4$)NR$^4$R$^4$, aa) —S(O)$_p$R$^4$, bb) —SO$_2$NR$^4$R$^4$, and cc) R$^4$;

R$^3$ is selected from the group consisting of:
a) —OR$^4$, b) —NR$^4$R$^4$, c) —C(O)R$^4$, d) —C(O)OR$^4$, e) —OC(O)R$^4$, f) —C(O)NR$^4$R$^4$, g) —NR$^4$C(O)R$^4$, h)

—OC(O)NR$^4$R$^4$, i) —NR$^4$C(O)OR$^4$, j) —NR$^4$C(O)NR$^4$R$^4$, k) —C(S)R$^4$, l) —C(S)OR$^4$, m) —OC(S)R$^4$, n) —C(S)NR$^4$R$^4$, o) —NR$^4$C(S)R$^4$, p) —OC(S)NR$^4$R$^4$, q) —NR$^4$C(S)OR$^4$, r) —NR$^4$C(S)NR$^4$R$^4$, s) —NR$^4$C(NR$^4$)NR$^4$R$^4$, t) —S(O)$_p$R$^4$, u) —SO$_2$NR$^4$R$^4$, and v) R$^4$;

R$^4$, at each occurrence, independently is selected from the group consisting of:
a) H, b) C$_{1-6}$ alkyl, c) C$_{2-6}$ alkenyl, d) C$_{2-6}$ alkynyl, e) C$_{3-14}$ saturated, unsaturated, or aromatic carbocycle, f) 3-14 membered saturated, unsaturated, or aromatic heterocycle comprising one or more heteroatoms selected from the group consisting of nitrogen, oxygen, and sulfur, g) —C(O)—C$_{1-6}$ alkyl, h) —C(O)—C$_{2-6}$ alkenyl, i) —C(O)—C$_{2-6}$ alkynyl, j) —C(O)—C$_{3-14}$ saturated, unsaturated, or aromatic carbocycle, k) —C(O)-3-14 membered saturated, unsaturated, or aromatic heterocycle comprising one or more heteroatoms selected from the group consisting of nitrogen, oxygen, and sulfur, l) —C(O)O—C$_{1-6}$ alkyl, m) —C(O)O—C$_{2-6}$ alkenyl, n) —C(O)O—C$_{2-6}$ alkynyl, o) —C(O)O—C$_{3-14}$ saturated, unsaturated, or aromatic carbocycle, and p) —C(O)O-3-14 membered saturated, unsaturated, or aromatic heterocycle comprising one or more heteroatoms selected from the group consisting of nitrogen, oxygen, and sulfur,
    wherein any of b)-p) optionally is substituted with one or more R$^5$ groups;

R$^5$, at each occurrence, is independently selected from the group consisting of:
a) F, b) Cl, c) Br, d) I, e) =O, f) =S, g) =NR$^6$, h) =NOR$^6$, i) =N—NR$^6$R$^6$, j) —CF$_3$, k) —OR$^6$, l) —CN, m) —NO$_2$, n) —NR$^6$R$^6$, o) —C(O)R$^6$, p) —C(O)OR$^6$, q) —OC(O)R$^6$, r) —C(O)NR$^6$R$^6$, s) —NR$^6$C(O)R$^6$, t) —OC(O)NR$^6$R$^6$, u) —NR$^6$C(O)OR$^6$, v) —NR$^6$C(O)NR$^6$R$^6$, w) —C(S)R$^6$, x) —C(S)OR$^6$, y) —OC(S)R$^6$, z) —C(S)NR$^6$R$^6$, aa) —NR$^6$C(S)R$^6$, bb) —OC(S)NR$^6$R$^6$, cc) —NR$^6$C(S)OR$^6$, dd) —NR$^6$C(S)NR$^6$R$^6$, ee) —NR$^6$C(NR$^6$)NR$^6$R$^6$, ff) —S(O)$_p$R$^6$, gg) —SO$_2$NR$^6$R$^6$, and hh) R$^6$;

R$^6$, at each occurrence, independently is selected from the group consisting of:
a) H, b) C$_{1-6}$ alkyl, c) C$_{2-6}$ alkenyl, d) C$_{2-6}$ alkynyl, e) C$_{3-14}$ saturated, unsaturated, or aromatic carbocycle, f) 3-14 membered saturated, unsaturated, or aromatic heterocycle comprising one or more heteroatoms selected from the group consisting of nitrogen, oxygen, and sulfur, g) —C(O)—C$_{1-6}$ alkyl, h) —C(O)—C$_{2-6}$ alkenyl, i) —C(O)—C$_{2-6}$ alkynyl, j) —C(O)—C$_{3-14}$ saturated, unsaturated, or aromatic carbocycle, k) —C(O)-3-14 membered saturated, unsaturated, or aromatic heterocycle comprising one or more heteroatoms selected from the group consisting of nitrogen, oxygen, and sulfur, l) —C(O)O—C$_{1-6}$ alkyl, m) —C(O)O—C$_{2-6}$ alkenyl, n) —C(O)O—C$_{2-6}$ alkynyl, o) —C(O)O—C$_{3-14}$ saturated, unsaturated, or aromatic carbocycle, and p) —C(O)O-3-14 membered saturated, unsaturated, or aromatic heterocycle comprising one or more heteroatoms selected from the group consisting of nitrogen, oxygen, and sulfur,
    wherein any of b)-p) optionally is substituted with one or more R$^7$ groups;

R$^7$, at each occurrence, independently is selected from the group consisting of:
a) F, b) Cl, c) Br, d) I, e) =O, f) =S, g) =NR$^8$, h) =NOR$^8$, i) =N—NR$^8$R$^8$, j) —CF$_3$, k) —OR$^8$, l) —CN, m) —NO$_2$, n) —NR$^8$R$^8$, o) —C(O)R$^8$, p) —C(O)OR$^8$, q) —OC(O)R$^8$, r) —C(O)NR$^8$R$^8$, s) —NR$^8$C(O)R$^8$, t) —OC(O)NR$^8$R$^8$, u) —NR$^8$C(O)OR$^8$, v) —NR$^8$C(O)NR$^8$R$^8$, w) —C(S)R$^8$, x) —C(S)OR$^8$, y) —OC(S)R$^8$, z) —C(S)NR$^8$R$^8$, aa) —NR$^8$C(S)R$^8$, bb) —OC(S)NR$^8$R$^8$, cc) —NR$^8$C(S)OR$^8$, dd) —NR$^8$C(S)NR$^8$R$^8$, ee) —NR$^8$C(NR$^8$)NR$^8$R$^8$, ff) —S(O)$_p$R$^8$, gg) —SO$_2$NR$^8$R$^8$, hh) C$_{1-6}$ alkyl, ii) C$_{2-6}$ alkenyl, jj) C$_{2-6}$ alkynyl, kk) C$_{3-14}$ saturated, unsaturated, or aromatic carbocycle, and ll) 3-14 membered saturated, unsaturated, or aromatic heterocycle comprising one or more heteroatoms selected from the group consisting of nitrogen, oxygen, and sulfur,
    wherein any of hh)-ll) optionally is substituted with one or more moieties selected from the group consisting of R$^8$, F, Cl, Br, I, —CF$_3$, —OR$^8$, —SR$^8$, —CN, —NO$_2$, —NR$^8$R$^8$, —C(O)R$^8$, —C(O)OR$^8$, —OC(O)R$^8$, —C(O)NR$^8$R$^8$, —NR$^8$C(O)R$^8$, —OC(O)NR$^8$R$^8$, —NR$^8$C(O)OR$^8$, —NR$^8$C(O)NR$^8$R$^8$, —C(S)R$^8$, —C(S)OR$^8$, —OC(S)R$^8$, —C(S)NR$^8$R$^8$, —NR$^8$C(S)R$^8$, —OC(S)NR$^8$R$^8$, —NR$^8$C(S)OR$^8$, —NR$^8$C(S)NR$^8$R$^8$, —NR$^8$C(NR$^8$)NR$^8$R$^8$, —SO$_2$NR$^8$R$^8$, and —S(O)$_p$R$^8$;

R$^8$, at each occurrence, independently is selected from the group consisting of:
a) H, b) C$_{1-6}$ alkyl, c) C$_{2-6}$ alkenyl, d) C$_{2-6}$ alkynyl, e) C$_{3-14}$ saturated, unsaturated, or aromatic carbocycle, f) 3-14 membered saturated, unsaturated, or aromatic heterocycle comprising one or more heteroatoms selected from the group consisting of nitrogen, oxygen, and sulfur, g) —C(O)—C$_{1-6}$ alkyl, h) —C(O)—C$_{2-6}$ alkenyl, i) —C(O)—C$_{2-6}$ alkynyl, j) —C(O)—C$_{3-14}$ saturated, unsaturated, or aromatic carbocycle, k) —C(O)-3-14 membered saturated, unsaturated, or aromatic heterocycle comprising one or more heteroatoms selected from the group consisting of nitrogen, oxygen, and sulfur, l) —C(O)O—C$_{1-6}$ alkyl, m) —C(O)O—C$_{2-6}$ alkenyl, n) —C(O)O—C$_{2-6}$ alkynyl, o) —C(O)O—C$_{3-14}$ saturated, unsaturated, or aromatic carbocycle, and p) —C(O)O-3-14 membered saturated, unsaturated, or aromatic heterocycle comprising one or more heteroatoms selected from the group consisting of nitrogen, oxygen, and sulfur,
    wherein any of b)-p) optionally is substituted with one or more moieties selected from the group consisting of F, Cl, Br, I, —CF$_3$, —OH, —OCH$_3$, —SH, —SCH$_3$, —CN, —NO$_2$, —NH$_2$, —NHCH$_3$, —N(CH$_3$)$_2$, —C(O)CH$_3$, —C(O)OCH$_3$, —C(O)NH$_2$, —NHC(O)CH$_3$, —SO$_2$NH$_2$, —SO$_2$NHCH$_3$, —SO$_2$N(CH$_3$)$_2$, and —S(O)$_p$CH$_3$;

m is 0, 1, 2, 3, or 4;
n is 0, 1, 2, 3, or 4; and
p, at each occurrence, independently is 0, 1, or 2,
and wherein the compound does not have the formula corresponding to any of the structures listed in Table 1.

TABLE 1
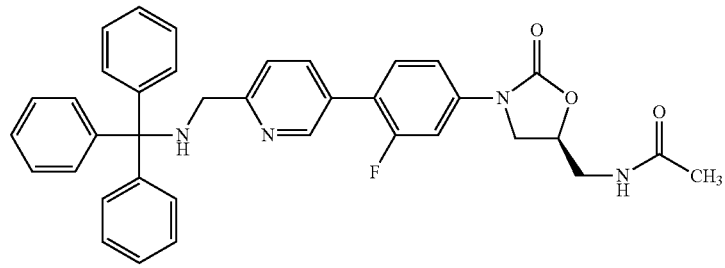 [SMILES: CC(=O)NC[C@H]1CN(c2ccc(-c3ccc(CNC(c4ccccc4)(c4ccccc4)c4ccccc4)nc3)c(F)c2)C(=O)O1]
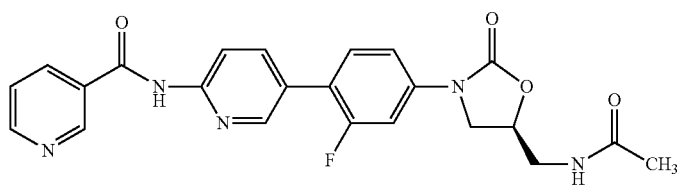 [SMILES: CC(=O)NC[C@H]1CN(c2ccc(-c3ccc(NC(=O)c4cccnc4)nc3)c(F)c2)C(=O)O1]
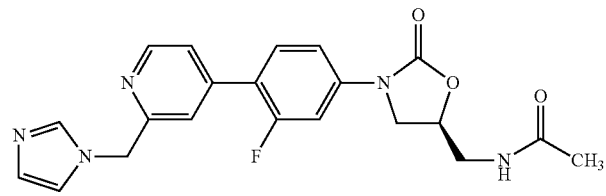 [SMILES: CC(=O)NC[C@H]1CN(c2ccc(-c3ccnc(Cn4ccnc4)c3)c(F)c2)C(=O)O1]
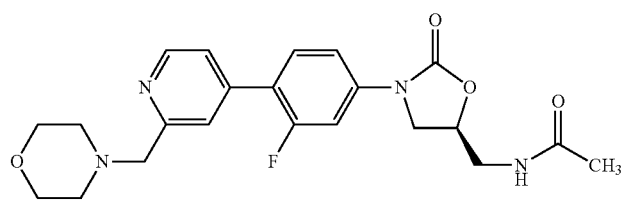 [SMILES: CC(=O)NC[C@H]1CN(c2ccc(-c3ccnc(CN4CCOCC4)c3)c(F)c2)C(=O)O1]
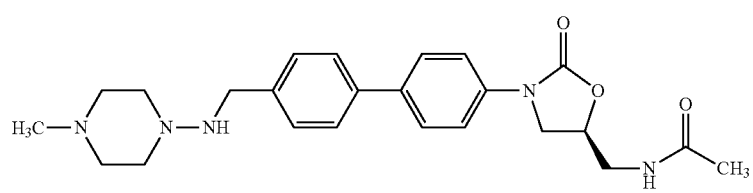 [SMILES: CC(=O)NC[C@H]1CN(c2ccc(-c3ccc(CNN4CCN(C)CC4)cc3)cc2)C(=O)O1]
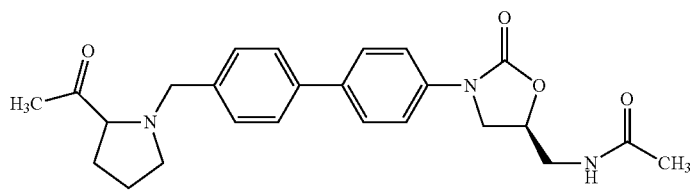 [SMILES: CC(=O)NC[C@H]1CN(c2ccc(-c3ccc(CN4CCCC4C(C)=O)cc3)cc2)C(=O)O1]
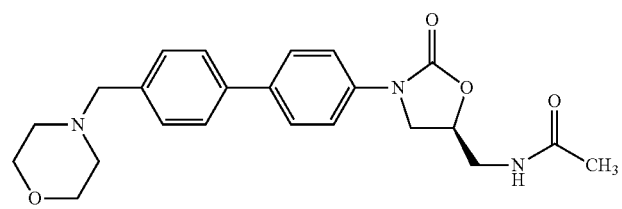 [SMILES: CC(=O)NC[C@H]1CN(c2ccc(-c3ccc(CN4CCOCC4)cc3)cc2)C(=O)O1]

TABLE 1-continued
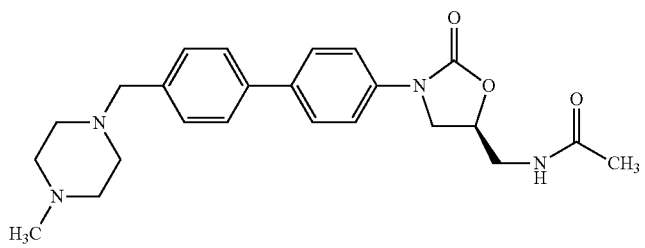 [SMILES: CC(=O)NC[C@H]1CN(c2ccc(-c3ccc(CN4CCN(C)CC4)cc3)cc2)C(=O)O1]
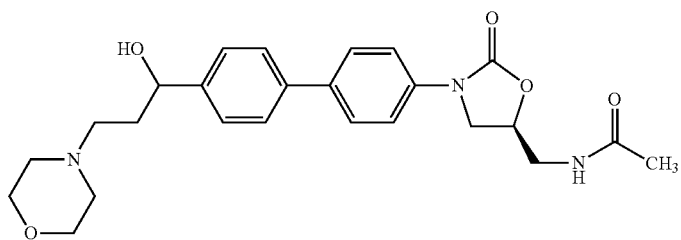 [SMILES: CC(=O)NC[C@H]1CN(c2ccc(-c3ccc(C(O)CCN4CCOCC4)cc3)cc2)C(=O)O1]
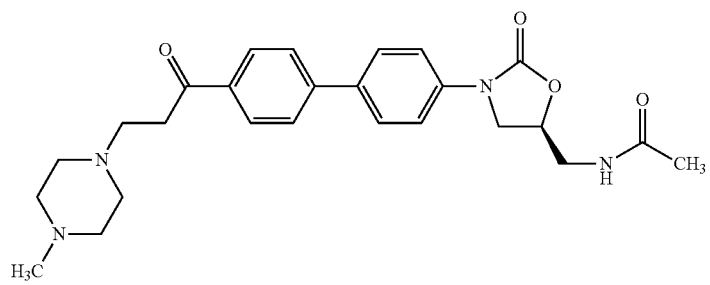 [SMILES: CC(=O)NC[C@H]1CN(c2ccc(-c3ccc(C(=O)CCN4CCN(C)CC4)cc3)cc2)C(=O)O1]
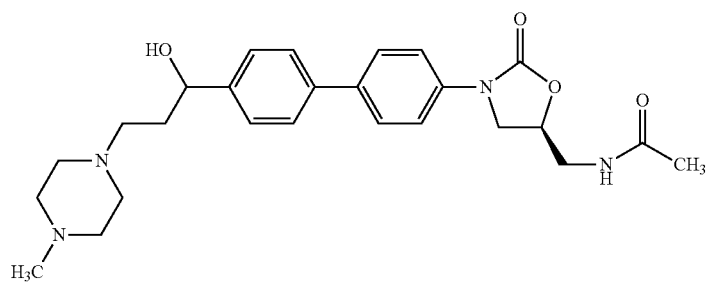 [SMILES: CC(=O)NC[C@H]1CN(c2ccc(-c3ccc(C(O)CCN4CCN(C)CC4)cc3)cc2)C(=O)O1]
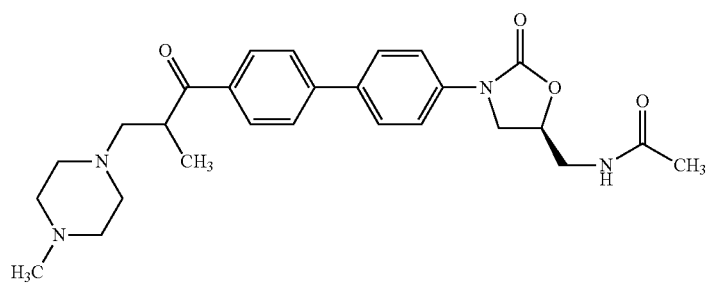 [SMILES: CC(=O)NC[C@H]1CN(c2ccc(-c3ccc(C(=O)C(C)CN4CCN(C)CC4)cc3)cc2)C(=O)O1]
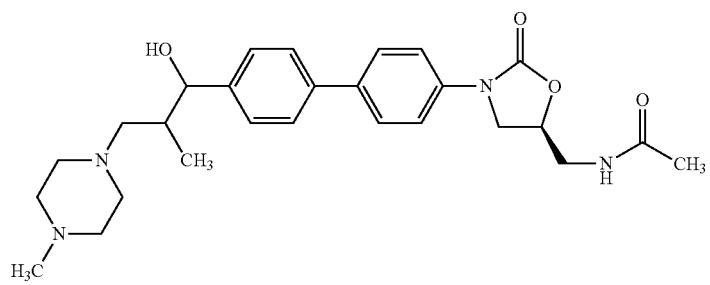 [SMILES: CC(=O)NC[C@H]1CN(c2ccc(-c3ccc(C(O)C(C)CN4CCN(C)CC4)cc3)cc2)C(=O)O1]

TABLE 1-continued
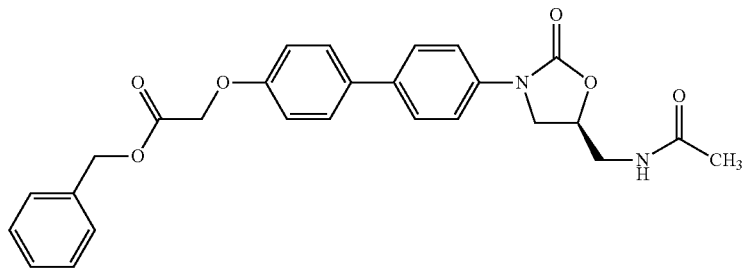 [SMILES: CC(=O)NC[C@H]1CN(c2ccc(-c3ccc(OCC(=O)OCc4ccccc4)cc3)cc2)C(=O)O1]
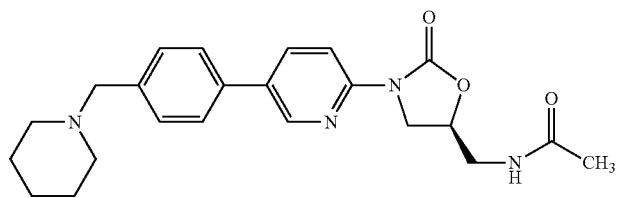 [SMILES: CC(=O)NC[C@H]1CN(c2ccc(-c3ccc(CN4CCCCC4)cc3)cn2)C(=O)O1]
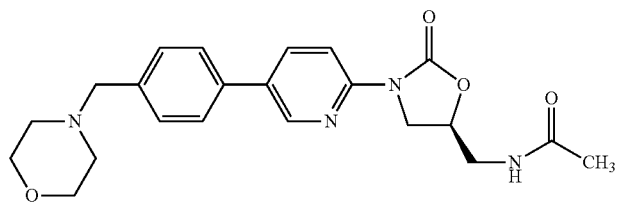 [SMILES: CC(=O)NC[C@H]1CN(c2ccc(-c3ccc(CN4CCOCC4)cc3)cn2)C(=O)O1]
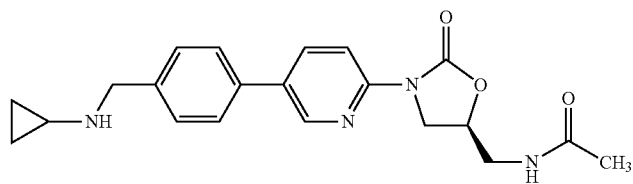 [SMILES: CC(=O)NC[C@H]1CN(c2ccc(-c3ccc(CNC4CC4)cc3)cn2)C(=O)O1]
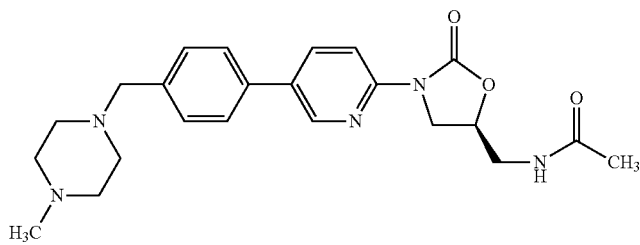 [SMILES: CC(=O)NC[C@H]1CN(c2ccc(-c3ccc(CN4CCN(C)CC4)cc3)cn2)C(=O)O1]
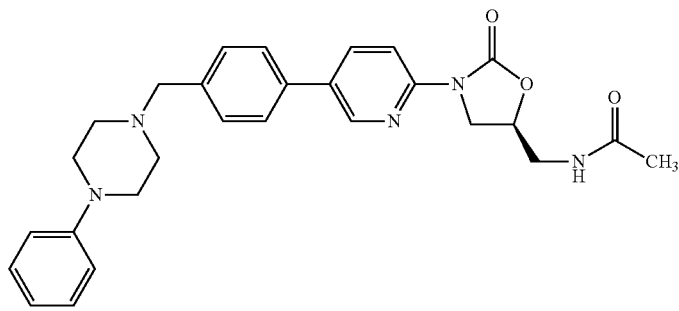 [SMILES: CC(=O)NC[C@H]1CN(c2ccc(-c3ccc(CN4CCN(c5ccccc5)CC4)cc3)cn2)C(=O)O1]

TABLE 1-continued
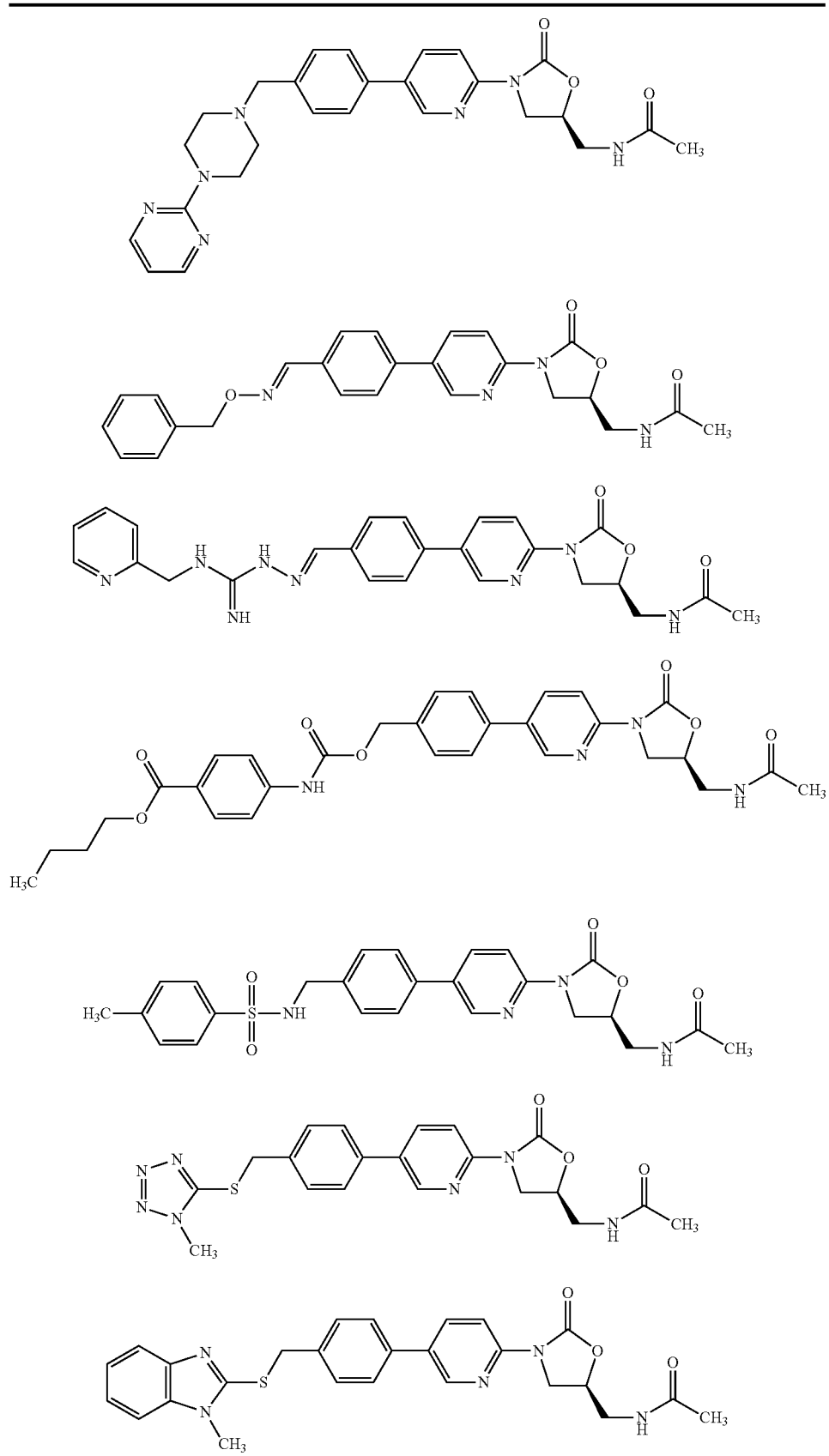

TABLE 1-continued

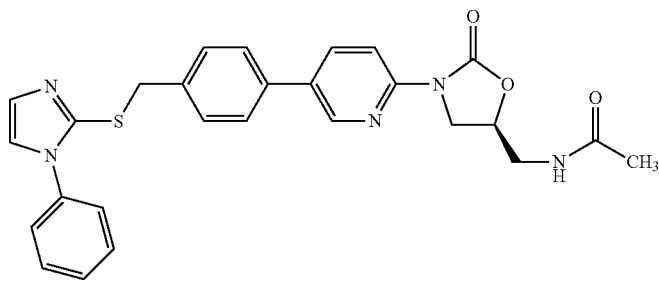 [SMILES: CC(=O)NC[C@H]1CN(c2ccc(-c3ccc(CSc4nccn4-c4ccccc4)cc3)cn2)C(=O)O1]

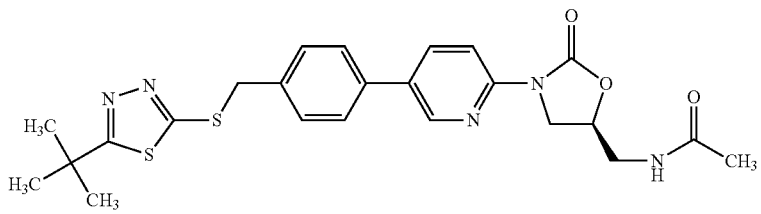 [SMILES: CC(=O)NC[C@H]1CN(c2ccc(-c3ccc(CSc4nnc(C(C)(C)C)s4)cc3)cn2)C(=O)O1]

Particular embodiments of the invention include compounds having the formula:

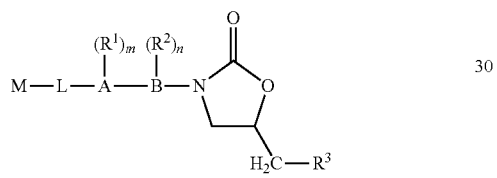

or a pharmaceutically acceptable salt, ester or prodrug thereof, wherein A, B, L, M, $R^1$, $R^2$, $R^3$, m, and n are defined above.

Other embodiments include compounds having the formula:

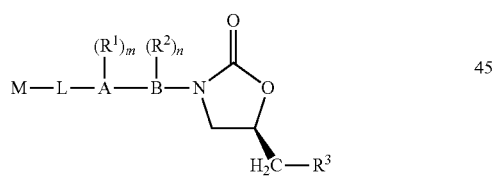

or a pharmaceutically acceptable salt, ester or prodrug thereof, wherein A, B, L, M, $R^1$, $R^2$, $R^3$, m, and n are defined as described above.

Particular compounds include those where A is selected from the group consisting of phenyl and pyridyl; B is selected from the group consisting of phenyl and pyridyl; m is 0, 1, or 2; and n is 0, 1, or 2.

In some embodiments, A-B is:

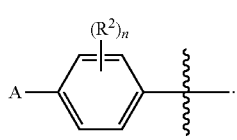

wherein A, $R^2$, and n are defined as described above. In particular embodiments, A-B is:

wherein A is defined as described above.

In various embodiments, A-B is:

wherein B is defined as described in above.

In some embodiments, $R^3$ is —NHC(O)$R^4$. Particular compounds according to these embodiments include those where $R^4$ is —CH$_3$ or

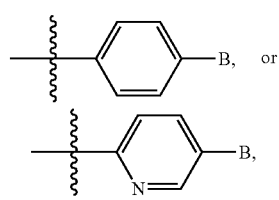

Particular embodiments of the invention include compounds having the formula:

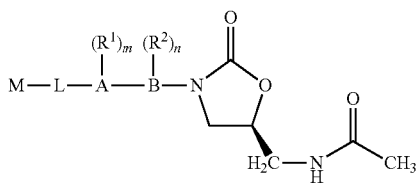

or a pharmaceutically acceptable salt, ester or prodrug thereof, wherein A, B, L, M, R¹, R², m, and n are defined as described above.

Other embodiments of the invention include compounds having the formula:

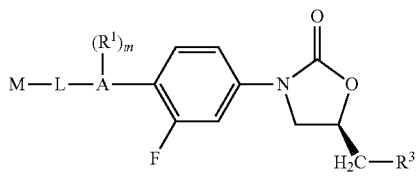

or a pharmaceutically acceptable salt, ester or prodrug thereof, wherein A, L, M, R¹, R³, and m are defined as described above.

Still other embodiments of the invention include compounds having the formula:

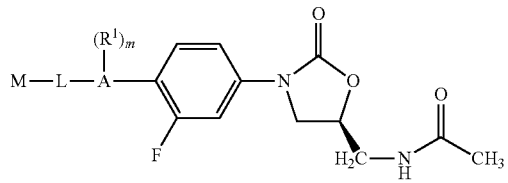

or a pharmaceutically acceptable salt, ester or prodrug thereof, wherein A, L, M, R¹, and m are defined as described above.

Some embodiments of the invention include compounds having the formula:

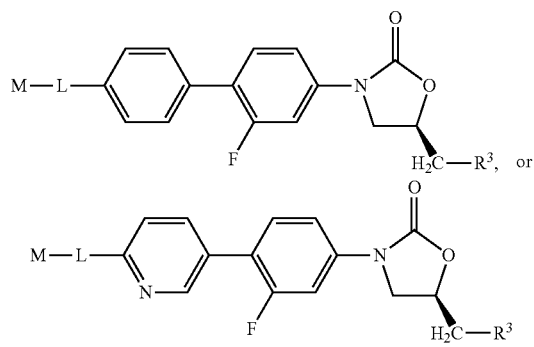

or a pharmaceutically acceptable salt, ester or prodrug thereof, wherein L, M, and R³ are defined as described above. Particular compounds according to these embodiments include those wherein R³ is —NHC(O)CH₃.

Other embodiments of the invention include compounds having the formula:

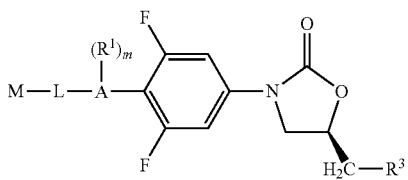

or a pharmaceutically acceptable salt, ester or prodrug thereof, wherein A, L, M, R¹, R³, and m are defined as described above.

Still other embodiments of the invention include compounds having the formula:

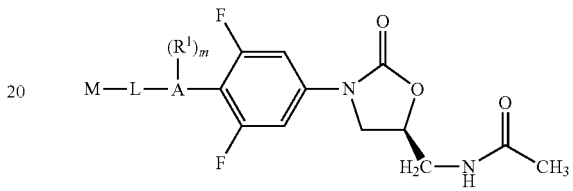

or a pharmaceutically acceptable salt, ester or prodrug thereof, wherein A, L, M, R¹, and m are defined as described above.

Some embodiments of the invention include compounds having the formula:

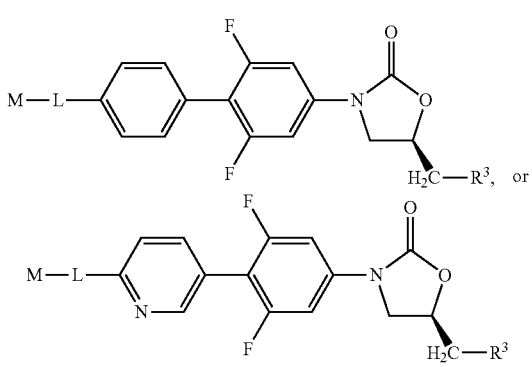

or a pharmaceutically acceptable salt, ester or prodrug thereof, wherein L, M, and R³ are defined as described above. Particular compounds according to these embodiments include those wherein R³ is —NHC(O)CH₃.

In some embodiments, M-L is M-L¹, and L¹ is $C_{1-6}$ alkyl. In particular embodiments, M-L¹ is M-CH₂—.

In other embodiments, M-L is M-L¹-X-L², and X is —NR⁴—. In particular compounds according to these embodiments, X is —NH—, —N(O)—, or —N(OR⁴)—, where R⁴ is H or $C_{1-6}$ alkyl. Other compounds include those where X is

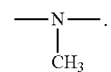

In certain compounds according to these embodiments, L¹ is $C_{1-6}$ alkyl, and L² is $C_{1-6}$ alkyl. In some embodiments, L¹ is —CH₂— and L² is —CH₂—. Particular examples of compounds according to these embodiments include those where M-L is M-CH$_2$—NH—CH$_2$— or

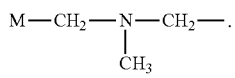

In still other embodiments, M-L is M-S-L$^1$-NR$^4$-L$^2$, wherein L$^1$ is C$_{1-6}$ alkyl, and L$^2$ is C$_{1-6}$ alkyl. In particular compounds according to these embodiments, M-L is M-S—CH$_2$CH$_2$—NH—CH$_2$—.

In particular embodiments, M is selected from the group consisting of:
a) phenyl, b) pyridyl, c) pyrazinyl, d) pyrimidinyl, e) pyridazinyl, f) oxiranyl, g) aziridinyl, h) furanyl, i) thiophenyl, j) pyrrolyl, k) oxazolyl, l) isoxazolyl, m) imidazolyl, n) pyrazolyl, o) isothiazolyl, p) thiazolyl, q) triazolyl, r) tetrazolyl, s) indolyl, t) purinyl, u) benzofuranyl, v) benzoxazolyl, w) benzisoxazolyl, x) quinolinyl, y) isoquinolinyl, z) quinoxalinyl, aa) quinazolinyl, bb) cinnolinyl, cc) cyclopropyl, dd) cyclobutyl, ee) cyclopentyl, ff) cyclohexyl, gg) cycloheptyl, hh) oxetanyl, ii) tetrahydrofuranyl, jj) tetrahydropyranyl, kk) azetidinyl, ll) pyrrolidinyl, mm) piperidinyl, nn) thietanyl, oo) tetrahydrothiophenyl, pp) tetrahydrothiopyranyl, qq) piperazinyl, rr) quinuclidinyl, ss) 1-azabicyclo[2.2.1]hyeptanyl, tt) morpholinyl, uu) thiomorpholinyl, vv) thiooxomorpholinyl, ww) thiodioxomorpholinyl, and xx) benzothiophenyl
wherein any of a)-xx) optionally is substituted with one or more R$^5$ groups. In particular embodiments, M is 4-isoxazolyl, [1,2,3]triazol-1-yl, 3H-[1,2,3]triazol-4-yl, 1H-tetrazol-5-yl, piperidin-1-yl, or pyrolidin-1-yl.

In preferred embodiments, A is phenyl, substituted phenyl, pyridyl, or substituted pyridyl. Under certain circumstances, when A is pyridin-4-yl substituted with M-L at the 2 position, M-L is not (imidazol-1-yl)methyl or (morpholin-4-yl)methyl.

In preferred embodiments, B is phenyl or substituted phenyl. More preferably, B is substituted phenyl. Preferred substituents include halogens, and in particular, fluorine. Under certain circumstances, when B is unsubstituted phenyl, M-L is selected from the group consisting of M-X, M-L$^1$-X, M-L$^1$-X-L$^2$, M-X-L$^1$-X-L$^2$, M-X—X—, M-L$^1$-X—X—, M-X—X-L$^2$, and M-L$^1$-X—X-L$^2$. Under certain circumstances, when B is pyridin-2-yl substituted with A at the 5 position, M-L is selected from the group consisting of M-X, M-L$^1$-X, M-L$^1$-X-L$^2$, M-L$^1$-X-L$^2$-X, M-X—X—, M-X—X-L$^2$, and M-L$^1$-X—X-L$^2$.

In another aspect, the invention provides a pharmaceutical composition comprising an effective amount of one or more of the foregoing compounds and a pharmaceutically acceptable carrier. Suitable formulating agents are described in detail in section 5 hereinbelow.

One or more of the foregoing compounds may also be incorporated into a medical device. For example, a medical device, such as a medical stent, can contain or be coated with one or more of the compounds of the invention.

In another aspect, the invention provides a method for treating a microbial infection, a fungal infection, a viral infection, a parasitic disease, a proliferative disease, an inflammatory disease, or a gastrointestinal motility disorder in a mammal. The method involves administering an effective amount of one or more compounds or pharmaceutical compositions of the invention, for example, via oral, parenteral or topical routes.

The invention provides a method of treating a disorder in a mammal comprising the step of administering to the mammal an effective amount of one or more compounds of the invention thereby to ameliorate a symptom of a particular disorder. Such a disorder can be selected from the group consisting of a skin infection, nosocomial pneumonia, postviral pneumonia, an abdominal infection, a urinary tract infection, bacteremia, septicemia, endocarditis, an atrioventricular shunt infection, a vascular access infection, meningitis, surgical prophylaxis, a peritoneal infection, a bone infection, a joint infection, a methicillin-resistant *Staphylococcus aureus* infection, a vancomycin-resistant Enterococci infection, a linezolid-resistant organism infection, and tuberculosis.

3. Synthesis of the Compounds of the Invention

The invention provides methods and intermediates for making compounds of the present invention. The following schemes depict some exemplary chemistries available for synthesizing the compounds of the invention. It will be appreciated, however, that the desired compounds may be synthesized using other alternative chemistries known in the art.

The following examples illustrate some of the compounds of the present invention. Compounds of general structures Ia through IVb (wherein X is CH or N) can be synthesized by the chemistries exemplified below in the following schemes.

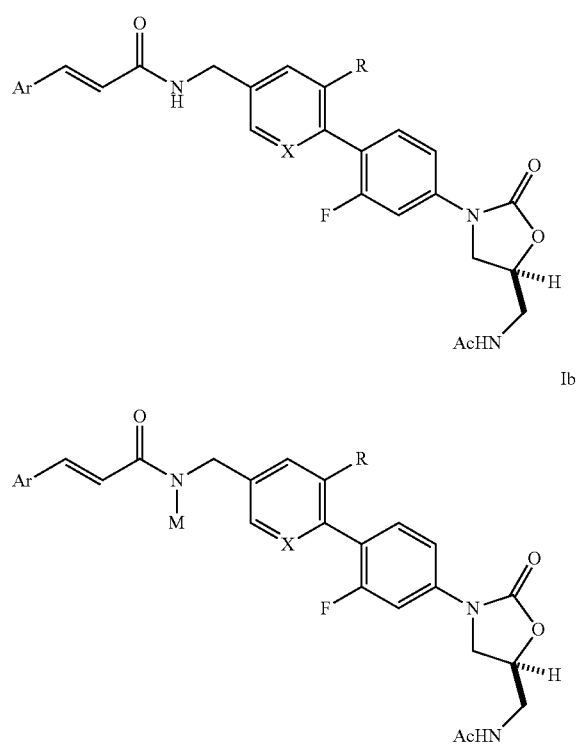

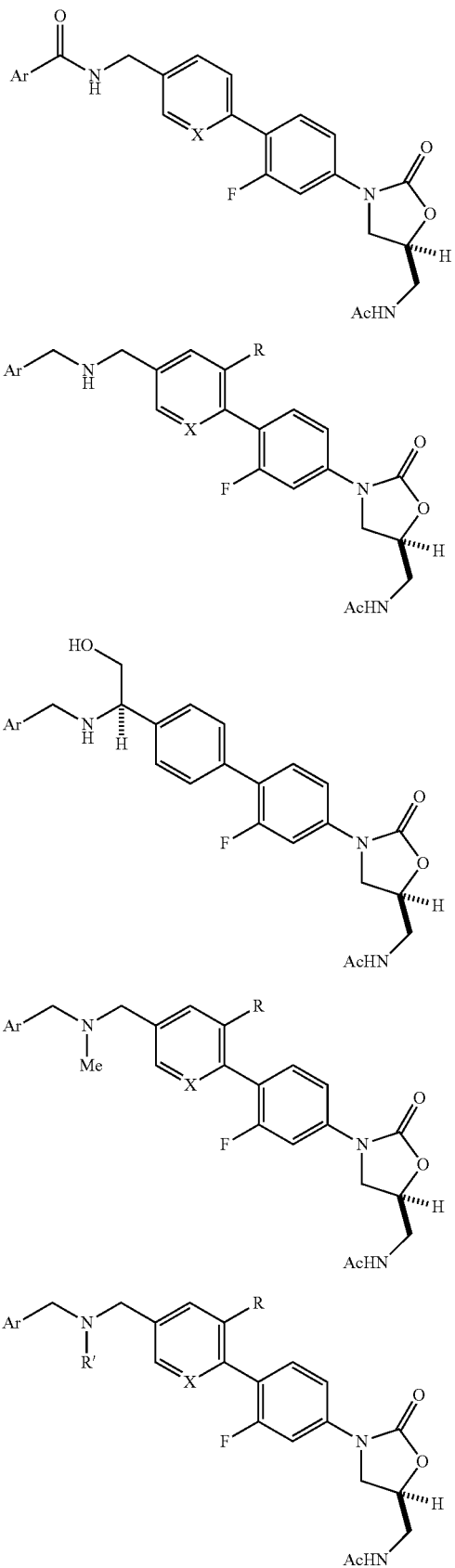

Scheme A exemplifies the synthesis of biaryl amine intermediate 5, which is useful in producing certain compounds of the present invention. Known iodoaryl oxazolidinone intermediate 1 (see U.S. Pat. Nos. 5,523,403 and 5,565,571) is coupled to a substituted aryl boronic acid (the Suzuki reaction) to produce biaryl alcohol 2. Other coupling reactions (for example, the Stille reaction) using alternate coupling intermediates easily obtained or synthesized by those skilled in the art could also be employed to synthesize target biaryl intermediates similar to 2. These alternate coupling reactions are within the scope of the present invention. Alcohol 2 is then converted to amine 5 by chemistry well known to those skilled in the art.

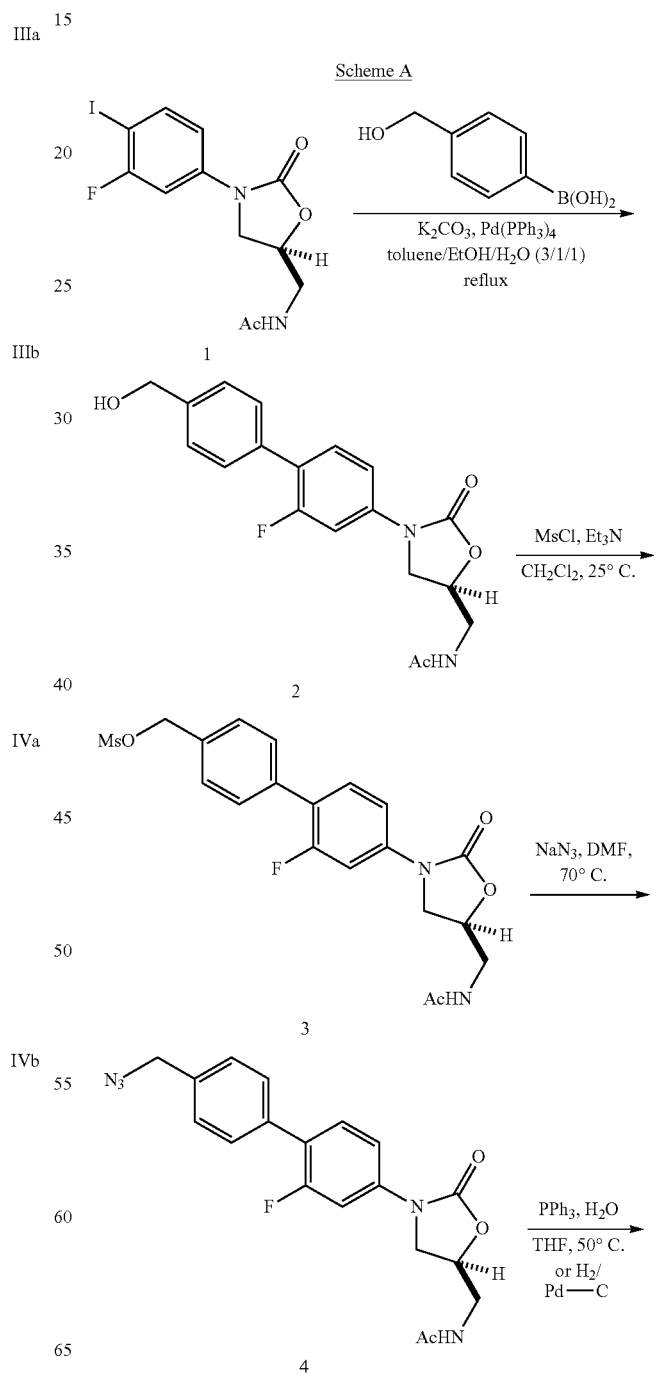

Scheme A

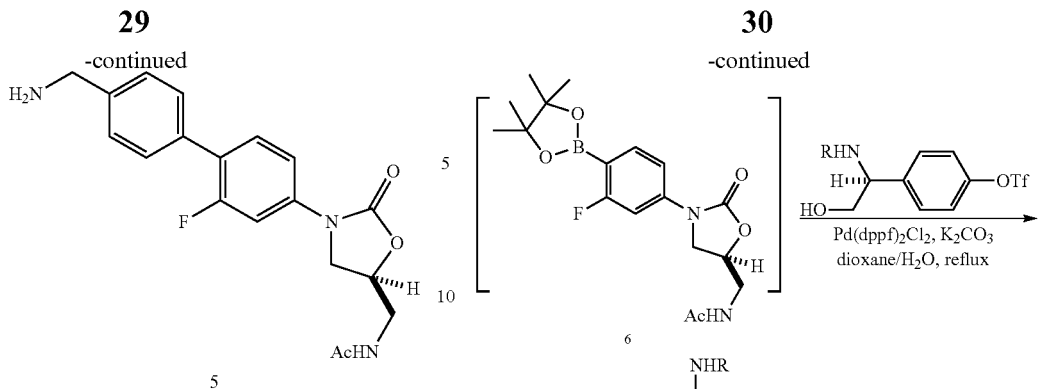

Scheme B illustrates the synthesis of intermediates 7 and 8 of the present invention using Suzuki coupling chemistry between boronic acids and aryl triflates. Boronic ester 6 is treated with an appropriate aryl triflate to yield the BOC-protected biaryl 7. The BOC group of 7 is removed to provide amine 8, an intermediate useful in the synthesis of certain compounds of the present invention.

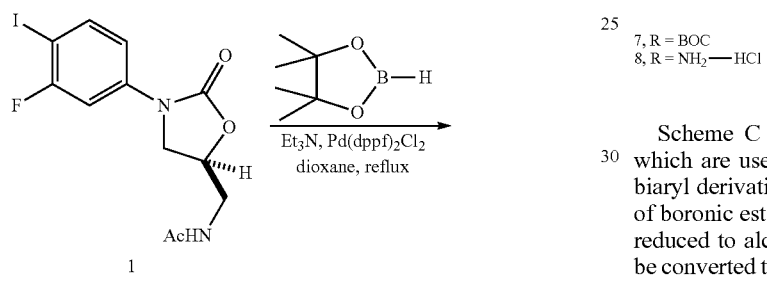

7, R = BOC
8, R = NH$_2$—HCl

Scheme C depicts the synthesis of intermediates 9-13, which are useful in producing certain methoxy-substituted biaryl derivatives of the present invention. Suzuki coupling of boronic ester 6 produces biaryl aldehyde 9, which can be reduced to alcohol 10. Mesylation of 10 yields 11 that can be converted to azide 12. Reduction of azide 12 yields amine 13.

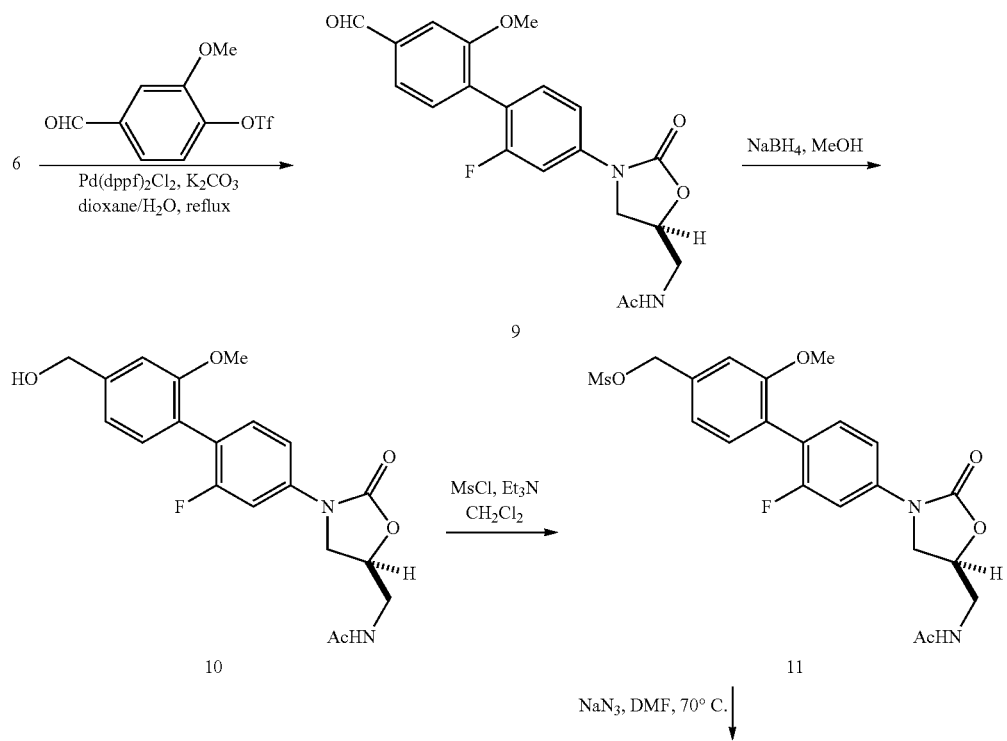

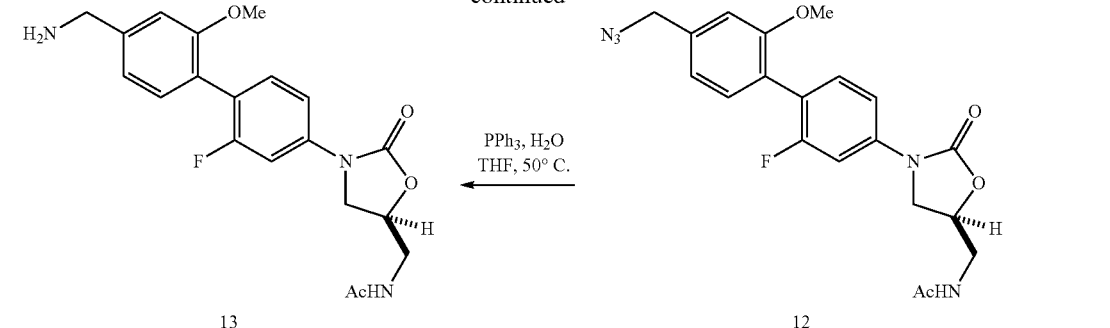
Scheme D depicts the synthesis of pyridyl intermediates, which are useful for the synthesis of compounds of the present invention, via similar chemistry to that shown in Scheme C. Coupling of boronic ester 6 to a halopyridine aldehyde produces biaryl aldehyde 14. Aldehyde 14 serves as the precursor to intermediates 15-18 via chemistry described above.
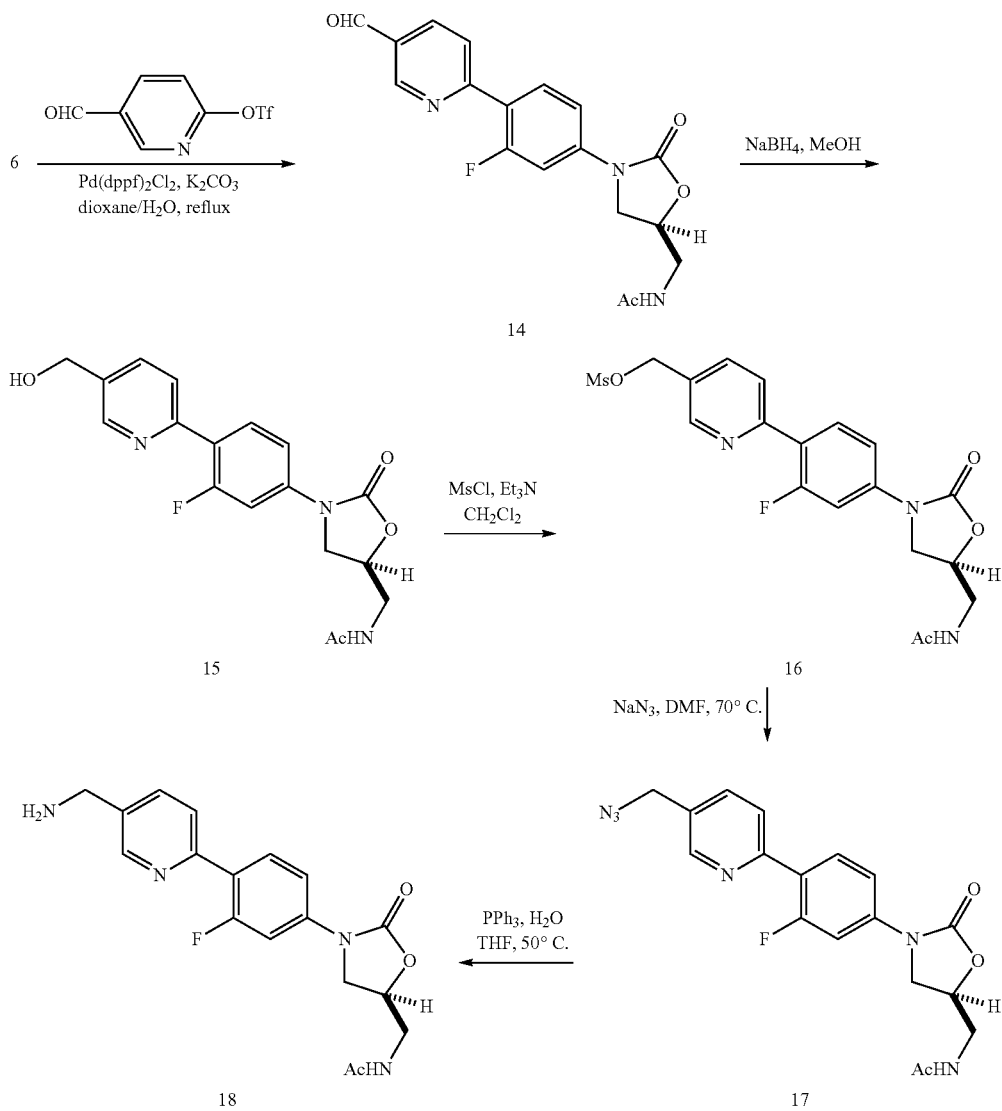

Biaryl aldehyde 19 (Scheme E) can be synthesized from a Suzuki coupling of iodide 1 and 4-formylphenylboronic acid. Scheme E illustrates how intermediate aldehydes of type 19, 9, and 14 can be converted via reductive amination chemistry to other amines, such as amines 20-22, which are useful as intermediates for the synthesis of certain compounds of the invention.

Scheme E

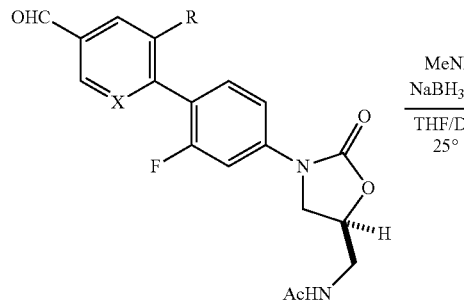

19, X = CH, R = H
9, X = CH, R = OMe
14, X = N, R = H

20, X = CH, R = H
21, X = CH, R = OMe
22, X = N, R = H

Scheme F depicts the general synthesis of compounds of type Ia and Ib from amines of type 5, 13, 18, and 20-22. Compounds of type Ia and Ib are synthesized via acylation of amines 5, 13 and 18 and 20-22 with the appropriate acids using, for example, 1-(3-dimethylaminopropyl)-3-ethylcarbodiimide hydrochloride (EDCI) as the coupling agent. Compounds 4001-4007 were specifically synthesized from amine 5 and the appropriate carboxylic acids.

Scheme F

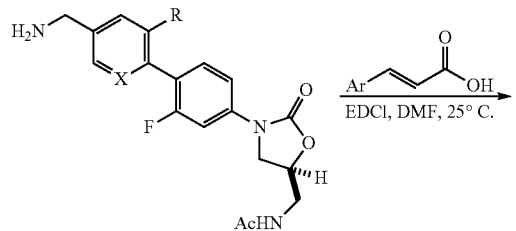

5, X = CH, R = H
13, X = CH, R = OMe
18, X = N, R = H

Ia

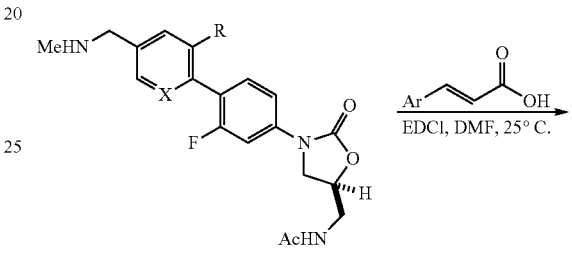

20, X = CH, R = H
21, X = CH, R = OMe
22, X = N, R = H

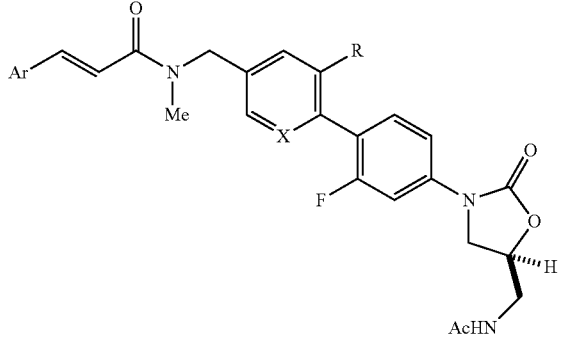

Ib

Scheme G highlights the synthesis of compounds of general structure II from amines of type 5 and 18. The amine can be acylated with carboxylic acids using EDCI (or other commonly employed peptide coupling reagents known in the art) to afford amides II. Acid chlorides can be purchased or synthesized and allowed to react with amines 5 and 18, in the presence of bases such as triethylamine, to also produce amides II. Alternatively, carboxylic acids can be pre-loaded onto a solid polymeric support, such as a tetrafluorophenol containing resin (TFP resin), and reacted with amines to yield amide products of general structure II (such as compounds 4008-4015).

Scheme G

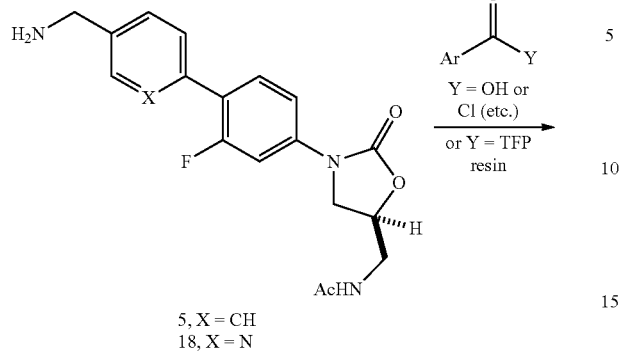

5, X = CH
18, X = N

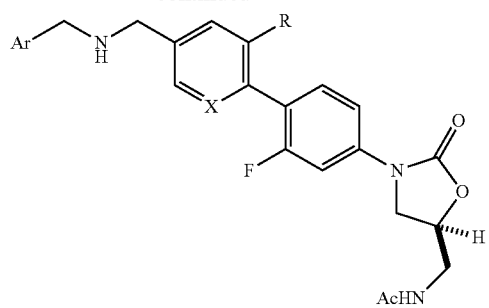

IIIa

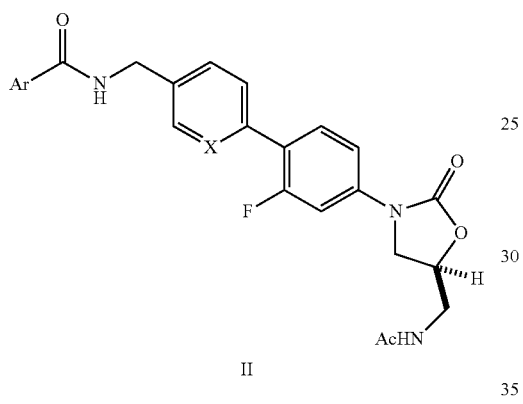

II

Scheme H illustrates the synthesis of compounds of general structure IIIa from amines of type 5, 13, and 18 using reductive amination chemistry. For example, biaryl amine compounds 4016-4028 are synthesized in this manner.

Scheme H

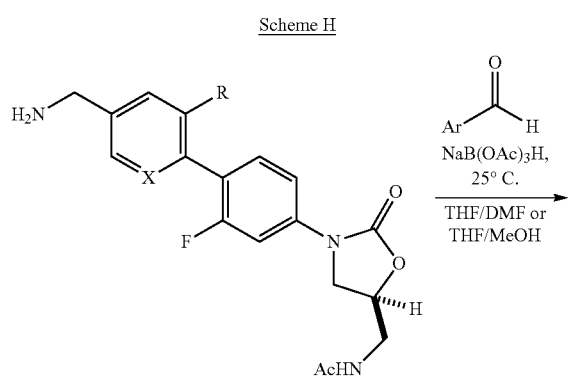

5, X = CH, R = H
13, X = CH, R = OMe
18, X = N, R = H

Scheme I depicts the synthesis of general structure IIIb of the present invention from amine intermediate 8. For example, compounds 4029-4031 are synthesized using this reductive amination chemistry.

Scheme I

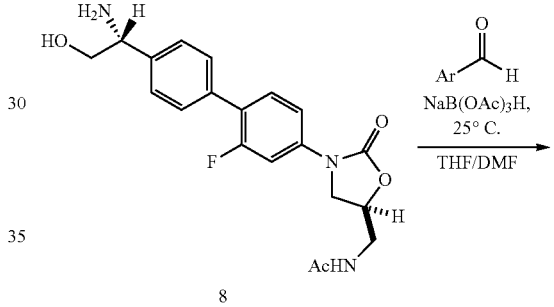

8

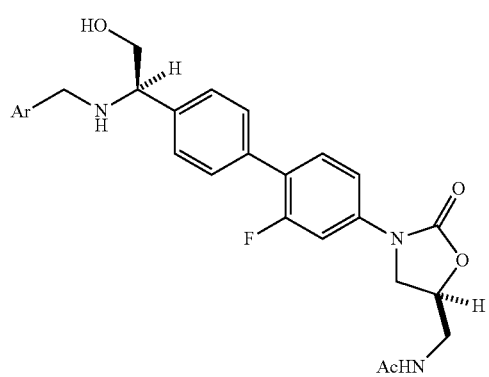

IIIb

Scheme J shows the synthesis of compounds of general structure IVa and IVb. Amines 20, 21, and 22 can be converted to tertiary amines IVa, such as compounds 4032-4034 and 4036, using standard reductive amination chemistry employed earlier for other derivatives. This reductive amination chemistry can be employed on biaryl aldehyde intermediates such as 19, 9, and 14 to yield optionally substituted amines of general structure IVb, illustrated by compound 4037.

Scheme J

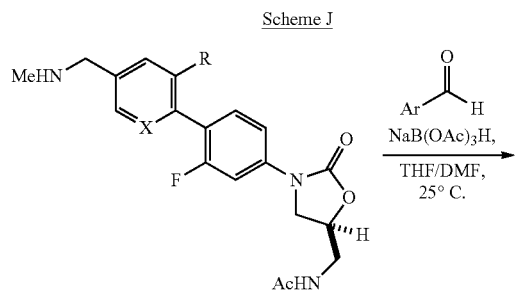

20, X = CH, R = H
21, X = CH, R = OMe
22, X = N, R = H

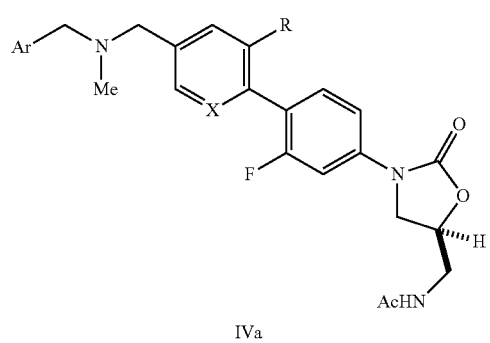

IVa

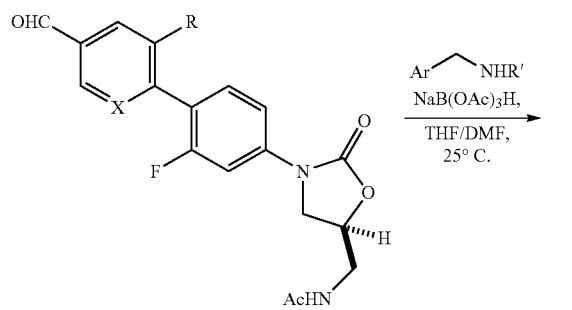

19, X = CH, R = H
9, X = CH, R = OMe
14, X = N, R = H

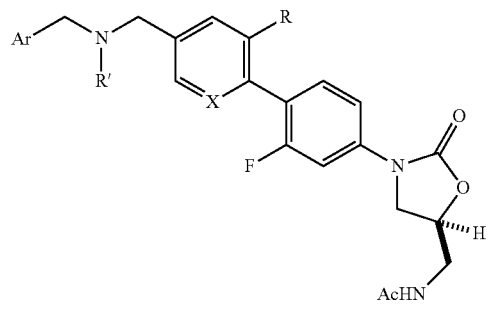

IVb

It should be noted that, when X is N, any of the synthetic routes described above may be used to produce compounds having any regioisomer of pyridine (e.g., pyridin-2-yl or pyridin-3-yl).

In addition, the invention provides alternative approaches for synthesizing compounds of the invention. In one approach, the method includes the step of combining a compound of formula (I):

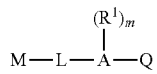

with a compound of formula (II):

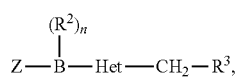

in a solvent in the presence of a base and a palladium catalyst, wherein
Q is a boronate having the formula $-BY_2$, wherein
Y, at each occurrence, independently is selected from the group consisting of:
a) —OH, and b) —O—$C_{1-4}$ alkyl,
alternatively, two Y groups taken together are selected from the group consisting of:
a) —OC($R^4$)($R^4$)C($R^4$)($R^4$)O—, and b) —OC($R^4$)($R^4$)CH$_2$C($R^4$)($R^4$)O—, alternatively, two Y groups taken together with the boron to which they are bound comprise a $BF_3$ alkali metal salt;
Z is selected from the group consisting of:
a) I, b) Br, c) Cl, and d) $R^4OSO_3$—; and
A, B, Het, L, M, $R^1$, $R^2$, $R^3$, $R^4$, m, and n are defined as described above.

In another approach, the method includes the step of combining a compound of formula (III):

with a compound of formula (IV):

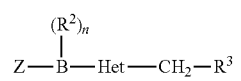

in a solvent in the presence of a base and a palladium catalyst, wherein A, B, Het, L, M, $R^1$, $R^2$, $R^3$, $R^4$, Q, Z, m, and n are defined as described above.

In either approach, Z can be I. Furthermore, Q can be —$BF_2$.KF or

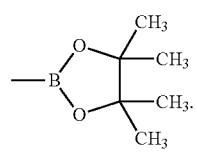

In some embodiments, the base is selected from the group consisting of an alkali metal hydroxide, an alkali metal carbonate, an alkali metal fluoride, a trialkyl amine, and mixtures thereof. Examples of suitable bases include potassium carbonate, sodium carbonate, potassium fluoride, triethylamine, diisopropylethylamine, and mixtures thereof. In particular embodiments, the ratio of equivalents of base to equivalents of compound (I) or compound (III) is about 3:1.

In some embodiments, the palladium catalyst is a ligand coordinated palladium (0) catalyst, such as a tetrakis(trialkylphosphine) palladium (0) or a tetrakis(triarylphosphine) palladium (0) catalyst. An example of a suitable palladium catalyst is tetrakis(triphenylphosphine) palladium (0). In particular embodiments, the ratio of the equivalents of tetrakis(triphenylphosphine) palladium (0) to the equivalents of compound (I) or compound (III) is about 1:20.

In some embodiments, the solvent comprises an aqueous solvent. In other embodiments, the solvent comprises a mixture of water and an organic solvent, wherein the organic solvent is selected from the group consisting of methanol, ethanol, propanol, isopropanol, butanol, isobutanol, secondary butanol, tertiary butanol, benzene, toluene, tetrahydrofuran, dimethylformamide, 1,2-diethyl ether, dimethoxyethane, diisopropyl ether, methyltertiarybutyl ether, methoxymethyl ether, 2-methoxyethyl ether, 1,4-dioxane, 1,3-dioxolane, and mixtures thereof. In a particular embodiment, the solvent is a mixture of water, toluene, and ethanol in a ratio, for example, of about 1:3:1 by volume.

In some embodiments, the method is carried out at a temperature between about 20° C. and about 100° C. In other embodiments, the process is carried out at the reflux temperature of the solvent.

4. Characterization of Compounds of the Invention

Compounds designed, selected and/or optimized by methods described above, once produced, may be characterized using a variety of assays known to those skilled in the art to determine whether the compounds have biological activity. For example, the molecules may be characterized by conventional assays, including but not limited to those assays described below, to determine whether they have a predicted activity, binding activity and/or binding specificity.

Furthermore, high-throughput screening may be used to speed up analysis using such assays. As a result, it may be possible to rapidly screen the molecules described herein for activity, for example, as anti-cancer, anti-bacterial, anti-fungal, anti-parasitic or anti-viral agents. Also, it may be possible to assay how the compounds interact with a ribosome or ribosomal subunit and/or are effective as modulators (for example, inhibitors) of protein synthesis using techniques known in the art. General methodologies for performing high-throughput screening are described, for example, in Devlin, *High Throughput Screening*, (Marcel Dekker, 1998); and U.S. Pat. No. 5,763,263. High-throughput assays can use one or more different assay techniques including, but not limited to, those described below.

(1) Surface Binding Studies.

A variety of binding assays may be useful in screening new molecules for their binding activity. One approach includes surface plasmon resonance (SPR) that can be used to evaluate the binding properties of molecules of interest with respect to a ribosome, ribosomal subunit or a fragment thereof.

SPR methodologies measure the interaction between two or more macromolecules in real-time through the generation of a quantum-mechanical surface plasmon. One device, (BIAcore Biosensor® from Pharmacia Biosensor, Piscatawy, N.J.) provides a focused beam of polychromatic light to the interface between a gold film (provided as a disposable biosensor "chip") and a buffer compartment that can be regulated by the user. A 100 nm thick "hydrogel" composed of carboxylated dextran that provides a matrix for the covalent immobilization of analytes of interest is attached to the gold film. When the focused light interacts with the free electron cloud of the gold film, plasmon resonance is enhanced. The resulting reflected light is spectrally depleted in wavelengths that optimally evolved the resonance. By separating the reflected polychromatic light into its component wavelengths (by means of a prism), and determining the frequencies that are depleted, the BIAcore establishes an optical interface which accurately reports the behavior of the generated surface plasmon resonance. When designed as above, the plasmon resonance (and thus the depletion spectrum) is sensitive to mass in the evanescent field (which corresponds roughly to the thickness of the hydrogel). If one component of an interacting pair is immobilized to the hydrogel, and the interacting partner is provided through the buffer compartment, the interaction between the two components can be measured in real time based on the accumulation of mass in the evanescent field and its corresponding effects of the plasmon resonance as measured by the depletion spectrum. This system permits rapid and sensitive real-time measurement of the molecular interactions without the need to label either component.

(2) Fluorescence Polarization.

Fluorescence polarization (FP) is a measurement technique that can readily be applied to protein-protein, protein-ligand, or RNA-ligand interactions in order to derive $IC_{50}$s and Kds of the association reaction between two molecules. In this technique one of the molecules of interest is conjugated with a fluorophore. This is generally the smaller molecule in the system (in this case, the compound of interest). The sample mixture, containing both the ligand-probe conjugate and the ribosome, ribosomal subunit or fragment thereof, is excited with vertically polarized light. Light is absorbed by the probe fluorophores, and re-emitted a short time later. The degree of polarization of the emitted light is measured. Polarization of the emitted light is dependent on several factors, but most importantly on viscosity of the solution and on the apparent molecular weight of the fluorophore. With proper controls, changes in the degree of polarization of the emitted light depends only on changes in the apparent molecular weight of the fluorophore, which in-turn depends on whether the probe-ligand conjugate is free in solution, or is bound to a receptor. Binding assays based on FP have a number of important advantages, including the measurement of $IC_{50}$s and Kds under true homogenous equilibrium conditions, speed of analysis and amenity to automation, and ability to screen in cloudy suspensions and colored solutions.

(3) Protein Synthesis.

It is contemplated that, in addition to characterization by the foregoing biochemical assays, the compound of interest may also be characterized as a modulator (for example, an inhibitor of protein synthesis) of the functional activity of the ribosome or ribosomal subunit.

Furthermore, more specific protein synthesis inhibition assays may be performed by administering the compound to a whole organism, tissue, organ, organelle, cell, a cellular or subcellular extract, or a purified ribosome preparation and observing its pharmacological and inhibitory properties by determining, for example, its inhibition constant ($IC_{50}$) for inhibiting protein synthesis. Incorporation of $^3H$ leucine or $^{35}S$ methionine, or similar experiments can be performed to investigate protein synthesis activity. A change in the amount or the rate of protein synthesis in the cell in the presence of a molecule of interest indicates that the molecule is a modulator of protein synthesis. A decrease in the rate or the amount of protein synthesis indicates that the molecule is a inhibitor of protein synthesis.

Furthermore, the compounds may be assayed for anti-proliferative or anti-infective properties on a cellular level. For example, where the target organism is a microorganism, the activity of compounds of interest may be assayed by growing the microorganisms of interest in media either containing or lacking the compound. Growth inhibition may be indicative that the molecule may be acting as a protein synthesis inhibitor. More specifically, the activity of the compounds of interest against bacterial pathogens may be demonstrated by the ability of the compound to inhibit growth of defined strains of human pathogens. For this purpose, a panel of bacterial strains can be assembled to include a variety of target pathogenic species, some containing resistance mechanisms that have been characterized. Use of such a panel of organisms permits the determination of structure-activity relationships not only in regards to potency and spectrum, but also with a view to obviating resistance mechanisms. The assays may be performed in microtiter trays according to conventional methodologies as published by The National Committee for Clinical Laboratory Standards (NCCLS) guidelines (NCCLS. M7-A5-Methods for Dilution Antimicrobial Susceptibility Tests for Bacteria That Grow Aerobically; Approved Standard-Fifth Edition. NCCLS Document M100-S12/M7 (ISBN 1-56238-394-9)).

5. Formulation and Administration

The compounds of the invention may be useful in the prevention or treatment of a variety of human or other animal disorders, including for example, bacterial infection, fungal infections, viral infections, parasitic diseases, and cancer. It is contemplated that, once identified, the active molecules of the invention may be incorporated into any suitable carrier prior to use. The dose of active molecule, mode of administration and use of suitable carrier will depend upon the intended recipient and target organism. The formulations, both for veterinary and for human medical use, of compounds according to the present invention typically include such compounds in association with a pharmaceutically acceptable carrier.

The carrier(s) should be "acceptable" in the sense of being compatible with the other ingredients of the formulations and not deleterious to the recipient. Pharmaceutically acceptable carriers, in this regard, are intended to include any and all solvents, dispersion media, coatings, anti-bacterial and anti-fungal agents, isotonic and absorption delaying agents, and the like, compatible with pharmaceutical administration. The use of such media and agents for pharmaceutically active substances is known in the art. Except insofar as any conventional media or agent is incompatible with the active compound, use thereof in the compositions is contemplated. Supplementary active compounds (identified or designed according to the invention and/or known in the art) also can be incorporated into the compositions. The formulations may conveniently be presented in dosage unit form and may be prepared by any of the methods well known in the art of pharmacy/microbiology. In general, some formulations are prepared by bringing the compound into association with a liquid carrier or a finely divided solid carrier or both, and then, if necessary, shaping the product into the desired formulation.

A pharmaceutical composition of the invention should be formulated to be compatible with its intended route of administration. Examples of routes of administration include oral or parenteral, for example, intravenous, intradermal, inhalation, transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

Useful solutions for oral or parenteral administration can be prepared by any of the methods well known in the pharmaceutical art, described, for example, in *Remington's Pharmaceutical Sciences*, 18th ed. (Mack Publishing Company, 1990). Formulations for parenteral administration can also include glycocholate for buccal administration, methoxysalicylate for rectal administration, or citric acid for vaginal administration. The parenteral preparation can be enclosed in ampoules, disposable syringes or multiple dose vials made of glass or plastic. Suppositories for rectal administration also can be prepared by mixing the drug with a non-irritating excipient such as cocoa butter, other glycerides, or other compositions which are solid at room temperature and liquid at body temperatures. Formulations also can include, for example, polyalkylene glycols such as polyethylene glycol, oils of vegetable origin, and hydrogenated naphthalenes. Formulations for direct administration can include glycerol and other compositions of high viscosity. Other potentially useful parenteral carriers for these drugs include ethylene-vinyl acetate copolymer particles, osmotic pumps, implantable infusion systems, and liposomes. Formulations for inhalation administration can contain as excipients, for example, lactose, or can be aqueous solutions containing, for example, polyoxyethylene-9-lauryl ether, glycocholate and deoxycholate, or oily solutions for administration in the form of nasal drops, or as a gel to be applied intranasally. Retention enemas also can be used for rectal delivery.

Formulations of the present invention suitable for oral administration may be in the form of: discrete units such as capsules, gelatin capsules, sachets, tablets, troches, or lozenges, each containing a predetermined amount of the drug; a powder or granular composition; a solution or a suspension in an aqueous liquid or non-aqueous liquid; or an oil-in-water emulsion or a water-in-oil emulsion. The drug may also be administered in the form of a bolus, electuary or paste. A tablet may be made by compressing or molding the drug optionally with one or more accessory ingredients. Compressed tablets may be prepared by compressing, in a suitable machine, the drug in a free-flowing form such as a powder or granules, optionally mixed by a binder, lubricant, inert diluent, surface active or dispersing agent. Molded tablets may be made by molding, in a suitable machine, a mixture of the powdered drug and suitable carrier moistened with an inert liquid diluent.

Oral compositions generally include an inert diluent or an edible carrier. For the purpose of oral therapeutic administration, the active compound can be incorporated with excipients. Oral compositions prepared using a fluid carrier for use as a mouthwash include the compound in the fluid carrier and are applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying which yields a powder of the active ingredient plus any additional desired ingredient from a previously sterile-filtered solution thereof.

Formulations suitable for intra-articular administration may be in the form of a sterile aqueous preparation of the drug that may be in microcrystalline form, for example, in the form of an aqueous microcrystalline suspension. Liposomal formulations or biodegradable polymer systems may also be used to present the drug for both intra-articular and ophthalmic administration.

Formulations suitable for topical administration, including eye treatment, include liquid or semi-liquid preparations such as liniments, lotions, gels, applicants, oil-in-water or water-in-oil emulsions such as creams, ointments or pastes; or solutions or suspensions such as drops. Formulations for topical administration to the skin surface can be prepared by dispersing the drug with a dermatologically acceptable carrier such as a lotion, cream, ointment or soap. Particularly useful are carriers capable of forming a film or layer over the skin to localize application and inhibit removal. For topical administration to internal tissue surfaces, the agent can be dispersed in a liquid tissue adhesive or other substance known to enhance adsorption to a tissue surface. For example, hydroxypropylcellulose or fibrinogen/thrombin solutions can be used to advantage. Alternatively, tissue-coating solutions, such as pectin-containing formulations can be used.

For inhalation treatments, inhalation of powder (self-propelling or spray formulations) dispensed with a spray can, a nebulizer, or an atomizer can be used. Such formulations can be in the form of a fine powder for pulmonary administration from a powder inhalation device or self-propelling powder-dispensing formulations. In the case of self-propelling solution and spray formulations, the effect may be achieved either by choice of a valve having the desired spray characteristics (i.e., being capable of producing a spray having the desired particle size) or by incorporating the active ingredient as a suspended powder in controlled particle size. For administration by inhalation, the compounds also can be delivered in the form of an aerosol spray from pressured container or dispenser which contains a suitable propellant, e.g., a gas such as carbon dioxide, or a nebulizer.

Systemic administration also can be by transmucosal or transdermal means. For transmucosal or transdermal administration, penetrants appropriate to the barrier to be permeated are used in the formulation. Such penetrants generally are known in the art, and include, for example, for transmucosal administration, detergents and bile salts. Transmucosal administration can be accomplished through the use of nasal sprays or suppositories. For transdermal administration, the active compounds typically are formulated into ointments, salves, gels, or creams as generally known in the art.

The active compounds may be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art, for example, as described in U.S. Pat. No. 4,522,811.

Oral or parenteral compositions can be formulated in dosage unit form for ease of administration and uniformity of dosage. Dosage unit form refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals. Furthermore, administration can be by periodic injections of a bolus, or can be made more continuous by intravenous, intramuscular or intraperitoneal administration from an external reservoir (e.g., an intravenous bag).

Where adhesion to a tissue surface is desired the composition can include the drug dispersed in a fibrinogen-thrombin composition or other bioadhesive. The compound then can be painted, sprayed or otherwise applied to the desired tissue surface. Alternatively, the drugs can be formulated for parenteral or oral administration to humans or other mammals, for example, in effective amounts, e.g., amounts that provide appropriate concentrations of the drug to target tissue for a time sufficient to induce the desired effect.

Where the active compound is to be used as part of a transplant procedure, it can be provided to the living tissue or organ to be transplanted prior to removal of tissue or organ from the donor. The compound can be provided to the donor host. Alternatively or, in addition, once removed from the donor, the organ or living tissue can be placed in a preservation solution containing the active compound. In all cases, the active compound can be administered directly to the desired tissue, as by injection to the tissue, or it can be provided systemically, either by oral or parenteral administration, using any of the methods and formulations described herein and/or known in the art. Where the drug comprises part of a tissue or organ preservation solution, any commercially available preservation solution can be used to advantage. For example, useful solutions known in the art include Collins solution, Wisconsin solution, Belzer solution, Eurocollins solution and lactated Ringer's solution.

Active compound as identified or designed by the methods described herein can be administered to individuals to treat disorders (prophylactically or therapeutically). In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a drug as well as tailoring the dosage and/or therapeutic regimen of treatment with the drug.

In therapeutic use for treating, or combating, bacterial infections in mammals, the compounds or pharmaceutical compositions thereof will be administered orally, parenterally and/or topically at a dosage to obtain and maintain a concentration, that is, an amount, or blood-level or tissue level of active component in the animal undergoing treatment which will be anti-microbially effective. The term "effective amount" is understood to mean that the compound of the invention is present in or on the recipient in an amount sufficient to elicit biological activity, for example, anti-microbial activity, anti-fungal activity, anti-viral activity, anti-parasitic activity, and/or anti-proliferative activity. Generally, an effective amount of dosage of active component will be in the range of from about 0.1 to about 100, more preferably from about 1.0 to about 50 mg/kg of body weight/day. The amount administered will also likely depend on such variables as the type and extent of disease or indication to be treated, the overall health status of the particular patient, the relative biological efficacy of the compound delivered, the formulation of the drug, the presence and types of excipients in the formulation, and the route of administration. Also, it is to be understood that the initial dosage administered may be increased beyond the above upper level in order to rapidly achieve the desired blood-level or tissue level, or the initial dosage may be smaller than the optimum and the daily dosage may be progressively increased during the course of treatment depending on the particular situation. If desired, the daily dose may also be divided into multiple doses for administration, for example, two to four times per day.

6. Examples

Exemplary compounds synthesized in accordance with the invention are listed in Table 2.

TABLE 2

| Compound Number | Structure |
|---|---|
| 1001 | 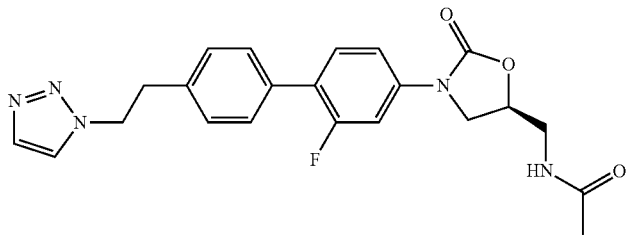 [SMILES: CC(=O)NC[C@H]1CN(c2ccc(-c3ccc(CCn4ccnn4)cc3)c(F)c2)C(=O)O1]<br>N-{3-[2-Fluoro-4'-(2-[1,2,3]triazol-1-yl-ethyl)-biphenyl-4-yl]-2-oxo-oxazolidin-5-(S)-ylmethyl}-acetamide |
| 1002 | 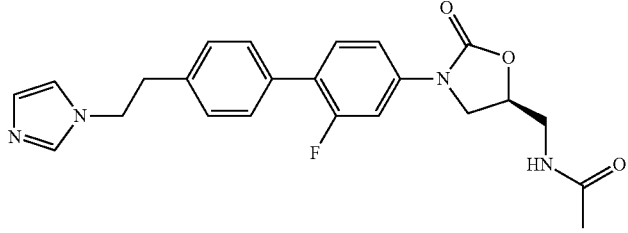 [SMILES: CC(=O)NC[C@H]1CN(c2ccc(-c3ccc(CCn4ccnc4)cc3)c(F)c2)C(=O)O1]<br>N-{3-[2-Fluoro-4'-(2-imidazol-1-yl-ethyl)-biphenyl-4-yl]-2-oxo-oxazolidin-5-(S)-ylmethyl}-acetamide |

TABLE 2-continued

| Compound Number | Structure |
| --- | --- |
| 1003 | 2-(4-{4'-[5-(S)-(Acetylamino-methyl)-2-oxo-oxazolidin-3-yl]-2'-fluoro-biphenyl-4-ylmethyl}-piperazin-1-yl)-acetamide |
| 1004 | N-{3-[4'-(4-Cyanomethyl-piperazin-1-ylmethyl)-2-fluoro-biphenyl-4-yl]-2-oxo-oxazolidin-5-(S)-ylmethyl}-acetamide |
| 1005 | N-{3-[4'-(4-Cyanomethyl-piperazin-1-ylmethyl)-2,3'-difluoro-biphenyl-4-yl]-2-oxo-oxazolidin-5-(S)-ylmethyl}-acetamide |
| 1006 | N-{3-[2-Fluoro-4'-(4-formyl-piperazin-1-ylmethyl)-biphenyl-4-yl]-2-oxo-oxazolidin-5-(S)-ylmethyl}-acetamide |

TABLE 2-continued

| Compound Number | Structure |
|---|---|
| 1007 | N-{3-[2-Fluoro-4'-(1H-tetrazol-5-ylmethyl)-biphenyl-4-yl]-2-oxo-oxazolidin-5-(S)-ylmethyl}-acetamide |
| 1008 | N-[3-(2-Fluoro-4'-imidazol-1-ylmethyl-biphenyl-4-yl)-2-oxo-oxazolidin-5-(S)-ylmethyl]-acetamide |
| 1009 | N-[3-(2,3'-Difluoro-4'-[1,2,3]triazol-1-ylmethyl-biphenyl-4-yl)-2-oxo-oxazolidin-5-(S)-ylmethyl]-acetamide |
| 1010 | N-[3-(2,3'-Difluoro-4'-imidazol-1-ylmethyl-biphenyl-4-yl)-2-oxo-oxazolidin-5-(S)-ylmethyl]-acetamide |
| 1011 | N-{3-[4'-(4-Aminomethyl-[1,2,3]triazol-1-ylmethyl)-2-fluoro-biphenyl-4-yl]-2-oxo-oxazolidin-5-(S)-ylmethyl}-acetamide |

TABLE 2-continued

| Compound Number | Structure |
|---|---|
| 1012 | 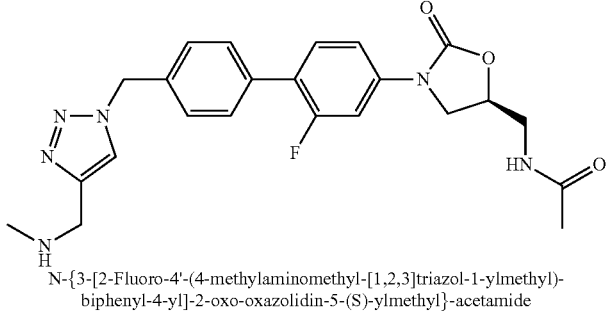<br>N-{3-[2-Fluoro-4'-(4-methylaminomethyl-[1,2,3]triazol-1-ylmethyl)-biphenyl-4-yl]-2-oxo-oxazolidin-5-(S)-ylmethyl}-acetamide |
| 1013 | 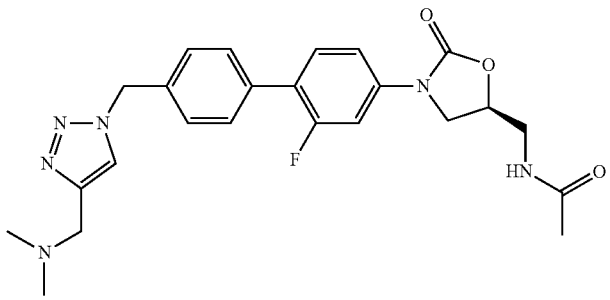 [SMILES: CC(=O)NC[C@H]1CN(c2ccc(-c3ccc(Cn4cc(CN(C)C)nn4)cc3)c(F)c2)C(=O)O1]<br>N-{3-[4'-(4-Dimethylaminomethyl-[1,2,3]triazol-1-ylmethyl)-2-fluoro-biphenyl-4-yl]-2-oxo-oxazolidin-5-(S)-ylmethyl}-acetamide |
| 1014 | 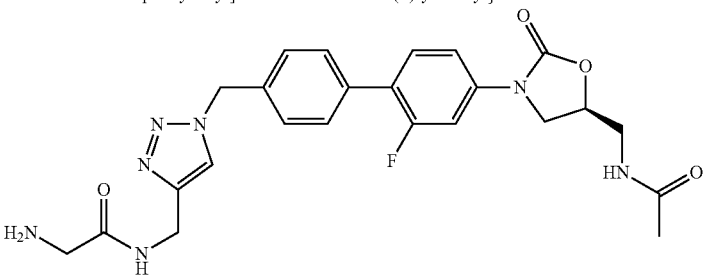<br>N-(1-{4'-[5-(S)-(Acetylamino-methyl)-2-oxo-oxazolidin-3-yl]-2'-fluoro-biphenyl-4-ylmethyl}-1H-[1,2,3]triazol-4-ylmethyl)-2-amino-acetamide |
| 1015 | 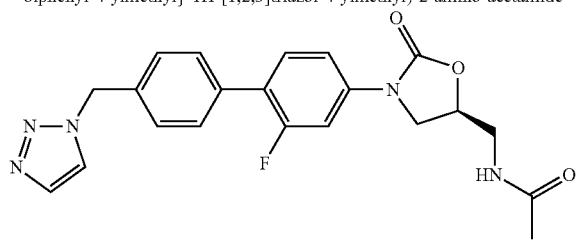<br>N-[3-(2-Fluoro-4'-[1,2,3]triazol-1-ylmethyl-biphenyl-4-yl)-2-oxo-oxazolidin-5-(S)-ylmethyl]-acetamide |
| 1016 | 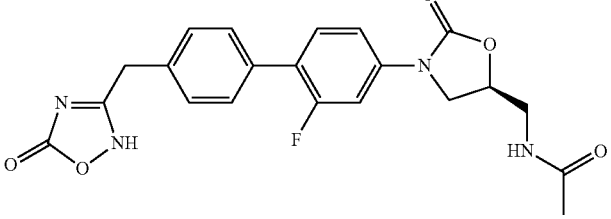<br>N-{3-[2-Fluoro-4'-(5-(S)-oxo-2,5-(S)-dihydro-[1,2,4]oxadiazol-3-ylmethyl)-biphenyl-4-yl]-2-oxo-oxazolidin-5-(S)-ylmethyl}-acetamide |

TABLE 2-continued

| Compound Number | Structure |
| --- | --- |
| 1017 | N-{3-[2-Fluoro-4'-(5-(S)-methyl-[1,2,4]oxadiazol-3-ylmethyl)-biphenyl-4-yl]-2-oxo-oxazolidin-5-(S)-ylmethyl}-acetamide |
| 1018 | N-{3-[2,6-Difluoro-4'-(4-hydroxymethyl-[1,2,3]triazol-1-ylmethyl)-biphenyl-4-yl]-2-oxo-oxazolidin-5-(S)-ylmethyl}-acetamide |
| 1019 | N-{3-[4'-(4-Dimethylaminomethyl-[1,2,3]triazol-1-ylmethyl)-2,6-difluoro-biphenyl-4-yl]-2-oxo-oxazolidin-5-(S)-ylmethyl}-acetamide |
| 1020 | N-[3-(2-Fluoro-4'-{2-[(tetrahydro-furan-2-ylmethyl)-amino]-thiazol-4-ylmethyl}-biphenyl-4-yl)-2-oxo-oxazolidin-5-(S)-ylmethyl]-acetamide |

TABLE 2-continued

| Compound Number | Structure |
|---|---|
| 1021 | N-(3-{2-Fluoro-4'-[2-(3-methoxy-benzylamino)-thiazol-4-ylmethyl]-biphenyl-4-yl}-2-oxo-oxazolidin-5-(S)-ylmethyl)-acetamide |
| 1022 | N-{3-[4'-(3-Cyano-azetidin-1-ylmethyl)-2-fluoro-biphenyl-4-yl]-2-oxo-oxazolidin-5-(S)-ylmethyl}-acetamide |
| 1023 | N-[3-(2-Fluoro-4'-[1,2,3]triazol-2-ylmethyl-biphenyl-4-yl)-2-oxo-oxazolidin-5-(S)-ylmethyl]-acetamide |
| 1024 | N-{3-[4'-(5-Amino-tetrazol-2-ylmethyl)-2-fluoro-biphenyl-4-yl]-2-oxo-oxazolidin-5-(S)-ylmethyl}-acetamide |

TABLE 2-continued

| Compound Number | Structure |
|---|---|
| 1025 | 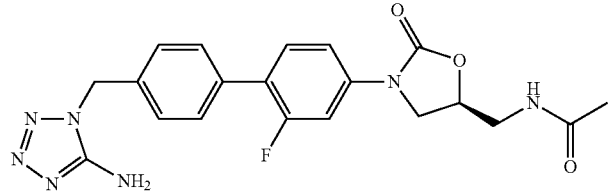<br>N-{3-[4'-(5-Amino-tetrazol-1-ylmethyl)-2-fluoro-biphenyl-4-yl]-2-oxo-oxazolidin-5-(S)-ylmethyl}-acetamide |
| 1026 | 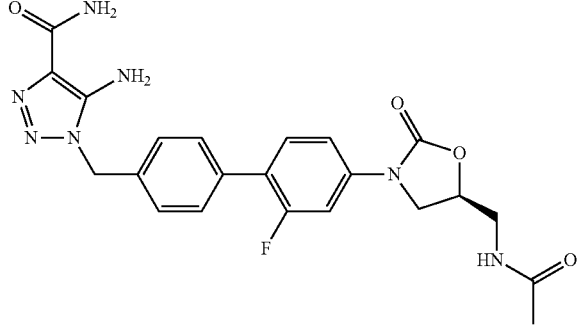 [SMILES: CC(=O)NC[C@H]1CN(c2ccc(-c3ccc(Cn4nnc(C(N)=O)c4N)cc3)c(F)c2)C(=O)O1]<br>1-{4'-[5-(S)-(Acetylamino-methyl)-2-oxo-oxazolidin-3-yl]-2'-fluoro-biphenyl-4-ylmethyl}-5-amino-1H-[1,2,3]triazole-4-carboxylic acid amide |
| 1027 | 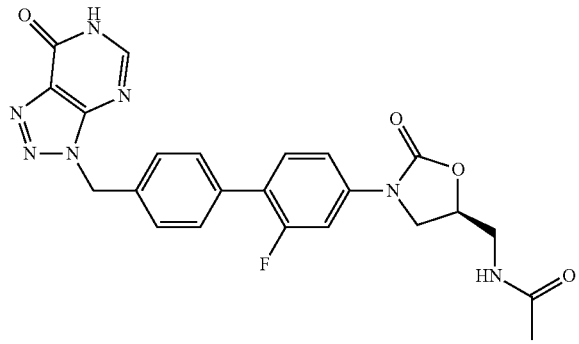 [SMILES: CC(=O)NC[C@H]1CN(c2ccc(-c3ccc(Cn4nnc5c(=O)[nH]cnc54)cc3)c(F)c2)C(=O)O1]<br>N-{3-[2-Fluoro-4'-(7-oxo-6,7-dihydro-[1,2,3]triazolo[4,5-d]pyrimidin-3-ylmethyl)-biphenyl-4-yl]-2-oxo-oxazolidin-5-(S)-ylmethyl}-acetamide |
| 1028 | 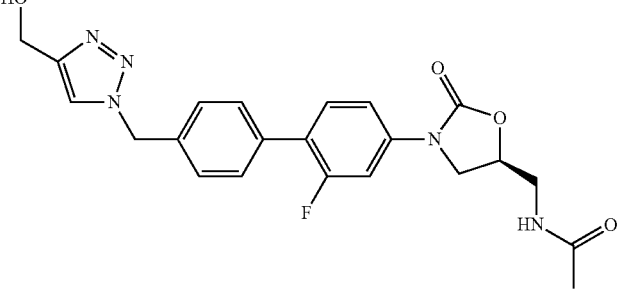<br>N-{3-[2-Fluoro-4'-(4-hydroxymethyl-[1,2,3]triazol-1-ylmethyl)-biphenyl-4-yl]-2-oxo-oxazolidin-5-(S)-ylmethyl}-acetamide |

TABLE 2-continued

| Compound Number | Structure |
|---|---|
| 1029 | 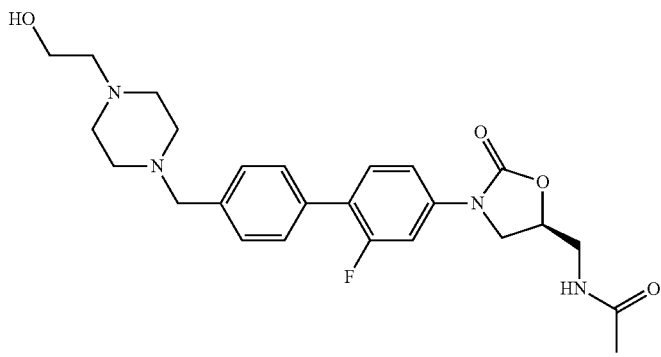 [SMILES: CC(=O)NC[C@H]1CN(c2ccc(-c3ccc(CN4CCN(CCO)CC4)cc3)c(F)c2)C(=O)O1]<br>N-(3-{2-Fluoro-4'-[4-(2-hydroxy-ethyl)-piperazin-1-ylmethyl]-biphenyl-4-yl}-2-oxo-oxazolidin-5-(S)-ylmethyl)-acetamide |
| 1030 | 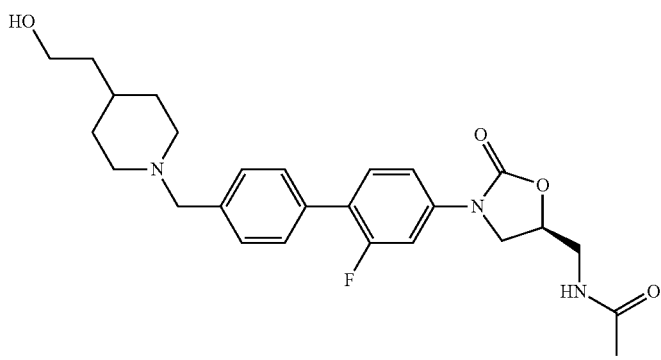 [SMILES: CC(=O)NC[C@H]1CN(c2ccc(-c3ccc(CN4CCC(CCO)CC4)cc3)c(F)c2)C(=O)O1]<br>N-(3-{2-Fluoro-4'-[4-(2-hydroxy-ethyl)-piperidin-1-ylmethyl]-biphenyl-4-yl}-2-oxo-oxazolidin-5-(S)-ylmethyl)-acetamide |
| 1031 | 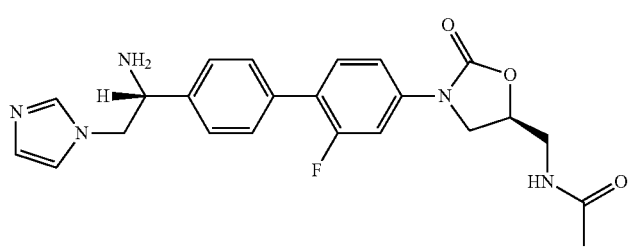 [SMILES: CC(=O)NC[C@H]1CN(c2ccc(-c3ccc([C@@H](N)Cn4ccnc4)cc3)c(F)c2)C(=O)O1]<br>N-{3-[4'-(R)-(1-Amino-2-imidazol-1-yl-ethyl)-2-fluoro-biphenyl-4-yl]-2-oxo-oxazolidin-5-(S)-ylmethyl}-acetamide |
| 1032 | 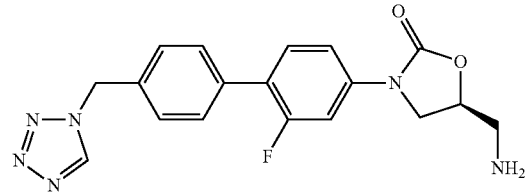 [SMILES: NC[C@H]1CN(c2ccc(-c3ccc(Cn4cnnn4)cc3)c(F)c2)C(=O)O1]<br>5-(S)-Aminomethyl-3-(2-fluoro-4'-tetrazol-1-ylmethyl-biphenyl-4-yl)-oxazolidin-2-one |

| Compound Number | Structure |
|---|---|
| 1033 | 2-Chloro-N-[3-(2-fluoro-4'-tetrazol-1-ylmethyl-biphenyl-4-yl)-2-oxo-oxazolidin-5-(S)-ylmethyl]-acetamide |
| 1034 | 2,2-Dichloro-N-[3-(2-fluoro-4'-tetrazol-1-ylmethyl-biphenyl-4-yl)-2-oxo-oxazolidin-5-(S)-ylmethyl]-acetamide |
| 1035 | N-{3-[3-Fluoro-4-(6-tetrazol-1-ylmethyl-pyridin-3-yl)-phenyl]-2-oxo-oxazolidin-5-(S)-ylmethyl}-acetamide |
| 1036 | N-{3-[3-Fluoro-4-(6-[1,2,3]triazol-1-ylmethyl-pyridin-3-yl)-phenyl]-2-oxo-oxazolidin-5-(S)-ylmethyl}-acetamide |
| 1037 | N-[3-(2-Fluoro-4'-[1,2,4]triazol-1-ylmethyl-biphenyl-4-yl)-2-oxo-oxazolidin-5-(S)-ylmethyl]-acetamide |

TABLE 2-continued

| Compound Number | Structure |
|---|---|
| 1038 | 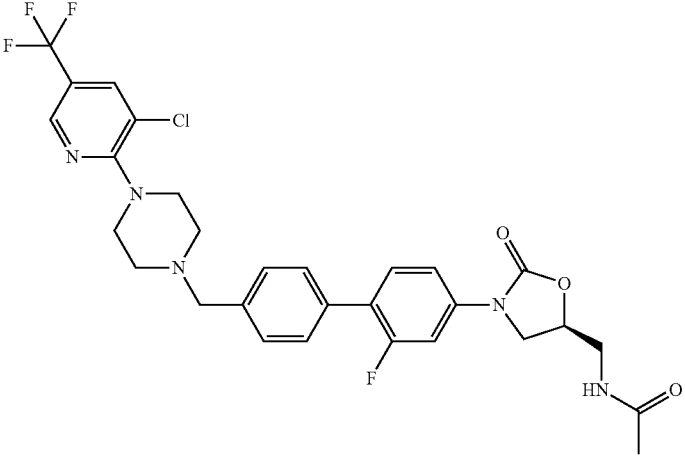 [SMILES: CC(=O)NC[C@H]1CN(c2ccc(-c3ccc(CN4CCN(c5ncc(C(F)(F)F)cc5Cl)CC4)cc3)c(F)c2)C(=O)O1]<br>N-(3-{4'-[4-(3-Chloro-5-trifluoromethyl-pyridin-2-yl)-piperazin-1-ylmethyl]-2-fluoro-biphenyl-4-yl}-2-oxo-oxazolidin-5-(S)-ylmethyl)-acetamide |
| 1039 | 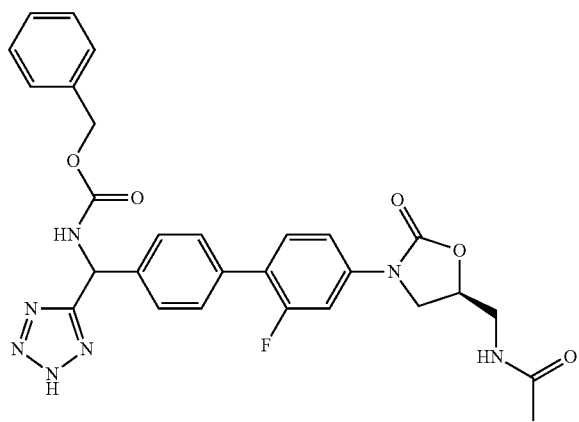 [SMILES: CC(=O)NC[C@H]1CN(c2ccc(-c3ccc(C(NC(=O)OCc4ccccc4)c4nn[nH]n4)cc3)c(F)c2)C(=O)O1]<br>[{4'-[5-(S)-(Acetylamino-methyl)-2-oxo-oxazolidin-3-yl]-2'-fluoro-biphenyl-4-yl}-(2H-tetrazol-5-(R/S)-yl)-methyl]-carbamic acid benzyl ester |
| 1040 | 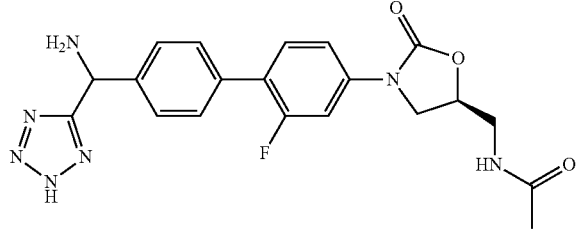 [SMILES: CC(=O)NC[C@H]1CN(c2ccc(-c3ccc(C(N)c4nn[nH]n4)cc3)c(F)c2)C(=O)O1]<br>N-(3-{4'-[Amino-(2H-tetrazol-5-(R/S)-yl)-methyl]-2-fluoro-biphenyl-4-yl}-2-oxo-oxazolidin-5-(S)-ylmethyl)-acetamide |

TABLE 2-continued

| Compound Number | Structure |
|---|---|
| 1041 | [{4'-[5-(S)-(Acetylamino-methyl)-2-oxo-oxazolidin-3-yl]-2'-fluoro-biphenyl-4-yl}-(2-methyl-2H-tetrazol-5-(R/S)-yl)-methyl]-carbamic acid benzyl ester |
| 1042 | N-(3-{4'-[Amino-(2-methyl-2H-tetrazol-5-(R/S)-yl)-methyl]-2-fluoro-biphenyl-4-yl}-2-oxo-oxazolidin-5-(S)-ylmethyl)-acetamide |
| 1043 | N-[3-(2-Fluoro-4'-pyrazol-1-ylmethyl-biphenyl-4-yl)-2-oxo-oxazolidin-5-(S)-ylmethyl]-acetamide |
| 1044 | N-(3-{2-Fluoro-4'-[2-(4-formyl-piperazin-1-yl)-1-(S)-hydroxy-ethyl]-biphenyl-4-yl}-2-oxo-oxazolidin-5-(S)-ylmethyl)-acetamide |

TABLE 2-continued

| Compound Number | Structure |
|---|---|
| 1045 | N-(3-{2-Fluoro-4'-[1-(R)-(4-formyl-piperazin-1-yl)-2-hydroxy-ethyl]-biphenyl-4-yl}-2-oxo-oxazolidin-5-(S)-ylmethyl)-acetamide |
| 1046 | N-{3-[2-Fluoro-4'-(1-(S)-hydroxy-2-imidazol-1-yl-ethyl)-biphenyl-4-yl]-2-oxo-oxazolidin-5-(S)-ylmethyl}-acetamide |
| 1047 | N-[3-(2-Fluoro-4'-tetrazol-1-ylmethyl-biphenyl-4-yl)-2-oxo-oxazolidin-5-(S)-ylmethyl]-acetamide |
| 1048 | N-[3-(2,6-Difluoro-4'-tetrazol-1-ylmethyl-biphenyl-4-yl)-2-oxo-oxazolidin-5-(S)-ylmethyl]-acetamide |
| 1049 | 1-{4'-[5-(S)-(Acetylamino-methyl)-2-oxo-oxazolidin-3-yl]-2'-fluoro-biphenyl-4-ylmethyl}-1H-pyrazole-4-carboxylic acid ethyl ester |

TABLE 2-continued

| Compound Number | Structure |
|---|---|
| 1050 | N-{3-[2-Fluoro-4'-(4-hydroxymethyl-imidazol-1-ylmethyl)-biphenyl-4-yl]-2-oxo-oxazolidin-5-(S)-ylmethyl}-acetamide |
| 1051 | 1-{4'-[5-(S)-(Acetylamino-methyl)-2-oxo-oxazolidin-3-yl]-2'-fluoro-biphenyl-4-ylmethyl}-1H-pyrazole-4-carboxylic acid |
| 1052 | N-{3-[2-Fluoro-4'-(4-methyl-pyrazol-1-ylmethyl)-biphenyl-4-yl]-2-oxo-oxazolidin-5-(S)-ylmethyl}-acetamide |
| 1053 | N-{3-[4'-(3-Amino-pyrazol-1-ylmethyl)-2-fluoro-biphenyl-4-yl]-2-oxo-oxazolidin-5-(S)-ylmethyl}-acetamide |
| 1054 | N-[3-(2-Fluoro-4'-pyrrol-1-ylmethyl-biphenyl-4-yl)-2-oxo-oxazolidin-5-(S)-ylmethyl]-acetamide |

| Compound Number | Structure |
|---|---|
| 1055 | 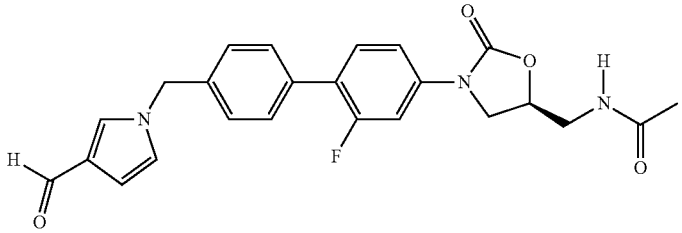 [SMILES: CC(=O)NC[C@H]1CN(c2ccc(-c3ccc(Cn4ccc(C=O)c4)cc3)c(F)c2)C(=O)O1]<br>N-{3-[2-Fluoro-4'-(3-formyl-pyrrol-1-ylmethyl)-biphenyl-4-yl]-2-oxo-oxazolidin-5-(S)-ylmethyl}-acetamide |
| 1056 | 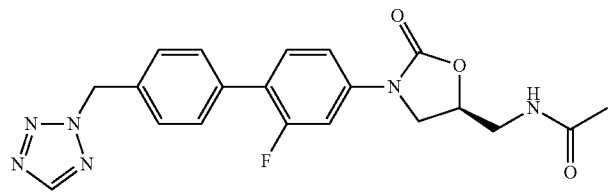 [SMILES: CC(=O)NC[C@H]1CN(c2ccc(-c3ccc(Cn4ncnn4)cc3)c(F)c2)C(=O)O1]<br>N-[3-(2-Fluoro-4'-tetrazol-2-ylmethyl-biphenyl-4-yl)-2-oxo-oxazolidin-5-(S)-ylmethyl]-acetamide |
| 1057 | 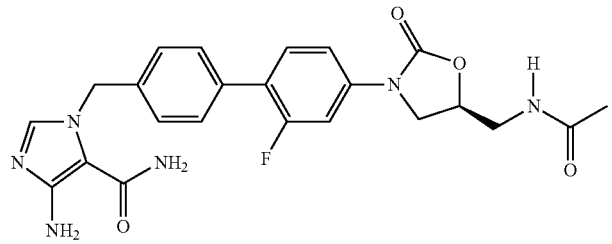 [SMILES: CC(=O)NC[C@H]1CN(c2ccc(-c3ccc(Cn4cnc(N)c4C(N)=O)cc3)c(F)c2)C(=O)O1]<br>3-{4'-[5-(S)-(Acetylamino-methyl)-2-oxo-oxazolidin-3-yl]-2'-fluoro-biphenyl-4-ylmethyl}-5-amino-3H-imidazole-4-carboxylic acid amide |
| 1058 | 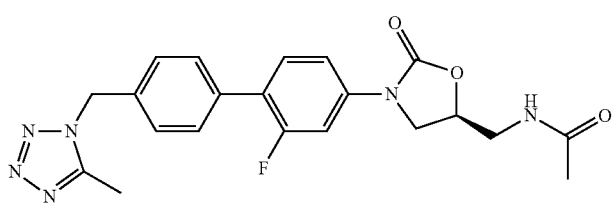 [SMILES: CC(=O)NC[C@H]1CN(c2ccc(-c3ccc(Cn4nnnc4C)cc3)c(F)c2)C(=O)O1]<br>N-{3-[2-Fluoro-4'-(5-methyl-tetrazol-1-ylmethyl)-biphenyl-4-yl]-2-oxo-oxazolidin-5-(S)-ylmethyl}-acetamide |
| 1059 | 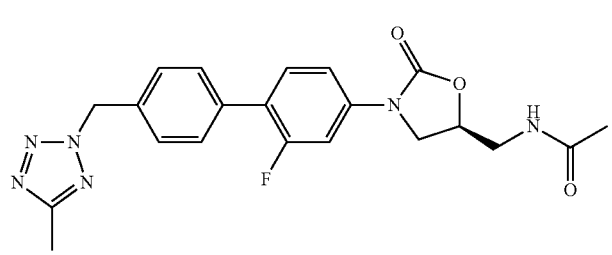 [SMILES: CC(=O)NC[C@H]1CN(c2ccc(-c3ccc(Cn4nnc(C)n4)cc3)c(F)c2)C(=O)O1]<br>N-{3-[2-Fluoro-4'-(5-methyl-tetrazol-2-ylmethyl)-biphenyl-4-yl]-2-oxo-oxazolidin-5-(S)-ylmethyl}-acetamide |

| Compound Number | Structure |
|---|---|
| 1060 | N-(3-{2-Fluoro-4'-[1-(R)-hydroxy-2-(1H-tetrazol-5-yl)-ethyl]-biphenyl-4-yl}-2-oxo-oxazolidin-5-(S)-ylmethyl)-acetamide |
| 1061 | N-{3-[2-Fluoro-4'-(1-(S)-hydroxy-2-[1,2,3]triazol-1-yl-ethyl)-biphenyl-4-yl]-2-oxo-oxazolidin-5-(S)-ylmethyl}-acetamide |
| 1062 | N-{3-[4'-(2-Azetidin-1-yl-1-(S)-hydroxy-ethyl)-2-fluoro-biphenyl-4-yl]-2-oxo-oxazolidin-5-(S)-ylmethyl}-acetamide |
| 1063 | N-{3-[4'-(1-(R)-Azetidin-1-yl-2-hydroxy-ethyl)-2-fluoro-biphenyl-4-yl]-2-oxo-oxazolidin-5-(S)-ylmethyl}-acetamide |
| 1064 | N-[3-(2-Fluoro-4'-thiomorpholin-4-ylmethyl-biphenyl-4-yl)-2-oxo-oxazolidin-5-(S)-ylmethyl]-acetamide |

TABLE 2-continued

| Compound Number | Structure |
|---|---|
| 1065 | N-{3-[2-Fluoro-4'-(1-oxo-1lambda*4*-thiomorpholin-4-ylmethyl)-biphenyl-4-yl]-2-oxo-oxazolidin-5-(S)-ylmethyl}-acetamide |
| 1066 | N-{3-[2-Fluoro-4'-(2-methyl-imidazol-1-ylmethyl)-biphenyl-4-yl]-2-oxo-oxazolidin-5-(S)-ylmethyl}-acetamide |
| 1067 | N-{3-[2-Fluoro-4'-(5-methyl-imidazol-1-ylmethyl)-biphenyl-4-yl]-2-oxo-oxazolidin-5-(S)-ylmethyl}-acetamide |
| 1068 | N-{3-[4'-(2,4-Dimethyl-imidazol-1-ylmethyl)-2-fluoro-biphenyl-4-yl]-2-oxo-oxazolidin-5-(S)-ylmethyl}-acetamide |
| 1069 | N-{3-[4'-(3-Amino-[1,2,4]triazol-1-ylmethyl)-2-fluoro-biphenyl-4-yl]-2-oxo-oxazolidin-5-(S)-ylmethyl}-acetamide |

TABLE 2-continued

| Compound Number | Structure |
|---|---|
| 1070 | N-[3-(2-Fluoro-4'-thiazolidin-3-ylmethyl-biphenyl-4-yl)-2-oxo-oxazolidin-5-(S)-ylmethyl]-acetamide |
| 1071 | N-{3-[3-Fluoro-4-(6-pyrrol-1-ylmethyl-pyridin-3-yl)-phenyl]-2-oxo-oxazolidin-5-(S)-ylmethyl}-acetamide |
| 1072 | N-{3-[3-Fluoro-4-(6-[1,2,4]triazol-1-ylmethyl-pyridin-3-yl)-phenyl]-2-oxo-oxazolidin-5-(S)-ylmethyl}-acetamide |
| 1073 | N-{3-[2-Fluoro-4'-(2-hydroxy-1-(R)-[1,2,3]triazol-1-yl-ethyl)-biphenyl-4-yl]-2-oxo-oxazolidin-5-(S)-ylmethyl}-acetamide |
| 1074 | N-(3-{4'-[1-(R)-(3,3-Difluoro-piperidin-1-yl)-2-hydroxy-ethyl]-2-fluoro-biphenyl-4-yl}-2-oxo-oxazolidin-5-(S)-ylmethyl)-acetamide |

TABLE 2-continued

| Compound Number | Structure |
|---|---|
| 1075 | N-(3-{4'-[2-(3,3-Difluoro-piperidin-1-yl)-1-(S)-hydroxy-ethyl]-2-fluoro-biphenyl-4-yl}-2-oxo-oxazolidin-5-(S)-ylmethyl)-acetamide |
| 1076 | N-{3-[3-Fluoro-4-(6-pyrazol-1-ylmethyl-pyridin-3-yl)-phenyl]-2-oxo-oxazolidin-5-(S)-ylmethyl}-acetamide |
| 1077 | N-{3-[3-Fluoro-4-(6-imidazol-1-ylmethyl-pyridin-3-yl)-phenyl]-2-oxo-oxazolidin-5-(S)-ylmethyl}-acetamide |
| 1078 | N-{3-[2-Fluoro-4'-(2-methylsulfanyl-4,5-dihydro-imidazol-1-ylmethyl)-biphenyl-4-yl]-2-oxo-oxazolidin-5-(S)-ylmethyl}-acetamide |
| 1079 | N-{3-[2-Fluoro-4'-(5-methylsulfanyl-tetrazol-1-ylmethyl)-biphenyl-4-yl]-2-oxo-oxazolidin-5-(S)-ylmethyl}-acetamide |

TABLE 2-continued

| Compound Number | Structure |
|---|---|
| 1080 | N-{3-[2-Fluoro-4'-(5-methylsulfanyl-tetrazol-2-ylmethyl)-biphenyl-4-yl]-2-oxo-oxazolidin-5-(S)-ylmethyl}-acetamide |
| 1081 | N-{3-[4'-(5-Ethylsulfanyl-tetrazol-1-ylmethyl)-2-fluoro-biphenyl-4-yl]-2-oxo-oxazolidin-5-(S)-ylmethyl}-acetamide |
| 1082 | N-{3-[4'-(5-Ethylsulfanyl-tetrazol-2-ylmethyl)-2-fluoro-biphenyl-4-yl]-2-oxo-oxazolidin-5-(S)-ylmethyl}-acetamide |
| 1083 | N-{3-[4'-(5-Chloro-tetrazol-1-ylmethyl)-2-fluoro-biphenyl-4-yl]-2-oxo-oxazolidin-5-(S)-ylmethyl}-acetamide |
| 1084 | 3-(2-Fluoro-4'-imidazol-1-ylmethyl-biphenyl-4-yl)-5-(R)-[1,2,3]triazol-1-ylmethyl-oxazolidin-2-one |

| Compound Number | Structure |
|---|---|
| 1085 | 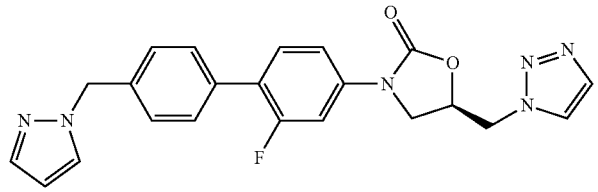 [SMILES: O=C1O[C@@H](Cn2ccnn2)CN1c1ccc(-c2ccc(Cn3cccn3)cc2)c(F)c1]<br>3-(2-Fluoro-4'-pyrazol-1-ylmethyl-biphenyl-4-yl)-5-(R)-[1,2,3]triazol-1-ylmethyl-oxazolidin-2-one |
| 1086 | 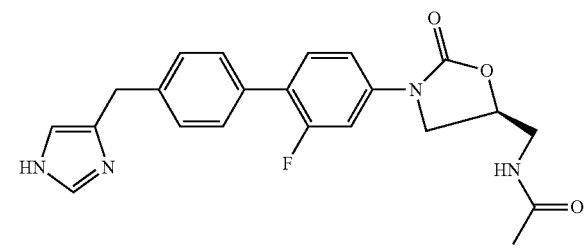 [SMILES: CC(=O)NC[C@H]1CN(c2ccc(-c3ccc(Cc4c[nH]cn4)cc3)c(F)c2)C(=O)O1]<br>N-{3-[2-Fluoro-4'-(1H-imidazol-4-ylmethyl)-biphenyl-4-yl]-2-oxo-oxazolidin-5-(S)-ylmethyl}-acetamide |
| 1087 | 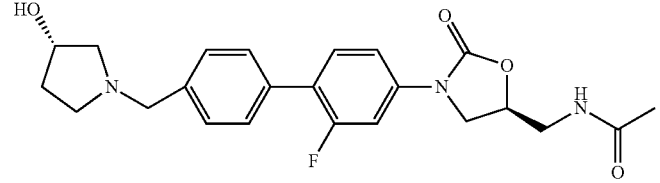 [SMILES: CC(=O)NC[C@H]1CN(c2ccc(-c3ccc(CN4CC[C@H](O)C4)cc3)c(F)c2)C(=O)O1]<br>N-{3-[2-Fluoro-4'-(3-(S)-hydroxy-pyrrolidin-1-ylmethyl)-biphenyl-4-yl]-2-oxo-oxazolidin-5-(S)-ylmethyl}-acetamide |
| 1088 | 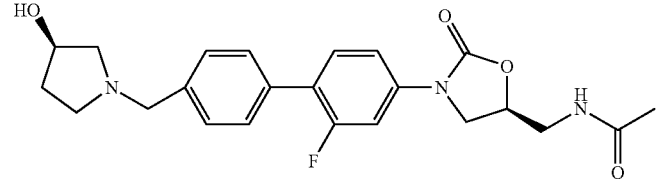 [SMILES: CC(=O)NC[C@H]1CN(c2ccc(-c3ccc(CN4CC[C@@H](O)C4)cc3)c(F)c2)C(=O)O1]<br>N-{3-[2-Fluoro-4'-(3-(R)-hydroxy-pyrrolidin-1-ylmethyl)-biphenyl-4-yl]-2-oxo-oxazolidin-5-(S)-ylmethyl}-acetamide |
| 1089 | 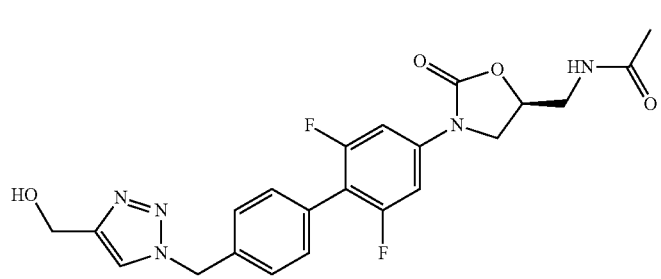 [SMILES: CC(=O)NC[C@H]1CN(c2cc(F)c(-c3ccc(Cn4cc(CO)nn4)cc3)c(F)c2)C(=O)O1]<br>N-{3-[2,6-Difluoro-4'-(4-hydroxymethyl-[1,2,3]triazol-1-ylmethyl)-biphenyl-4-yl]-2-oxo-oxazolidin-5-(S)-ylmethyl}-acetamide |

TABLE 2-continued

| Compound Number | Structure |
|---|---|
| 1090 | 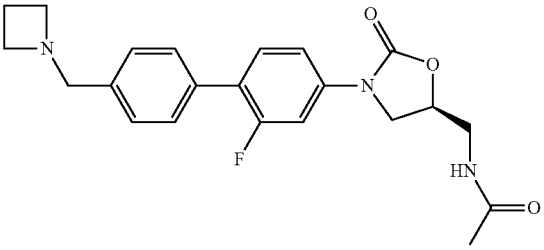 [SMILES: CC(=O)NC[C@H]1CN(c2ccc(-c3ccc(CN4CCC4)cc3)c(F)c2)C(=O)O1]
N-[3-(4'-Azetidin-1-ylmethyl-2-fluoro-biphenyl-4-yl)-2-oxo-oxazolidin-5-(S)-ylmethyl]-acetamide |
| 1091 | 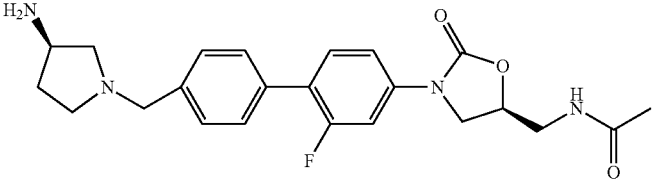 [SMILES: CC(=O)NC[C@H]1CN(c2ccc(-c3ccc(CN4CC[C@@H](N)C4)cc3)c(F)c2)C(=O)O1]
N-{3-[4'-(3-(R)-Amino-pyrrolidin-1-ylmethyl)-2-fluoro-biphenyl-4-yl]-2-oxo-oxazolidin-5-(S)-ylmethyl}-acetamide |
| 1092 | 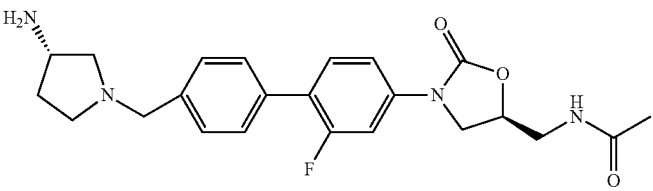 [SMILES: CC(=O)NC[C@H]1CN(c2ccc(-c3ccc(CN4CC[C@H](N)C4)cc3)c(F)c2)C(=O)O1]
N-{3-[4'-(3-(S)-Amino-pyrrolidin-1-ylmethyl)-2-fluoro-biphenyl-4-yl]-2-oxo-oxazolidin-5-(S)-ylmethyl}-acetamide |
| 1093 | 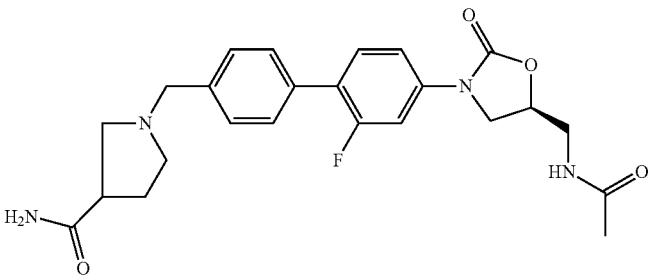 [SMILES: CC(=O)NC[C@H]1CN(c2ccc(-c3ccc(CN4CCC(C(N)=O)C4)cc3)c(F)c2)C(=O)O1]
1-{4'-[5-(S)-(Acetylamino-methyl)-2-oxo-oxazolidin-3-yl]-2'-fluoro-biphenyl-4-ylmethyl}-pyrrolidine-3-(R/S)-carboxylic acid amide |
| 1094 | 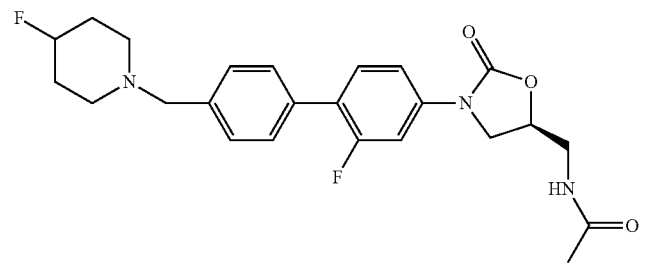 [SMILES: CC(=O)NC[C@H]1CN(c2ccc(-c3ccc(CN4CCC(F)CC4)cc3)c(F)c2)C(=O)O1]
N-{3-[2-Fluoro-4'-(4-fluoro-piperidin-1-ylmethyl)-biphenyl-4-yl]-2-oxo-oxazolidin-5-(S)-ylmethyl}-acetamide |

TABLE 2-continued

| Compound Number | Structure |
|---|---|
| 1095 | 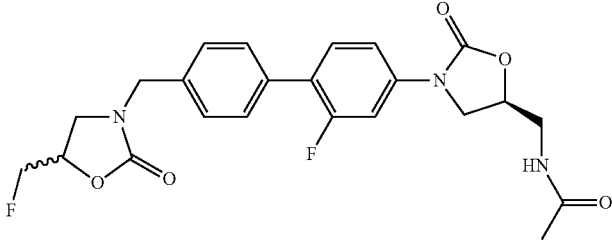 [SMILES: CC(=O)NC[C@H]1CN(c2ccc(-c3ccc(CN4CC(CF)OC4=O)cc3)c(F)c2)C(=O)O1]<br>N-{3-[2-Fluoro-4'-(5-fluoromethyl-2-oxo-oxazolidin-3-(R/S)ylmethyl)-biphenyl-4-yl]-2-oxo-oxazolidin-5-(S)-ylmethyl}-acetamide |
| 1096 | 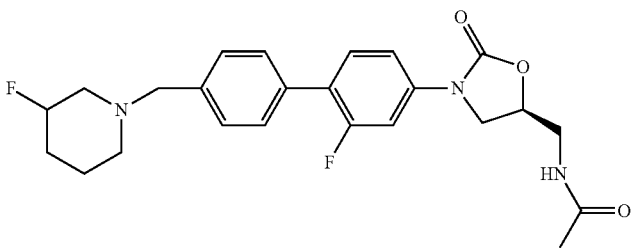 [SMILES: CC(=O)NC[C@H]1CN(c2ccc(-c3ccc(CN4CCCC(F)C4)cc3)c(F)c2)C(=O)O1]<br>N-{3-[2-Fluoro-4'-(3-(R/S)-fluoro-piperidin-1-ylmethyl)-biphenyl-4-yl]-2-oxo-oxazolidin-5-(S)-ylmethyl}-acetamide |
| 1097 | 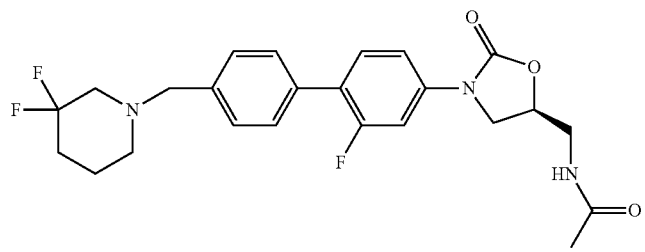 [SMILES: CC(=O)NC[C@H]1CN(c2ccc(-c3ccc(CN4CCCC(F)(F)C4)cc3)c(F)c2)C(=O)O1]<br>N-{3-[4'-(3,3-Difluoro-piperidin-1-ylmethyl)-2-fluoro-biphenyl-4-yl]-2-oxo-oxazolidin-5-(S)-ylmethyl}-acetamide |
| 1098 | 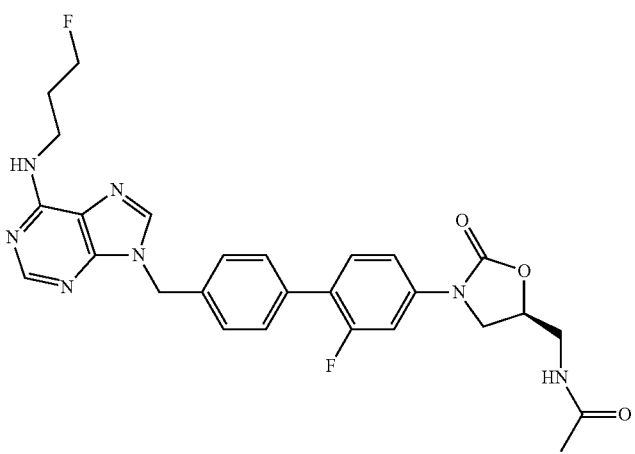 [SMILES: CC(=O)NC[C@H]1CN(c2ccc(-c3ccc(Cn4cnc5c(NCCCF)ncnc54)cc3)c(F)c2)C(=O)O1]<br>N-(3-{2-Fluoro-4'-[6-(3-fluoro-propylamino)-purin-9-ylmethyl]-biphenyl-4-yl}-2-oxo-oxazolidin-5-(S)-ylmethyl)-acetamide |

TABLE 2-continued

| Compound Number | Structure |
|---|---|
| 1099 | 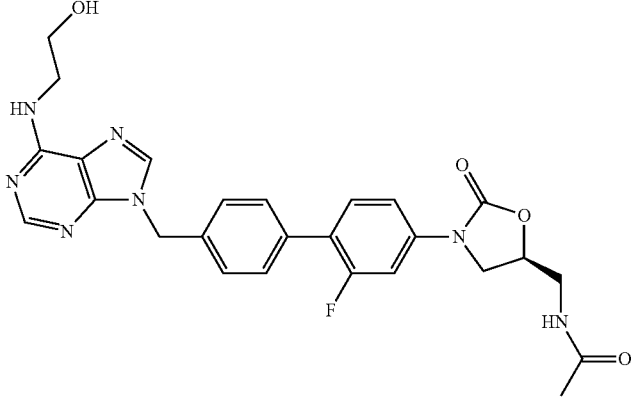 [SMILES: CC(=O)NC[C@H]1CN(c2ccc(-c3ccc(Cn4cnc5c(NCCO)ncnc54)cc3)c(F)c2)C(=O)O1]  N-(3-{2-Fluoro-4'-[6-(2-hydroxy-ethylamino)-purin-9-ylmethyl]-biphenyl-4-yl}-2-oxo-oxazolidin-5-(S)-ylmethyl)-acetamide |
| 1100 | 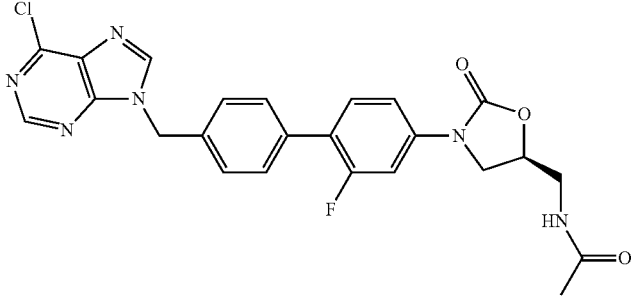 [SMILES: CC(=O)NC[C@H]1CN(c2ccc(-c3ccc(Cn4cnc5c(Cl)ncnc54)cc3)c(F)c2)C(=O)O1]  N-{3-[4'-(6-Chloro-purin-9-ylmethyl)-2-fluoro-biphenyl-4-yl]-2-oxo-oxazolidin-5-(S)-ylmethyl}-acetamide |
| 1101 | 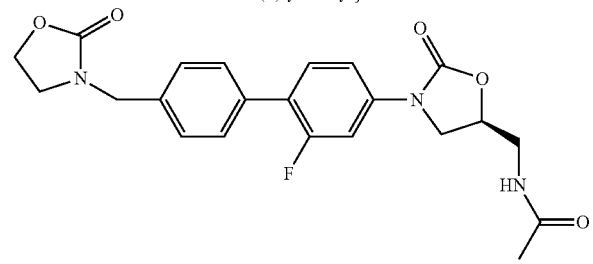  N-{3-[2-Fluoro-4'-(2-oxo-oxazolidin-3-ylmethyl)-biphenyl-4-yl]-2-oxo-oxazolidin-5-(S)-ylmethyl}-acetamide |
| 1102 | 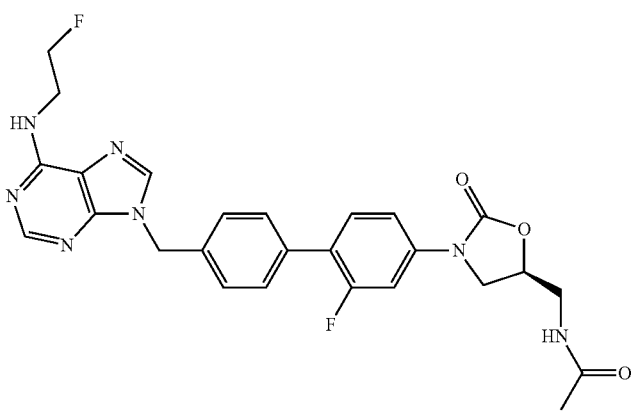 [SMILES: CC(=O)NC[C@H]1CN(c2ccc(-c3ccc(Cn4cnc5c(NCCF)ncnc54)cc3)c(F)c2)C(=O)O1]  N-(3-{2-Fluoro-4'-[6-(2-fluoro-ethylamino)-purin-9-ylmethyl]-biphenyl-4-yl}-2-oxo-oxazolidin-5-(S)-ylmethyl)-acetamide |

TABLE 2-continued
| Compound Number | Structure |
|---|---|
| 1103 | 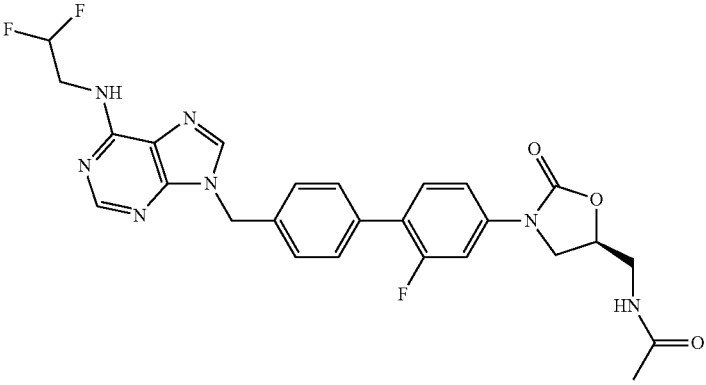 [SMILES: CC(=O)NC[C@H]1CN(c2ccc(-c3ccc(Cn4cnc5c(NCC(F)F)ncnc54)cc3)c(F)c2)C(=O)O1]<br>N-(3-{4'-[6-(2,2-Difluoro-ethylamino)-purin-9-ylmethyl]-2-fluoro-biphenyl-4-yl}-2-oxo-oxazolidin-5-(S)-ylmethyl)-acetamide |
| 1104 | 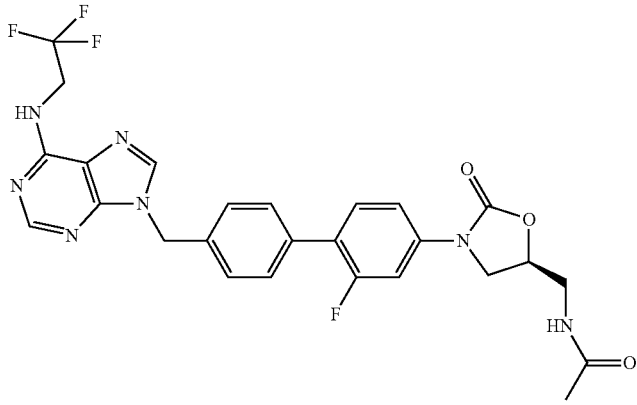 [SMILES: CC(=O)NC[C@H]1CN(c2ccc(-c3ccc(Cn4cnc5c(NCC(F)(F)F)ncnc54)cc3)c(F)c2)C(=O)O1]<br>N-(3-{2-Fluoro-4'-[6-(2,2,2-trifluoro-ethylamino)-purin-9-ylmethyl]-biphenyl-4-yl}-2-oxo-oxazolidin-5-(S)-ylmethyl)-acetamide |
| 1105 | 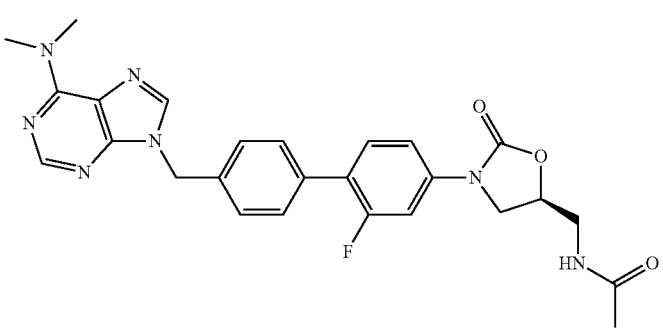 [SMILES: CC(=O)NC[C@H]1CN(c2ccc(-c3ccc(Cn4cnc5c(N(C)C)ncnc54)cc3)c(F)c2)C(=O)O1]<br>N-{3-[4'-(6-Dimethylamino-purin-9-ylmethyl)-2-fluoro-biphenyl-4-yl]-2-oxo-oxazolidin-5-(S)-ylmethyl}-acetamide |

TABLE 2-continued

| Compound Number | Structure |
|---|---|
| 1106 | 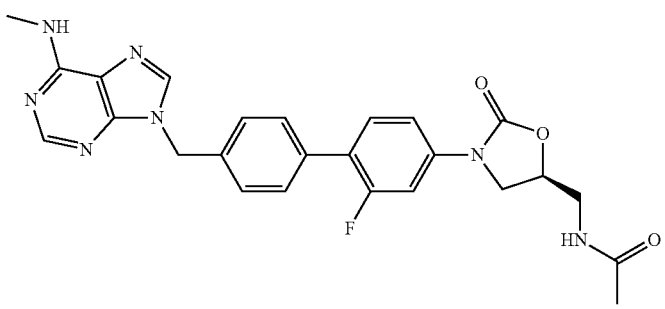 [SMILES: CNc1ncnc2c1ncn2Cc1ccc(-c2ccc(N3C[C@H](CNC(C)=O)OC3=O)cc2F)cc1]<br>N-{3-[2-Fluoro-4'-(6-methylamino-purin-9-ylmethyl)-biphenyl-4-yl]-2-oxo-oxazolidin-5-(S)-ylmethyl}-acetamide |
| 1107 | 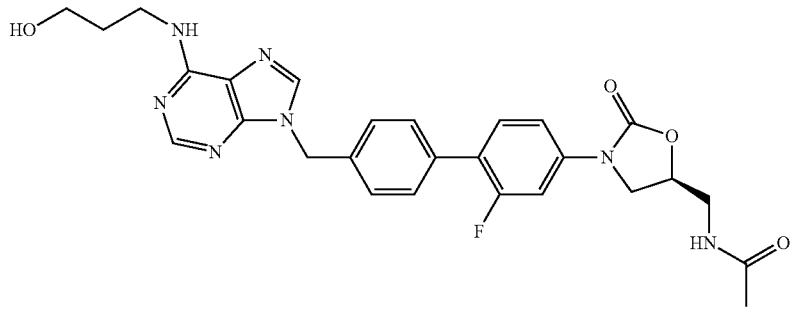 [SMILES: CC(=O)NC[C@H]1CN(c2ccc(-c3ccc(Cn4cnc5c(NCCCO)ncnc54)cc3)c(F)c2)C(=O)O1]<br>N-(3-{2-Fluoro-4'-[6-(3-hydroxy-propylamino)-purin-9-ylmethyl]-biphenyl-4-yl}-2-oxo-oxazolidin-5-(S)-ylmethyl)-acetamide |
| 1108 | 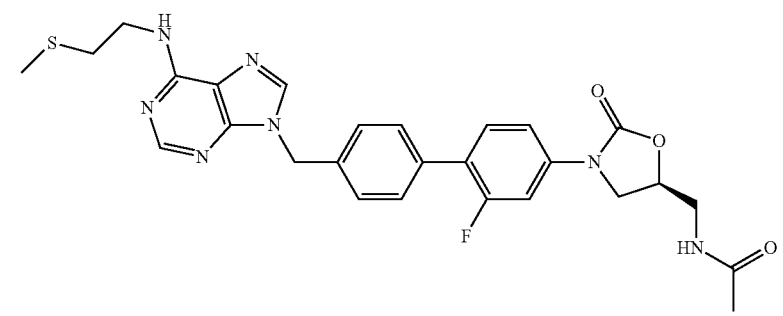 [SMILES: CSCCNc1ncnc2c1ncn2Cc1ccc(-c2ccc(N3C[C@H](CNC(C)=O)OC3=O)cc2F)cc1]<br>N-(3-{2-Fluoro-4'-[6-(2-methylsulfanyl-ethylamino)-purin-9-ylmethyl]-biphenyl-4-yl}-2-oxo-oxazolidin-5-(S)-ylmethyl)-acetamide |
| 1109 | 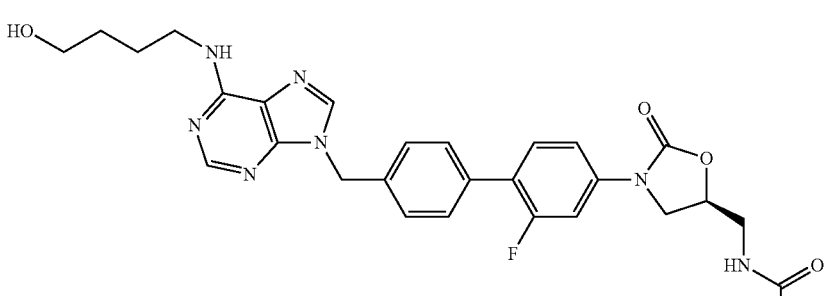<br>N-(3-{2-Fluoro-4'-[6-(4-hydroxy-butylamino)-purin-9-ylmethyl]-biphenyl-4-yl}-2-oxo-oxazolidin-5-(S)-ylmethyl)-acetamide |

TABLE 2-continued

| Compound Number | Structure |
|---|---|
| 1110 | N-{3-[4'-(6-Amino-purin-9-ylmethyl)-2-fluoro-biphenyl-4-yl]-2-oxo-oxazolidin-5-(S)-ylmethyl}-acetamide |
| 1111 | N-{3-[2-Fluoro-4'-(6-oxo-1,6-dihydro-purin-9-ylmethyl)-biphenyl-4-yl]-2-oxo-oxazolidin-5-(S)-ylmethyl}-acetamide |
| 1112 | N-[3-(2-Fluoro-4'-isoxazolidin-2-ylmethyl-biphenyl-4-yl)-2-oxo-oxazolidin-5-(S)-ylmethyl]-acetamide |
| 1113 | N-{3-[4'-(2-Amino-imidazol-1-ylmethyl)-2-fluoro-biphenyl-4-yl]-2-oxo-oxazolidin-5-(S)-ylmethyl}-acetamide |

TABLE 2-continued

| Compound Number | Structure |
| --- | --- |
| 1114 | N-{3-[2-Fluoro-4'-(7-oxo-4,5-dihydro-[1,2,3]triazolo[1,5-c]pyrimidin-6-ylmethyl)-biphenyl-4-yl]-2-oxo-oxazolidin-5-(S)-ylmethyl}-acetamide |
| 1115 | N-[3-(2-Fluoro-4'-pyrrolidin-1-ylmethyl-biphenyl-4-yl)-2-oxo-oxazolidin-5-(S)-ylmethyl]-acetamide |
| 1116 | N-[3-(2-Fluoro-4'-piperidin-1-ylmethyl-biphenyl-4-yl)-2-oxo-oxazolidin-5-(S)-ylmethyl]-acetamide |
| 1117 | N-{3-[2-Fluoro-4'-(1-(S)-hydroxy-2-morpholin-4-yl-ethyl)-biphenyl-4-yl]-2-oxo-oxazolidin-5-(S)-ylmethyl}-acetamide |
| 1118 | N-{3-[2-Fluoro-4'-(2-hydroxy-1-(R)-morpholin-4-yl-ethyl)-biphenyl-4-yl]-2-oxo-oxazolidin-5-(S)-ylmethyl}-acetamide |

TABLE 2-continued

| Compound Number | Structure |
|---|---|
| 1119 | 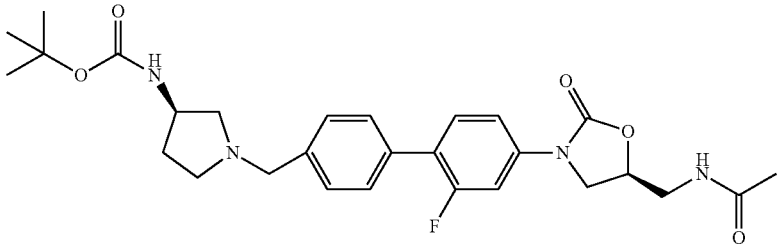 [SMILES: CC(=O)NC[C@H]1CN(c2ccc(-c3ccc(CN4CC[C@@H](NC(=O)OC(C)(C)C)C4)cc3)c(F)c2)C(=O)O1]<br>(1-{4'-[5-(S)-(Acetylamino-methyl)-2-oxo-oxazolidin-3-yl]-2'-fluoro-biphenyl-4-ylmethyl}-pyrrolidin-3-(R)-yl)-carbamic acid tert-butyl ester |
| 1120 | 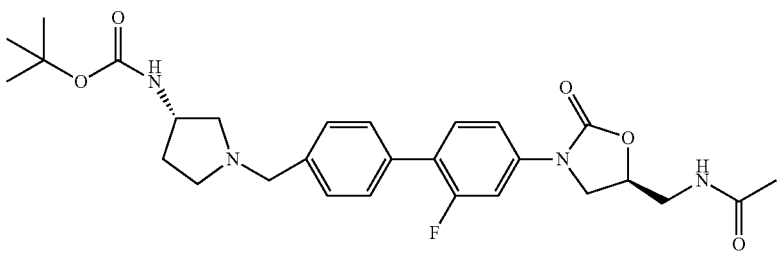 [SMILES: CC(=O)NC[C@H]1CN(c2ccc(-c3ccc(CN4CC[C@H](NC(=O)OC(C)(C)C)C4)cc3)c(F)c2)C(=O)O1]<br>(1-{4'-[5-(S)-(Acetylamino-methyl)-2-oxo-oxazolidin-3-yl]-2'-fluoro-biphenyl-4-ylmethyl}-pyrrolidin-3-(S)-yl)-carbamic acid tert-butyl ester |
| 1121 | 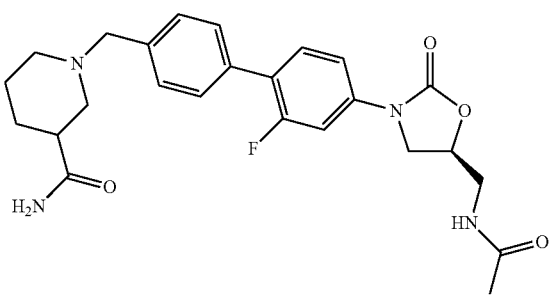 [SMILES: CC(=O)NC[C@H]1CN(c2ccc(-c3ccc(CN4CCCC(C(N)=O)C4)cc3)c(F)c2)C(=O)O1]<br>1-{4'-[5-(S)-(Acetylamino-methyl)-2-oxo-oxazolidin-3-yl]-2'-fluoro-biphenyl-4-ylmethyl}-piperidine-3-(R/S)-carboxylic acid amide |
| 1122 | 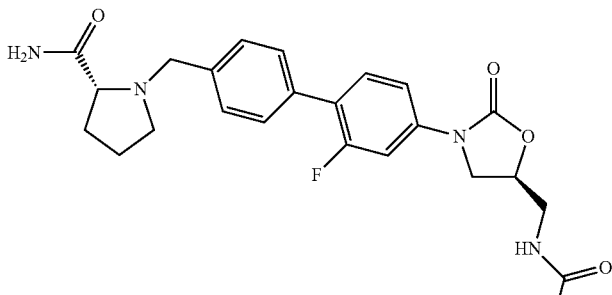<br>1-{4'-[5-(S)-(Acetylamino-methyl)-2-oxo-oxazolidin-3-yl]-2'-fluoro-biphenyl-4-ylmethyl}-pyrrolidine-2-(S)-carboxylic acid amide |

TABLE 2-continued

| Compound Number | Structure |
|---|---|
| 1123 | N-{3-[2-Fluoro-4'-(3-oxo-piperazin-1-ylmethyl)-biphenyl-4-yl]-2-oxo-oxazolidin-5-(S)-ylmethyl}-acetamide |
| 1124 | N-{3-[4'-(2,2-Dimethyl-4-oxo-imidazolidin-1-ylmethyl)-2-fluoro-biphenyl-4-yl]-2-oxo-oxazolidin-5-(S)-ylmethyl}-acetamide |
| 1125 | 1-{4'-[5-(S)-(Acetylamino-methyl)-2-oxo-oxazolidin-3-yl]-2'-fluoro-biphenyl-4-ylmethyl}-azetidine-3-(R/S)-carboxylic acid amide |
| 1126 | 1-{4'-[5-(Acetylamino-methyl)-2-oxo-oxazolidin-3-yl]-2'-fluoro-biphenyl-4-ylmethyl}-azetidine-2-carboxylic acid amide |
| 1127 | N-{3-[2-Fluoro-4'-(2-oxo-piperazin-1-ylmethyl)-biphenyl-4-yl]-2-oxo-oxazolidin-5-(S)-ylmethyl}-acetamide |

TABLE 2-continued

| Compound Number | Structure |
|---|---|
| 1128 | 2-(4-{4'-[5-(S)-(Acetylamino-methyl)-2-oxo-oxazolidin-3-yl]-2'-fluoro-biphenyl-4-ylmethyl}-3-oxo-piperazin-1-yl)-acetamide |
| 1129 | N-{3-[4'-(4-Cyanomethyl-2-oxo-piperazin-1-ylmethyl)-2-fluoro-biphenyl-4-yl]-2-oxo-oxazolidin-5-(S)-ylmethyl}-acetamide |
| 1130 | N-{3-[2-Fluoro-4'-(2-oxo-4-[1,2,3]thiadiazol-4-ylmethyl-piperazin-1-ylmethyl)-biphenyl-4-yl]-2-oxo-oxazolidin-5-(S)-ylmethyl}-acetamide |
| 2001 | N-{3-[2-Fluoro-4'-(5-methyl-isoxazol-3-yloxymethyl)-biphenyl-4-yl]-2-oxo-oxazolidin-5-(S)-ylmethyl}-acetamide |
| 2002 | N-{3-[2-Fluoro-4'-([1,2,4]triazol-4-ylaminomethyl)-biphenyl-4-yl]-2-oxo-oxazolidin-5-(S)-ylmethyl}-acetamide |

TABLE 2-continued

| Compound Number | Structure |
|---|---|
| 2003 | N-(3-{2-Fluoro-4'-[(3-methyl-isoxazol-5-ylamino)-methyl]-biphenyl-4-yl}-2-oxo-oxazolidin-5-(S)-ylmethyl)-acetamide |
| 2004 | N-(3-{2-Fluoro-4'-[(5-methyl-isoxazol-3-ylamino)-methyl]-biphenyl-4-yl}-2-oxo-oxazolidin-5-(S)-ylmethyl)-acetamide |
| 2005 | 4-({4'-[5-(S)-(Acetylamino-methyl)-2-oxo-oxazolidin-3-yl]-2'-fluoro-biphenyl-4-ylmethyl}-amino)-piperidine-1-carboxylic acid ethyl ester |
| 2006 | N-(3-{4'-[(1-Aza-bicyclo[2.2.2]oct-3-ylamino)-methyl]-2-fluoro-biphenyl-4-yl}-2-oxo-oxazolidin-5-(S)-ylmethyl)-acetamide |
| 2007 | 2-({4'-[5-(S)-(Acetylamino-methyl)-2-oxo-oxazolidin-3-yl]-2'-fluoro-biphenyl-4-ylmethyl}-amino)-benzamide |

TABLE 2-continued

| Compound Number | Structure |
|---|---|
| 2008 | 2-({4-[5-(S)-(Acetylamino-methyl)-2-oxo-oxazolidin-3-yl]-2'-fluoro-biphenyl-4-ylmethyl}-amino)-thiophene-3-carboxylic acid amide |
| 2009 | N-(3-{2-Fluoro-4'-[(3-oxo-isoxazolidin-4-(R)-ylamino)-methyl]-biphenyl-4-yl}-2-oxo-oxazolidin-5-(S)-ylmethyl)-acetamide |
| 2010 | N-(3-{2-Fluoro-4'-[(3-oxo-isoxazolidin-4-(S)-ylamino)-methyl]-biphenyl-4-yl}-2-oxo-oxazolidin-5-(S)-ylmethyl)-acetamide |
| 2011 | N-{3-[4'-(Azetidin-3-(R/S)-ylaminomethyl)-2-fluoro-biphenyl-4-yl]-2-oxo-oxazolidin-5-(S)-ylmethyl}-acetamide |
| 2012 | N-(3-{4'-[(3-Aminomethyl-[1,2,4]thiadiazol-5-ylamino)-methyl]-2-fluoro-biphenyl-4-yl}-2-oxo-oxazolidin-5-(S)-ylmethyl)-acetamide |

TABLE 2-continued

| Compound Number | Structure |
|---|---|
| 2013 | N-[5-({4'-[5-(S)-(Acetylamino-methyl)-2-oxo-oxazolidin-3-yl]-2'-fluoro-biphenyl-4-ylmethyl}-amino)-[1,2,4]thiadiazol-3-ylmethyl]-2-(S)-amino-propionamide |
| 2014 | 2,6-Diamino-hexanoic acid [5-({4'-[5-(acetylamino-methyl)-2-oxo-oxazolidin-3-yl]-2'-fluoro-biphenyl-4-ylmethyl}-amino)-[1,2,4]thiadiazol-3-ylmethyl]-amide |
| 2015 | N-{3-[2-Fluoro-4'-(1-methyl-1H-tetrazol-5-ylsulfanylmethyl)-biphenyl-4-yl]-2-oxo-oxazolidin-5-(S)-ylmethyl}-acetamide |
| 2016 | N-{3-[2-Fluoro-4'-(3H-[1,2,3]triazol-4-ylsulfanylmethyl)-biphenyl-4-yl]-2-oxo-oxazolidin-5-(S)-ylmethyl}-acetamide |
| 2017 | N-{3-[4'-(4,6-Dioxo-1,4,5,6-tetrahydro-pyrimidin-2-ylsulfanylmethyl)-2-fluoro-biphenyl-4-yl]-2-oxo-oxazolidin-5-(S)-ylmethyl}-acetamide |

TABLE 2-continued

| Compound Number | Structure |
|---|---|
| 2018 | N-{3-[2-Fluoro-4'-(pyridin-2-ylsulfanylmethyl)-biphenyl-4-yl]-2-oxo-oxazolidin-5-(S)-ylmethyl}-acetamide |
| 2019 | N-{3-[2-Fluoro-4'-(pyridin-4-ylsulfanylmethyl)-biphenyl-4-yl]-2-oxo-oxazolidin-5-(S)-ylmethyl}-acetamide |
| 2020 | N-{3-[2-Fluoro-4'-(1-methyl-1H-tetrazole-5-sulfinylmethyl)-biphenyl-4-yl]-2-oxo-oxazolidin-5-(S)-ylmethyl}-acetamide |
| 2021 | N-{3-[2-Fluoro-4'-(3H-[1,2,3]triazole-4-sulfinylmethyl)-biphenyl-4-yl]-2-oxo-oxazolidin-5-(S)-ylmethyl}-acetamide |
| 2022 | N-{3-[2-Fluoro-4'-(pyridine-4-sulfinylmethyl)-biphenyl-4-yl]-2-oxo-oxazolidin-5-(S)-ylmethyl}-acetamide |

TABLE 2-continued

| Compound Number | Structure |
|---|---|
| 2023 | N-{3-[2-Fluoro-4'-(pyridine-2-sulfinylmethyl)-biphenyl-4-yl]-2-oxo-oxazolidin-5-(S)-ylmethyl}-acetamide |
| 2024 | N-{3-[2-Fluoro-4'-(1-methyl-1H-tetrazole-5-sulfonylmethyl)-biphenyl-4-yl]-2-oxo-oxazolidin-5-(S)-ylmethyl}-acetamide |
| 2025 | N-{3-[2-Fluoro-4'-(3H-[1,2,3]triazole-4-sulfonylmethyl)-biphenyl-4-yl]-2-oxo-oxazolidin-5-(S)-ylmethyl}-acetamide |
| 2026 | N-(3-{2-Fluoro-4'-[2-(3H-[1,2,3]triazol-4-ylsulfanyl)-ethyl]-biphenyl-4-yl}-2-oxo-oxazolidin-5-(S)-ylmethyl)-acetamide |
| 2027 | N-(3-{4'-[1-(2-Dimethylamino-ethyl)-1H-tetrazol-5-ylsulfanylmethyl]-2-fluoro-biphenyl-4-yl}-2-oxo-oxazolidin-5-(S)-ylmethyl)-acetamide |

TABLE 2-continued

| Compound Number | Structure |
|---|---|
| 2028 | 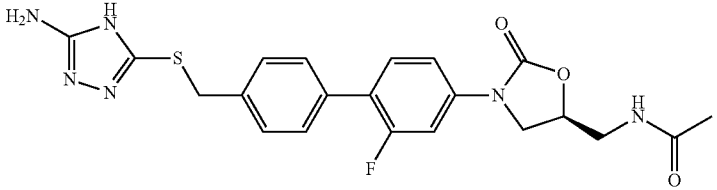 [SMILES: CC(=O)NC[C@H]1CN(c2ccc(-c3ccc(CSc4nnc(N)[nH]4)cc3)c(F)c2)C(=O)O1]<br>N-{3-[4'-(5-Amino-4H-[1,2,4]triazol-3-ylsulfanylmethyl)-2-fluoro-biphenyl-4-yl]-2-oxo-oxazolidin-5-(S)-ylmethyl}-acetamide |
| 2029 | 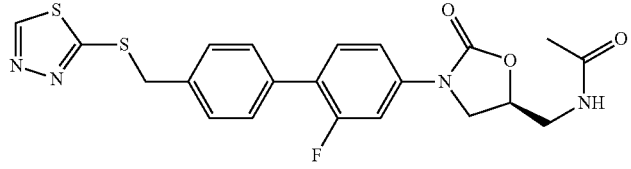<br>N-{3-[2-Fluoro-4'-([1,3,4]thiadiazol-2-ylsulfanylmethyl)-biphenyl-4-yl]-2-oxo-oxazolidin-5-(S)-ylmethyl}-acetamide |
| 2030 | 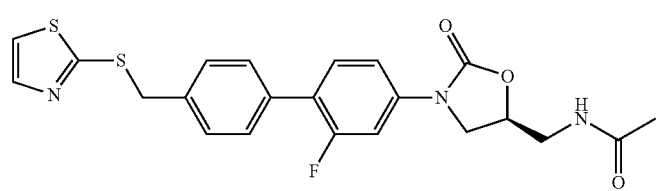 [SMILES: CC(=O)NC[C@H]1CN(c2ccc(-c3ccc(CSc4nccs4)cc3)c(F)c2)C(=O)O1]<br>N-{3-[2-Fluoro-4'-(thiazol-2-ylsulfanylmethyl)-biphenyl-4-yl]-2-oxo-oxazolidin-5-(S)-ylmethyl}-acetamide |
| 2031 | 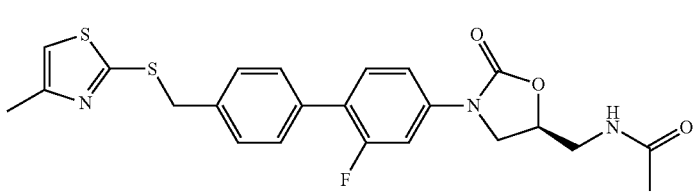 [SMILES: CC(=O)NC[C@H]1CN(c2ccc(-c3ccc(CSc4nc(C)cs4)cc3)c(F)c2)C(=O)O1]<br>N-{3-[2-Fluoro-4'-(4-methyl-thiazol-2-ylsulfanylmethyl)-biphenyl-4-yl]-2-oxo-oxazolidin-5-(S)-ylmethyl}-acetamide |
| 2032 | 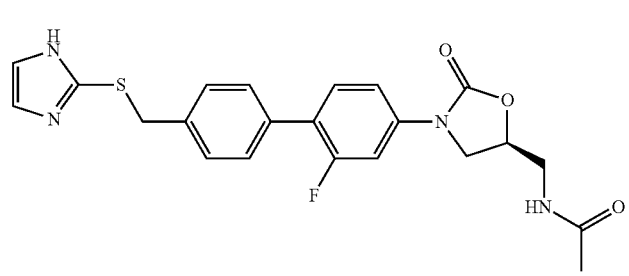 [SMILES: CC(=O)NC[C@H]1CN(c2ccc(-c3ccc(CSc4ncc[nH]4)cc3)c(F)c2)C(=O)O1]<br>N-{3-[2-Fluoro-4'-(1H-imidazol-2-ylsulfanylmethyl)-biphenyl-4-yl]-2-oxo-oxazolidin-5-(S)-ylmethyl}-acetamide |

TABLE 2-continued

| Compound Number | Structure |
|---|---|
| 2033 | N-{3-[2-Fluoro-4'-(2-methyl-2H-[1,2,4]triazol-3-ylsulfanylmethyl)-biphenyl-4-yl]-2-oxo-oxazolidin-5-(S)-ylmethyl}-acetamide |
| 2034 | N-{3-[2-Fluoro-4'-(2-methyl-2H-[1,2,4]triazol-3-ylsulfanylmethyl)-biphenyl-4-yl]-2-oxo-oxazolidin-5-(S)-ylmethyl}-acetamide |
| 2035 | N-{3-[2-Fluoro-4'-([1,3,4]thiadiazole-2-sulfinylmethyl)-biphenyl-4-yl]-2-oxo-oxazolidin-5-(S)-ylmethyl}-acetamide |
| 2036 | N-{3-[2-Fluoro-4'-(thiazole-2-sulfinylmethyl)-biphenyl-4-yl]-2-oxo-oxazolidin-5-(S)-ylmethyl}-acetamide |

TABLE 2-continued

| Compound Number | Structure |
|---|---|
| 2037 | N-{3-[2-Fluoro-4'-(4-methyl-thiazole-2-sulfinylmethyl)-biphenyl-4-yl]-2-oxo-oxazolidin-5-(S)-ylmethyl}-acetamide |
| 2038 | N-{3-[2-Fluoro-4'-(1H-imidazole-2-sulfinylmethyl)-biphenyl-4-yl]-2-oxo-oxazolidin-5-(S)-ylmethyl}-acetamide |
| 2039 | N-{3-[2-Fluoro-4'-(2-methyl-2H-[1,2,4]triazole-3-sulfinylmethyl)-biphenyl-4-yl]-2-oxo-oxazolidin-5-(S)-ylmethyl}-acetamide |
| 2040 | N-(3-{3-Fluoro-4-[6-(3H-[1,2,3]triazol-4-ylsulfanylmethyl)-pyridin-3-yl]-phenyl}-2-oxo-oxazolidin-5-(S)-ylmethyl)-acetamide |
| 2041 | N-{3-[2-Fluoro-4'-(pyridin-2-yl-hydrazonomethyl)-biphenyl-4-yl]-2-oxo-oxazolidin-5-(S)-ylmethyl}-acetamide |

TABLE 2-continued

| Compound Number | Structure |
|---|---|
| 2042 | N-(3-{2-Fluoro-4'-[(4-trifluoromethyl-pyrimidin-2-yl)-hydrazonomethyl]-biphenyl-4-yl}-2-oxo-oxazolidin-5-(S)-ylmethyl)-acetamide |
| 2043 | N-(3-{2-Fluoro-4'-[(1-methyl-1H-imidazole-4-sulfonylamino)-methyl]-biphenyl-4-yl}-2-oxo-oxazolidin-5-(S)-ylmethyl)-acetamide |
| 2044 | N-(3-{2-Fluoro-4'-[(6-morpholin-4-yl-pyridine-3-sulfonylamino)-methyl]-biphenyl-4-yl}-2-oxo-oxazolidin-5-(S)-ylmethyl)-acetamide |
| 2045 | N-{3-[2-Fluoro-4'-(pyridin-3-ylsulfamoylmethyl)-biphenyl-4-yl]-2-oxo-oxazolidin-5-(S)-ylmethyl}-acetamide |

TABLE 2-continued

| Compound Number | Structure |
|---|---|
| 2046 | N-{3-[2-Fluoro-4'-([1,2,4]triazol-4-ylaminomethyl)-biphenyl-4-yl]-2-oxo-oxazolidin-5-(S)-ylmethyl}-acetamide |
| 2047 | N-{3-[2-Fluoro-4'-(2H-[1,2,4]triazol-3-ylsulfanylmethyl)-biphenyl-4-yl]-2-oxo-oxazolidin-5-(S)-ylmethyl}-acetamide |
| 2048 | N-{3-[2-Fluoro-4'-(N'-pyridin-2-yl-hydrazinomethyl)-biphenyl-4-yl]-2-oxo-oxazolidin-5-(S)-ylmethyl}-acetamide |
| 2049 | N-(3-{4'-[N'-(4,5-Dihydro-1H-imidazol-2-yl)-hydrazinomethyl]-2-fluoro-biphenyl-4-yl}-2-oxo-oxazolidin-5-(S)-ylmethyl)-acetamide |
| 2050 | N-{3-[2-Fluoro-4'-(isoxazol-3-ylaminomethyl)-biphenyl-4-yl]-2-oxo-oxazolidin-5-(S)-ylmethyl}-acetamide |

TABLE 2-continued

| Compound Number | Structure |
|---|---|
| 2051 | N-(3-{2-Fluoro-4'-[(quinoline-8-sulfonylamino)-methyl]-biphenyl-4-yl}-2-oxo-oxazolidin-5-(S)-ylmethyl)-acetamide |
| 2052 | N-(3-{2-Fluoro-4'-[(1-methyl-1H-imidazole-4-sulfonylamino)-methyl]-biphenyl-4-yl}-2-oxo-oxazolidin-5-(S)-ylmethyl)-acetamide |
| 2053 | N-(3-{2-Fluoro-4'-[(6-morpholin-4-yl-pyridine-3-sulfonylamino)-methyl]-biphenyl-4-yl}-2-oxo-oxazolidin-5-(S)-ylmethyl)-acetamide |
| 2054 | N-{3-[2-Fluoro-4'-pyridin-3-ylsulfamoylmethyl)-biphenyl-4-yl]2-oxo-oxazolidin-5-(S)-ylmethyl}acetamide |
| 2055 | 5-({4'-[5-(S)-(Acetylamino-methyl)-2-oxo-oxazolidin-3-yl]-2'-fluoro-biphenyl-4-ylmethyl}-amino)-3H-imidazole-4-carboxylic acid amide |

TABLE 2-continued

| Compound Number | Structure |
|---|---|
| 2056 | N-{3-[2-Fluoro-4'-(morpholin-4-yliminomethyl)-biphenyl-4-yl]-2-oxo-oxazolidin-5-(S)-ylmethyl}-acetamide |
| 2057 | N-(3-{2-Fluoro-4'-[(4-methyl-piperazin-1-ylamino)-methyl]-biphenyl-4-yl}-2-oxo-oxazolidin-5-(S)-ylmethyl)-acetamide |
| 2058 | N-(3-{2-Fluoro-4'-[(4-trifluoromethyl-benzenesulfonylamino)-methyl]-biphenyl-4-yl}-2-oxo-oxazolidin-5-(S)-ylmethyl)-acetamide |
| 2059 | N-(3-{2-Fluoro-4'-[(2-oxo-piperidin-3-(S)-ylamino)-methyl]-biphenyl-4-yl}-2-oxo-oxazolidin-5-(S)-ylmethyl)-acetamide |

TABLE 2-continued

| Compound Number | Structure |
|---|---|
| 3001 | N-{3-[2-Fluoro-4'-(pyridin-4-ylmethylsulfanyl)-biphenyl-4-yl]-2-oxo-oxazolidin-5-(S)-ylmethyl}-acetamide |
| 3002 | N-{3-[2-Fluoro-4'-(pyridin-4-ylmethanesulfinyl)-biphenyl-4-yl]-2-oxo-oxazolidin-5-(S)-ylmethyl}-acetamide |
| 3003 | N-{3-[2-Fluoro-4'-(pyridin-4-ylmethanesulfonyl)-biphenyl-4-yl]-2-oxo-oxazolidin-5-(S)-ylmethyl}-acetamide |
| 3004 | N-{3-[2-Fluoro-4'-(1-oxy-pyridin-4-ylmethanesulfonyl)-biphenyl-4-yl]-2-oxo-oxazolidin-5-(S)-ylmethyl}-acetamide |
| 3005 | N-(3-{2-Fluoro-4'-[(pyridin-4-ylmethyl)-sulfamoyl]-biphenyl-4-yl}-2-oxo-oxazolidin-5-(S)-ylmethyl)-acetamide |

TABLE 2-continued

| Compound Number | Structure |
|---|---|
| 3006 | N-(3-{2-Fluoro-4'-[(pyridin-2-ylmethyl)-sulfamoyl]-biphenyl-4-yl}-2-oxo-oxazolidin-5-(S)-ylmethyl)-acetamide |
| 3007 | N-{3-[2-Fluoro-4'-(2-pyridin-2-yl-ethylsulfamoyl)-biphenyl-4-yl]-2-oxo-oxazolidin-5-(S)-ylmethyl}-acetamide |
| 4001 | N-{4'-[5-(S)-(Acetylamino-methyl)-2-oxo-oxazolidin-3-yl]-2'-fluoro-biphenyl-4-ylmethyl}-3-(6-methyl-2,4-dioxo-1,2,3,4-tetrahydro-pyrimidin-5-yl)-acrylamide |
| 4002 | N-{4'-[5-(S)-(Acetylamino-methyl)-2-oxo-oxazolidin-3-yl]-2'-fluoro-biphenyl-4-ylmethyl}-3-pyridin-3-yl-acrylamide |

TABLE 2-continued

| Compound Number | Structure |
|---|---|
| 4003 | 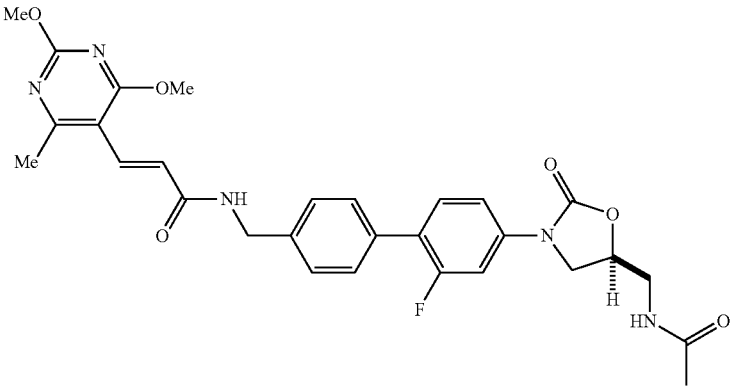 [SMILES: COc1nc(C)c(/C=C/C(=O)NCc2ccc(-c3ccc(N4C[C@H](CNC(C)=O)OC4=O)cc3F)cc2)c(OC)n1]<br>N-{4'-[5-(S)-(Acetylamino-methyl)-2-oxo-oxazolidin-3-yl]-2'-fluoro-biphenyl-4-ylmethyl}-3-(2,4-dimethoxy-6-methyl-pyrimidin-5-yl)-acrylamide |
| 4004 | 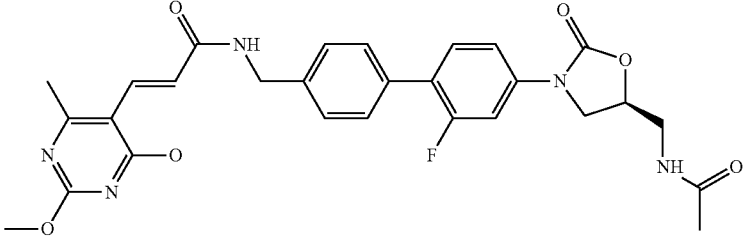 [SMILES: COc1nc(C)c(/C=C/C(=O)NCc2ccc(-c3ccc(N4C[C@H](CNC(C)=O)OC4=O)cc3F)cc2)c(O)n1]<br>N-{4'-[5-(S)-(Acetylamino-methyl)-2-oxo-oxazolidin-3-yl]-2'-fluoro-biphenyl-4-ylmethyl}-3-(4-hydroxy-2-methoxy-6-methyl-pyrimidin-5-yl)-acrylamide |
| 4005 | 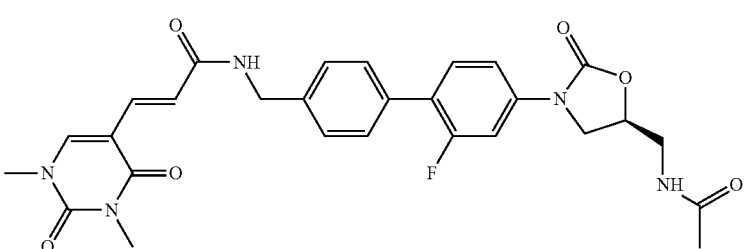<br>N-{4'-[5-(S)-(Acetylamino-methyl)-2-oxo-oxazolidin-3-yl]-2'-fluoro-biphenyl-4-ylmethyl}-3-(1,3-dimethyl-2,4-dioxo-1,2,3,4-tetrahydro-pyrimidin-5-yl)-acrylamide |
| 4006 | 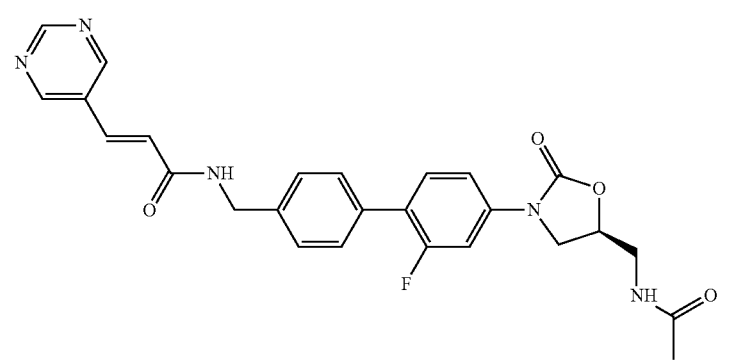 [SMILES: CC(=O)NC[C@H]1CN(c2ccc(-c3ccc(CNC(=O)/C=C/c4cncnc4)cc3)c(F)c2)C(=O)O1]<br>N-{4'-[5-(S)-(Acetylamino-methyl)-2-oxo-oxazolidin-3-yl]-2'-fluoro-biphenyl-4-ylmethyl}-3-pyrimidin-5-yl-acrylamide |

TABLE 2-continued

| Compound Number | Structure |
|---|---|
| 4007 | 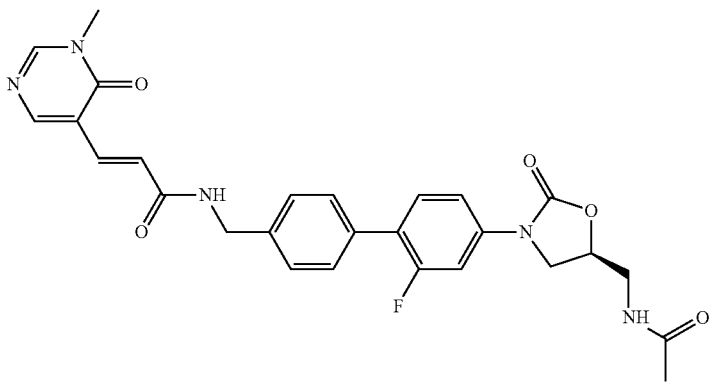 [SMILES: CC(=O)NC[C@H]1CN(c2ccc(-c3ccc(CNC(=O)/C=C/c4cncn(C)c4=O)cc3)c(F)c2)C(=O)O1]<br>N-{4'-[5-(S)-(Acetylamino-methyl)-2-oxo-oxazolidin-3-yl]-2'-fluoro-biphenyl-4-ylmethyl}-3-(1-methyl-6-oxo-1,6-dihydro-pyrimidin-5-yl)-acrylamide |
| 4008 | 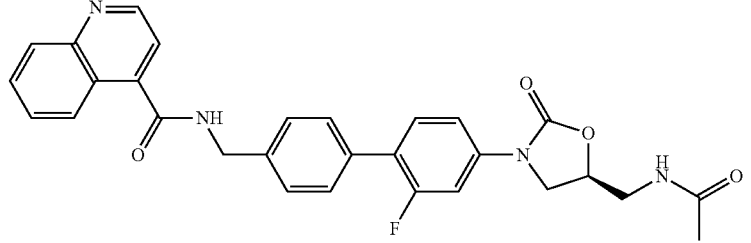 [SMILES: CC(=O)NC[C@H]1CN(c2ccc(-c3ccc(CNC(=O)c4ccnc5ccccc45)cc3)c(F)c2)C(=O)O1]<br>Quinoline-4-carboxylic acid {4'-[5-(S)-(acetylamino-methyl)-2-oxo-oxazolidin-3-yl]-2'-fluoro-biphenyl-4-ylmethyl}-amide |
| 4009 | 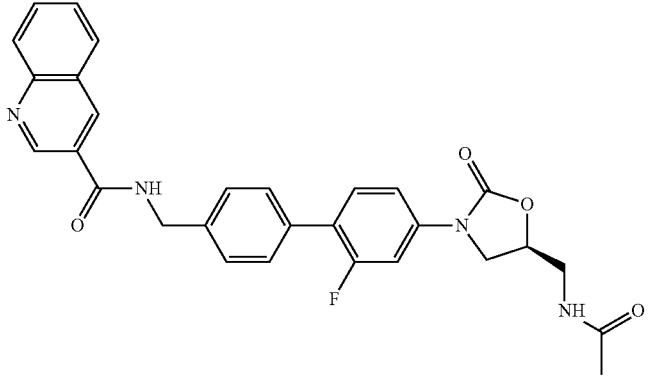 [SMILES: CC(=O)NC[C@H]1CN(c2ccc(-c3ccc(CNC(=O)c4cnc5ccccc5c4)cc3)c(F)c2)C(=O)O1]<br>Quinoline-3-carboxylic acid {4'-[5-(S)-(acetylamino-methyl)-2-oxo-oxazolidin-3-yl]-2'-fluoro-biphenyl-4-ylmethyl}-amide |
| 4010 | 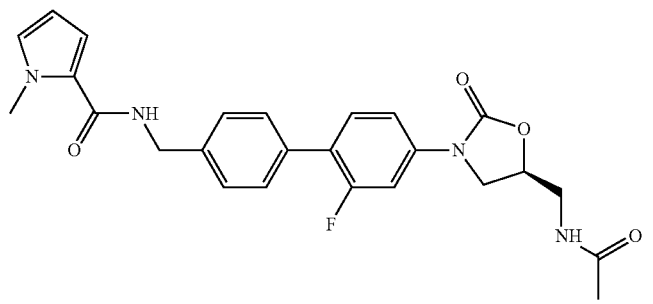 [SMILES: CC(=O)NC[C@H]1CN(c2ccc(-c3ccc(CNC(=O)c4cccn4C)cc3)c(F)c2)C(=O)O1]<br>1-Methyl-1H-pyrrole-2-carboxylic acid {4'-[5-(S)-(acetylamino-methyl)-2-oxo-oxazolidin-3-yl]-2'-fluoro-biphenyl-4-ylmethyl}-amide |

TABLE 2-continued

| Compound Number | Structure |
|---|---|
| 4011 | 1H-Indole-6-carboxylic acid {4'-[5-(S)-(acetylamino-methyl)-2-oxo-oxazolidin-3-yl]-2'-fluoro-biphenyl-4-ylmethyl}-amide |
| 4012 | N-{4'-[5-(S)-(Acetylamino-methyl)-2-oxo-oxazolidin-3-yl]-2'-fluoro-biphenyl-4-ylmethyl}-3-methanesulfonyl-benzamide |
| 4013 | N-{4'-[5-(S)-(Acetylamino-methyl)-2-oxo-oxazolidin-3-yl]-2'-fluoro-biphenyl-4-ylmethyl}-4-fluoro-benzamide |
| 4014 | Benzo[1,3]dioxole-5-carboxylic acid {4'-[5-(S)-(acetylamino-methyl)-2-oxo-oxazolidin-3-yl]-2'-fluoro-biphenyl-4-ylmethyl}-amide |

TABLE 2-continued

| Compound Number | Structure |
|---|---|
| 4015 | 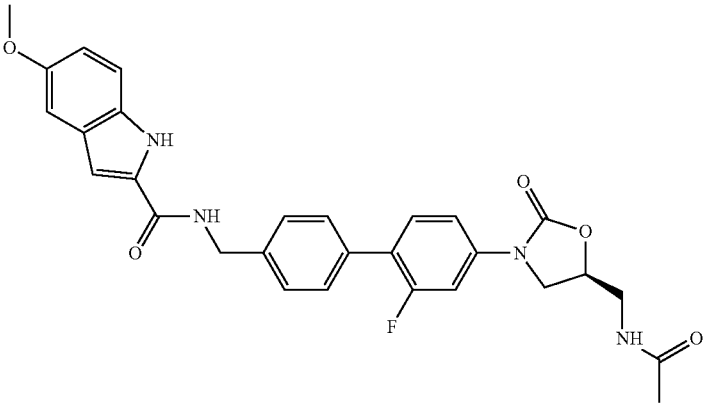 [SMILES: COc1ccc2[nH]c(C(=O)NCc3ccc(-c4ccc(N5C[C@H](CNC(C)=O)OC5=O)cc4F)cc3)cc2c1]<br>5-Methoxy-1H-indole-2-carboxylic acid {4'-[5-(S)-(acetylamino-methyl)-2-oxo-oxazolidin-3-yl]-2'-fluoro-biphenyl-4-ylmethyl}-amide |
| 4016 | 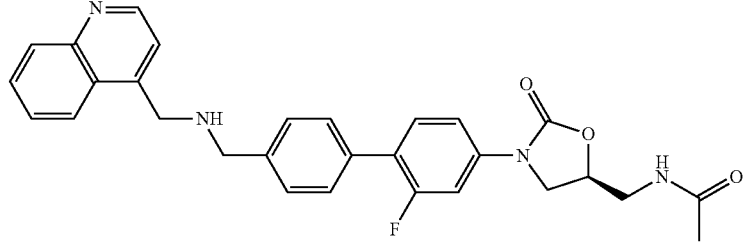 [SMILES: CC(=O)NC[C@H]1CN(c2ccc(-c3ccc(CNCc4ccnc5ccccc45)cc3)c(F)c2)C(=O)O1]<br>N-[3-(2-Fluoro-4'-{[(quinolin-4-ylmethyl)-amino]-methyl}-biphenyl-4-yl)-2-oxo-oxazolidin-5-(S)-ylmethyl]-acetamide |
| 4017 | 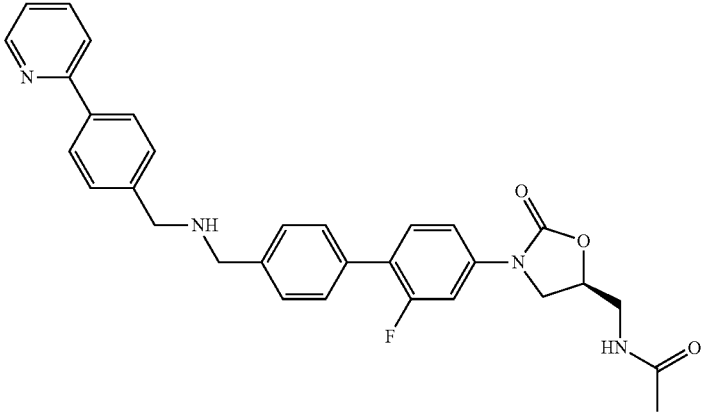 [SMILES: CC(=O)NC[C@H]1CN(c2ccc(-c3ccc(CNCc4ccc(-c5ccccn5)cc4)cc3)c(F)c2)C(=O)O1]<br>N-(3-{2-Fluoro-4'-[(4-pyridin-2-yl-benzylamino)-methyl]-biphenyl-4-yl}-2-oxo-oxazolidin-5-(S)-ylmethyl)-acetamide |
| 4018 | 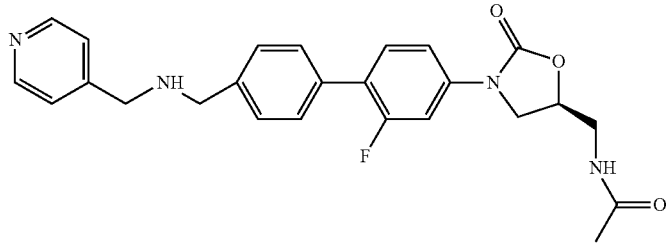 [SMILES: CC(=O)NC[C@H]1CN(c2ccc(-c3ccc(CNCc4ccncc4)cc3)c(F)c2)C(=O)O1]<br>N-[3-(2-Fluoro-4'-{[(pyridin-4-ylmethyl)-amino]-methyl}-biphenyl-4-yl)-2-oxo-oxazolidin-5-(S)-ylmethyl]-acetamide |

TABLE 2-continued

| Compound Number | Structure |
|---|---|
| 4019 | 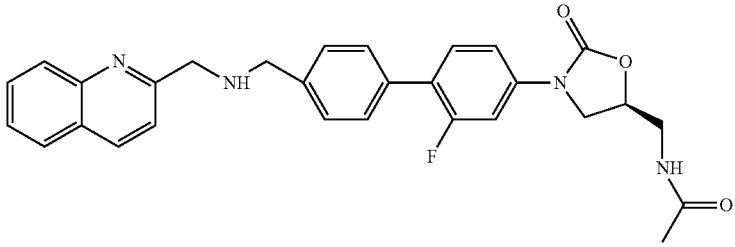 [SMILES: CC(=O)NC[C@H]1CN(c2ccc(-c3ccc(CNCc4ccc5ccccc5n4)cc3)c(F)c2)C(=O)O1]<br>N-[3-(2-Fluoro-4'-{[(quinolin-2-ylmethyl)-amino]-methyl}-biphenyl-4-yl)-2-oxo-oxazolidin-5-(S)-ylmethyl]-acetamide |
| 4020 | 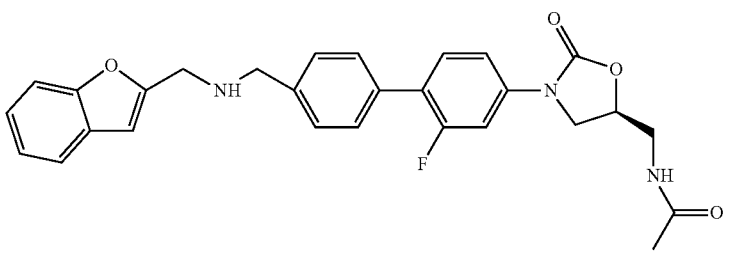 [SMILES: CC(=O)NC[C@H]1CN(c2ccc(-c3ccc(CNCc4cc5ccccc5o4)cc3)c(F)c2)C(=O)O1]<br>N-[3-(4'-{[(Benzofuran-2-ylmethyl)-amino]-methyl}-2-fluoro-biphenyl-4-yl)-2-oxo-oxazolidin-5-(S)-ylmethyl]-acetamide |
| 4021 | 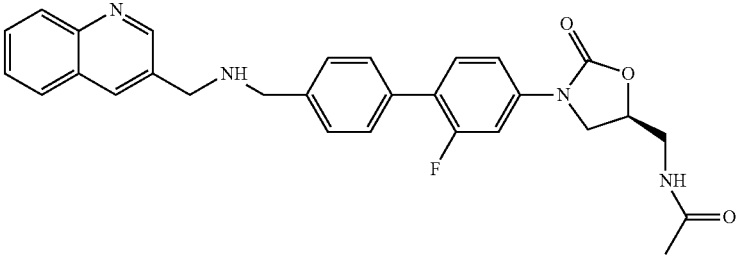 [SMILES: CC(=O)NC[C@H]1CN(c2ccc(-c3ccc(CNCc4cnc5ccccc5c4)cc3)c(F)c2)C(=O)O1]<br>N-[3-(2-Fluoro-4'-{[(quinolin-3-ylmethyl)-amino]-methyl}-biphenyl-4-yl)-2-oxo-oxazolidin-5-(S)-ylmethyl]-acetamide |
| 4022 | 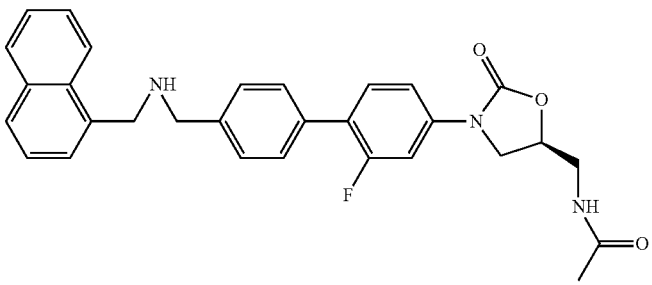 [SMILES: CC(=O)NC[C@H]1CN(c2ccc(-c3ccc(CNCc4cccc5ccccc45)cc3)c(F)c2)C(=O)O1]<br>N-[3-(2-Fluoro-4'-{[(naphthalen-1-ylmethyl)-amino]-methyl}-biphenyl-4-yl)-2-oxo-oxazolidin-5-(S)-ylmethyl]-acetamide |
| 4023 | 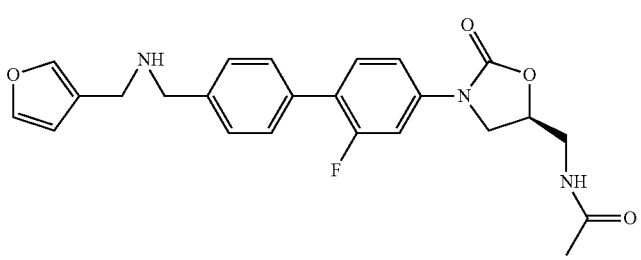 [SMILES: CC(=O)NC[C@H]1CN(c2ccc(-c3ccc(CNCc4ccoc4)cc3)c(F)c2)C(=O)O1]<br>N-[3-(2-Fluoro-4'-{[(furan-3-ylmethyl)-amino]-methyl}-biphenyl-4-yl)-2-oxo-oxazolidin-5-(S)-ylmethyl]-acetamide |

TABLE 2-continued

| Compound Number | Structure |
|---|---|
| 4024 | 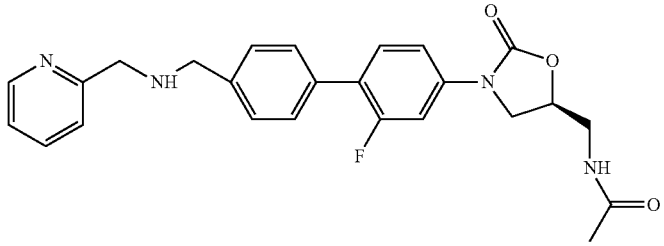 [SMILES: CC(=O)NC[C@H]1CN(c2ccc(-c3ccc(CNCc4ccccn4)cc3)c(F)c2)C(=O)O1]<br>N-[3-(2-Fluoro-4'-{[(pyridin-2-ylmethyl)-amino]-methyl}-biphenyl-4-yl)-2-oxo-oxazolidin-5-(S)-ylmethyl]-acetamide |
| 4025 | 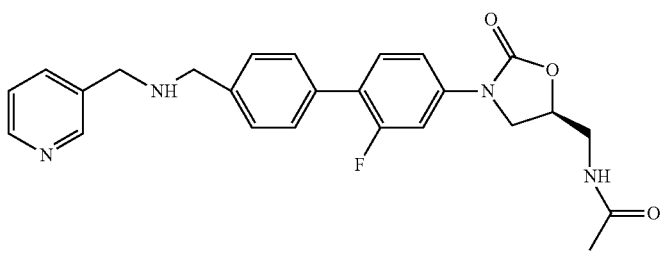 [SMILES: CC(=O)NC[C@H]1CN(c2ccc(-c3ccc(CNCc4cccnc4)cc3)c(F)c2)C(=O)O1]<br>N-[3-(2-Fluoro-4'-{[(pyridin-3-ylmethyl)-amino]-methyl}-biphenyl-4-yl)-2-oxo-oxazolidin-5-(S)-ylmethyl]-acetamide |
| 4026 | 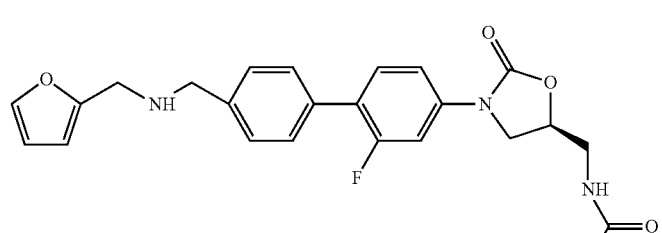<br>N-[3-(2-Fluoro-4'-{[(furan-2-ylmethyl)-amino]-methyl}-biphenyl-4-yl)-2-oxo-oxazolidin-5-(S)-ylmethyl]-acetamide |
| 4027 | 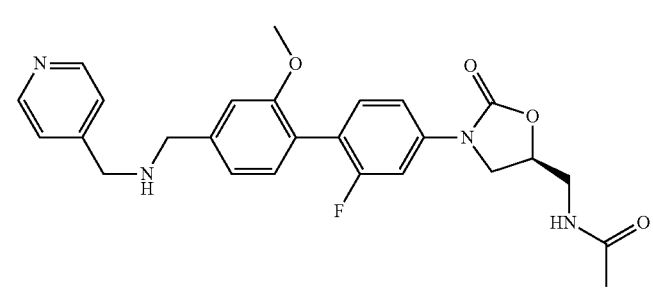 [SMILES: COc1cc(CNCc2ccncc2)ccc1-c1ccc(N2C[C@H](CNC(C)=O)OC2=O)cc1F]<br>N-[3-(2-Fluoro-2'-methoxy-4'-{[(pyridin-4-ylmethyl)-amino]-methyl}-biphenyl-4-yl)-2-oxo-oxazolidin-5-(S)-ylmethyl]-acetamide |
| 4028 | 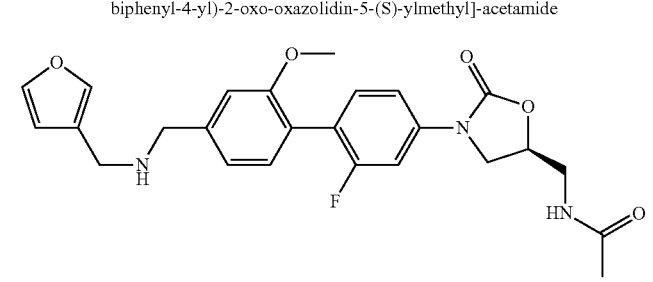<br>N-[3-(2-Fluoro-4'-{[(furan-3-ylmethyl)-amino]-methyl}-2'-methoxy-biphenyl-4-yl)-2-oxo-oxazolidin-5-(S)-ylmethyl]-acetamide |

| Compound Number | Structure |
|---|---|
| 4029 | 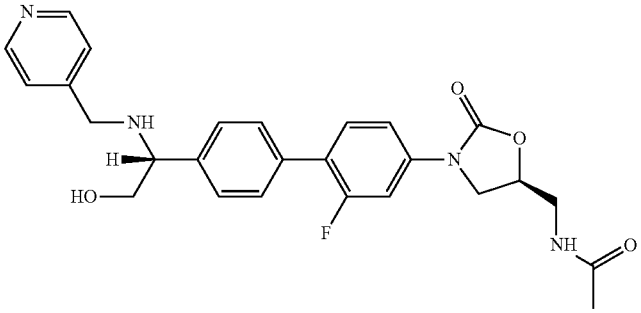 [SMILES: CC(=O)NC[C@H]1CN(c2ccc(-c3ccc([C@H](CO)NCc4ccncc4)cc3)c(F)c2)C(=O)O1]<br>N-[3-(2-Fluoro-4'-{2-hydroxy-1-(R)-[(pyridin-4-ylmethyl)-amino]-ethyl}-biphenyl-4-yl)-2-oxo-oxazolidin-5-(S)-ylmethyl]-acetamide |
| 4030 | 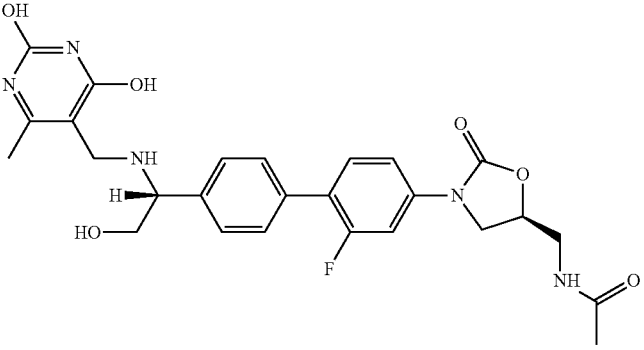 [SMILES: CC(=O)NC[C@H]1CN(c2ccc(-c3ccc([C@H](CO)NCc4c(C)nc(O)nc4O)cc3)c(F)c2)C(=O)O1]<br>N-[3-(4'-{1-(R)-[(2,4-Dihydroxy-6-methyl-pyrimidin-5-ylmethyl)-amino]-2-hydroxy-ethyl}-2-fluoro-biphenyl-4-yl)-2-oxo-oxazolidin-5-(S)-ylmethyl]-acetamide |
| 4031 | 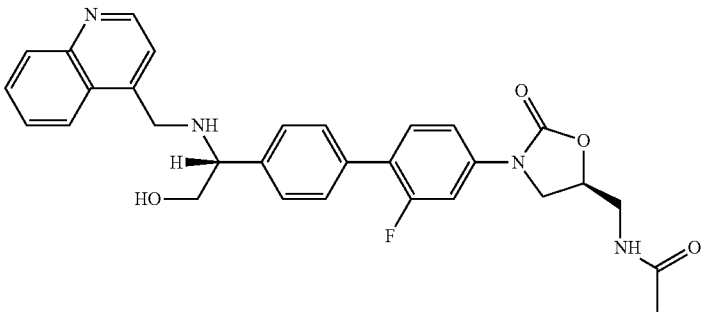 [SMILES: CC(=O)NC[C@H]1CN(c2ccc(-c3ccc([C@H](CO)NCc4ccnc5ccccc45)cc3)c(F)c2)C(=O)O1]<br>N-[3-(2-Fluoro-4'-{2-hydroxy-1-(R)-[(quinolin-4-ylmethyl)-amino]-ethyl}-biphenyl-4-yl)-2-oxo-oxazolidin-5-(S)-ylmethyl]-acetamide |
| 4032 | 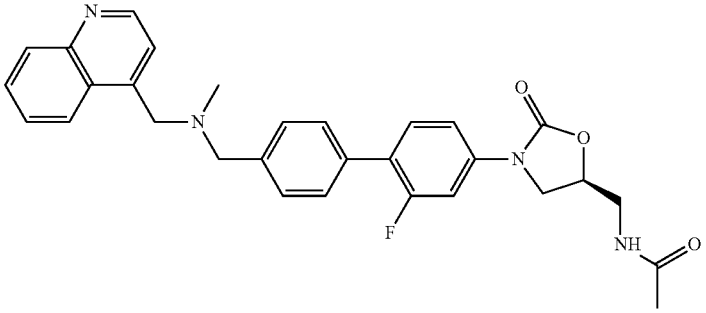 [SMILES: CC(=O)NC[C@H]1CN(c2ccc(-c3ccc(CN(C)Cc4ccnc5ccccc45)cc3)c(F)c2)C(=O)O1]<br>N-(3-{2-Fluoro-4'-[(methyl-quinolin-4-ylmethyl-amino)-methyl]-biphenyl-4-yl}-2-oxo-oxazolidin-5-(S)-ylmethyl)-acetamide |

TABLE 2-continued

| Compound Number | Structure |
|---|---|
| 4033 | N-(3-{2-Fluoro-2'-methoxy-4'-[(methyl-pyridin-4-ylmethyl-amino)-methyl]-biphenyl-4-yl}-2-oxo-oxazolidin-5-(S)-ylmethyl)-acetamide |
| 4034 | N-(3-{2-Fluoro-4'-[(furan-3-ylmethyl-methyl-amino)-methyl]-2'-methoxy-biphenyl-4-yl}-2-oxo-oxazolidin-5-(S)-ylmethyl)-acetamide |
| 4035 | N-(3-{4'-[(Ethyl-pyridin-4-ylmethyl-amino)-methyl]-2-fluoro-biphenyl-4-yl}-2-oxo-oxazolidin-5-(S)-ylmethyl)-acetamide |
| 4036 | N-[3-(4'-{[(2,4-Dihydroxy-6-methyl-pyrimidin-5-ylmethyl)-methyl-amino]-methyl}-2-fluoro-biphenyl-4-yl)-2-oxo-oxazolidin-5-(S)-ylmethyl]-acetamide |

TABLE 2-continued

| Compound Number | Structure |
|---|---|
| 4037 | N-[3-(4'-{[Bis-(4-hydroxy-3-methoxy-benzyl)-amino]-methyl}-2-fluoro-biphenyl-4-yl)-2-oxo-oxazolidin-5-(S)-ylmethyl]-acetamide |
| 4038 | N-[3-(2-Fluoro-4'-{[(isoxazol-4-ylmethyl)-amino]-methyl}-biphenyl-4-yl)-2-oxo-oxazolidin-5-(S)-ylmethyl]-acetamide |
| 4039 | N-(3-{2-Fluoro-2'-methoxy-4'-[(methyl-pyridin-4-ylmethyl-amino)-methyl]-biphenyl-4-yl}-2-oxo-oxazolidin-5-(S)-ylmethyl)-acetamide |
| 4040 | N-[3-(2-Fluoro-2'-methoxy-4'-{[(pyridin-4-ylmethyl)-amino]-methyl}-biphenyl-4-yl)-2-oxo-oxazolidin-5-(S)-ylmethyl]-acetamide |

TABLE 2-continued

| Compound Number | Structure |
|---|---|
| 4041 | N-(3-{2-Fluoro-2'-methoxy-4'-[(methyl-pyridin-4-ylmethyl-amino)-methyl]-biphenyl-4-yl}-2-oxo-oxazolidin-5-(S)-ylmethyl)-acetamide |
| 4042 | N-[3-(2-Fluoro-4'-{[(furan-3-ylmethyl)-amino]-methyl}-2'-methoxy-biphenyl-4-yl)-2-oxo-oxazolidin-5-(S)-ylmethyl]-acetamide |
| 4043 | N-(3-{2-Fluoro-4'-[(furan-3-ylmethyl-methyl-amino)-methyl]-2'-methoxy-biphenyl-4-yl}-2-oxo-oxazolidin-5-(S)-ylmethyl)-acetamide |
| 4044 | N-(3-{2-Fluoro-4'-[(methyl-pyridin-4-ylmethyl-amino)-methyl]-biphenyl-4-yl}-2-oxo-oxazolidin-5-(S)-ylmethyl)-acetamide |

TABLE 2-continued

| Compound Number | Structure |
|---|---|
| 4045 | N-(3-{2-Fluoro-4'-[(methyl-pyridin-2-ylmethyl-amino)-methyl]-biphenyl-4-yl}-2-oxo-oxazolidin-5-(S)-ylmethyl)-acetamide |
| 4046 | N-[3-(4'-{[(3,5-Dichloro-benzyl)-methyl-amino]-methyl}-2-fluoro-biphenyl-4-yl)-2-oxo-oxazolidin-5-(S)-ylmethyl]-acetamide |
| 4047 | N-(3-{2-Fluoro-4'-[(methyl-pyridin-3-ylmethyl-amino)-methyl]-biphenyl-4-yl}-2-oxo-oxazolidin-5-(S)-ylmethyl)-acetamide |
| 4048 | N-[3-(2-Fluoro-4'-{[(1H-pyrrol-2-ylmethyl)-amino]-methyl}-biphenyl-4-yl)-2-oxo-oxazolidin-5-(S)-ylmethyl]-acetamide |

TABLE 2-continued

| Compound Number | Structure |
|---|---|
| 4049 | 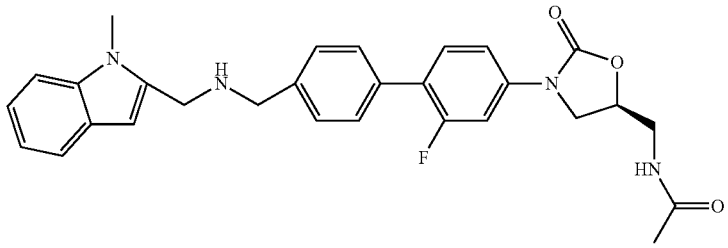 [SMILES: CC(=O)NC[C@H]1CN(c2ccc(-c3ccc(CNCc4cc5ccccc5n4C)cc3)c(F)c2)C(=O)O1]  N-[3-(2-Fluoro-4'-{[(1-methyl-1H-indol-2-ylmethyl)-amino]-methyl}-biphenyl-4-yl)-2-oxo-oxazolidin-5-(S)-ylmethyl]-acetamide |
| 4050 | 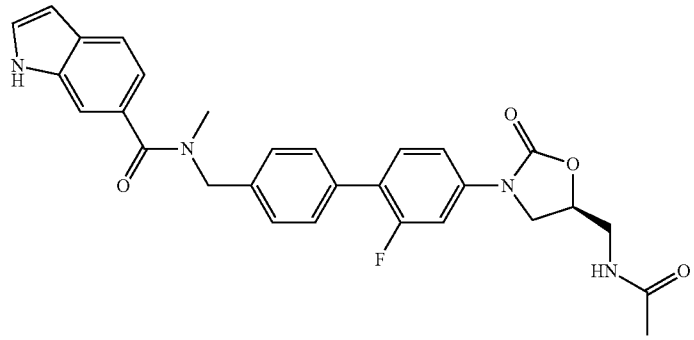 [SMILES: CC(=O)NC[C@H]1CN(c2ccc(-c3ccc(CN(C)C(=O)c4ccc5cc[nH]c5c4)cc3)c(F)c2)C(=O)O1]  1H-Indole-6-carboxylic acid {4'-[5-(S)-(acetylamino-methyl)-2-oxo-oxazolidin-3-yl]-2'-fluoro-biphenyl-4-ylmethyl}-methyl-amide |
| 4051 | 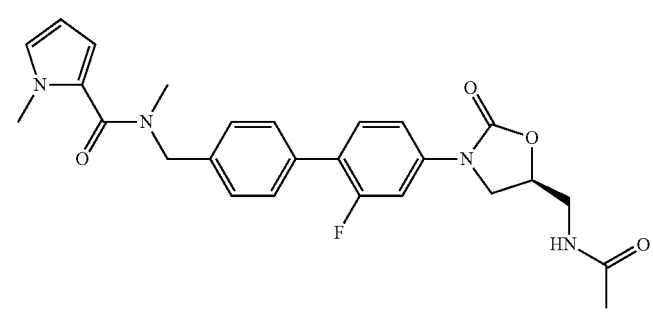 [SMILES: CC(=O)NC[C@H]1CN(c2ccc(-c3ccc(CN(C)C(=O)c4cccn4C)cc3)c(F)c2)C(=O)O1]  1-Methyl-1H-pyrrole-2-carboxylic acid {4'-[5-(S)-(acetylamino-methyl)-2-oxo-oxazolidin-3-yl]-2'-fluoro-biphenyl-4-ylmethyl}-methyl-amide |
| 4052 | 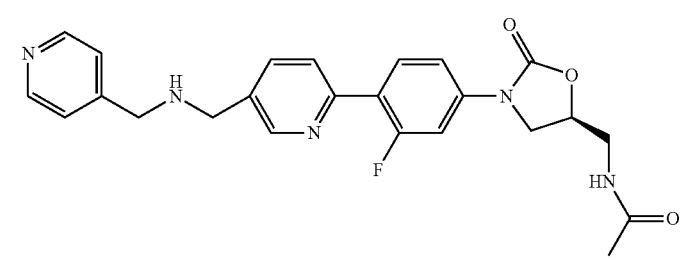 [SMILES: CC(=O)NC[C@H]1CN(c2ccc(-c3ccc(CNCc4ccncc4)cn3)c(F)c2)C(=O)O1]  N-{3-[3-Fluoro-4-(5-{[(pyridin-4-ylmethyl)-amino]-methyl}-pyridin-2-yl)-phenyl]-2-oxo-oxazolidin-5-(S)-ylmethyl}-acetamide |

TABLE 2-continued

| Compound Number | Structure |
|---|---|
| 4053 | N-{3-[3-Fluoro-4-(5-{[(furan-3-ylmethyl)-amino]-methyl}-pyridin-2-yl)-phenyl]-2-oxo-oxazolidin-5-(S)-ylmethyl}-acetamide |
| 4054 | N-[3-(2-Fluoro-4'-{[(6-methoxy-pyridin-3-ylmethyl)-amino]-methyl}-biphenyl-4-yl)-2-oxo-oxazolidin-5-(S)-ylmethyl]-acetamide |
| 4055 | N-[3-(2-Fluoro-4'-{[(6-methoxy-pyridin-3-ylmethyl)-methyl-amino]-methyl}-biphenyl-4-yl)-2-oxo-oxazolidin-5-(S)-ylmethyl]-acetamide |
| 4056 | N-(3-{4'-[(2,5-Bis-trifluoromethyl-benzylamino)-methyl]-2-fluoro-biphenyl-4-yl}-2-oxo-oxazolidin-5-(S)-ylmethyl)-acetamide |

| Compound Number | Structure |
|---|---|
| 4057 | N-[3-(2-Fluoro-4'-{[(6-methyl-2,4-dioxo-1,2,3,4-tetrahydro-pyrimidin-5-ylmethyl)-amino]-methyl}-biphenyl-4-yl)-2-oxo-oxazolidin-5-(S)-ylmethyl]-acetamide |
| 4058 | N-[3-(2-Fluoro-4'-{[(furan-3-ylmethyl)-amino]-methyl}-2'-methoxy-biphenyl-4-yl)-2-oxo-oxazolidin-5-(S)-ylmethyl]-acetamide |
| 4059 | N-[3-(2-Fluoro-4'-{[(1-methyl-1H-pyrrol-2-ylmethyl)-amino]-methyl}-biphenyl-4-yl)-2-oxo-oxazolidin-5-(S)-ylmethyl]-acetamide |
| 4060 | N-[3-(2-Fluoro-4'-{[(isoquinolin-4-ylmethyl)-amino]-methyl}-biphenyl-4-yl)-2-oxo-oxazolidin-5-(S)-ylmethyl]-acetamide |

TABLE 2-continued

| Compound Number | Structure |
|---|---|
| 4061 | 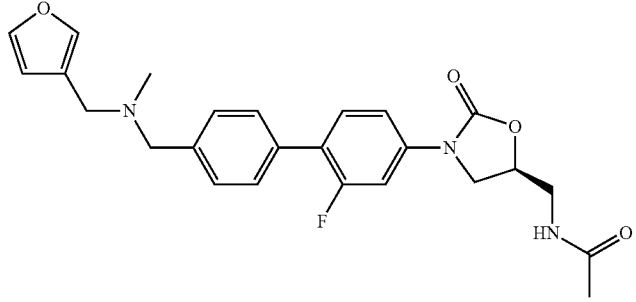 [SMILES: CC(=O)NC[C@H]1CN(c2ccc(-c3ccc(CN(C)Cc4ccoc4)cc3)c(F)c2)C(=O)O1]<br>N-(3-{2-Fluoro-4'-[(furan-3-ylmethyl-methyl-amino)-methyl]-biphenyl-4-yl}-2-oxo-oxazolidin-5-(S)-ylmethyl)-acetamide |
| 4062 | 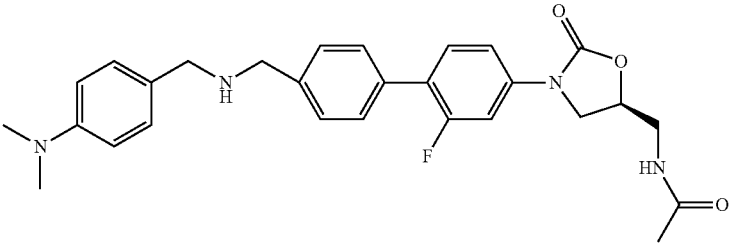 [SMILES: CC(=O)NC[C@H]1CN(c2ccc(-c3ccc(CNCc4ccc(N(C)C)cc4)cc3)c(F)c2)C(=O)O1]<br>N-(3-{4'-[(4-Dimethylamino-benzylamino)-methyl]-2-fluoro-biphenyl-4-yl}-2-oxo-oxazolidin-5-(S)-ylmethyl)-acetamide |
| 4063 | 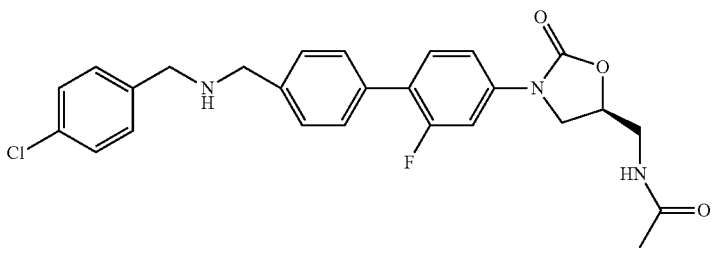 [SMILES: CC(=O)NC[C@H]1CN(c2ccc(-c3ccc(CNCc4ccc(Cl)cc4)cc3)c(F)c2)C(=O)O1]<br>N-(3-{4'-[(4-Chloro-benzylamino)-methyl]-2-fluoro-biphenyl-4-yl}-2-oxo-oxazolidin-5-(S)-ylmethyl)-acetamide |
| 4064 | 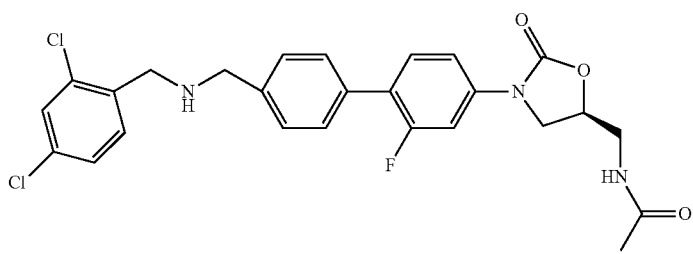 [SMILES: CC(=O)NC[C@H]1CN(c2ccc(-c3ccc(CNCc4ccc(Cl)cc4Cl)cc3)c(F)c2)C(=O)O1]<br>N-(3-{4'-[(2,4-Dichloro-benzylamino)-methyl]-2-fluoro-biphenyl-4-yl}-2-oxo-oxazolidin-5-(S)-ylmethyl)-acetamide |

TABLE 2-continued

| Compound Number | Structure |
|---|---|
| 4065 | 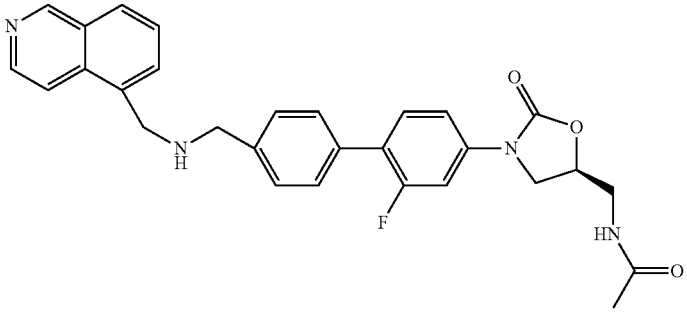 [SMILES: CC(=O)NC[C@H]1CN(c2ccc(-c3ccc(CNCc4cccc5cnccc45)cc3)c(F)c2)C(=O)O1]<br>N-[3-(2-Fluoro-4'-{[(isoquinolin-5-ylmethyl)-amino]-methyl}-biphenyl-4-yl)-2-oxo-oxazolidin-5-(S)-ylmethyl]-acetamide |
| 4066 | 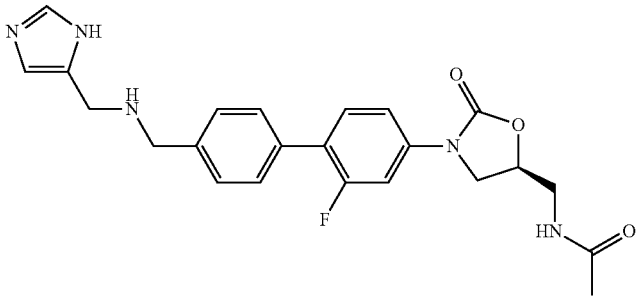 [SMILES: CC(=O)NC[C@H]1CN(c2ccc(-c3ccc(CNCc4cnc[nH]4)cc3)c(F)c2)C(=O)O1]<br>N-[3-(2-Fluoro-4'-{[(3H-imidazol-4-ylmethyl)-amino]-methyl}-biphenyl-4-yl)-2-oxo-oxazolidin-5-(S)-ylmethyl]-acetamide |
| 4067 | 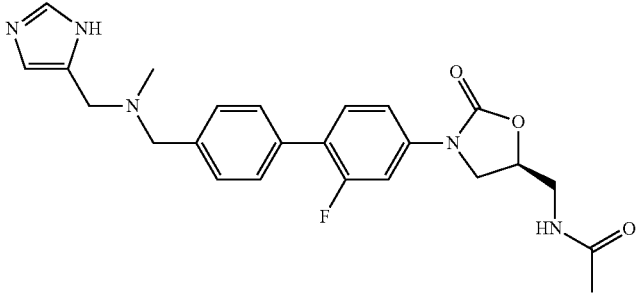 [SMILES: CC(=O)NC[C@H]1CN(c2ccc(-c3ccc(CN(C)Cc4cnc[nH]4)cc3)c(F)c2)C(=O)O1]<br>N-[3-(2-Fluoro-4'-{[(3H-imidazol-4-ylmethyl)-methyl-amino]-methyl}-biphenyl-4-yl)-2-oxo-oxazolidin-5-(S)-ylmethyl]-acetamide |
| 4068 | 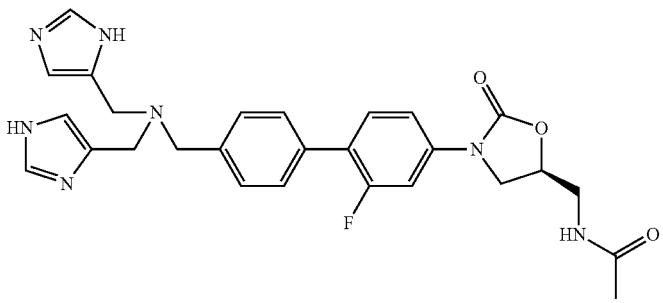 [SMILES: CC(=O)NC[C@H]1CN(c2ccc(-c3ccc(CN(Cc4c[nH]cn4)Cc4cnc[nH]4)cc3)c(F)c2)C(=O)O1]<br>N-[3-(2-Fluoro-4'-{[(1H-imidazol-4-ylmethyl)-(3H-imidazol-4-ylmethyl)-amino]-methyl}-biphenyl-4-yl)-2-oxo-oxazolidin-5-(S)-ylmethyl]-acetamide |

| Compound Number | Structure |
|---|---|
| 4069 | 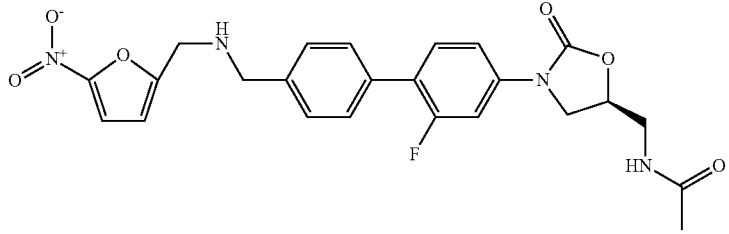 [SMILES: CC(=O)NC[C@H]1CN(c2ccc(-c3ccc(CNCc4ccc([N+](=O)[O-])o4)cc3)c(F)c2)C(=O)O1]<br>N-[3-(2-Fluoro-4'-{[(5-nitro-furan-2-ylmethyl)-amino]-methyl}-biphenyl-4-yl)-2-oxo-oxazolidin-5-(S)-ylmethyl]-acetamide |
| 4070 | 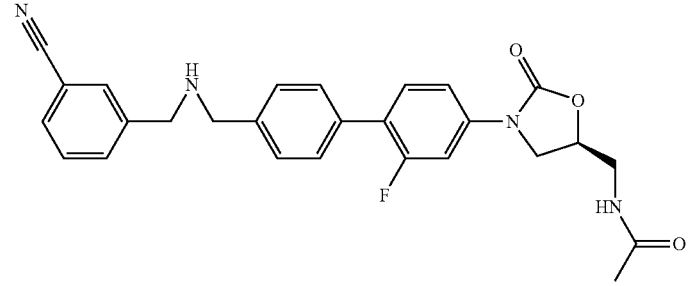 [SMILES: CC(=O)NC[C@H]1CN(c2ccc(-c3ccc(CNCc4cccc(C#N)c4)cc3)c(F)c2)C(=O)O1]<br>N-(3-{4'-[(3-Cyano-benzylamino)-methyl]-2-fluoro-biphenyl-4-yl}-2-oxo-oxazolidin-5-(S)-ylmethyl)-acetamide |
| 4071 | 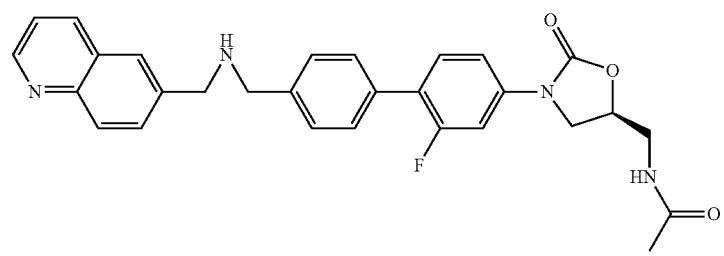 [SMILES: CC(=O)NC[C@H]1CN(c2ccc(-c3ccc(CNCc4ccc5ncccc5c4)cc3)c(F)c2)C(=O)O1]<br>N-[3-(2-Fluoro-4'-{[(quinolin-6-ylmethyl)-amino]-methyl}-biphenyl-4-yl)-2-oxo-oxazolidin-5-(S)-ylmethyl]-acetamide |
| 4072 | 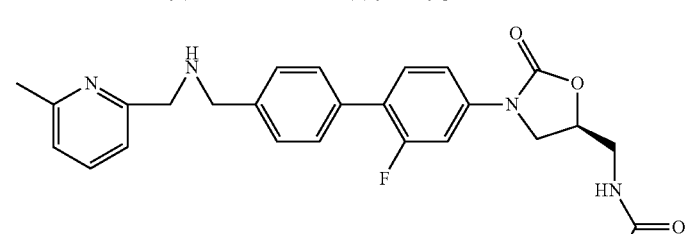<br>N-[3-(2-Fluoro-4'-{[(6-methyl-pyridin-2-ylmethyl)-amino]-methyl}-biphenyl-4-yl)-2-oxo-oxazolidin-5-(S)-ylmethyl]-acetamide |
| 4073 | 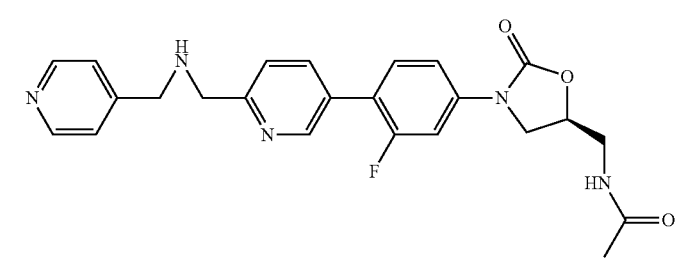 [SMILES: CC(=O)NC[C@H]1CN(c2ccc(-c3ccc(CNCc4ccncc4)nc3)c(F)c2)C(=O)O1]<br>N-{3-[3-Fluoro-4-(6-{[(pyridin-4-ylmethyl)-amino]-methyl}-pyridin-3-yl)-phenyl]-2-oxo-oxazolidin-5-(S)-ylmethyl}-acetamide |

TABLE 2-continued

| Compound Number | Structure |
|---|---|
| 4074 | N-[3-(2-Fluoro-4'-{[(thiazol-2-ylmethyl)-amino]-methyl}-biphenyl-4-yl)-2-oxo-oxazolidin-5-(S)-ylmethyl]-acetamide |
| 4075 | N-[3-(2-Fluoro-4'-{[(5-hydroxymethyl-furan-2-ylmethyl)-amino]-methyl}-biphenyl-4-yl)-2-oxo-oxazolidin-5-(S)-ylmethyl]-acetamide |
| 4076 | N-[3-(2-Fluoro-4'-{[(1-methyl-1H-imidazol-2-ylmethyl)-amino]-methyl}-biphenyl-4-yl)-2-oxo-oxazolidin-5-(S)-ylmethyl]-acetamide |
| 4077 | N-[3-(4'-{[(Benzo[b]thiophen-3-ylmethyl)-amino]-methyl}-2-fluoro-biphenyl-4-yl)-2-oxo-oxazolidin-5-(S)-ylmethyl]-acetamide |
| 4078 | N-[3-(4'-{[(5-Bromo-furan-2-ylmethyl)-amino]-methyl}-2-fluoro-biphenyl-4-yl)-2-oxo-oxazolidin-5-(S)-ylmethyl]-acetamide |

TABLE 2-continued

| Compound Number | Structure |
|---|---|
| 4079 | N-(3-{2-Fluoro-4'-[(3-imidazol-1-yl-propylamino)-methyl]-biphenyl-4-yl}-2-oxo-oxazolidin-5-(S)-ylmethyl)-acetamide |
| 4080 | N-{3-[2-Fluoro-4'-(N-pyridin-4-ylmethyl-carbamimidoyl)-biphenyl-4-yl]-2-oxo-oxazolidin-5-(S)-ylmethyl}-acetamide |
| 4081 | N-[3-(2-Fluoro-4'-{[(5-methyl-furan-2-ylmethyl)-amino]-methyl}-biphenyl-4-yl)-2-oxo-oxazolidin-5-(S)-ylmethyl]-acetamide |
| 4082 | N-[3-(2-Fluoro-4'-{[(5-methyl-3H-imidazol-4-ylmethyl)-amino]-methyl}-biphenyl-4-yl)-2-oxo-oxazolidin-5-(S)-ylmethyl]-acetamide |
| 4083 | N-[3-(2-Fluoro-4'-{[(1H-indol-3-ylmethyl)-amino]-methyl}-biphenyl-4-yl)-2-oxo-oxazolidin-5-(S)-ylmethyl]-acetamide |

| Compound Number | Structure |
|---|---|
| 4084 | 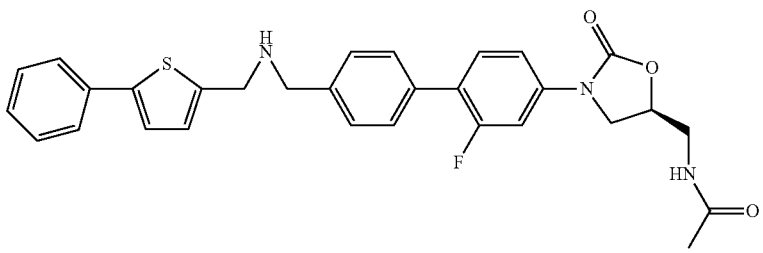 [SMILES: CC(=O)NC[C@H]1CN(c2ccc(-c3ccc(CNCc4ccc(-c5ccccc5)s4)cc3)c(F)c2)C(=O)O1]<br>N-[3-(2-Fluoro-4'-{[(5-phenyl-thiophen-2-ylmethyl)-amino]-methyl}-biphenyl-4-yl)-2-oxo-oxazolidin-5-(S)-ylmethyl]-acetamide |
| 4085 | 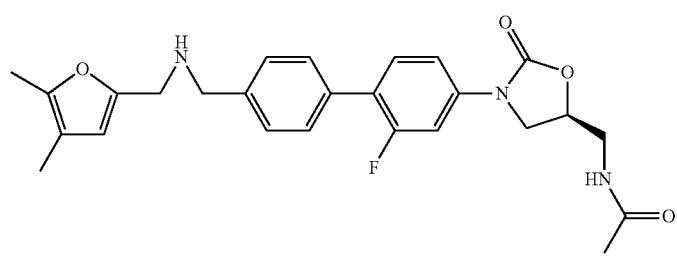 [SMILES: CC(=O)NC[C@H]1CN(c2ccc(-c3ccc(CNCc4cc(C)c(C)o4)cc3)c(F)c2)C(=O)O1]<br>N-[3-(4'-{[(4,5-Dimethyl-furan-2-ylmethyl)-amino]-methyl}-2-fluoro-biphenyl-4-yl)-2-oxo-oxazolidin-5-(S)-ylmethyl]-acetamide |
| 4086 | 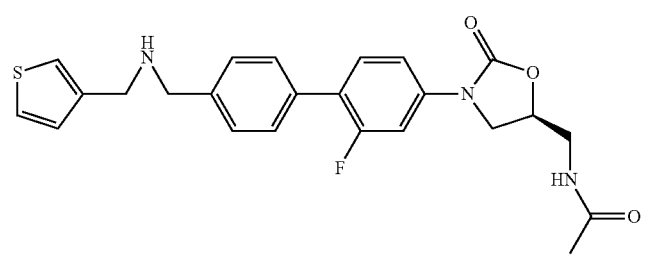 [SMILES: CC(=O)NC[C@H]1CN(c2ccc(-c3ccc(CNCc4ccsc4)cc3)c(F)c2)C(=O)O1]<br>N-[3-(2-Fluoro-4'-{[(thiophen-3-ylmethyl)-amino]-methyl}-biphenyl-4-yl)-2-oxo-oxazolidin-5-(S)-ylmethyl]-acetamide |
| 4087 | 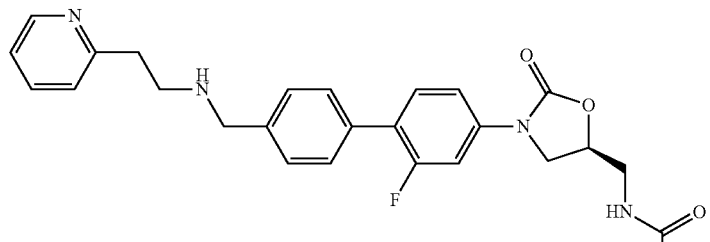<br>N-(3-{2-Fluoro-4'-[(2-pyridin-2-yl-ethylamino)-methyl]-biphenyl-4-yl}-2-oxo-oxazolidin-5-(S)-ylmethyl)-acetamide |

TABLE 2-continued

| Compound Number | Structure |
|---|---|
| 4088 | N-[2-Oxo-3-(2,2',3'-trifluoro-4'-{[(furan-2-ylmethyl)-amino]-methyl}-biphenyl-4-yl)-oxazolidin-5-(S)-ylmethyl]-acetamide |
| 4089 | N-[2-Oxo-3-(2,2',3'-trifluoro-4'-{[(pyridin-4-ylmethyl)-amino]-methyl}-biphenyl-4-yl)-oxazolidin-5-(S)-ylmethyl]-acetamide |
| 4090 | N-[2-Oxo-3-(2,2',3'-trifluoro-4'-{[(pyridin-2-ylmethyl)-amino]-methyl}-biphenyl-4-yl)-oxazolidin-5-(S)-ylmethyl]-acetamide |
| 4091 | N-[3-(2-Fluoro-4'-{[(1H-imidazol-2-ylmethyl)-amino]-methyl}-biphenyl-4-yl)-2-oxo-oxazolidin-5-(S)-ylmethyl]-acetamide |

TABLE 2-continued

| Compound Number | Structure |
|---|---|
| 4092 | 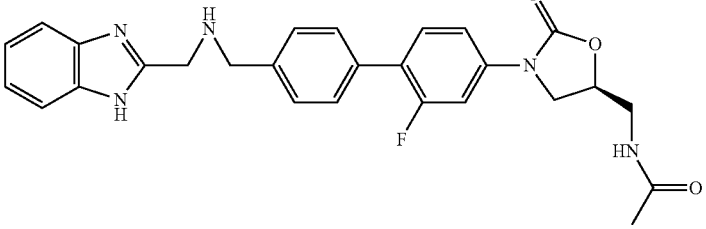<br>N-[3-(4'-{[(1H-Benzoimidazol-2-ylmethyl)-amino]-methyl}-2-fluoro-biphenyl-4-yl)-2-oxo-oxazolidin-5-(S)-ylmethyl]-acetamide |
| 4093 | 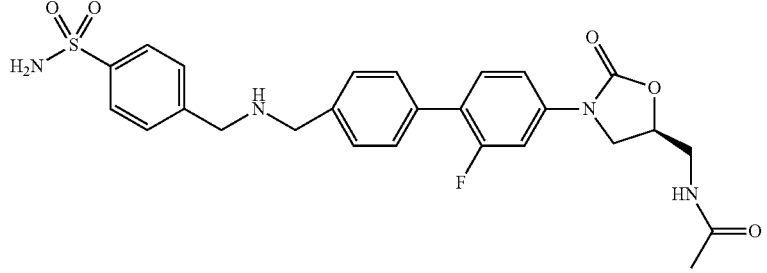 [SMILES: CC(=O)NC[C@H]1CN(c2ccc(-c3ccc(CNCc4ccc(S(N)(=O)=O)cc4)cc3)c(F)c2)C(=O)O1]<br>N-(3-{2-Fluoro-4'-[(4-sulfamoyl-benzylamino)-methyl]-biphenyl-4-yl}-2-oxo-oxazolidin-5-(S)-ylmethyl)-acetamide |
| 4094 | 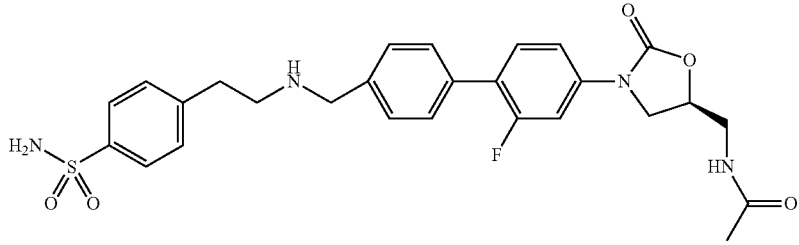 [SMILES: CC(=O)NC[C@H]1CN(c2ccc(-c3ccc(CNCCc4ccc(S(N)(=O)=O)cc4)cc3)c(F)c2)C(=O)O1]<br>N-[3-(2-Fluoro-4'-{[2-(4-sulfamoyl-phenyl)-ethylamino]-methyl}-biphenyl-4-yl)-2-oxo-oxazolidin-5-(S)-ylmethyl]-acetamide |
| 4095 | 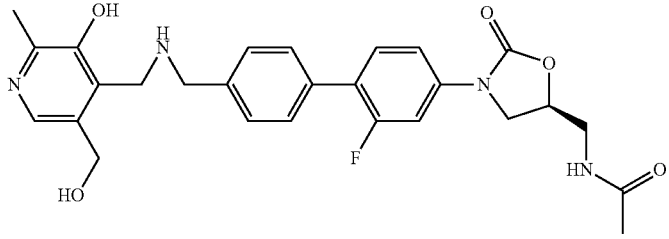 [SMILES: CC(=O)NC[C@H]1CN(c2ccc(-c3ccc(CNCc4c(CO)cnc(C)c4O)cc3)c(F)c2)C(=O)O1]<br>N-[3-(2-Fluoro-4'-{[(3-hydroxy-5-hydroxymethyl-2-methyl-pyridin-4-ylmethyl)-amino]-methyl}-biphenyl-4-yl)-2-oxo-oxazolidin-5-(S)-ylmethyl]-acetamide |
| 4096 | 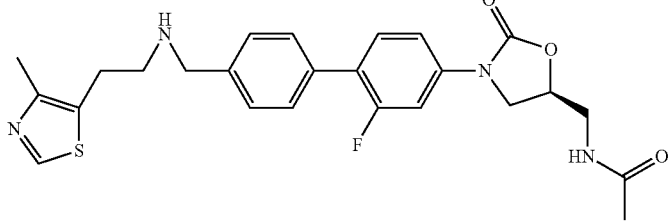<br>N-[3-(2-Fluoro-4'-{[2-(4-methyl-thiazol-5-yl)-ethylamino]-methyl}-biphenyl-4-yl)-2-oxo-oxazolidin-5-(S)-ylmethyl]-acetamide |

TABLE 2-continued

| Compound Number | Structure |
|---|---|
| 4097 | 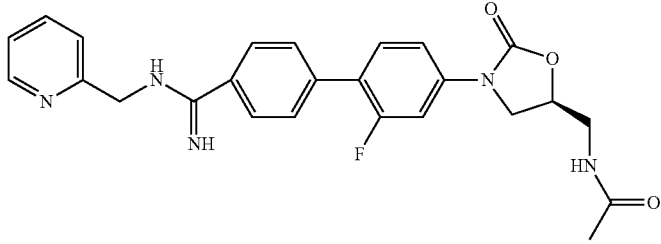<br>N-{3-[2-Fluoro-4'-(N-pyridin-2-ylmethyl-carbamimidoyl)-biphenyl-4-yl]-2-oxo-oxazolidin-5-(S)-ylmethyl}-acetamide |
| 4098 | 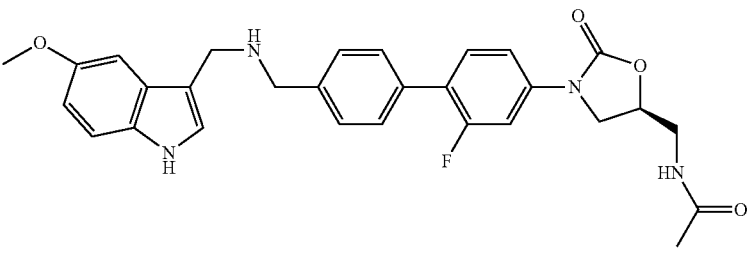 [SMILES: COc1ccc2[nH]cc(CNCc3ccc(-c4ccc(N5C[C@H](CNC(C)=O)OC5=O)cc4F)cc3)c2c1]<br>N-[3-(2-Fluoro-4'-{[(5-methoxy-1H-indol-3-ylmethyl)-amino]-methyl}-biphenyl-4-yl)-2-oxo-oxazolidin-5-(S)-ylmethyl]-acetamide |
| 4099 | 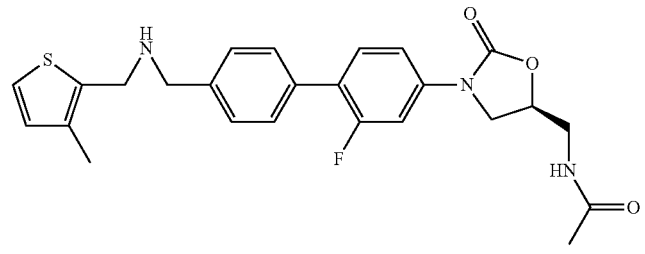 [SMILES: CC(=O)NC[C@H]1CN(c2ccc(-c3ccc(CNCc4sccc4C)cc3)c(F)c2)C(=O)O1]<br>N-[3-(2-Fluoro-4'-{[(3-methyl-thiophen-2-ylmethyl)-amino]-methyl}-biphenyl-4-yl)-2-oxo-oxazolidin-5-(S)-ylmethyl]-acetamide |
| 4100 | 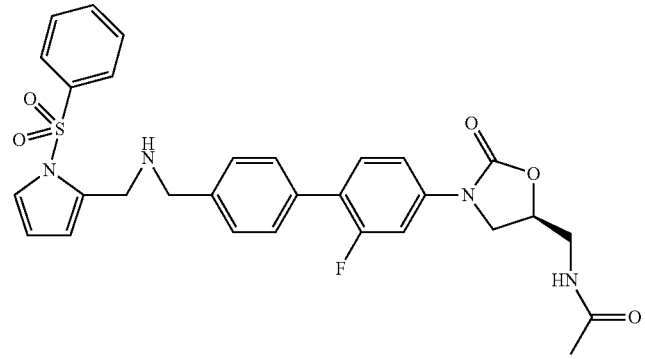 [SMILES: CC(=O)NC[C@H]1CN(c2ccc(-c3ccc(CNCc4cccn4S(=O)(=O)c4ccccc4)cc3)c(F)c2)C(=O)O1]<br>N-[3-(4'-{[(1-Benzenesulfonyl-1H-pyrrol-2-ylmethyl)-amino]-methyl}-2-fluoro-biphenyl-4-yl)-2-oxo-oxazolidin-5-(S)-ylmethyl]-acetamide |

TABLE 2-continued

| Compound Number | Structure |
|---|---|
| 4101 | N-[3-(4'-{[(2,4-Dioxo-1,2,3,4-tetrahydro-pyrimidin-5-ylmethyl)-amino]-methyl}-2-fluoro-biphenyl-4-yl)-2-oxo-oxazolidin-5-(S)-ylmethyl]-acetamide |
| 4102 | 4'-[5-(S)-(Acetylamino-methyl)-2-oxo-oxazolidin-3-yl]-2'-fluoro-biphenyl-4-carboxylic acid (pyridin-4-ylmethyl)-amide |
| 4103 | N-[3-(4'-{[(2,5-Dimethyl-furan-3-ylmethyl)-amino]-methyl}-2-fluoro-biphenyl-4-yl)-2-oxo-oxazolidin-5-(S)-ylmethyl]-acetamide |
| 4104 | N-[3-(2-Fluoro-4'-{[(5-methyl-3-phenyl-isoxazol-4-ylmethyl)-amino]-methyl}-biphenyl-4-yl)-2-oxo-oxazolidin-5-(S)-ylmethyl]-acetamide |
| 4105 | N-[3-(2-Fluoro-4'-{[(5-methyl-2-trifluoromethyl-furan-3-ylmethyl)-amino]-methyl}-biphenyl-4-yl)-2-oxo-oxazolidin-5-(S)-ylmethyl]-acetamide |

TABLE 2-continued

| Compound Number | Structure |
|---|---|
| 4106 | 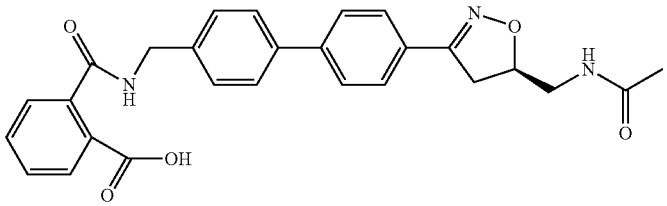 [SMILES: CC(=O)NC[C@H]1CC(c2ccc(-c3ccc(CNC(=O)c4ccccc4C(=O)O)cc3)cc2)=NO1]<br>N-{4'-[5-(R)-(Acetylamino-methyl)-4,5-dihydro-isoxazol-3-yl]-biphenyl-4-ylmethyl}-phthalamic acid |
| 4107 | 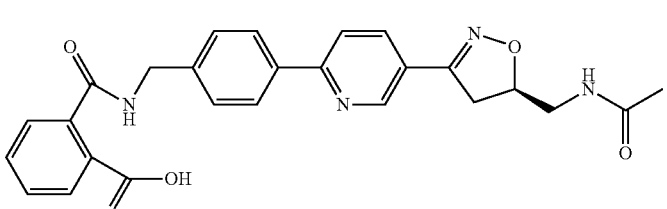<br>N-(4-{5-[5-(R)-(Acetylamino-methyl)-4,5-(S)-dihydro-isoxazol-3-yl]-pyridin-2-yl}-benzyl)-phthalamic acid |
| 4108 | 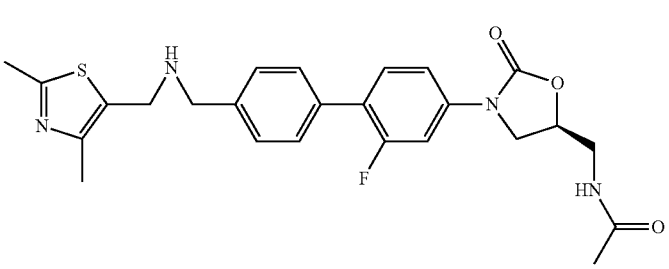 [SMILES: CC(=O)NC[C@H]1CN(c2ccc(-c3ccc(CNCc4sc(C)nc4C)cc3)c(F)c2)C(=O)O1]<br>N-[3-(4'-{[(2,4-Dimethyl-thiazol-5-ylmethyl)-amino]-methyl}-2-fluoro-biphenyl-4-yl)-2-oxo-oxazolidin-5-(S)-ylmethyl]-acetamide |
| 4109 | 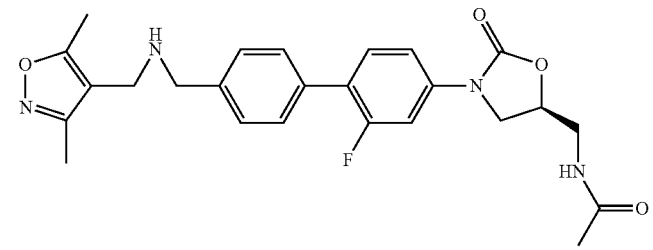<br>N-[3-(4'-{[(3,5-Dimethyl-isoxazol-4-ylmethyl)-amino]-methyl}-2-fluoro-biphenyl-4-yl)-2-oxo-oxazolidin-5-(S)-ylmethyl]-acetamide |
| 4110 | 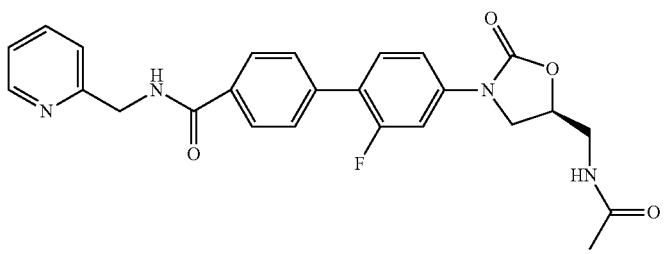 [SMILES: CC(=O)NC[C@H]1CN(c2ccc(-c3ccc(C(=O)NCc4ccccn4)cc3)c(F)c2)C(=O)O1]<br>4'-[5-(S)-(Acetylamino-methyl)-2-oxo-oxazolidin-3-yl]-2'-fluoro-biphenyl-4-carboxylic acid (pyridin-2-ylmethyl)-amide |

TABLE 2-continued

| Compound Number | Structure |
|---|---|
| 4111 | 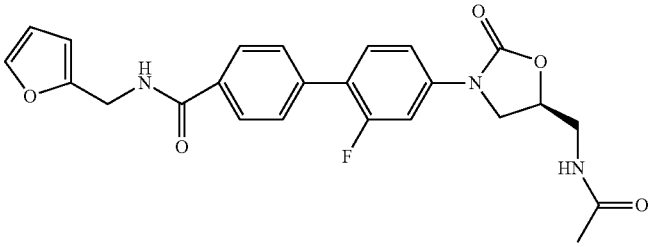 [SMILES: CC(=O)NC[C@H]1CN(c2ccc(-c3ccc(C(=O)NCc4ccco4)cc3)c(F)c2)C(=O)O1]<br>4'-[5-(S)-(Acetylamino-methyl)-2-oxo-oxazolidin-3-yl]-2'-fluoro-biphenyl-4-carboxylic acid (furan-2-ylmethyl)-amide |
| 4112 | 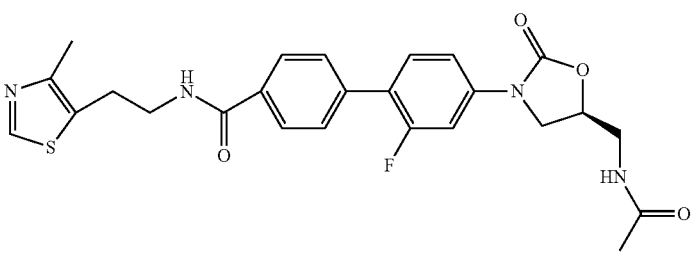 [SMILES: CC(=O)NC[C@H]1CN(c2ccc(-c3ccc(C(=O)NCCc4scnc4C)cc3)c(F)c2)C(=O)O1]<br>4'-[5-(S)-(Acetylamino-methyl)-2-oxo-oxazolidin-3-yl]-2'-fluoro-biphenyl-4-carboxylic acid [2-(4-methyl-thiazol-5-yl)-ethyl]-amide |
| 4113 | 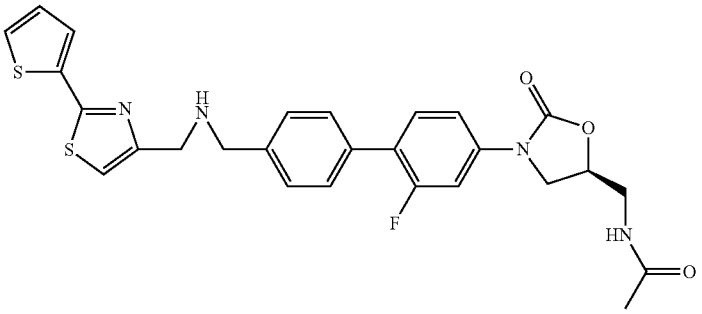 [SMILES: CC(=O)NC[C@H]1CN(c2ccc(-c3ccc(CNCc4csc(-c5cccs5)n4)cc3)c(F)c2)C(=O)O1]<br>N-[3-(2-Fluoro-4'-{[(2-thiophen-2-yl-thiazol-4-ylmethyl)-amino]-methyl}-biphenyl-4-yl)-2-oxo-oxazolidin-5-(S)-ylmethyl]-acetamide |
| 4114 | 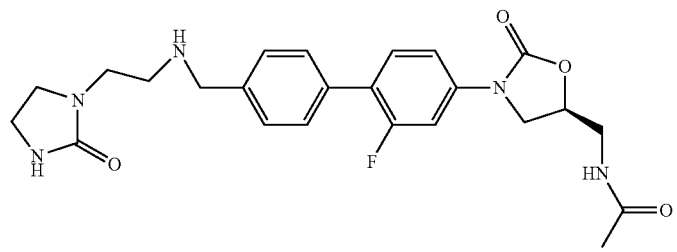 [SMILES: CC(=O)NC[C@H]1CN(c2ccc(-c3ccc(CNCCN4CCNC4=O)cc3)c(F)c2)C(=O)O1]<br>N-[3-(2-Fluoro-4'-{[2-(2-oxo-imidazolidin-1-yl)-ethylamino]-methyl}-biphenyl-4-yl)-2-oxo-oxazolidin-5-(S)-ylmethyl]-acetamide |
| 4115 | 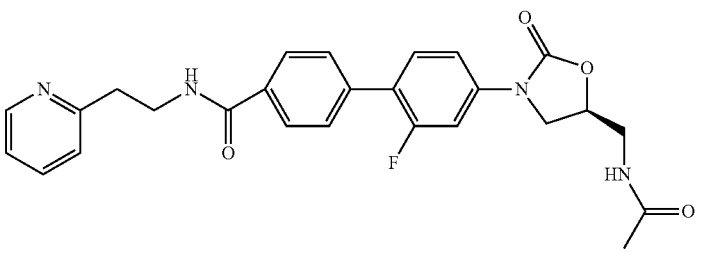 [SMILES: CC(=O)NC[C@H]1CN(c2ccc(-c3ccc(C(=O)NCCc4ccccn4)cc3)c(F)c2)C(=O)O1]<br>4'-[5-(S)-(Acetylamino-methyl)-2-oxo-oxazolidin-3-yl]-2'-fluoro-biphenyl-4-carboxylic acid (2-pyridin-2-yl-ethyl)-amide |

TABLE 2-continued

| Compound Number | Structure |
|---|---|
| 4116 | 4'-[5-(S)-(Acetylamino-methyl)-2-oxo-oxazolidin-3-yl]-2'-fluoro-biphenyl-4-carboxylic acid [2-(3H-imidazol-4-yl)-ethyl]-amide |
| 4117 | N-[3-(2-Fluoro-4'-{[(2-morpholin-4-yl-pyridin-3-ylmethyl)-amino]-methyl}-biphenyl-4-yl)-2-oxo-oxazolidin-5-(S)-ylmethyl]-acetamide |
| 4118 | N-[3-(2-Fluoro-4'-{[(6-morpholin-4-yl-pyridin-3-ylmethyl)-amino]-methyl}-biphenyl-4-yl)-2-oxo-oxazolidin-5-(S)-ylmethyl]-acetamide |
| 4119 | N-[3-(2-Fluoro-4'-{[(5-pyridin-2-yl-thiophen-2-ylmethyl)-amino]-methyl}-biphenyl-4-yl)-2-oxo-oxazolidin-5-(S)-ylmethyl]-acetamide |
| 4120 | 5-[({4'-[5-(S)-(Acetylamino-methyl)-2-oxo-oxazolidin-3-yl]-2'-fluoro-biphenyl-4-ylmethyl}-amino)-methyl]-2-methyl-furan-3-carboxylic acid methyl ester |

TABLE 2-continued

| Compound Number | Structure |
|---|---|
| 4121 | 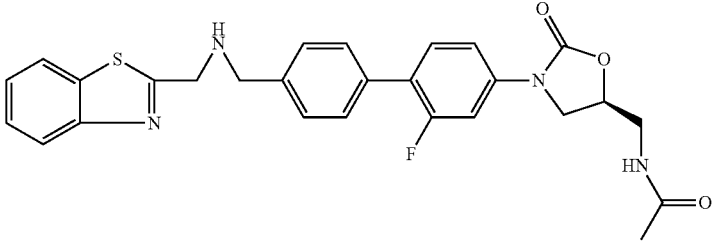 [SMILES: CC(=O)NC[C@H]1CN(c2ccc(-c3ccc(CNCc4nc5ccccc5s4)cc3)c(F)c2)C(=O)O1]<br>N-[3-(4'-{[(Benzothiazol-2-ylmethyl)-amino]-methyl}-2-fluoro-biphenyl-4-yl)-2-oxo-oxazolidin-5-(S)-ylmethyl]-acetamide |
| 4122 | 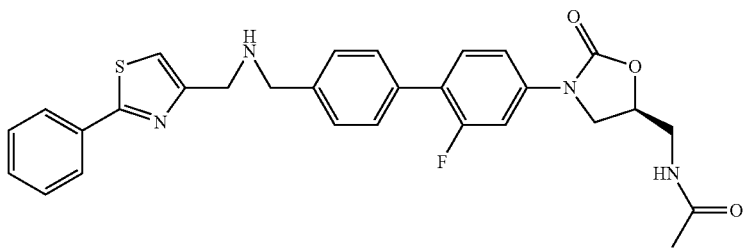 [SMILES: CC(=O)NC[C@H]1CN(c2ccc(-c3ccc(CNCc4csc(-c5ccccc5)n4)cc3)c(F)c2)C(=O)O1]<br>N-[3-(2-Fluoro-4'-{[(2-phenyl-thiazol-4-ylmethyl)-amino]-methyl}-biphenyl-4-yl)-2-oxo-oxazolidin-5-(S)-ylmethyl]-acetamide |
| 4123 | 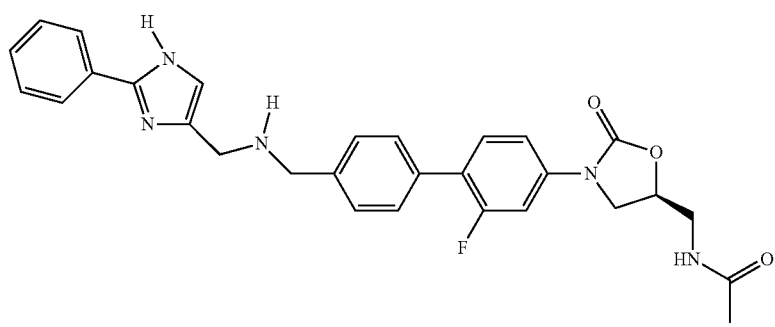 [SMILES: CC(=O)NC[C@H]1CN(c2ccc(-c3ccc(CNCc4c[nH]c(-c5ccccc5)n4)cc3)c(F)c2)C(=O)O1]<br>N-[3-(2-Fluoro-4'-{[(2-phenyl-1H-imidazol-4-ylmethyl)-amino]-methyl}-biphenyl-4-yl)-2-oxo-oxazolidin-5-(S)-ylmethyl]-acetamide |
| 4124 | 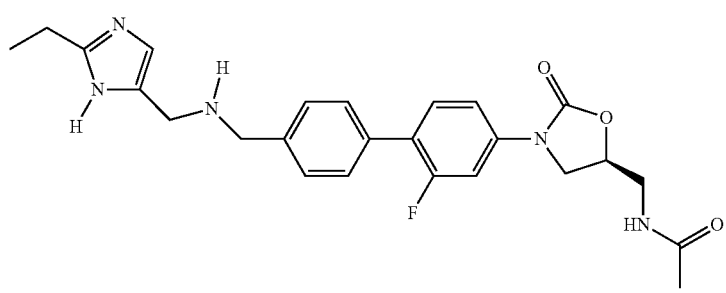 [SMILES: CCc1ncc(CNCc2ccc(-c3ccc(N4C[C@H](CNC(C)=O)OC4=O)cc3F)cc2)[nH]1]<br>N-[3-(4'-{[(2-Ethyl-3H-imidazol-4-ylmethyl)-amino]-methyl}-2-fluoro-biphenyl-4-yl)-2-oxo-oxazolidin-5-(S)-ylmethyl]-acetamide |

TABLE 2-continued

| Compound Number | Structure |
|---|---|
| 4125 | 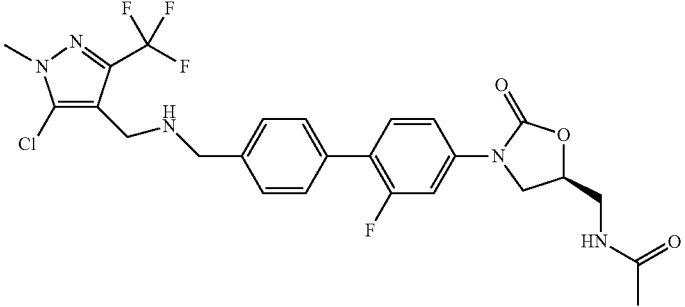 [SMILES: CC(=O)NC[C@H]1CN(c2ccc(-c3ccc(CNCc4c(C(F)(F)F)nn(C)c4Cl)cc3)c(F)c2)C(=O)O1]<br>N-[3-(4'-{[(5-Chloro-1-methyl-3-trifluoromethyl-1H-pyrazol-4-ylmethyl)-amino]-methyl}-2-fluoro-biphenyl-4-yl)-2-oxo-oxazolidin-5-(S)-ylmethyl]-acetamide |
| 4126 | 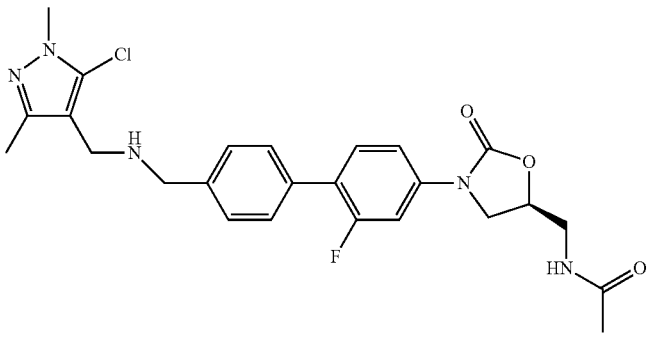 [SMILES: CC(=O)NC[C@H]1CN(c2ccc(-c3ccc(CNCc4c(C)nn(C)c4Cl)cc3)c(F)c2)C(=O)O1]<br>N-[3-(4'-{[(5-Chloro-1,3-dimethyl-1H-pyrazol-4-ylmethyl)-amino]-methyl}-2-fluoro-biphenyl-4-yl)-2-oxo-oxazolidin-5-(S)-ylmethyl]-acetamide |
| 4127 | 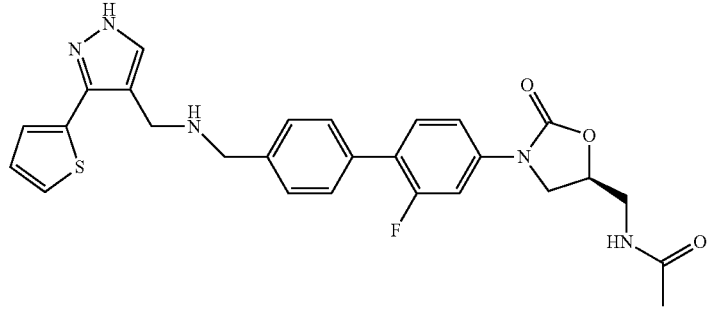 [SMILES: CC(=O)NC[C@H]1CN(c2ccc(-c3ccc(CNCc4c[nH]nc4-c4cccs4)cc3)c(F)c2)C(=O)O1]<br>N-[3-(2-Fluoro-4'-{[(3-thiophen-2-yl-1H-pyrazol-4-ylmethyl)-amino]-methyl}-biphenyl-4-yl)-2-oxo-oxazolidin-5-(S)-ylmethyl]-acetamide |
| 4128 | 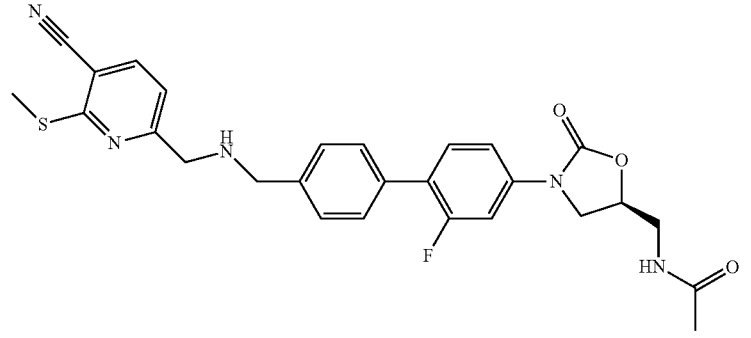 [SMILES: CSc1nc(CNCc2ccc(-c3ccc(N4C[C@H](CNC(C)=O)OC4=O)cc3F)cc2)ccc1C#N]<br>N-[3-(4'-{[(5-Cyano-6-methylsulfanyl-pyridin-2-ylmethyl)-amino]-methyl}-2-fluoro-biphenyl-4-yl)-2-oxo-oxazolidin-5-(S)-ylmethyl]-acetamide |

TABLE 2-continued

| Compound Number | Structure |
|---|---|
| 4129 | 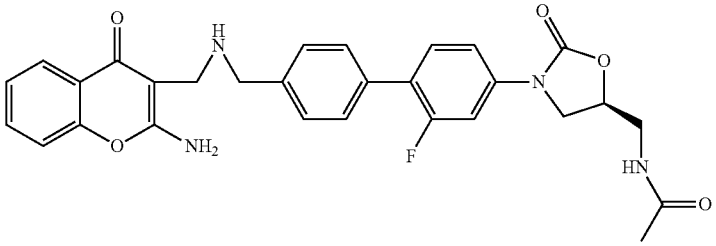 [SMILES: CC(=O)NC[C@H]1CN(c2ccc(-c3ccc(CNCc4c(N)oc5ccccc5c4=O)cc3)c(F)c2)C(=O)O1]<br>N-[3-(4'-{[(2-Amino-4-oxo-4H-chromen-3-ylmethyl)-amino]-methyl}-2-fluoro-biphenyl-4-yl)-2-oxo-oxazolidin-5-(S)-ylmethyl]-acetamide |
| 4130 | 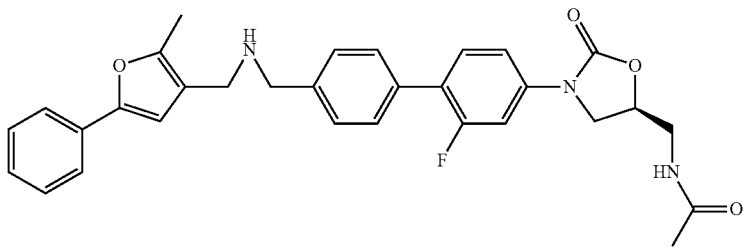 [SMILES: CC(=O)NC[C@H]1CN(c2ccc(-c3ccc(CNCc4cc(-c5ccccc5)oc4C)cc3)c(F)c2)C(=O)O1]<br>N-[3-(2-Fluoro-4'-{[(2-methyl-5-phenyl-furan-3-ylmethyl)-amino]-methyl}-biphenyl-4-yl)-2-oxo-oxazolidin-5-(S)-ylmethyl]-acetamide |
| 4131 | 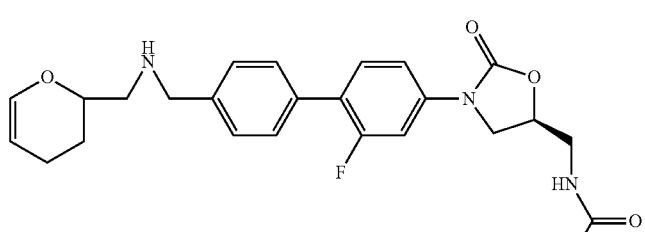<br>N-[3-(4'-{[(3,4-Dihydro-2H-pyran-2-ylmethyl)-amino]-methyl}-2-fluoro-biphenyl-4-yl)-2-oxo-oxazolidin-5-(S)-ylmethyl]-acetamide |
| 4132 | 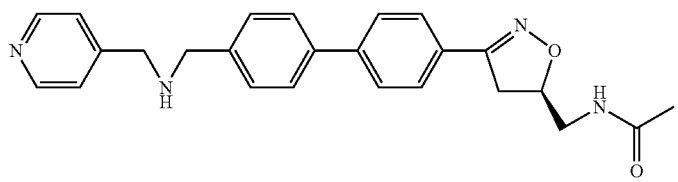 [SMILES: CC(=O)NC[C@H]1CC(c2ccc(-c3ccc(CNCc4ccncc4)cc3)cc2)=NO1]<br>N-[3-(4'-{[(Pyridin-4-ylmethyl)-amino]-methyl}-biphenyl-4-yl)-4,5-dihydro-isoxazol-5-(R)-ylmethyl]-acetamide |
| 4133 | 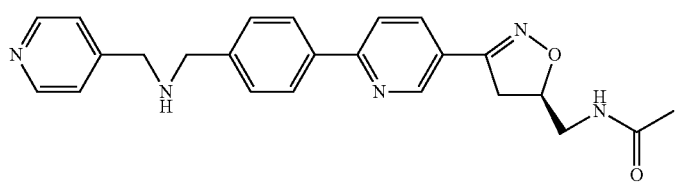 [SMILES: CC(=O)NC[C@H]1CC(c2ccc(-c3ccc(CNCc4ccncc4)cc3)nc2)=NO1]<br>N-{3-[6-(4-{[(Pyridin-4-ylmethyl)-amino]-methyl}-phenyl)-pyridin-3-yl]-4,5-dihydro-isoxazol-5-(R)-ylmethyl}-acetamide |

TABLE 2-continued

| Compound Number | Structure |
|---|---|
| 4134 | 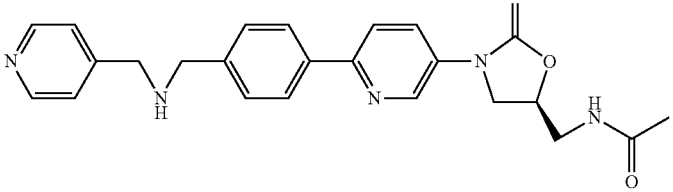<br>N-{2-Oxo-3-[6-(4-{[(pyridin-4-ylmethyl)-amino]-methyl}-phenyl)-pyridin-3-yl]-oxazolidin-5-(S)-ylmethyl}-acetamide |
| 4135 | 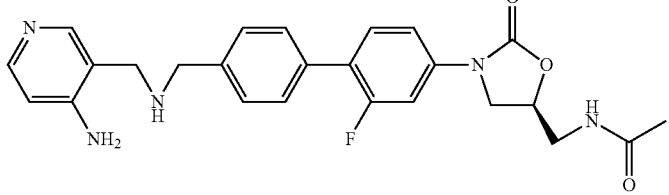<br>N-[3-(4'-{[(4-Amino-pyridin-3-ylmethyl)-amino]-methyl}-2-fluoro-biphenyl-4-yl)-2-oxo-oxazolidin-5-(S)-ylmethyl]-acetamide |
| 4136 | 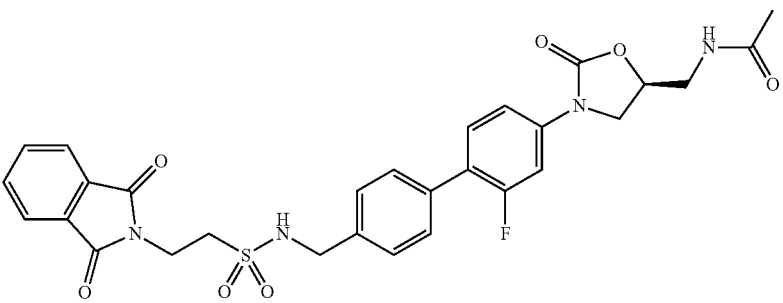 [SMILES: CC(=O)NC[C@H]1CN(c2ccc(-c3ccc(CNS(=O)(=O)CCN4C(=O)c5ccccc5C4=O)cc3)c(F)c2)C(=O)O1]<br>N-[3-(4'-{[2-(1,3-Dioxo-1,3-dihydro-isoindol-2-yl)-ethanesulfonylamino]-methyl}-2-fluoro-biphenyl-4-yl)-2-oxo-oxazolidin-5-(S)-ylmethyl]-acetamide |
| 4137 | 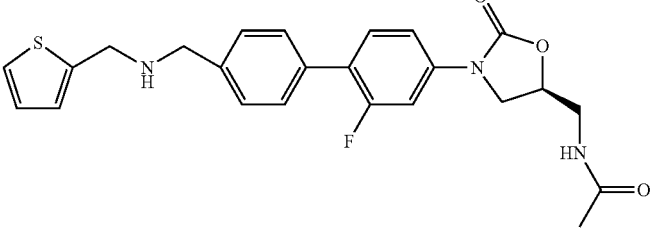<br>N-[3-(2-Fluoro-4'-{[(thiophen-2-ylmethyl)-amino]-methyl}-biphenyl-4-yl)-2-oxo-oxazolidin-5-(S)-ylmethyl]-acetamide |
| 4138 | 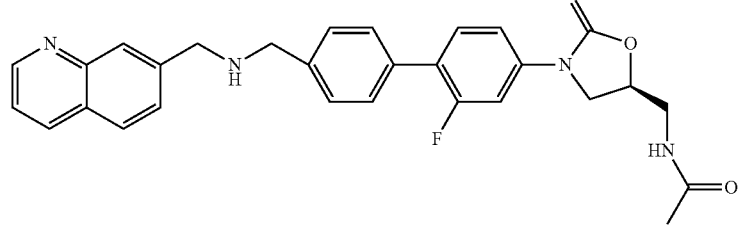<br>N-[3-(2-Fluoro-4'-{[(quinolin-7-ylmethyl)-amino]-methyl}-biphenyl-4-yl)-2-oxo-oxazolidin-5-(S)-ylmethyl]-acetamide |

| Compound Number | Structure |
|---|---|
| 4139 | N-[3-(4'-{[(4-Chloro-1-methyl-1H-pyrazol-3-ylmethyl)-amino]-methyl}-2-fluoro-biphenyl-4-yl)-2-oxo-oxazolidin-5-(S)-ylmethyl]-acetamide |
| 4140 | N-[3-(2-Fluoro-4'-{[(3-methyl-[1,2,4]oxadiazol-5-ylmethyl)-amino]-methyl}-biphenyl-4-yl)-2-oxo-oxazolidin-5-(S)-ylmethyl]-acetamide |
| 4141 | N-[3-(2-Fluoro-4'-{[(5-methyl-[1,2,4]oxadiazol-3-ylmethyl)-amino]-methyl}-biphenyl-4-yl)-2-oxo-oxazolidin-5-(S)-ylmethyl]-acetamide |
| 4142 | N-{4'-[5-(S)-(Acetylamino-methyl)-2-oxo-oxazolidin-3-yl]-2'-fluoro-biphenyl-4-ylmethyl}-isonicotinamide |
| 4143 | 4'-[5-(S)-(Acetylamino-methyl)-2-oxo-oxazolidin-3-yl]-2'-fluoro-biphenyl-4-carboxylic acid (thiazol-2-ylmethyl)-amide |

TABLE 2-continued

| Compound Number | Structure |
|---|---|
| 4144 | N-[3-(2-Fluoro-4'-{1-(R/S)-[(furan-3-ylmethyl)-amino]-ethyl}-biphenyl-4-yl)-2-oxo-oxazolidin-5-(S)-ylmethyl]-acetamide |
| 4145 | N-[3-(2-Fluoro-4'-{1-(R/S)-[(thiazol-2-ylmethyl)-amino]-ethyl}-biphenyl-4-yl)-2-oxo-oxazolidin-5-(S)-ylmethyl]-acetamide |
| 4146 | N-[3-(2-Fluoro-4'-{[(5-methyl-2-phenyl-2H-[1,2,3]triazol-4-ylmethyl)-amino]-methyl}-biphenyl-4-yl)-2-oxo-oxazolidin-5-(S)-ylmethyl]-acetamide |
| 4147 | N-(3-{2-Fluoro-4'-[(4-pyrrol-1-yl-benzylamino)-methyl]-biphenyl-4-yl}-2-oxo-oxazolidin-5-(S)-ylmethyl)-acetamide |
| 4148 | N-[3-(2-Fluoro-4'-{[3-(5-methyl-1H-pyrazol-4-yl)-propylamino]-methyl}-biphenyl-4-yl)-2-oxo-oxazolidin-5-(S)-ylmethyl]-acetamide |

TABLE 2-continued

| Compound Number | Structure |
|---|---|
| 4149 | N-[3-(2-Fluoro-4'-{2-[(pyridin-4-ylmethyl)-amino]-ethyl}-biphenyl-4-yl)-2-oxo-oxazolidin-5-(S)-ylmethyl]-acetamide |
| 4150 | N-[3-(2-Fluoro-4'-{[2-(R/S)-(1-methyl-pyrrolidin-2-yl)-ethylamino]-methyl}-biphenyl-4-yl)-2-oxo-oxazolidin-5-(S)-ylmethyl]-acetamide |
| 4151 | N-[3-(2-Fluoro-4'-{[(2-methoxy-pyridin-3-ylmethyl)-amino]-methyl}-biphenyl-4-yl)-2-oxo-oxazolidin-5-(S)-ylmethyl]-acetamide |
| 4152 | N-[3-(4'-{[(2-Amino-pyridin-3-ylmethyl)-amino]-methyl}-2-fluoro-biphenyl-4-yl)-2-oxo-oxazolidin-5-(S)-ylmethyl]-acetamide |
| 4153 | N-[3-(2-Fluoro-4'-{[(pyrrolidin-3-(R/S)-ylmethyl)-amino]-methyl}-biphenyl-4-yl)-2-oxo-oxazolidin-5-(S)-ylmethyl]-acetamide |

| Compound Number | Structure |
|---|---|
| 4154 | 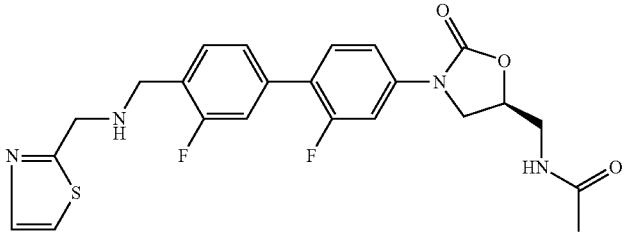 [SMILES: CC(=O)NC[C@H]1CN(c2ccc(-c3ccc(CNCc4nccs4)c(F)c3)c(F)c2)C(=O)O1]<br>N-[3-(2,3'-Difluoro-4'-{[(thiazol-2-ylmethyl)-amino]-methyl}-biphenyl-4-yl)-2-oxo-oxazolidin-5-(S)-ylmethyl]-acetamide |
| 4155 | 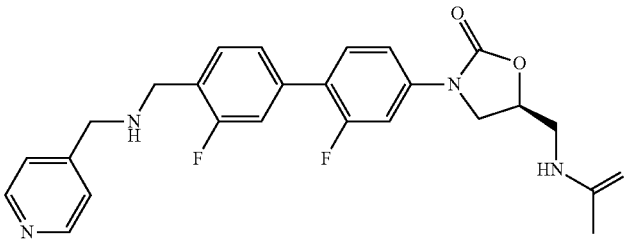<br>N-[3-(2,3'-Difluoro-4'-{[(pyridin-4-ylmethyl)-amino]-methyl}-biphenyl-4-yl)-2-oxo-oxazolidin-5-(S)-ylmethyl]-acetamide |
| 4156 | 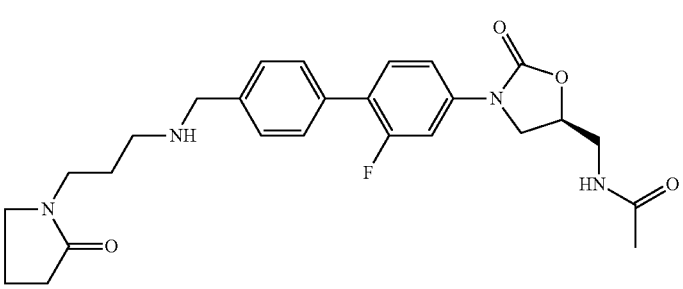 [SMILES: CC(=O)NC[C@H]1CN(c2ccc(-c3ccc(CNCCCN4CCCC4=O)cc3)c(F)c2)C(=O)O1]<br>N-[3-(2-Fluoro-4'-{[3-(2-oxo-pyrrolidin-1-yl)-propylamino]-methyl}-biphenyl-4-yl)-2-oxo-oxazolidin-5-(S)-ylmethyl]-acetamide |
| 4157 | 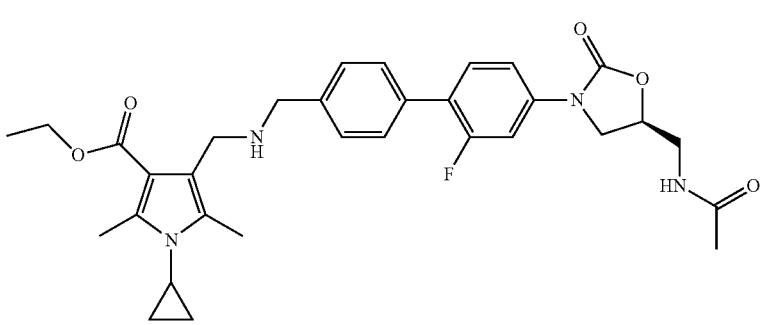 [SMILES: CCOC(=O)c1c(CNCc2ccc(-c3ccc(N4C[C@H](CNC(C)=O)OC4=O)cc3F)cc2)c(C)n(C2CC2)c1C]<br>4-[({4'-[5-(S)-(Acetylamino-methyl)-2-oxo-oxazolidin-3-yl]-2'-fluoro-biphenyl-4-ylmethyl}-amino)-methyl]-1-cyclopropyl-2,5-dimethyl-1H-pyrrole-3-carboxylic acid ethyl ester |

TABLE 2-continued

| Compound Number | Structure |
|---|---|
| 4158 | N-{3-[2-Fluoro-4'-({[5-(3-sulfamoyl-phenyl)-furan-2-ylmethyl]-amino}-methyl)-biphenyl-4-yl]-2-oxo-oxazolidin-5-(S)-ylmethyl}-acetamide |
| 4159 | N-(3-{2-Fluoro-4'-[(1-pyridin-4-(R/S)-yl-ethylamino)-methyl]-biphenyl-4-yl}-2-oxo-oxazolidin-5-(S)-ylmethyl)-acetamide |
| 4160 | N-(3-{2-Fluoro-4'-[1-(R/S)-(1-pyridin-4-(R/S)-yl-ethylamino)-ethyl]-biphenyl-4-yl}-2-oxo-oxazolidin-5-(S)-ylmethyl)-acetamide |
| 4161 | N-[3-(4'-{[(5-Ethyl-furan-2-ylmethyl)-amino]-methyl}-2-fluoro-biphenyl-4-yl)-2-oxo-oxazolidin-5-(S)-ylmethyl]-acetamide |
| 4162 | N-[3-(4'-{[(5-Ethyl-thiophen-2-ylmethyl)-amino]-methyl}-2-fluoro-biphenyl-4-yl)-2-oxo-oxazolidin-5-(S)-ylmethyl]-acetamide |

TABLE 2-continued

| Compound Number | Structure |
|---|---|
| 4163 | N-[3-(2-Fluoro-4'-{[(1,3,5-trimethyl-1H-pyrazol-4-ylmethyl)-amino]-methyl}-biphenyl-4-yl)-2-oxo-oxazolidin-5-(S)-ylmethyl]-acetamide |
| 4164 | N-[3-(2,3'-Difluoro-4'-{[([1,2,3]thiadiazol-4-ylmethyl)-amino]-methyl}-biphenyl-4-yl)-2-oxo-oxazolidin-5-(S)-ylmethyl]-acetamide |
| 4165 | N-[3-(2-Fluoro-4'-{[(2-methyl-1H-imidazol-4-ylmethyl)-amino]-methyl}-biphenyl-4-yl)-2-oxo-oxazolidin-5-(S)-ylmethyl]-acetamide |
| 4166 | N-[3-(2-Fluoro-3'-{[([1,2,3]thiadiazol-4-ylmethyl)-amino]-methyl}-biphenyl-4-yl)-2-oxo-oxazolidin-5-(S)-ylmethyl]-acetamide |
| 4167 | N-[3-(2-Fluoro-4'-{[(5-methylsulfanyl-thiophen-2-ylmethyl)-amino]-methyl}-biphenyl-4-yl)-2-oxo-oxazolidin-5-(S)-ylmethyl]-acetamide |

TABLE 2-continued

| Compound Number | Structure |
|---|---|
| 4168 | 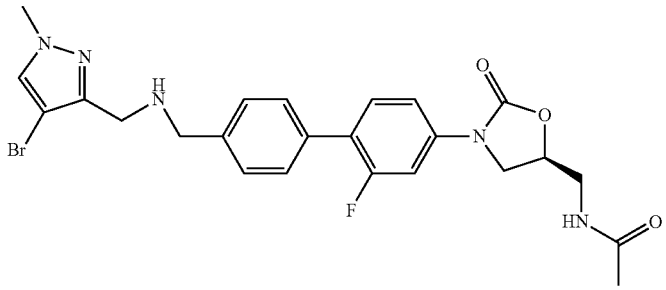 [SMILES: CC(=O)NC[C@H]1CN(c2ccc(-c3ccc(CNCc4nn(C)cc4Br)cc3)c(F)c2)C(=O)O1]<br>N-[3-(4'-{[(4-Bromo-1-methyl-1H-pyrazol-3-ylmethyl)-amino]-methyl}-2-fluoro-biphenyl-4-yl)-2-oxo-oxazolidin-5-(S)-ylmethyl]-acetamide |
| 4169 | 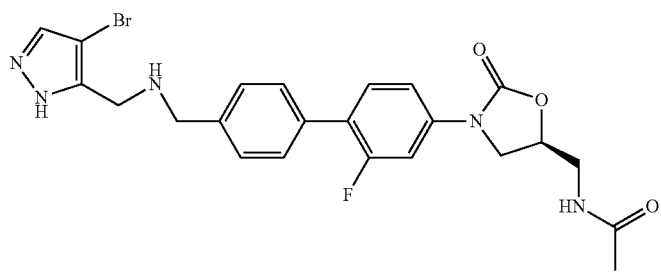 [SMILES: CC(=O)NC[C@H]1CN(c2ccc(-c3ccc(CNCc4[nH]ncc4Br)cc3)c(F)c2)C(=O)O1]<br>N-[3-(4'-{[(4-Bromo-2H-pyrazol-3-ylmethyl)-amino]-methyl}-2-fluoro-biphenyl-4-yl)-2-oxo-oxazolidin-5-(S)-ylmethyl]-acetamide |
| 4170 | 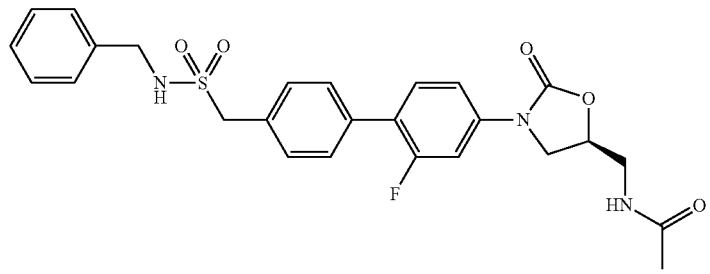 [SMILES: CC(=O)NC[C@H]1CN(c2ccc(-c3ccc(CS(=O)(=O)NCc4ccccc4)cc3)c(F)c2)C(=O)O1]<br>N-{3-[4'-(Benzylsulfamoyl-methyl)-2-fluoro-biphenyl-4-yl]-2-oxo-oxazolidin-5-(S)-ylmethyl}-acetamide |
| 4171 | 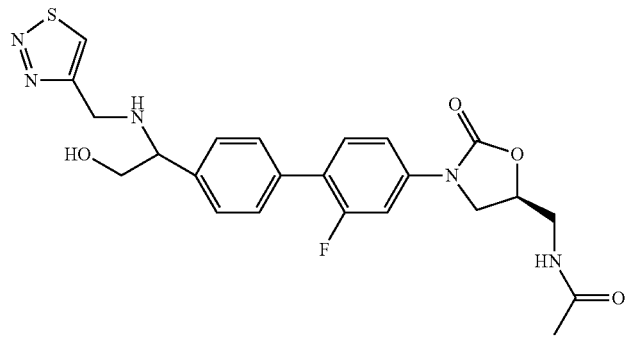 [SMILES: CC(=O)NC[C@H]1CN(c2ccc(-c3ccc(C(CO)NCc4csnn4)cc3)c(F)c2)C(=O)O1]<br>N-[3-(2-Fluoro-4'-{2-hydroxy-1-[([1,2,3]thiadiazol-4-(R/S)-ylmethyl)-amino]-ethyl}-biphenyl-4-yl)-2-oxo-oxazolidin-5-(S)-ylmethyl]-acetamide |

| Compound Number | Structure |
|---|---|
| 4172 | N-[3-(2-Fluoro-4'-{2-hydroxy-1-[([1,2,3]thiadiazol-4-(R/S)-ylmethyl)-amino]-ethyl}-biphenyl-4-yl)-2-oxo-oxazolidin-5-(S)-ylmethyl]-acetamide |
| 4173 | 4'-[5-(S)-(Acetylamino-methyl)-2-oxo-oxazolidin-3-yl]-2'-fluoro-biphenyl-4-carboxylic acid [1-carbamoyl-2-(S)-(3H-imidazol-4-yl)-ethyl]-amide |
| 4174 | 2-({4'-[5-(S)-(Acetylamino-methyl)-2-oxo-oxazolidin-3-yl]-2'-fluoro-biphenyl-4-ylmethyl}-amino)-3-(S)-(1H-imidazol-4-yl)-propionamide |
| 4175 | 2-({4'-[5-(S)-(Acetylamino-methyl)-2-oxo-oxazolidin-3-yl]-2'-fluoro-biphenyl-4-ylmethyl}-amino)-3-(S)-(1H-indol-3-yl)-propionamide |

TABLE 2-continued

| Compound Number | Structure |
|---|---|
| 4176 | N-[3-(2-Fluoro-2',5'-dimethyl-4'-{[(pyridin-4-ylmethyl)-amino]-methyl}-biphenyl-4-yl)-2-oxo-oxazolidin-5-(S)-ylmethyl]-acetamide |
| 4177 | N-(3-{4'-[(2,2-Difluoro-2-pyridin-2-yl-ethylamino)-methyl]-2-fluoro-biphenyl-4-yl}-2-oxo-oxazolidin-5-(S)-ylmethyl)-acetamide |
| 4178 | N-[3-(2-Fluoro-4'-{[(5-(S)-oxo-4,5-dihydro-1H-[1,2,4]triazol-3-ylmethyl)-amino]-methyl}-biphenyl-4-yl)-2-oxo-oxazolidin-5-(S)-ylmethyl]-acetamide |
| 4179 | N-[3-(2-Fluoro-4'-{[(3-fluoro-pyridin-4-ylmethyl)-amino]-methyl}-biphenyl-4-yl)-2-oxo-oxazolidin-5-(S)-ylmethyl]-acetamide |
| 4180 | N-[3-(2-Fluoro-4'-{[(5-methylamino-[1,2,4]thiadiazol-3-ylmethyl)-amino]-methyl}-biphenyl-4-yl)-2-oxo-oxazolidin-5-(S)-ylmethyl]-acetamide |

| Compound Number | Structure |
|---|---|
| 4181 | 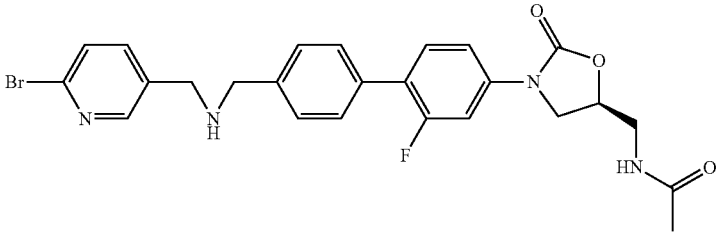 [SMILES: CC(=O)NC[C@H]1CN(c2ccc(-c3ccc(CNCc4ccc(Br)nc4)cc3)c(F)c2)C(=O)O1]<br>N-[3-(4'-{[(6-Bromo-pyridin-3-ylmethyl)-amino]-methyl}-2-fluoro-biphenyl-4-yl)-2-oxo-oxazolidin-5-(S)-ylmethyl]-acetamide |
| 4182 | 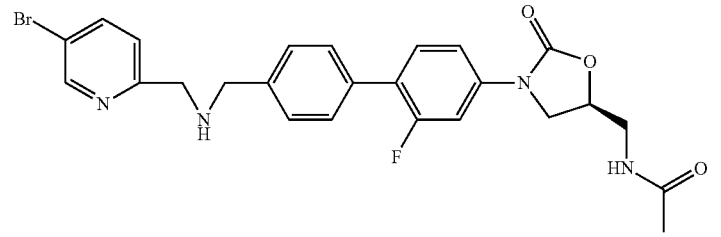 [SMILES: CC(=O)NC[C@H]1CN(c2ccc(-c3ccc(CNCc4ccc(Br)cn4)cc3)c(F)c2)C(=O)O1]<br>N-[3-(4'-{[(5-Bromo-pyridin-2-ylmethyl)-amino]-methyl}-2-fluoro-biphenyl-4-yl)-2-oxo-oxazolidin-5-(S)-ylmethyl]-acetamide |
| 4183 | 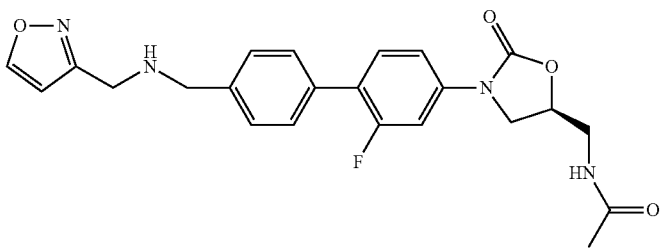 [SMILES: CC(=O)NC[C@H]1CN(c2ccc(-c3ccc(CNCc4ccon4)cc3)c(F)c2)C(=O)O1]<br>N-[3-(2-Fluoro-4'-{[(isoxazol-3-ylmethyl)-amino]-methyl}-biphenyl-4-yl)-2-oxo-oxazolidin-5-(S)-ylmethyl]-acetamide |
| 4184 | 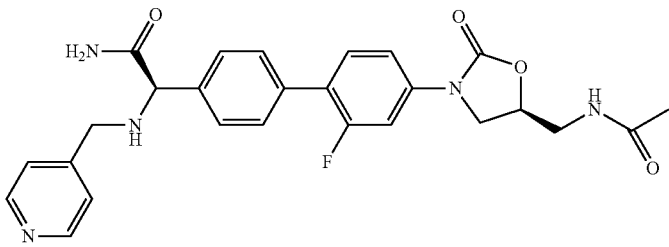 [SMILES: CC(=O)NC[C@H]1CN(c2ccc(-c3ccc([C@@H](NCc4ccncc4)C(N)=O)cc3)c(F)c2)C(=O)O1]<br>2-{4'-[5-(S)-(Acetylamino-methyl)-2-oxo-oxazolidin-3-yl]-2'-fluoro-biphenyl-4-yl}-2-(R)-[(pyridin-4-ylmethyl)-amino]-acetamide |
| 4185 | 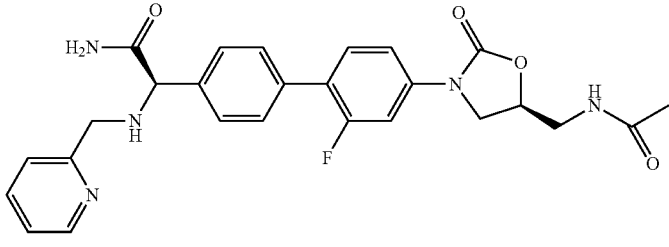 [SMILES: CC(=O)NC[C@H]1CN(c2ccc(-c3ccc([C@@H](NCc4ccccn4)C(N)=O)cc3)c(F)c2)C(=O)O1]<br>2-{4'-[5-(S)-(Acetylamino-methyl)-2-oxo-oxazolidin-3-yl]-2'-fluoro-biphenyl-4-yl}-2-(R)-[(pyridin-2-ylmethyl)-amino]-acetamide |

TABLE 2-continued

| Compound Number | Structure |
|---|---|
| 4186 | N-[3-(2-Fluoro-4'-{[(piperidin-4-ylmethyl)-amino]-methyl}-biphenyl-4-yl)-2-oxo-oxazolidin-5-(S)-ylmethyl]-acetamide |
| 4187 | 5-{4-[5-(S)-(Acetylamino-methyl)-2-oxo-oxazolidin-3-yl]-2-fluoro-phenyl}-pyridine-2-carboxylic acid (pyridin-2-ylmethyl)-amide |
| 4188 | 5-{4-[5-(S)-(Acetylamino-methyl)-2-oxo-oxazolidin-3-yl]-2-fluoro-phenyl}-pyridine-2-carboxylic acid (pyridin-4-ylmethyl)-amide |
| 4189 | 5-{4-[5-(S)-(Acetylamino-methyl)-2-oxo-oxazolidin-3-yl]-2-fluoro-phenyl}-pyridine-2-carboxylic acid (thiazol-2-ylmethyl)-amide |
| 4190 | 4'-[5-(S)-(Acetylamino-methyl)-2-oxo-oxazolidin-3-yl]-3,2'-difluoro-biphenyl-4-carboxylic acid (pyridin-2-ylmethyl)-amide |
| 4191 | 4'-[5-(S)-(Acetylamino-methyl)-2-oxo-oxazolidin-3-yl]-3,2'-difluoro-biphenyl-4-carboxylic acid [2-(3H-imidazol-4-yl)-ethyl]-amide |

TABLE 2-continued

| Compound Number | Structure |
|---|---|
| 4192 | N-{3-[2-Fluoro-4'-(pyridin-2-ylmethoxymethyl)-biphenyl-4-yl]-2-oxo-oxazolidin-5-(S)-ylmethyl}-acetamide |
| 4193 | N-{4'-[5-(S)-(Acetylamino-methyl)-2-oxo-oxazolidin-3-yl]-2'-fluoro-biphenyl-4-ylmethyl}-3-(1-methyl-6-oxo-1,6-dihydro-pyridin-3-yl)-acrylamide |
| 4194 | N-{4'-[5-(S)-(Acetylamino-methyl)-2-oxo-oxazolidin-3-yl]-2'-fluoro-biphenyl-4-ylmethyl}-3-(1-methyl-2-oxo-1,2-dihydro-pyridin-3-yl)-acrylamide |
| 4195 | N-(3-{3-Fluoro-4-[6-(pyridin-2-ylmethoxymethyl)-pyridin-3-yl]-phenyl}-2-oxo-oxazolidin-5-(S)-ylmethyl)-acetamide |

TABLE 2-continued

| Compound Number | Structure |
|---|---|
| 4196 | N-{3-[2-Fluoro-4'-(pyridin-4-ylmethoxymethyl)-biphenyl-4-yl]-2-oxo-oxazolidin-5-(S)-ylmethyl}-acetamide |
| 4197 | N-(3-{3-Fluoro-4-[5-(pyridin-2-ylmethoxymethyl)-pyridin-2-yl]-phenyl}-2-oxo-oxazolidin-5-(S)-ylmethyl)-acetamide |
| 4198 | N-{3-[2-Fluoro-4'-(1-oxy-pyridin-4-ylmethoxymethyl)-biphenyl-4-yl]-2-oxo-oxazolidin-5-(S)-ylmethyl}-acetamide |
| 4199 | N-[3-(2-Fluoro-4'-{1-(R)-hydroxy-2-[(oxazol-4-ylmethyl)-amino]-ethyl}-biphenyl-4-yl)-2-oxo-oxazolidin-5-(S)-ylmethyl]-acetamide |
| 4200 | N-[3-(2-Fluoro-4'-{2-hydroxy-1-(S)-[(oxazol-4-ylmethyl)-amino]-ethyl}-biphenyl-4-yl)-2-oxo-oxazolidin-5-(S)-ylmethyl]-acetamide |

TABLE 2-continued

| Compound Number | Structure |
|---|---|
| 4201 | N-[3-(2-Fluoro-4'-{1-(R)-hydroxy-2-[(pyridin-4-ylmethyl)-amino]-ethyl}-biphenyl-4-yl)-2-oxo-oxazolidin-5-(S)-ylmethyl]-acetamide |
| 4202 | N-[3-(2-Fluoro-4'-{2-hydroxy-1-(R)-[(pyridin-4-ylmethyl)-amino]-ethyl}-biphenyl-4-yl)-2-oxo-oxazolidin-5-(S)-ylmethyl]-acetamide |
| 4203 | N-[3-(2-Fluoro-4'-{[(pyrimidin-5-ylmethyl)-amino]-methyl}-biphenyl-4-yl)-2-oxo-oxazolidin-5-(S)-ylmethyl]-acetamide |
| 4204 | N-(3-{4'-[(Acetyl-[1,2,3]thiadiazol-4-ylmethyl-amino)-methyl]-2-fluoro-biphenyl-4-yl}-2-oxo-oxazolidin-5-(S)-ylmethyl)-acetamide |
| 4205 | 4'-[5-(S)-(Acetylamino-methyl)-2-oxo-oxazolidin-3-yl]-2'-fluoro-biphenyl-4-carboxylic acid (oxazol-4-ylmethyl)-amide |

TABLE 2-continued

| Compound Number | Structure |
|---|---|
| 4206 | N-[3-(2-Fluoro-4'-{[([1,2,4]thiadiazol-3-ylmethyl)-amino]-methyl}-biphenyl-4-yl)-2-oxo-oxazolidin-5-(S)-ylmethyl]-acetamide |
| 4207 | 2-(4-Chloro-benzylamino)-thiazole-4-carboxylic acid {4'-[5-(S)-(acetylamino-methyl)-2-oxo-oxazolidin-3-yl]-2'-fluoro-biphenyl-4-ylmethyl}-amide |
| 4208 | N-[3-(2-Fluoro-4'-{[(oxazol-5-ylmethyl)-amino]-methyl}-biphenyl-4-yl)-2-oxo-oxazolidin-5-(S)-ylmethyl]-acetamide |
| 4209 | N-[3-(4'-{[([1,3]Dioxolan-2-ylmethyl)-amino]-methyl}-2-fluoro-biphenyl-4-yl)-2-oxo-oxazolidin-5-(S)-ylmethyl]-acetamide |
| 4210 | N-(3-{2-Fluoro-4'-[(oxiranylmethyl-amino)-methyl]-biphenyl-4-yl}-2-oxo-oxazolidin-5-(S)-ylmethyl)-acetamide |

| Compound Number | Structure |
|---|---|
| 4211 | 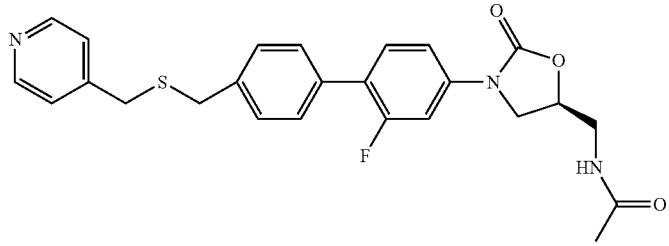 [SMILES: CC(=O)NC[C@H]1CN(c2ccc(-c3ccc(CSCc4ccncc4)cc3)c(F)c2)C(=O)O1]<br>N-{3-[2-Fluoro-4'-(pyridin-4-ylmethylsulfanylmethyl)-biphenyl-4-yl]-2-oxo-oxazolidin-5-(S)-ylmethyl}-acetamide |
| 4212 | 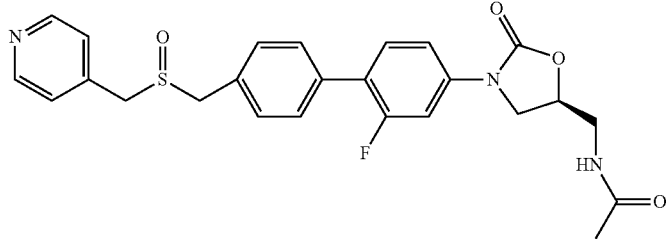 [SMILES: CC(=O)NC[C@H]1CN(c2ccc(-c3ccc(CS(=O)Cc4ccncc4)cc3)c(F)c2)C(=O)O1]<br>N-{3-[2-Fluoro-4'-(pyridin-4-ylmethanesulfinylmethyl)-biphenyl-4-yl]-2-oxo-oxazolidin-5-(S)-ylmethyl}-acetamide |
| 4213 | 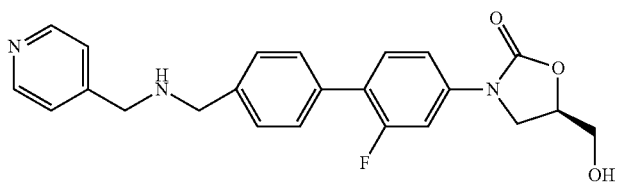 [SMILES: O=C1O[C@@H](CO)CN1c1ccc(-c2ccc(CNCc3ccncc3)cc2)c(F)c1]<br>3-(2-Fluoro-4'-{[(pyridin-4-ylmethyl)-amino]-methyl}-biphenyl-4-yl)-5-(R)-hydroxymethyl-oxazolidin-2-one |
| 4214 | 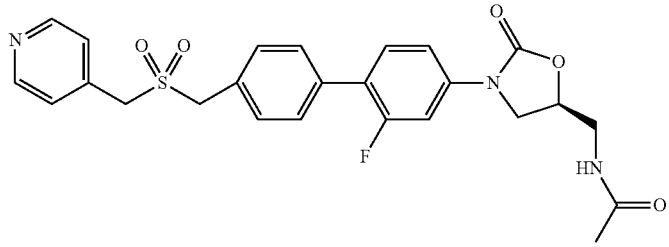 [SMILES: CC(=O)NC[C@H]1CN(c2ccc(-c3ccc(CS(=O)(=O)Cc4ccncc4)cc3)c(F)c2)C(=O)O1]<br>N-{3-[2-Fluoro-4'-(pyridin-4-ylmethanesulfonylmethyl)-biphenyl-4-yl]-2-oxo-oxazolidin-5-(S)-ylmethyl}-acetamide |

| Compound Number | Structure |
|---|---|
| 4215 | 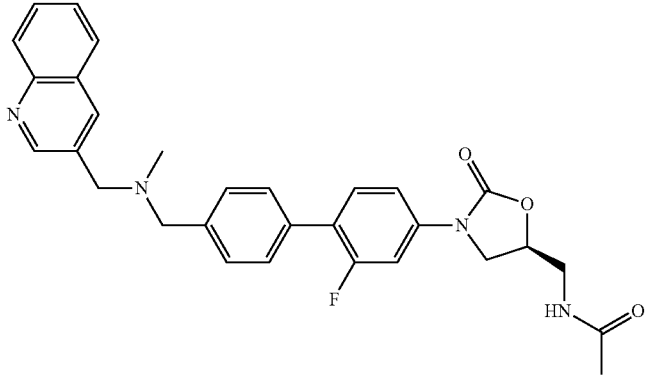 [SMILES: CC(=O)NC[C@H]1CN(c2ccc(-c3ccc(CN(C)Cc4cnc5ccccc5c4)cc3)c(F)c2)C(=O)O1]<br>N-(3-{2-Fluoro-4'-[(methyl-quinolin-3-ylmethyl-amino)-methyl]-biphenyl-4-yl}-2-oxo-oxazolidin-5-(S)-ylmethyl)-acetamide |
| 4216 | 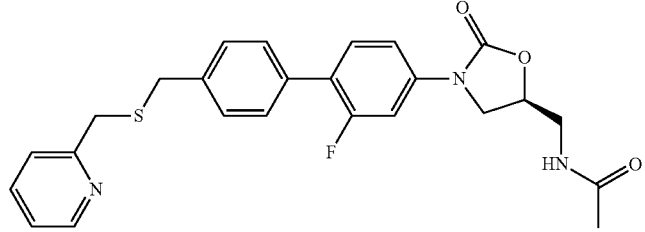 [SMILES: CC(=O)NC[C@H]1CN(c2ccc(-c3ccc(CSCc4ccccn4)cc3)c(F)c2)C(=O)O1]<br>N-{3-[2-Fluoro-4'-(pyridin-2-ylmethylsulfanylmethyl)-biphenyl-4-yl]-2-oxo-oxazolidin-5-(S)-ylmethyl}-acetamide |
| 4217 | 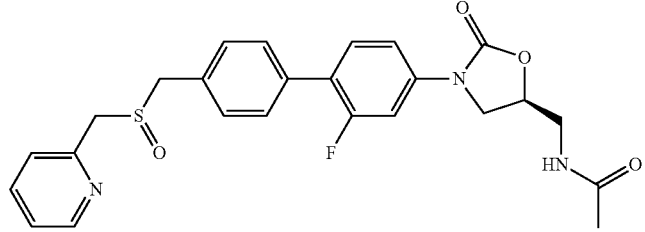 [SMILES: CC(=O)NC[C@H]1CN(c2ccc(-c3ccc(CS(=O)Cc4ccccn4)cc3)c(F)c2)C(=O)O1]<br>N-{3-[2-Fluoro-4'-(pyridin-2-ylmethanesulfinylmethyl)-biphenyl-4-yl]-2-oxo-oxazolidin-5-(S)-ylmethyl}-acetamide |
| 4218 | 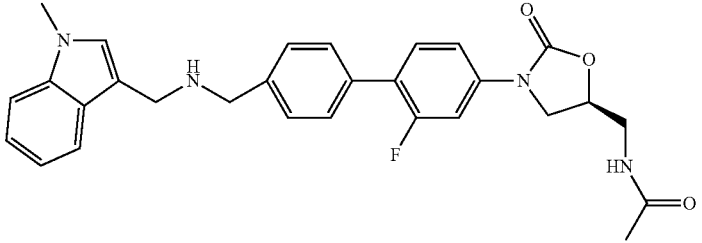 [SMILES: CC(=O)NC[C@H]1CN(c2ccc(-c3ccc(CNCc4cn(C)c5ccccc45)cc3)c(F)c2)C(=O)O1]<br>N-[3-(2-Fluoro-4'-{[(1-methyl-1H-indol-3-ylmethyl)-amino]-methyl}-biphenyl-4-yl)-2-oxo-oxazolidin-5-(S)-ylmethyl]-acetamide |

TABLE 2-continued

| Compound Number | Structure |
|---|---|
| 4219 | N-[3-(2-Fluoro-4'-{[(tetrahydro-furan-3-ylmethyl)-amino]-methyl}-biphenyl-4-yl)-2-oxo-oxazolidin-5-(S)-ylmethyl]-acetamide |
| 4220 | N-[3-(2-Fluoro-4'-{[(tetrahydro-furan-3-ylmethyl)-amino]-methyl}-biphenyl-4-yl)-2-oxo-oxazolidin-5-(S)-ylmethyl]-acetamide |
| 4221 | N-[3-(2-Fluoro-4'-{[(thiophen-2-ylmethyl)-amino]-methyl}-biphenyl-4-yl)-2-oxo-oxazolidin-5-(S)-ylmethyl]-acetamide |
| 4222 | N-{3-[2-Fluoro-4'-(N-furan-2-ylmethyl-carbamimidoyl)-biphenyl-4-yl]-2-oxo-oxazolidin-5-(S)-ylmethyl}-acetamide |
| 4223 | 5-{4-[5-(S)-(Acetylamino-methyl)-2-oxo-oxazolidin-3-yl]-2-fluoro-phenyl}-pyridine-2-carboxylic acid [2-(3H-imidazol-4-yl)-ethyl]-amide |

TABLE 2-continued

| Compound Number | Structure |
|---|---|
| 4224 | 4'-[5-(S)-(Acetylamino-methyl)-2-oxo-oxazolidin-3-yl]-2'-fluoro-biphenyl-4-carboxylic acid ([1,2,4]oxadiazol-3-ylmethyl)-amide |
| 4225 | 4'-[5-(S)-(Acetylamino-methyl)-2-oxo-oxazolidin-3-yl]-2'-fluoro-biphenyl-4-carboxylic acid ([1,2,4]thiadiazol-3-ylmethyl)-amide |
| 4226 | N-[3-(2-Fluoro-4'-oxiranylmethylsulfanylmethyl-biphenyl-4-yl)-2-oxo-oxazolidin-5-(S)-ylmethyl]-acetamide |
| 4227 | N-[3-(2-Fluoro-4'-{[2-(1H-imidazol-4-yl)-ethylamino]-methyl}-biphenyl-4-yl)-2-oxo-oxazolidin-5-(S)-ylmethyl]-acetamide |
| 4228 | N-[3-(2-Fluoro-4'-{[2-(5-methyl-3H-indol-3-yl)-ethylamino]-methyl}-biphenyl-4-yl)-2-oxo-oxazolidin-5-(S)-ylmethyl]-acetamide |

TABLE 2-continued

| Compound Number | Structure |
|---|---|
| 4229 | N-[3-(2-Fluoro-4'-{[(5-methyl-isoxazol-3-ylmethyl)-amino]-methyl}-biphenyl-4-yl)-2-oxo-oxazolidin-5-(S)-ylmethyl]-acetamide |
| 4230 | 3-(2-Fluoro-4'-{[(pyridin-4-ylmethyl)-amino]-methyl}-biphenyl-4-yl)-5-(R)-[1,2,4]triazol-1-ylmethyl-oxazolidin-2-one |
| 4231 | 3-(2-Fluoro-4'-{[(pyridin-4-ylmethyl)-amino]-methyl}-biphenyl-4-yl)-5-(R)-(1-methyl-1H-tetrazol-5-ylsulfanylmethyl)-oxazolidin-2-one |
| 4232 | N-[3-(2-Fluoro-4'-{1-(R/S)-[(pyridin-4-ylmethyl)-amino]-ethyl}-biphenyl-4-yl)-2-oxo-oxazolidin-5-(S)-ylmethyl]-acetamide |
| 4233 | N-[3-(2-Fluoro-4'-{[([1,2,4]oxadiazol-3-ylmethyl)-amino]-methyl}-biphenyl-4-yl)-2-oxo-oxazolidin-5-(S)-ylmethyl]-acetamide |

TABLE 2-continued

| Compound Number | Structure |
|---|---|
| 4234 | N-[3-(2-Fluoro-4'-{[(oxazol-4-ylmethyl)-amino]-methyl}-biphenyl-4-yl)-2-oxo-oxazolidin-5-(S)-ylmethyl]-acetamide |
| 4235 | N-{3-[3-Fluoro-4-(6-{[(oxazol-4-ylmethyl)-amino]-methyl}-pyridin-3-yl)-phenyl]-2-oxo-oxazolidin-5-(S)-ylmethyl}-acetamide |
| 4236 | N-(3-{2-Fluoro-4'-[N'-(pyridine-4-carbonyl)-hydrazinomethyl]-biphenyl-4-yl}-2-oxo-oxazolidin-5-(S)-ylmethyl)-acetamide |
| 4237 | N-(3-{2-Fluoro-4'-[N'-(pyridine-3-carbonyl)-hydrazinomethyl]-biphenyl-4-yl}-2-oxo-oxazolidin-5-(S)-ylmethyl)-acetamide |
| 4238 | N-[3-(2-Fluoro-4'-{[(oxazol-5-ylmethyl)-amino]-methyl}-biphenyl-4-yl)-2-oxo-oxazolidin-5-(S)-ylmethyl]-acetamide |

TABLE 2-continued

| Compound Number | Structure |
|---|---|
| 4239 | 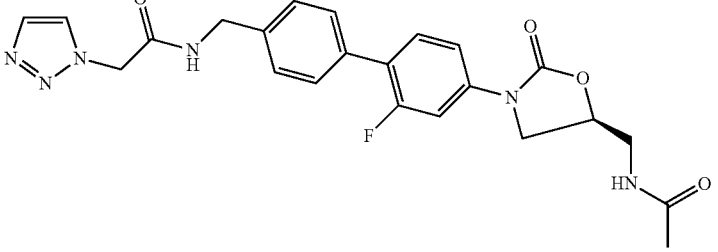<br>N-{4'-[5-(S)-(Acetylamino-methyl)-2-oxo-oxazolidin-3-yl]-2'-fluoro-biphenyl-4-ylmethyl}-2-[1,2,3]triazol-1-yl-acetamide |
| 4240 | 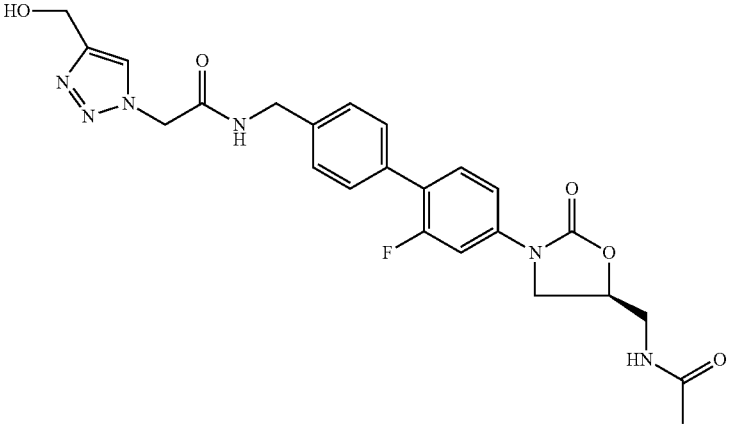 [SMILES: CC(=O)NC[C@H]1CN(c2ccc(-c3ccc(CNC(=O)Cn4cc(CO)nn4)cc3)c(F)c2)C(=O)O1]<br>N-{4'-[5-(S)-(Acetylamino-methyl)-2-oxo-oxazolidin-3-yl]-2'-fluoro-biphenyl-4-ylmethyl}-2-(4-hydroxymethyl-[1,2,3]triazol-1-yl)-acetamide |
| 4241 | 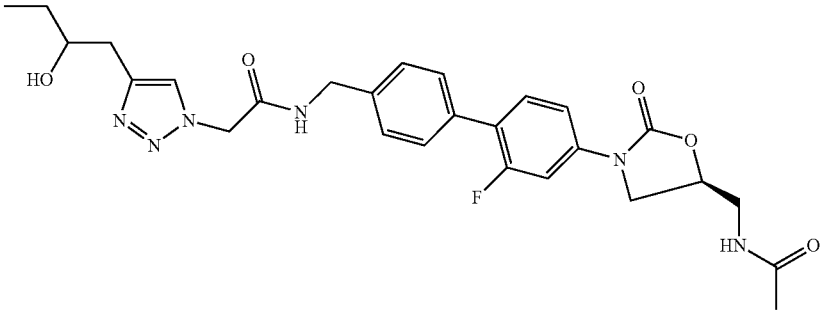 [SMILES: CCC(O)Cc1cn(CC(=O)NCc2ccc(-c3ccc(N4C[C@H](CNC(C)=O)OC4=O)cc3F)cc2)nn1]<br>N-{4'-[5-(S)-(Acetylamino-methyl)-2-oxo-oxazolidin-3-yl]-2'-fluoro-biphenyl-4-ylmethyl}-2-[4-(2-hydroxy-butyl)-[1,2,3]triazol-1-yl]-acetamide |
| 4242 | 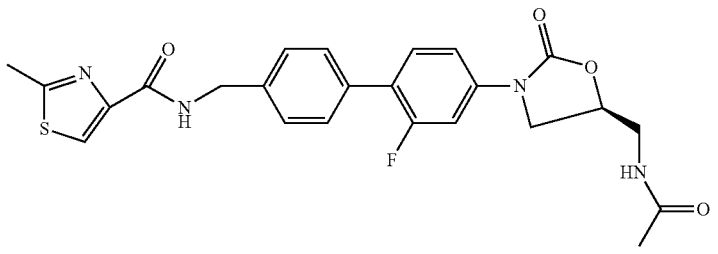 [SMILES: CC(=O)NC[C@H]1CN(c2ccc(-c3ccc(CNC(=O)c4csc(C)n4)cc3)c(F)c2)C(=O)O1]<br>2-Methyl-thiazole-4-carboxylic acid {4'-[5-(S)-(acetylamino-methyl)-2-oxo-oxazolidin-3-yl]-2'-fluoro-biphenyl-4-ylmethyl}-amide |

TABLE 2-continued

| Compound Number | Structure |
|---|---|
| 4243 | 2-Methyl-thiazole-4-carboxylic acid {4'-[5-(S)-(acetylamino-methyl)-2-oxo-oxazolidin-3-yl]-2'-fluoro-biphenyl-4-ylmethyl}-amide |
| 4244 | N-{3-[2-Fluoro-4'-([1,2,4]oxadiazol-3-ylmethylsulfanylmethyl)-biphenyl-4-yl]-2-oxo-oxazolidin-5-(S)-ylmethyl}-acetamide |
| 4245 | N-[3-(2-Fluoro-4'-{[(1-oxy-pyridin-4-ylmethyl)-amino]-methyl}-biphenyl-4-yl)-2-oxo-oxazolidin-5-(S)-ylmethyl]-acetamide |
| 4246 | N-{3-[4'-(2-Benzylamino-1-(S)-hydroxy-ethyl)-2-fluoro-biphenyl-4-yl]-2-oxo-oxazolidin-5-(S)-ylmethyl}-acetamide |
| 4247 | N-[3-(4'-{2-[Benzyl-(3-fluoro-propyl)-amino]-1-(S)-hydroxy-ethyl}-2-fluoro-biphenyl-4-yl)-2-oxo-oxazolidin-5-(S)-ylmethyl]-acetamide |

TABLE 2-continued

| Compound Number | Structure |
|---|---|
| 4248 | N-[3-(4'-{2-[Benzyl-(2-methylsulfanyl-ethyl)-amino]-1-(S)-hydroxy-ethyl}-2-fluoro-biphenyl-4-yl)-2-oxo-oxazolidin-5-(S)-ylmethyl]-acetamide |
| 4249 | N-[3-(4'-{2-[Benzyl-(3-chloro-3,3-difluoro-propyl)-amino]-1-(S)-hydroxy-ethyl}-2-fluoro-biphenyl-4-yl)-2-oxo-oxazolidin-5-(S)-ylmethyl]-acetamide |
| 4250 | N-(2-{4'-[5-(S)-(Acetylamino-methyl)-2-oxo-oxazolidin-3-yl]-2'-fluoro-biphenyl-4-yl}-2-(S)-hydroxy-ethyl)-N-benzyl-acetamide |
| 4251 | N-(3-{4'-[2-(Benzyl-methyl-amino)-1-(S)-hydroxy-ethyl]-2-fluoro-biphenyl-4-yl}-2-oxo-oxazolidin-5-(S)-ylmethyl)-acetamide |
| 4252 | N-{3-[3-Fluoro-4-(6-{[(isoxazol-4-ylmethyl)-amino]-methyl}-pyridin-3-yl)-phenyl]-2-oxo-oxazolidin-5-(S)-ylmethyl}-acetamide |

| Compound Number | Structure |
|---|---|
| 4253 | 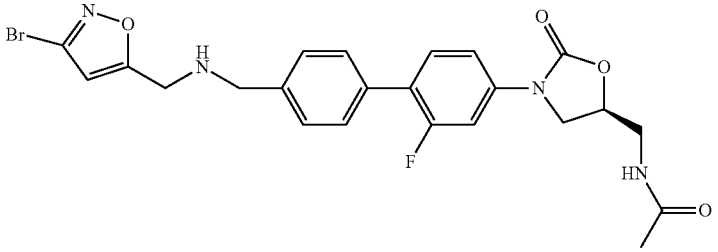 [SMILES: CC(=O)NC[C@H]1CN(c2ccc(-c3ccc(CNCc4cc(Br)no4)cc3)c(F)c2)C(=O)O1]<br>N-[3-(4'-{[(3-Bromo-isoxazol-5-ylmethyl)-amino]-methyl}-2-fluoro-biphenyl-4-yl)-2-oxo-oxazolidin-5-(S)-ylmethyl]-acetamide |
| 4254 | 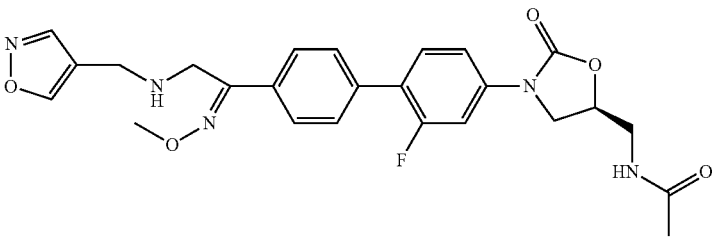 [SMILES: CO/N=C(\CNCc1cnoc1)c1ccc(-c2ccc(N3C[C@H](CNC(C)=O)OC3=O)cc2F)cc1]<br>N-[3-(2-Fluoro-4'-{2-[(isoxazol-4-ylmethyl)-amino]-1-methoxyimino-ethyl}-biphenyl-4-yl)-2-oxo-oxazolidin-5-(S)-ylmethyl]-acetamide |
| 4255 | 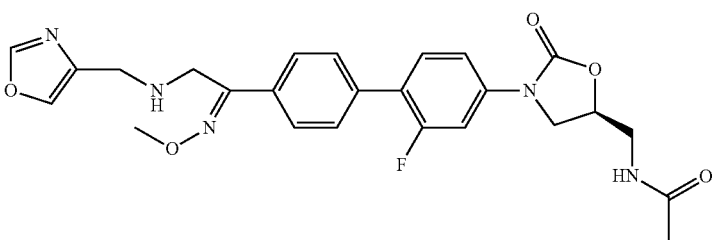 [SMILES: CO/N=C(\CNCc1cocn1)c1ccc(-c2ccc(N3C[C@H](CNC(C)=O)OC3=O)cc2F)cc1]<br>N-[3-(2-Fluoro-4'-{1-methoxyimino-2-[(oxazol-4-ylmethyl)-amino]-ethyl}-biphenyl-4-yl)-2-oxo-oxazolidin-5-(S)-ylmethyl]-acetamide |
| 4256 | 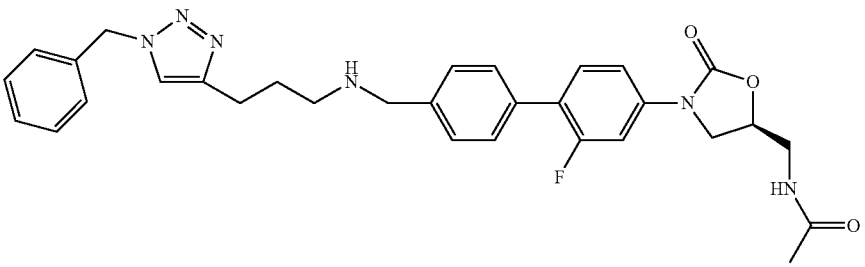 [SMILES: CC(=O)NC[C@H]1CN(c2ccc(-c3ccc(CNCCCc4cn(Cc5ccccc5)nn4)cc3)c(F)c2)C(=O)O1]<br>N-[3-(4'-{[3-(1-Benzyl-1H-[1,2,3]triazol-4-yl)-propylamino]-methyl}-2-fluoro-biphenyl-4-yl)-2-oxo-oxazolidin-5-(S)-ylmethyl]-acetamide |
| 4257 | 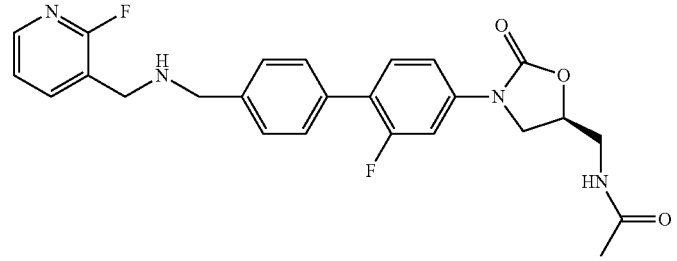 [SMILES: CC(=O)NC[C@H]1CN(c2ccc(-c3ccc(CNCc4cccnc4F)cc3)c(F)c2)C(=O)O1]<br>N-[3-(2-Fluoro-4'-{[(2-fluoro-pyridin-3-ylmethyl)-amino]-methyl}-biphenyl-4-yl)-2-oxo-oxazolidin-5-(S)-ylmethyl]-acetamide |

TABLE 2-continued

| Compound Number | Structure |
|---|---|
| 4258 | 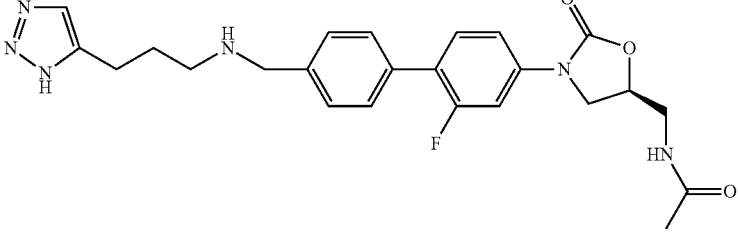<br>N-[3-(2-Fluoro-4'-{[3-(3H-[1,2,3]triazol-4-yl)-propylamino]-methyl}-biphenyl-4-yl)-2-oxo-oxazolidin-5-(S)-ylmethyl]-acetamide |
| 4259 | 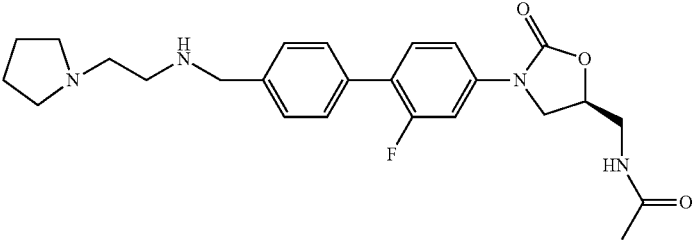 [SMILES: CC(=O)NC[C@H]1CN(c2ccc(-c3ccc(CNCCN4CCCC4)cc3)c(F)c2)C(=O)O1]<br>N-(3-{2-Fluoro-4'-[(2-pyrrolidin-1-yl-ethylamino)-methyl]-biphenyl-4-yl}-2-oxo-oxazolidin-5-(S)-ylmethyl)-acetamide |
| 4260 | 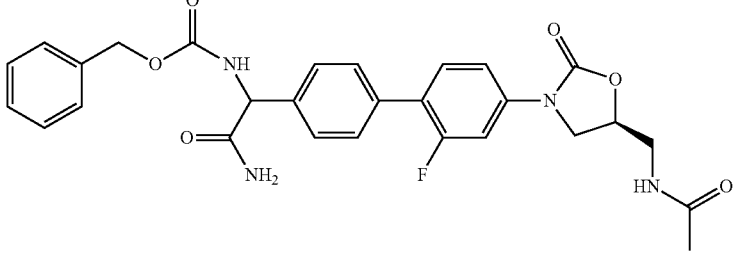<br>N-[3-(3-Fluoro-4-morpholin-4-yl-phenyl)-2-oxo-oxazolidin-5-(S)-ylmethyl]-3-(5-pyrimidin-2-yl-pyridin-2-yl)-propionamide |
| 4261 | 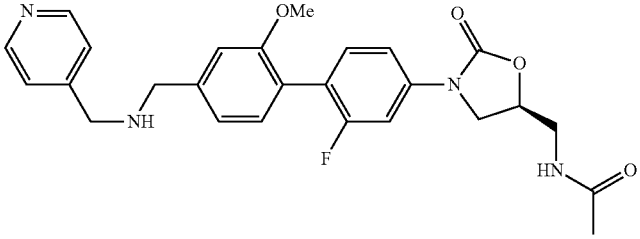 [SMILES: COc1cc(CNCc2ccncc2)ccc1-c1ccc(N2C[C@H](CNC(C)=O)OC2=O)cc1F]<br>N-[3-(2-Fluoro-2'-methoxy-4'-{[(pyridin-4-ylmethyl)-amino]-methyl}-biphenyl-4-yl)-2-oxo-oxazolidin-5-(S)-ylmethyl]-acetamide |
| 4262 | 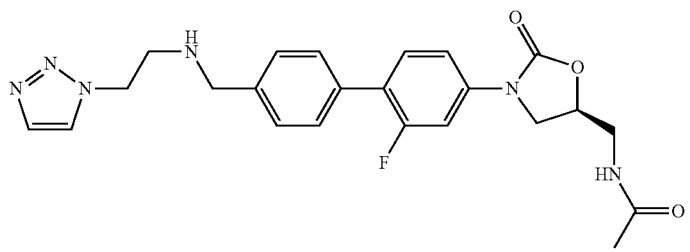 [SMILES: CC(=O)NC[C@H]1CN(c2ccc(-c3ccc(CNCCn4ccnn4)cc3)c(F)c2)C(=O)O1]<br>N-(3-{2-Fluoro-4'-[(2-[1,2,3]triazol-1-yl-ethylamino)-methyl]-biphenyl-4-yl}-2-oxo-oxazolidin-5-(S)-ylmethyl)-acetamide |

TABLE 2-continued

| Compound Number | Structure |
|---|---|
| 4263 | 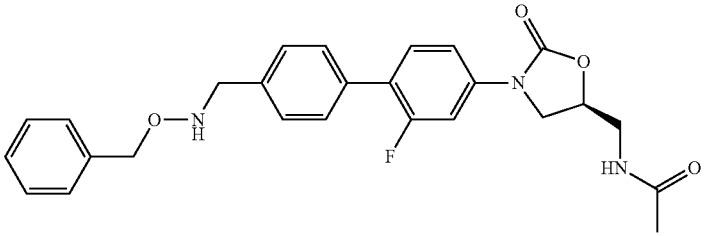 [SMILES: CC(=O)NC[C@H]1CN(c2ccc(-c3ccc(CNOCc4ccccc4)cc3)c(F)c2)C(=O)O1]
N-{3-[4'-(Benzyloxyamino-methyl)-2-fluoro-biphenyl-4-yl]-2-oxo-oxazolidin-5-(S)-ylmethyl}-acetamide |
| 4264 | 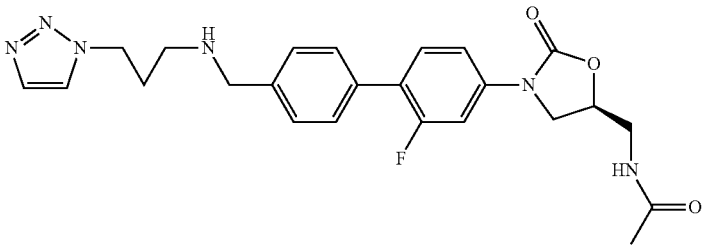 [SMILES: CC(=O)NC[C@H]1CN(c2ccc(-c3ccc(CNCCCn4ccnn4)cc3)c(F)c2)C(=O)O1]
N-(3-{2-Fluoro-4'-[(3-[1,2,3]triazol-1-yl-propylamino)-methyl]-biphenyl-4-yl}-2-oxo-oxazolidin-5-(S)-ylmethyl)-acetamide |
| 4265 | 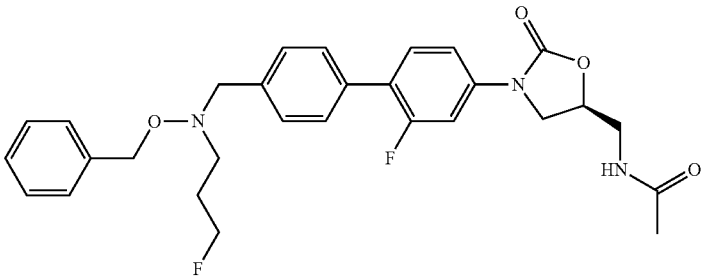 [SMILES: CC(=O)NC[C@H]1CN(c2ccc(-c3ccc(CN(CCCF)OCc4ccccc4)cc3)c(F)c2)C(=O)O1]
N-[3-(4'-{[Benzyloxy-(3-fluoro-propyl)-amino]-methyl}-2-fluoro-biphenyl-4-yl)-2-oxo-oxazolidin-5-(S)-ylmethyl]-acetamide |
| 4266 | 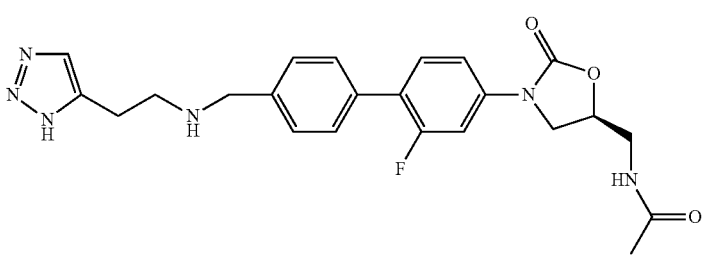 [SMILES: CC(=O)NC[C@H]1CN(c2ccc(-c3ccc(CNCCc4cnn[nH]4)cc3)c(F)c2)C(=O)O1]
N-[3-(2-Fluoro-4'-{[2-(3H-[1,2,3]triazol-4-yl)-ethylamino]-methyl}-biphenyl-4-yl)-2-oxo-oxazolidin-5-(S)-ylmethyl]-acetamide |
| 4267 | 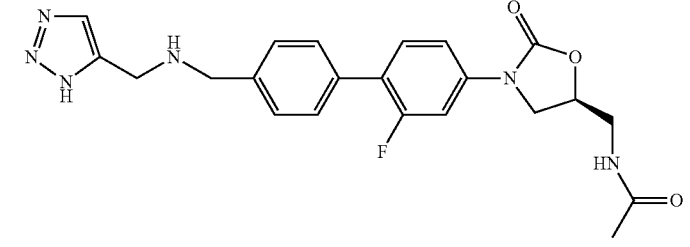 [SMILES: CC(=O)NC[C@H]1CN(c2ccc(-c3ccc(CNCc4cnn[nH]4)cc3)c(F)c2)C(=O)O1]
N-[3-(2-Fluoro-4'-{[(3H-[1,2,3]triazol-4-ylmethyl)-amino]-methyl}-biphenyl-4-yl)-2-oxo-oxazolidin-5-(S)-ylmethyl]-acetamide |

TABLE 2-continued

| Compound Number | Structure |
|---|---|
| 4268 | 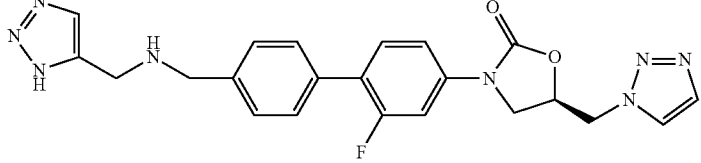<br>3-(2-Fluoro-4'-{[(3H-[1,2,3]triazol-4-ylmethyl)-amino]-methyl}-biphenyl-4-yl)-5-(R)-[1,2,3]triazol-1-ylmethyl-oxazolidin-2-one |
| 4269 | 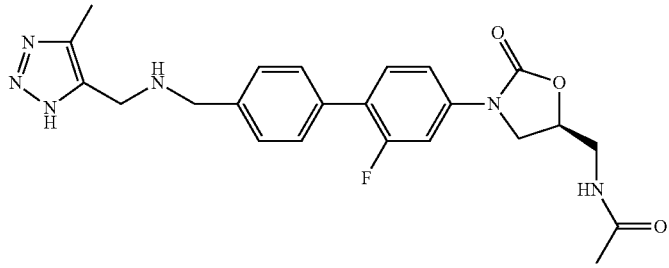 [SMILES: CC(=O)NC[C@H]1CN(c2ccc(-c3ccc(CNCc4[nH]nnc4C)cc3)c(F)c2)C(=O)O1]<br>N-[3-(2-Fluoro-4'-{[(5-methyl-3H-[1,2,3]triazol-4-ylmethyl)-amino]-methyl}-biphenyl-4-yl)-2-oxo-oxazolidin-5-(S)-ylmethyl]-acetamide |
| 4270 | 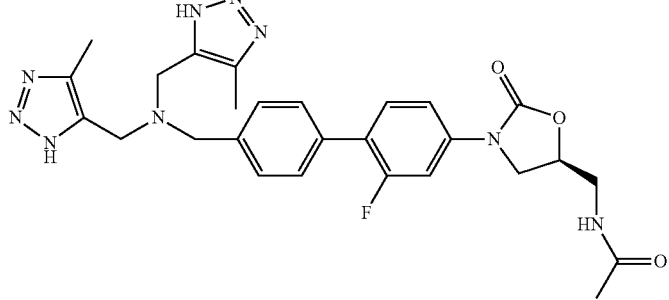<br>N-[3-(4'-{[Bis-(5-methyl-3H-[1,2,3]triazol-4-ylmethyl)-amino]-methyl}-2-fluoro-biphenyl-4-yl)-2-oxo-oxazolidin-5-(S)-ylmethyl]-acetamide |
| 4271 | 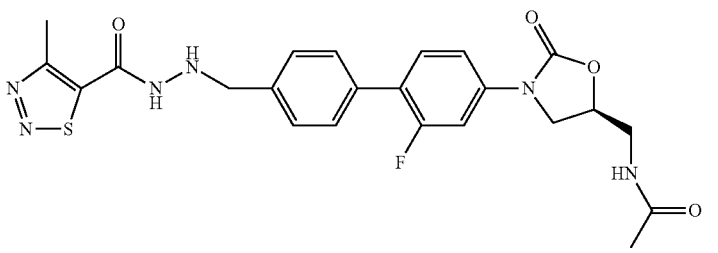 [SMILES: CC(=O)NC[C@H]1CN(c2ccc(-c3ccc(CNNC(=O)c4snnc4C)cc3)c(F)c2)C(=O)O1]<br>N-(3-{2-Fluoro-4'-[N'-(4-methyl-[1,2,3]thiadiazole-carbonyl)-hydrazinomethyl]-biphenyl-4-yl}-2-oxo-oxazolidin-5-(S)-ylmethyl)-acetamide |
| 4272 | 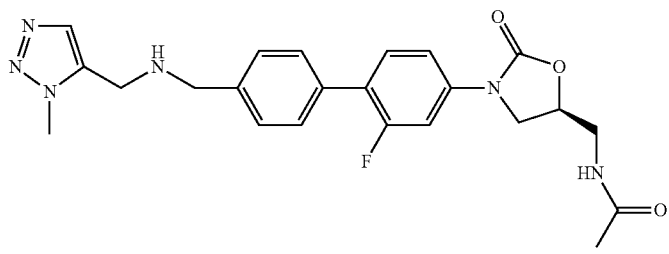 [SMILES: CC(=O)NC[C@H]1CN(c2ccc(-c3ccc(CNCc4cnnn4C)cc3)c(F)c2)C(=O)O1]<br>N-[3-(2-Fluoro-4'-{[(3-methyl-3H-[1,2,3]triazol-4-ylmethyl)-amino]-methyl}-biphenyl-4-yl)-2-oxo-oxazolidin-5-(S)-ylmethyl]-acetamide |

| Compound Number | Structure |
|---|---|
| 4273 | 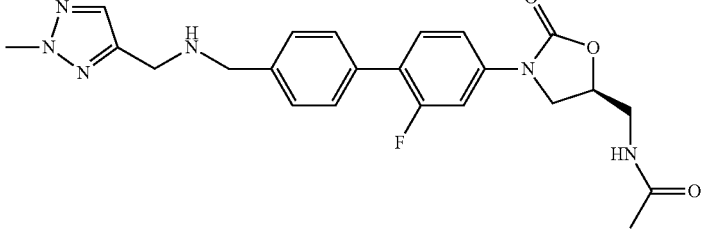<br>N-[3-(2-Fluoro-4'-{[(2-methyl-2H-[1,2,3]triazol-4-ylmethyl)-amino]-methyl}-biphenyl-4-yl)-2-oxo-oxazolidin-5-(S)-ylmethyl]-acetamide |
| 4274 | 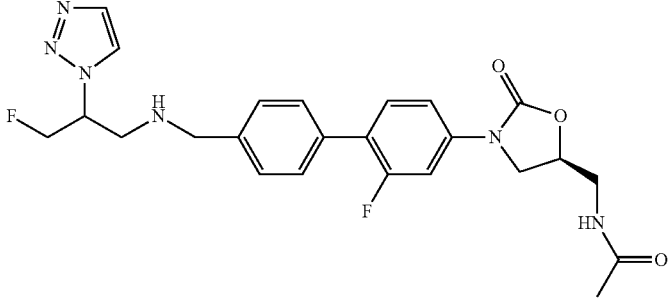 [SMILES: CC(=O)NC[C@H]1CN(c2ccc(-c3ccc(CNCC(CF)n4ccnn4)cc3)c(F)c2)C(=O)O1]<br>N-(3-{2-Fluoro-4'-[(3-fluoro-2-[1,2,3]triazol-1-yl-propylamino)-methyl]-biphenyl-4-yl}-2-oxo-oxazolidin-5-(S)-ylmethyl)-acetamide |
| 4275 | 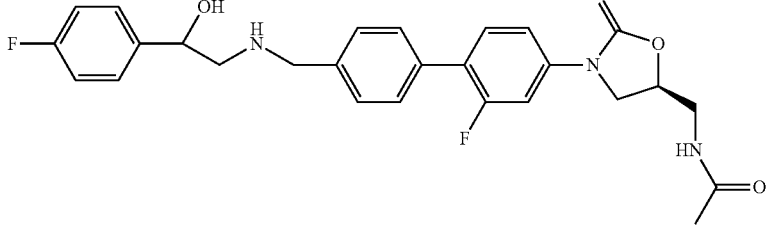<br>N-[3-(2-Fluoro-4'-{[2-(4-fluoro-phenyl)-2-(R/S)-hydroxy-ethylamino]-methyl}-biphenyl-4-yl)-2-oxo-oxazolidin-5-(S)-ylmethyl]-acetamide |
| 4276 | 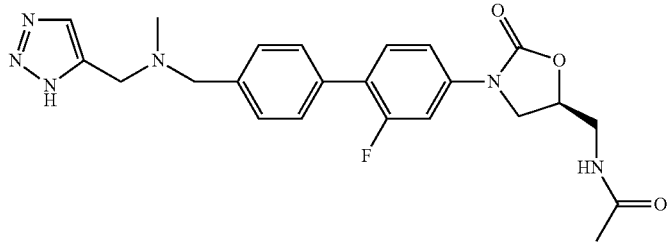<br>N-[3-(2-Fluoro-4'-{[methyl-(3H-[1,2,3]triazol-4-ylmethyl)-amino]-methyl}-biphenyl-4-yl)-2-oxo-oxazolidin-5-(S)-ylmethyl]-acetamide |
| 4277 | 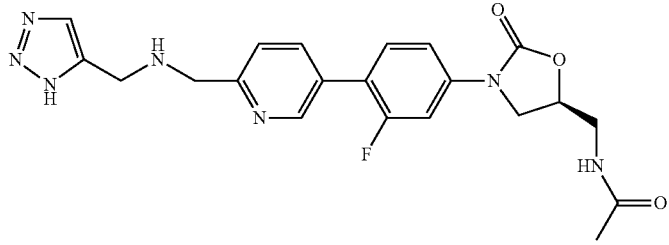 [SMILES: CC(=O)NC[C@H]1CN(c2ccc(-c3ccc(CNCc4cnn[nH]4)nc3)c(F)c2)C(=O)O1]<br>N-{3-[3-Fluoro-4-(6-{[(3H-[1,2,3]triazol-4-ylmethyl)-amino]-methyl}-pyridin-3-yl)-phenyl]-2-oxo-oxazolidin-5-(S)-ylmethyl}-acetamide |

TABLE 2-continued

| Compound Number | Structure |
|---|---|
| 4278 | N-[3-(2-Fluoro-4'-{[1-(R/S)-(3H-[1,2,3]triazol-4-yl)-ethylamino]-methyl}-biphenyl-4-yl)-2-oxo-oxazolidin-5-(S)-ylmethyl]-acetamide |
| 4279 | N-[3-(2-Fluoro-4'-{[(pyrrolidin-2-(R/S)-ylmethyl)-amino]-methyl}-biphenyl-4-yl)-2-oxo-oxazolidin-5-(S)-ylmethyl]-acetamide |
| 4280 | {4'-[5-(S)-(Acetylamino-methyl)-2-oxo-oxazolidin-3-yl]-2'-fluoro-biphenyl-4-ylmethyl}-(1-methyl-1H-tetrazol-5-ylmethyl)-carbamic acid tert-butyl ester |
| 4281 | {4'-[5-(S)-(Acetylamino-methyl)-2-oxo-oxazolidin-3-yl]-2'-fluoro-biphenyl-4-ylmethyl}-(2-methyl-2H-tetrazol-5-ylmethyl)-carbamic acid tert-butyl ester |

| Compound Number | Structure |
|---|---|
| 4282 | N-[3-(2-Fluoro-4'-{[(1H-tetrazol-5-ylmethyl)-amino]-methyl}-biphenyl-4-yl)-2-oxo-oxazolidin-5-(S)-ylmethyl]-acetamide |
| 4283 | N-[3-(2-Fluoro-4'-{[(1-methyl-1H-tetrazol-5-ylmethyl)-amino]-methyl}-biphenyl-4-yl)-2-oxo-oxazolidin-5-(S)-ylmethyl]-acetamide |
| 4284 | N-[3-(2-Fluoro-4'-{[(2-methyl-2H-tetrazol-5-ylmethyl)-amino]-methyl}-biphenyl-4-yl)-2-oxo-oxazolidin-5-(S)-ylmethyl]-acetamide |
| 4285 | N-[3-(2-Fluoro-4'-{[(N-hydroxy-pyridine-4-carboximidoyl)-amino]-methyl}-biphenyl-4-yl)-2-oxo-oxazolidin-5-(S)-ylmethyl]-acetamide |
| 4286 | N-[3-(4'-{2-[Benzyl-(2-methanesulfonyl-ethyl)-amino]-1-(S)-hydroxy-ethyl}-2-fluoro-biphenyl-4-yl)-2-oxo-oxazolidin-5-(S)-ylmethyl]-acetamide |

| Compound Number | Structure |
|---|---|
| 4287 | 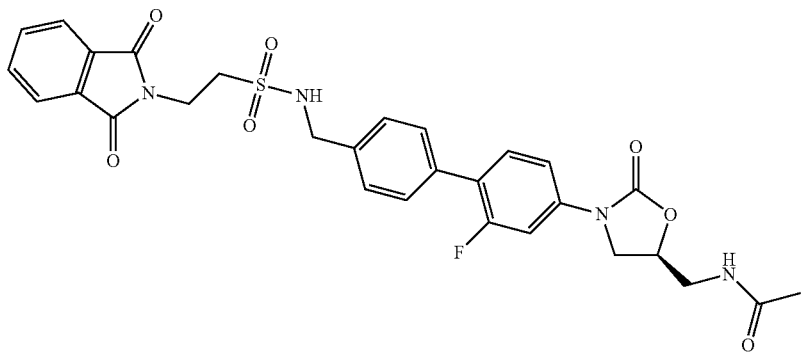 [SMILES: CC(=O)NC[C@H]1CN(c2ccc(-c3ccc(CNS(=O)(=O)CCN4C(=O)c5ccccc5C4=O)cc3)c(F)c2)C(=O)O1]<br>N-[3-(4'-{[2-(1,3-Dioxo-1,3-dihydro-isoindol-2-yl)-ethanesulfonylamino]-methyl}-2-fluoro-biphenyl-4-yl)-2-oxo-oxazolidin-5-(S)-ylmethyl]-acetamide |
| 4288 | 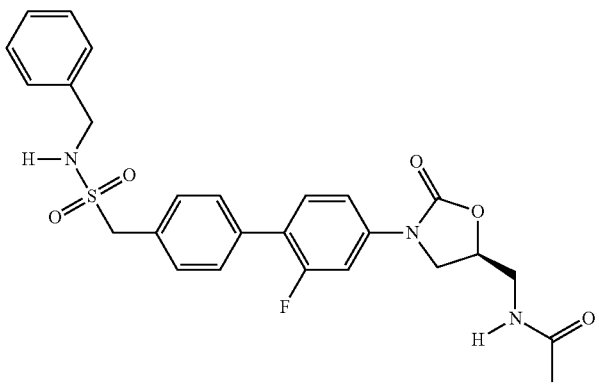 [SMILES: CC(=O)NC[C@H]1CN(c2ccc(-c3ccc(CS(=O)(=O)NCc4ccccc4)cc3)c(F)c2)C(=O)O1]<br>N-{3-[4'-(Benzylsulfamoyl-methyl)-2-fluoro-biphenyl-4-yl]-2-oxo-oxazolidin-5-(S)-ylmethyl}-acetamide |
| 4289 | 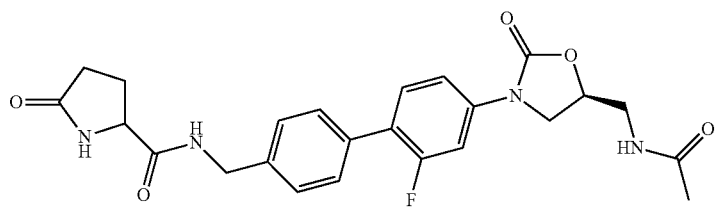 [SMILES: CC(=O)NC[C@H]1CN(c2ccc(-c3ccc(CNC(=O)C4CCC(=O)N4)cc3)c(F)c2)C(=O)O1]<br>5-Oxo-pyrrolidine-2-carboxylic acid {4'-[5-(S)-(acetylamino-methyl)-2-oxo-oxazolidin-3-yl]-2'-fluoro-biphenyl-4-ylmethyl}-amide |
| 4290 | 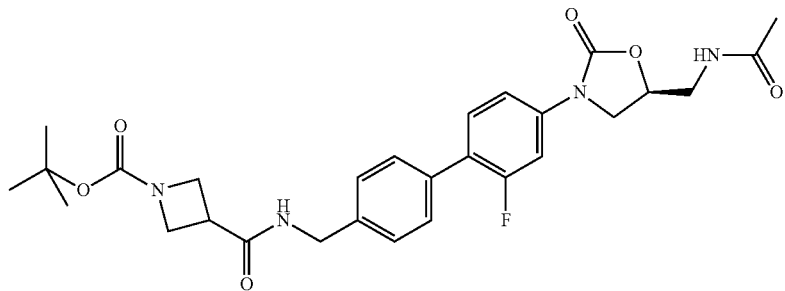 [SMILES: CC(=O)NC[C@H]1CN(c2ccc(-c3ccc(CNC(=O)C4CN(C(=O)OC(C)(C)C)C4)cc3)c(F)c2)C(=O)O1]<br>3-({4'-[5-(S)-(Acetylamino-methyl)-2-oxo-oxazolidin-3-yl]-2'-fluoro-biphenyl-4-ylmethyl}-carbamoyl)-azetidine-1-carboxylic acid tert-butyl ester |

TABLE 2-continued

| Compound Number | Structure |
|---|---|
| 4291 | Azetidine-3-carboxylic acid {4'-[5-(S)-(acetylamino-methyl)-2-oxo-oxazolidin-3-yl]-2'-fluoro-biphenyl-4-ylmethyl}-amide |
| 4292 | N-{4'-[5-(S)-(Acetylamino-methyl)-2-oxo-oxazolidin-3-yl]-2'-fluoro-biphenyl-4-ylmethyl}-2-(R)-amino-3-(3H-imidazol-4-yl)-propionamide |
| 4293 | 2-({4'-[5-(S)-(Acetylamino-methyl)-2-oxo-oxazolidin-3-yl]-2'-fluoro-biphenyl-4-ylmethyl}-amino)-2-pyridin-3-yl-acetamide |
| 4294 | N-{4'-[5-(S)-(Acetylamino-methyl)-2-oxo-oxazolidin-3-yl]-2'-fluoro-biphenyl-4-ylmethyl}-2-amino-2-pyridin-3-yl-acetamide |
| 4295 | 2-({4'-[5-(S)-(Acetylamino-methyl)-2-oxo-oxazolidin-3-yl]-2'-fluoro-biphenyl-4-ylmethyl}-carbamoyl)-azetidine-1-carboxylic acid tert-butyl ester |

TABLE 2-continued

| Compound Number | Structure |
|---|---|
| 4296 | 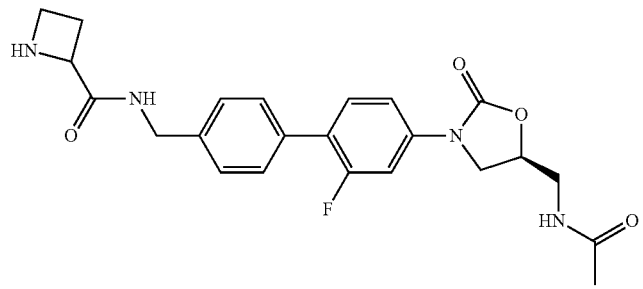 [SMILES: CC(=O)NC[C@H]1CN(c2ccc(-c3ccc(CNC(=O)C4CCN4)cc3)c(F)c2)C(=O)O1]<br>Azetidine-2-carboxylic acid {4'-[5-(S)-(acetylamino-methyl)-2-oxo-oxazolidin-3-yl]-2'-fluoro-biphenyl-4-ylmethyl}-amide |
| 4297 | 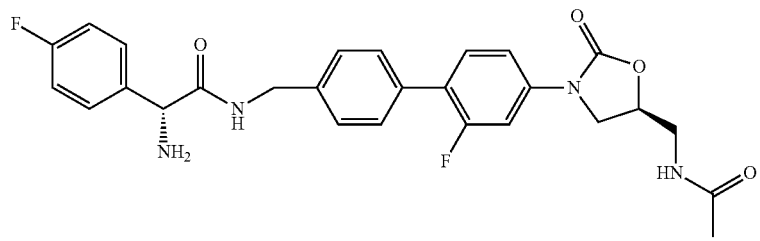 [SMILES: CC(=O)NC[C@H]1CN(c2ccc(-c3ccc(CNC(=O)[C@H](N)c4ccc(F)cc4)cc3)c(F)c2)C(=O)O1]<br>N-{4'-[5-(S)-(Acetylamino-methyl)-2-oxo-oxazolidin-3-yl]-2'-fluoro-biphenyl-4-ylmethyl}-2-(R)-amino-2-(4-fluoro-phenyl)-acetamide |
| 4298 | 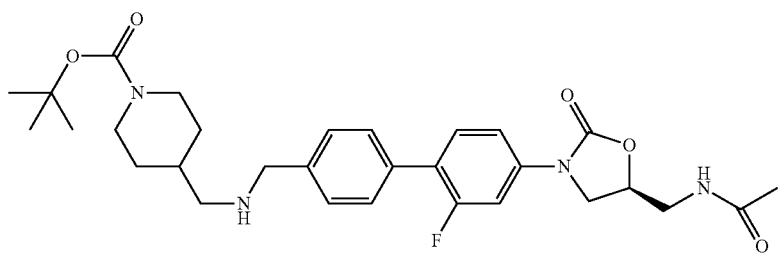 [SMILES: CC(=O)NC[C@H]1CN(c2ccc(-c3ccc(CNCC4CCN(C(=O)OC(C)(C)C)CC4)cc3)c(F)c2)C(=O)O1]<br>4-[({4'-[5-(S)-(Acetylamino-methyl)-2-oxo-oxazolidin-3-yl]-2'-fluoro-biphenyl-4-ylmethyl}-amino)-methyl]-piperidine-1-carboxylic acid tert-butylester |
| 4299 | 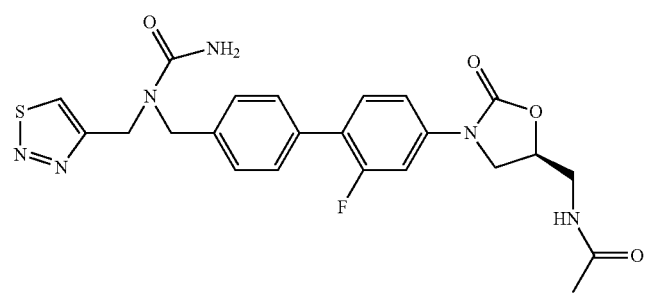 [SMILES: CC(=O)NC[C@H]1CN(c2ccc(-c3ccc(CN(Cc4csnn4)C(N)=O)cc3)c(F)c2)C(=O)O1]<br>N-{3-[2-Fluoro-4'-(1-[1,2,3]thiadiazol-4-ylmethyl-ureidomethyl)-biphenyl-4-yl]-2-oxo-oxazolidin-5-(S)-ylmethyl}-acetamide |

TABLE 2-continued

| Compound Number | Structure |
|---|---|
| 4300 | N-(3-{4'-[(Cyclopropylmethyl-amino)-methyl]-2-fluoro-biphenyl-4-yl}-2-oxo-oxazolidin-5-(S)-ylmethyl)-acetamide |
| 4301 | 4-(R)-Hydroxy-pyrrolidine-2-(S)-carboxylicacid {4'-[5-(S)-(acetylamino-methyl)-2-oxo-oxazolidin-3-yl]-2'-fluoro-biphenyl-4-ylmethyl}-amide |
| 4302 | N-{4'-[5-(S)-(Acetylamino-methyl)-2-oxo-oxazolidin-3-yl]-2'-fluoro-biphenyl-4-ylmethyl}-2-(S)-amino-3-pyridin-2-yl-propionamide |
| 4303 | [1-(S)-({4'-[5-(S)-(Acetylamino-methyl)-2-oxo-oxazolidin-3-yl]-2'-fluoro-biphenyl-4-ylmethyl}-carbamoyl)-2-pyridin-2-yl-ethyl]-carbamic acid tert-butyl ester |

TABLE 2-continued

| Compound Number | Structure |
|---|---|
| 4304 | [1-({4'-[5-(S)-(Acetylamino-methyl)-2-oxo-oxazolidin-3-yl]-2'-fluoro-biphenyl-4-ylmethyl}-carbamoyl)-cyclopropyl]-carbamic acid tert-butyl ester |
| 4305 | 2-({4'-[5-(S)-(Acetylamino-methyl)-2-oxo-oxazolidin-3-yl]-2'-fluoro-biphenyl-4-ylmethyl}-carbamoyl)-2,5-dihydro-pyrrole-1-(S)-carboxylic acid tert-butylester |
| 4306 | 2,5-Dihydro-1H-pyrrole-2-(S)-carboxylic acid {4'-[5-(S)-(acetylamino-methyl)-2-oxo-oxazolidin-3-yl]-2'-fluoro-biphenyl-4-ylmethyl}-amide |
| 4307 | N-{4'-[5-(S)-(Acetylamino-methyl)-2-oxo-oxazolidin-3-yl]-2'-fluoro-biphenyl-4-ylmethyl}-2-(R)-amino-3-(1H-indol-3-yl)-propionamide |

TABLE 2-continued

| Compound Number | Structure |
|---|---|
| 4308 | 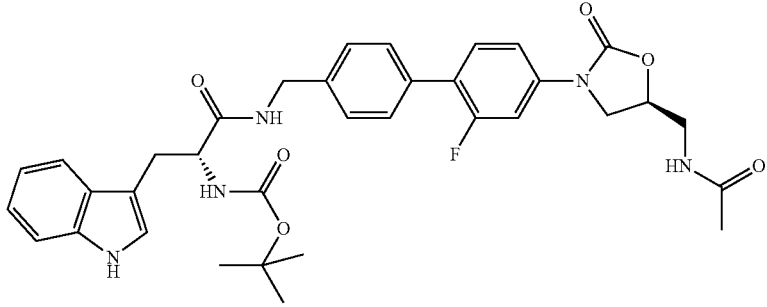 [SMILES: CC(=O)NC[C@H]1CN(c2ccc(-c3ccc(CNC(=O)[C@@H](Cc4c[nH]c5ccccc45)NC(=O)OC(C)(C)C)cc3)c(F)c2)C(=O)O1]<br>[1-(R)-({4'-[5-(S)-(Acetylamino-methyl)-2-oxo-oxazolidin-3-yl]-2'-fluoro-biphenyl-4-ylmethyl}-carbamoyl)-2-(1H-indol-3-yl)-ethyl]-carbamic acid tert-butyl ester |
| 4309 | 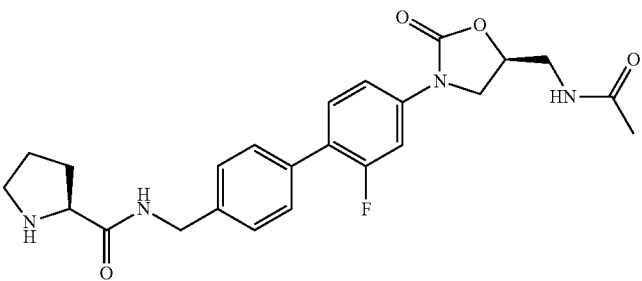 [SMILES: CC(=O)NC[C@H]1CN(c2ccc(-c3ccc(CNC(=O)[C@@H]4CCCN4)cc3)c(F)c2)C(=O)O1]<br>Pyrrolidine-2-(S)-carboxylic acid {4'-[5-(S)-(acetylamino-methyl)-2-oxo-oxazolidin-3-yl]-2'-fluoro-biphenyl-4-ylmethyl}-amide |
| 4310 | 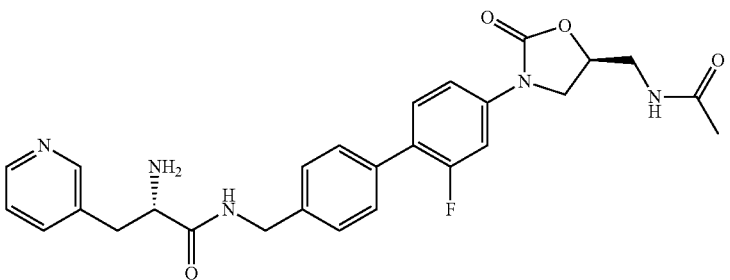 [SMILES: CC(=O)NC[C@H]1CN(c2ccc(-c3ccc(CNC(=O)[C@@H](N)Cc4cccnc4)cc3)c(F)c2)C(=O)O1]<br>N-{4'-[5-(S)-(Acetylamino-methyl)-2-oxo-oxazolidin-3-yl]-2'-fluoro-biphenyl-4-ylmethyl}-2-(R)-amino-3-pyridin-3-yl-propionamide |
| 4311 | 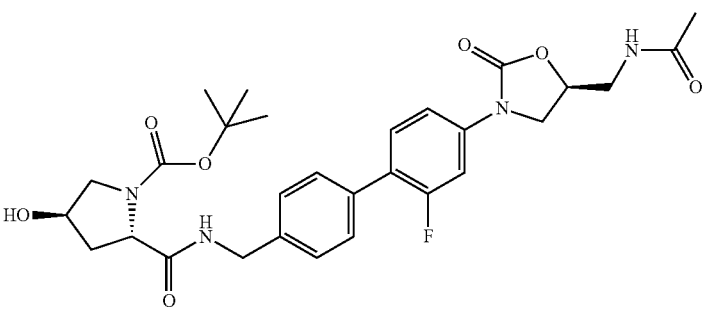 [SMILES: CC(=O)NC[C@H]1CN(c2ccc(-c3ccc(CNC(=O)[C@@H]4C[C@@H](O)CN4C(=O)OC(C)(C)C)cc3)c(F)c2)C(=O)O1]<br>2-({4'-[5-(S)-(Acetylamino-methyl)-2-oxo-oxazolidin-3-yl]-2'-fluoro-biphenyl-4-ylmethyl}-carbamoyl)-4-(R)-hydroxy-pyrrolidine-1-(S)-carboxylic acid tert-butyl ester |

TABLE 2-continued

| Compound Number | Structure |
|---|---|
| 4312 | 2-({4'-[5-(S)-(Acetylamino-methyl)-2-oxo-oxazolidin-3-yl]-2'-fluoro-biphenyl-4-ylmethyl}-amino)-3-(S)-(1H-indol-3-yl)-propionamide |
| 4313 | 2-({4'-[5-(S)-(Acetylamino-methyl)-2-oxo-oxazolidin-3-yl]-2'-fluoro-biphenyl-4-ylmethyl}-amino)-3-(1H-imidazol-4-yl)-propionamide |
| 4314 | N-(3-{2-Fluoro-4'-[(2-oxo-2-piperazin-1-yl-ethylamino)-methyl]-biphenyl-4-yl}-2-oxo-oxazolidin-5-(S)-ylmethyl)-acetamide |
| 4315 | 4-[2-({4'-[5-(S)-(Acetylamino-methyl)-2-oxo-oxazolidin-3-yl]-2'-fluoro-biphenyl-4-ylmethyl}-amino)-acetyl]-piperazine-1-carboxylic acid tert-butyl ester |
| 4316 | N-(3-{2-Fluoro-4'-[(2-morpholin-4-yl-2-oxo-ethylamino)-methyl]-biphenyl-4-yl}-2-oxo-oxazolidin-5-(S)-ylmethyl)-acetamide |

| Compound Number | Structure |
|---|---|
| 4317 | 3-[({4'-[5-(S)-(Acetylamino-methyl)-2-oxo-oxazolidin-3-yl]-2'-fluoro-biphenyl-4-ylmethyl}-amino)-methyl]-pyrrolidine-1-carboxylic acid tert-butyl ester |
| 4318 | N-(3-{2-Fluoro-4'-[(2-morpholin-4-yl-ethylamino)-methyl]-biphenyl-4-yl}-2-oxo-oxazolidin-5-(S)-ylmethyl)-acetamide |
| 4319 | Cyclopropanecarboxylic acid {4'-[5-(S)-(acetylamino-methyl)-2-oxo-oxazolidin-3-yl]-2'-fluoro-biphenyl-4-ylmethyl}-amide |
| 4320 | N-(3-{2-Fluoro-4'-[(furan-3-ylmethyl-methyl-amino)-methyl]-2'-methoxy-biphenyl-4-yl}-2-oxo-oxazolidin-5-(S)-ylmethyl)-acetamide |

TABLE 2-continued

| Compound Number | Structure |
|---|---|
| 4321 | 1-Amino-cyclopropanecarboxylic acid {4'-[5-(S)-(acetylamino-methyl)-2-oxo-oxazolidin-3-yl]-2'-fluoro-biphenyl-4-ylmethyl}-amide |
| 4322 | Piperazine-2-(R/S)-carboxylic acid {4'-[5-(S)-(acetylamino-methyl)-2-oxo-oxazolidin-3-yl]-2'-fluoro-biphenyl-4-ylmethyl}-amide |
| 5001 | N-[3-(2-Fluoro-4'-{[2-(3H-[1,2,3]triazol-4-ylsulfanyl)-ethylamino]-methyl}-biphenyl-4-yl)-2-oxo-oxazolidin-5-(S)-ylmethyl]-acetamide |
| 5002 | N-[3-(2-Fluoro-4'-{[3-(3H-[1,2,3]triazol-4-ylsulfanyl)-propylamino]-methyl}-biphenyl-4-yl)-2-oxo-oxazolidin-5-(S)-ylmethyl]-acetamide |
| 5003 | N-[3-(2-Fluoro-4'-{[2-([1,3,4]thiadiazol-2-ylsulfanyl)-ethylamino]-methyl}-biphenyl-4-yl)-2-oxo-oxazolidin-5-(S)-ylmethyl]-acetamide |

TABLE 2-continued

| Compound Number | Structure |
|---|---|
| 5004 | N-[3-(2-Fluoro-4'-{[2-(pyridin-2-ylsulfanyl)-ethylamino]-methyl}-biphenyl-4-yl)-2-oxo-oxazolidin-5-(S)-ylmethyl]-acetamide |
| 5005 | N-[3-(2-Fluoro-4'-{[2-(4H-[1,2,4]triazol-3-ylsulfanyl)-ethylamino]-methyl}-biphenyl-4-yl)-2-oxo-oxazolidin-5-(S)-ylmethyl]-acetamide |
| 5006 | N-[3-(2-Fluoro-4'-{[2-(thiazol-2-ylsulfanyl)-ethylamino]-methyl}-biphenyl-4-yl)-2-oxo-oxazolidin-5-(S)-ylmethyl]-acetamide |
| 5007 | 3-(2-Fluoro-4'-{[2-(3H-[1,2,3]triazol-4-ylsulfanyl)-ethylamino]-methyl}-biphenyl-4-yl)-5-(R)-[1,2,3]triazol-1-ylmethyl-oxazolidin-2-one |
| 5008 | N-[3-(2-Fluoro-4'-{[2-(1H-imidazol-2-ylsulfanyl)-ethylamino]-methyl}-biphenyl-4-yl)-2-oxo-oxazolidin-5-(S)-ylmethyl]-acetamide |

TABLE 2-continued

| Compound Number | Structure |
|---|---|
| 5009 | 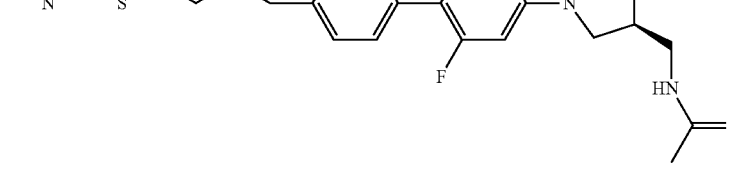<br>N-[3-(2-Fluoro-4'-{[2-(pyrimidin-2-ylsulfanyl)-ethylamino]-methyl}-biphenyl-4-yl)-2-oxo-oxazolidin-5-(S)-ylmethyl]-acetamide |
| 5010 | 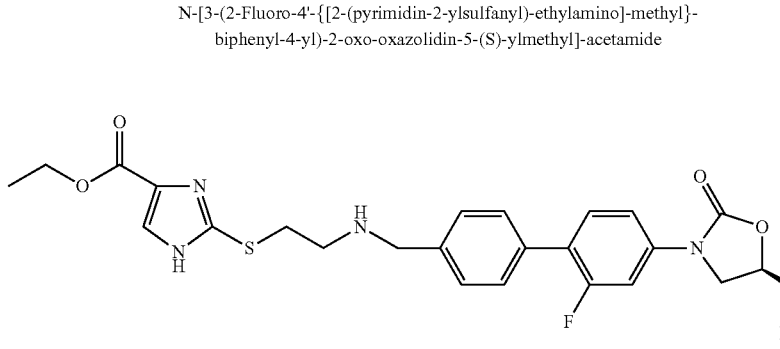<br>2-[2-({4'-[5-(S)-(Acetylamino-methyl)-2-oxo-oxazolidin-3-yl]-2'-fluoro-biphenyl-4-ylmethyl}-amino)-ethylsulfanyl]-1H-imidazole-4-carboxylic acid ethyl ester |
| 5011 | 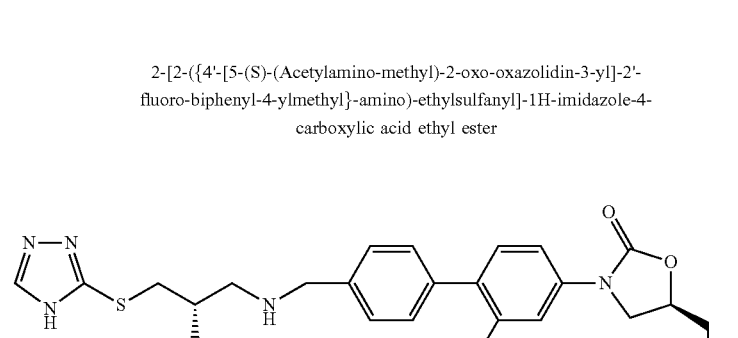<br>N-[3-(2-Fluoro-4'-{[2-(S)-(hydroxy-3-(4H-[1,2,4]triazol-3-ylsulfanyl)-propylamino]-methyl}-biphenyl-4-yl)-2-oxo-oxazolidin-5-(S)-ylmethyl]-acetamide |
| 5012 | 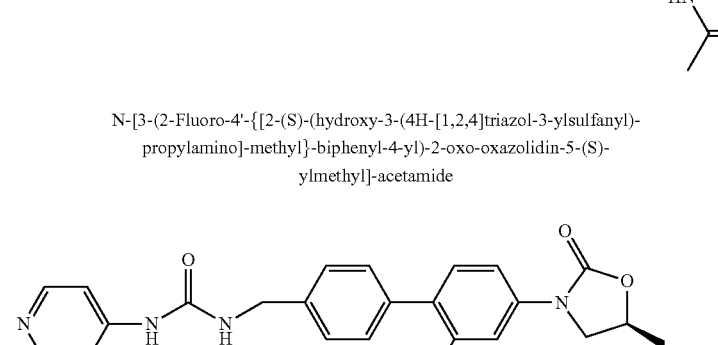<br>N-(3-{2-Fluoro-4'-[(3-pyridin-4-yl-ureido)-methyl]-biphenyl-4-yl}-2-oxo-oxazolidin-5-(S)-ylmethyl)-acetamide |

TABLE 2-continued

| Compound Number | Structure |
|---|---|
| 5013 | N-(3-{2-Fluoro-4'-[3-(3-fluoro-phenyl)-ureidomethyl]-biphenyl-4-yl}-2-oxo-oxazolidin-5-(S)-ylmethyl)-acetamide |
| 5014 | N-{4'-[5-(S)-(Acetylamino-methyl)-2-oxo-oxazolidin-3-yl]-2'-fluoro-biphenyl-4-ylmethyl}-2-(2,4-dichloro-phenoxy)-acetamide |
| 5015 | N-[3-(4'-{[3-(3-Chloro-5-trifluoromethyl-pyridin-2-ylamino)-propylamino]-methyl}-2-fluoro-biphenyl-4-yl)-2-oxo-oxazolidin-5-(S)-ylmethyl]-acetamide |

TABLE 2-continued

| Compound Number | Structure |
|---|---|
| 6001 | 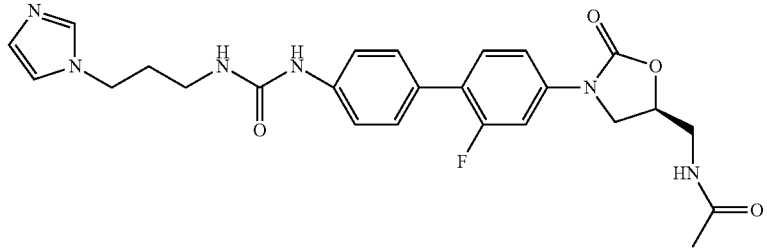 [SMILES: CC(=O)NC[C@H]1CN(c2ccc(-c3ccc(NC(=O)NCCCn4ccnc4)cc3)c(F)c2)C(=O)O1]<br>N-(3-{2-Fluoro-4'-[3-(3-imidazol-1-yl-propyl)-ureido]-biphenyl-4-yl}-2-oxo-oxazolidin-5-(S)-ylmethyl)-acetamide |
| 6002 | 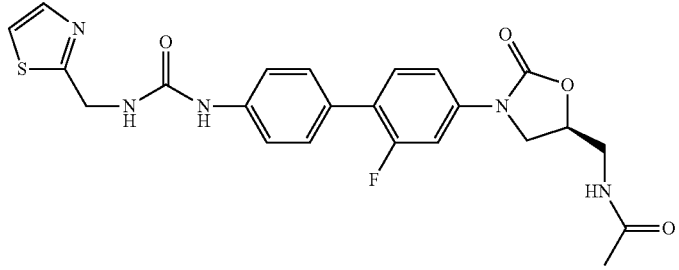 [SMILES: CC(=O)NC[C@H]1CN(c2ccc(-c3ccc(NC(=O)NCc4nccs4)cc3)c(F)c2)C(=O)O1]<br>N-{3-[2-Fluoro-4'-(3-thiazol-2-ylmethyl-ureido)-biphenyl-4-yl]-2-oxo-oxazolidin-5-(S)-ylmethyl}-acetamide |
| 6003 | 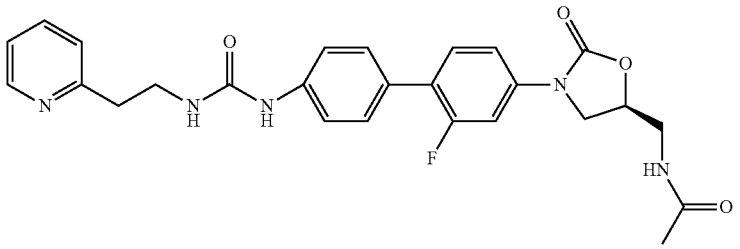 [SMILES: CC(=O)NC[C@H]1CN(c2ccc(-c3ccc(NC(=O)NCCc4ccccn4)cc3)c(F)c2)C(=O)O1]<br>N-(3-{2-Fluoro-4'-[3-(2-pyridin-2-yl-ethyl)-ureido]-biphenyl-4-yl}-2-oxo-oxazolidin-5-(S)-ylmethyl)-acetamide |
| 6004 | 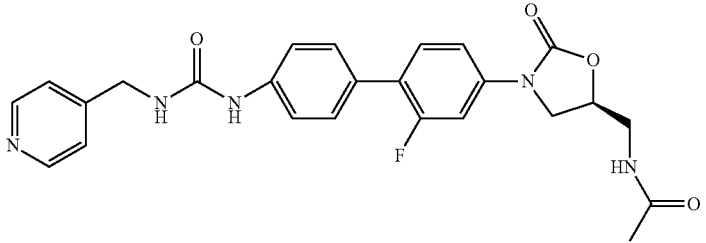 [SMILES: CC(=O)NC[C@H]1CN(c2ccc(-c3ccc(NC(=O)NCc4ccncc4)cc3)c(F)c2)C(=O)O1]<br>N-{3-[2-Fluoro-4'-(3-pyridin-4-ylmethyl-ureido)-biphenyl-4-yl]-2-oxo-oxazolidin-5-(S)-ylmethyl}-acetamide |
| 6005 | 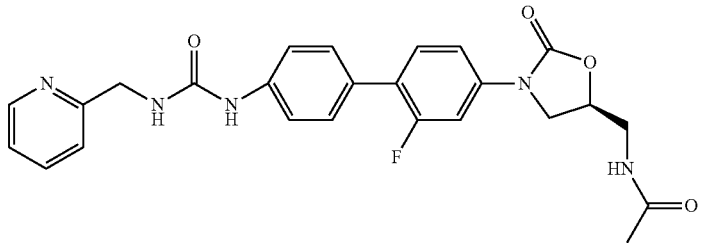 [SMILES: CC(=O)NC[C@H]1CN(c2ccc(-c3ccc(NC(=O)NCc4ccccn4)cc3)c(F)c2)C(=O)O1]<br>N-{3-[2-Fluoro-4'-(3-pyridin-2-ylmethyl-ureido)-biphenyl-4-yl]-2-oxo-oxazolidin-5-(S)-ylmethyl}-acetamide |

TABLE 2-continued

| Compound Number | Structure |
|---|---|
| 6006 | 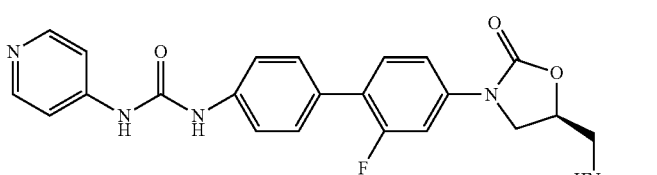 N-{3-[2-Fluoro-4'-(3-pyridin-4-yl-ureido)-biphenyl-4-yl]-2-oxo-oxazolidin-5-(S)-ylmethyl}-acetamide |

Nuclear magnetic resonance (NMR) spectra were obtained on a Bruker Avance 300 or Avance 500 spectrometer, or in some cases a GE-Nicolet 300 spectrometer. Common reaction solvents were either high performance liquid chromatography (HPLC) grade or American Chemical Society (ACS) grade, and anhydrous as obtained from the manufacturer unless otherwise noted. "Chromatography" or "purified by silica gel" refers to flash column chromatography using silica gel (EM Merck, Silica Gel 60, 230-400 mesh) unless otherwise noted.

Example 1

Synthesis of Biaryl Precursors

Scheme 1 depicts the synthesis of various biaryl intermediates useful in producing compounds of the present invention. Known iodoaryl oxazolidinone intermediate 50 (see U.S. Pat. Nos. 5,523,403 and 5,565,571) is coupled to a substituted aryl boronic acid (the Suzuki reaction) to produce biaryl alcohol 51. Mesylate 52, azide 53, and amine 54 are then synthesized using chemistry well known to those skilled in the art.

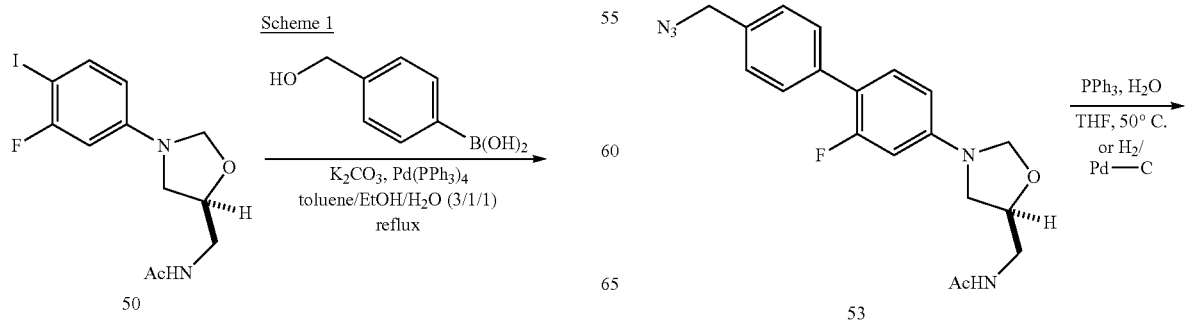

Scheme 1

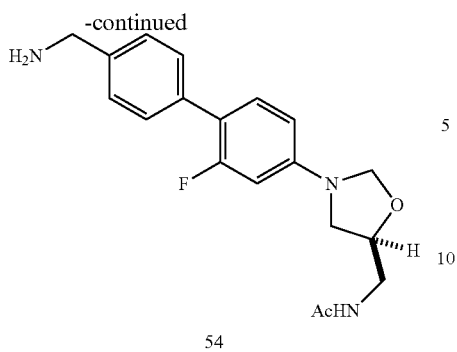

54

Synthesis of Alcohol 51

A suspension of N-[3-(3-fluoro-4-iodo-phenyl)-2-oxo-oxazolidin-5-ylmethyl]-acetamide 50 (14.0 g, 37 mmol) in toluene (120 mL) was treated with 4-(hydroxymethyl) phenylboronic acid (7.87 g, 51.8 mmol, 1.4 equiv), potassium carbonate ($K_2CO_3$, 15.32 g, 111 mmol, 3.0 equiv), ethanol (EtOH, 40 mL), and $H_2O$ (40 mL) at 25° C., and the resulting mixture was degassed three times under a steady stream of argon at 25° C. Tetrakis(triphenylphosphine)palladium ($Pd(PPh_3)_4$, 2.14 g, 1.85 mmol, 0.05 equiv) was subsequently added to the reaction mixture, and the resulting reaction mixture was degassed three times again before being warmed to gentle reflux for 6 h. When thin layer chromatography (TLC) and HPLC showed the coupling reaction was complete, the reaction mixture was cooled to room temperature before being treated with $H_2O$ (240 mL). The resulting mixture was then stirred at room temperature for 10 min before being cooled to 0-5° C. for 1 h. The solid precipitates were collected by filtration, washed with $H_2O$ (2×100 mL) and 20% ethyl acetate (EtOAc)/hexane (2×50 mL), and dried in vacuo. The crude desired N-[3-(2-Fluoro-4'-hydroxymethyl-biphenyl-4-yl)-2-oxo-oxazolidin-5-ylmethyl]-acetamide 51 (12.50 g, 94% yield) was obtained as off-white solids. This material was found to be essentially pure by HPLC and $^1$H NMR and was directly used in the subsequent reaction without further purification. $^1$H NMR (300 MHz, DMSO-$d_6$) δ 1.76 (s, 3H, COCH$_3$), 3.35 (t, 2H, J=5.4 Hz), 3.69 (dd, 1H, J=6.4, 9.2 Hz), 4.08 (t, 1H, J=9.1 Hz), 4.46 (d, 2H, J=5.7 Hz, CH$_2$OH), 4.68 (m, 1H), 5.16 (t, 1H, J=5.7 Hz, OH), 7.25-7.52 (m, 7H, aromatic-H), 8.18 (t, 1H, J=5.8 Hz, NHCOCH$_3$). LCMS (ESI) m/e 359 (M+H)$^+$.

Synthesis of Mesylate 52

A suspension of 51 (12.49 g, 34.90 mmol) in methylene chloride ($CH_2Cl_2$, 150 mL) was treated with triethylamine ($Et_3N$, 7.07 g, 9.7 mL, 70 mmol, 2.0 equiv) at 25° C., and the resulting mixture was cooled to 0-5° C. before being treated dropwise with methanesulfonyl chloride (4.80 g, 3.24 mL, 41.9 mmol, 1.2 equiv) at 0-5° C. The resulting reaction mixture was subsequently stirred at 0-5° C. for 2 h. When TLC and HPLC showed the reaction was complete, the reaction mixture was treated with $H_2O$ (100 mL) at 0-5° C. The mixture was then concentrated in vacuo to remove most of the $CH_2Cl_2$, and the resulting slurry was treated with $H_2O$ (150 mL). The mixture was stirred at room temperature for 10 min before being cooled to 0-5° C. for 30 min. The solid precipitates were collected by filtration, washed with $H_2O$ (2×100 mL) and 20% EtOAc/hexane (2×50 mL), and dried in vacuo. The crude desired methanesulfonic acid 4'-[5-(acetylamino-methyl)-2-oxo-oxazolidin-3-yl]-2'-fluoro-biphenyl-4-ylmethyl ester 52 (11.84 g, 78% yield) was obtained as off-white solids, which by TLC and HPLC was found to be essentially pure and was directly used in the subsequent reaction without further purification. LCMS (ESI) m/e 437 (M+H)$^+$.

Synthesis of Azide 53

A solution of 52 (9.27 g, 21.26 mmol) in anhydrous N,N-dimethylformamide (DMF, 50 mL) was treated with sodium azide (NaN$_3$, 5.53 g, 85.04 mmol, 4.0 equiv) at 25° C., and the resulting reaction mixture was warmed to 70-80° C. for 4 h. When TLC and HPLC showed the reaction was complete, the reaction mixture was cooled to room temperature before being treated with $H_2O$ (150 mL). The resulting mixture was stirred at room temperature for 10 min before being cooled to 0-5° C. for 1 h. The solid precipitates were collected by filtration, washed with $H_2O$ (2×100 mL) and 20% EtOAc/hexane (2×50 mL), and dried in vacuo. The crude desired N-[3-(4'-azidomethyl-2-fluoro-biphenyl-4-yl)-2-oxo-oxazolidin-5-ylmethyl]-acetamide 53 (7.16 g, 88% yield) was obtained as off-white solids. The material was found to be essentially pure by TLC and HPLC and was directly used in the subsequent reaction without further purification. LCMS (ESI) m/e 384 (M+H)$^+$.

Synthesis of Amine 54

A solution of 53 (7.16 g, 18.69 mmol) in tetrahydrofuran (THF) (100 mL) was treated with triphenylphosphine (PPh$_3$, 5.88 g, 22.43 mmol, 1.2 equiv) and $H_2O$ (3.6 g, 3.6 mL, 0.2 mmol, 11.0 equiv) at 25° C., and the resulting reaction mixture was warmed to 50-55° C. for 12 h. When TLC and HPLC showed the reduction reaction was complete, the reaction mixture was cooled to room temperature before the solvents were removed in vacuo. The residue was directly purified by flash column chromatography (0-15% MeOH—$CH_2Cl_2$ gradient elution) to afford the desired N-[3-(4'-Aminomethyl-2-fluoro-biphenyl-4-yl)-2-oxo-oxazolidin-5-ylmethyl]-acetamide 54 (5.82 g, 87% yield) as off-white crystals, which were of sufficient purity to be directly used in subsequent reactions. $^1$H NMR (300 MHz, DMSO-$d_6$) δ 1.85 (s, 3H, COCH$_3$), 3.04 (br. s, 2H, NH$_2$), 3.44 (t, 2H, J=5.4 Hz), 3.78 (m, 3H), 4.18 (t, 1H, J=9.1 Hz), 4.77 (m, 1H), 7.25-7.60 (m, 7H, aromatic-H), 8.20 (t, 1H, J=5.8 Hz, NHCOCH$_3$). LCMS (ESI) m/e 359 (M+2H)$^{2+}$.

Example 2

Synthesis of Triazole 1001 and Imidazole 1002

Scheme 2 illustrates the synthesis of triazole 1001 and imidazole 1002. Aryl bromide 60 was converted to boronic acid 61 which was used in a Suzuki coupling with aryl iodide 50 to afford alcohol 63 after desilylation. The alcohol was converted to mesylate 64 and then to azide 65. The cycloaddition of azide 65 with trimethylsilylacetylene followed by desilylation afforded triazole 1001. Alkylation of mesylate 64 with imidazole yielded compound 1002.

Scheme 2

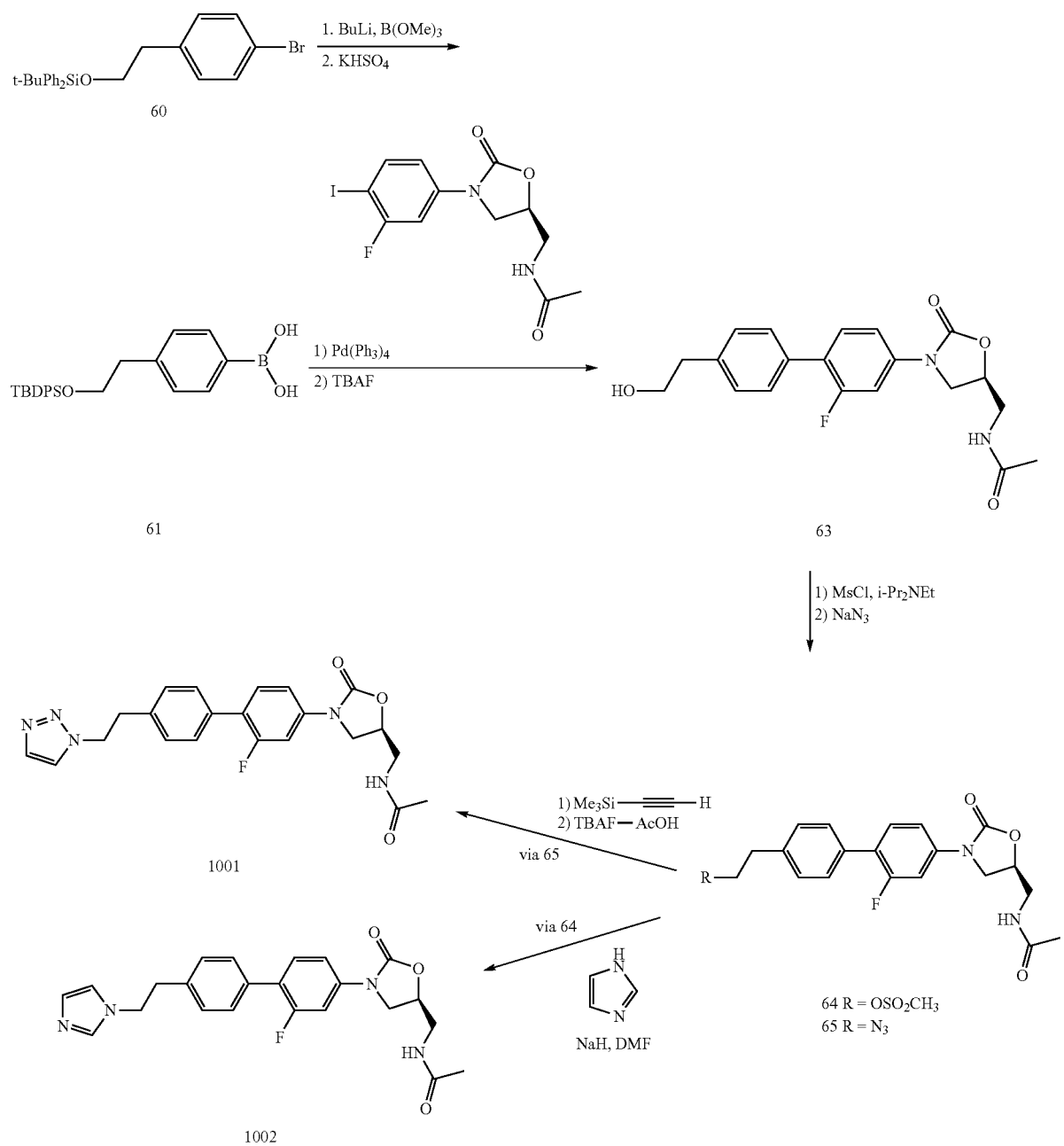

Synthesis of Bromide 60

To a solution of 4-bromophenethyl alcohol (5.60 g, 27.9 mmol), imidazole (3.80 g, 55.7 mmol) and a catalytic amount of 4-dimethylaminopyridine (DMAP) in DMF (55 mL) was added t-butyldiphenylchlorosilane (TBDPSCl, 7.20 mL, 27.9 mmol) at 0° C. and the mixture was stirred at ambient temperature for 72 h. The reaction was quenched with ice cold water (50 mL) and extracted with ether (4×50 mL). The combined ethereal layer was washed with water (4×100 mL), dried over anhydrous sodium sulfate ($Na_2SO_4$), concentrated and purified by flash chromatography (2% ethyl acetate in hexanes) to yield 10.6 g of 60.

Synthesis of Boronic Acid 61

To a solution of 60 (10.5 g, 24.0 mmol) in THF (50 mL) was added n-butyl lithium (n-BuLi, 2.5M in hexane, 11.5 mL, 28.8 mmol) at −78° C. and the mixture was stirred for 1 h before the addition of trimethyl borate (3.54 mL, 31.2 mmol). The solution was then stirred overnight at ambient temperature and quenched with 1M potassium hydrogen sulfate ($KHSO_4$, 25 mL). The resulting mixture was extracted with $CH_2Cl_2$ (3×50 mL), washed with brine (3×100 mL), dried (anhydrous $Na_2SO_4$), concentrated and purified by flash chromatography (25% ethyl acetate in hexanes) to yield 5 g of boronic acid 61 as mixture of acid and cyclic anhydrides.

Synthesis of Alcohol 63

To a mixture of boronic acid 61 (4.7 g, 11.7 mmol), known oxazolidinone 50 (4.00 g, 10.6 mmol; see U.S. Pat. Nos. 5,523,403 and 5,565,571), potassium carbonate ($K_2CO_3$, 4.40 g, 31.8 mmol) and $Pd(PPh_3)_4$ (0.613 g, 5 mol %) was added toluene (90 mL), ethanol (30 mL) and $H_2O$ (30 mL). The reaction mixture was refluxed overnight under argon atmosphere, concentrated and redissolved in $CH_2Cl_2$ (100 mL). The organic phase was washed with brine solution (2×100 mL), dried (anhydrous $Na_2SO_4$), concentrated and used for the next step without further purification. To a solution of this crude material in THF (70 mL) was added tetrabutylammonium fluoride (TBAF, 20 mL, 20 mmol) and the mixture was stirred overnight at ambient temperature. The reaction mixture was concentrated and washed with water (4×100 mL) to yield 3.5 g of 63. LCMS (ESI) m/z 373 (M+H).

Synthesis of Mesylate 64 and Azide 65

To a solution of 63 (1.0 g, 2.7 mmol) in $CH_2Cl_2$ (15 mL), DMF (4 mL) and N,N-diisopropylethylamine (Hunig's base, 0.75 mL, 4.05 mmol) was added methanesulfonyl chloride (0.32 mL, 2.7 mmol) at 0° C. After 2 h the reaction mixture was poured into $CH_2Cl_2$ (150 mL) and the organic layer was washed with water (3×100 mL), dried, concentrated to afford 64 as a solid. The crude solid 64 thus obtained was heated with $NaN_3$ (0.35 g, 5.4 mmol) at 90° C. overnight. The reaction mixture was poured into ethyl acetate (100 mL). The ethyl acetate layer was washed with water (3×50 mL), dried and concentrated to yield 1.1 g of pure azide 65. LCMS (ESI) m/z 398 (M+H).

Synthesis of Triazole 1001

A solution of azide 65 (100 mg, 0.252 mmol) and trimethylsilylacetylene (0.072 mL, 0.504 mmol) in DMF (3 mL) was heated at 90° C. until the azide was consumed. The reaction mixture was concentrated and treated with TBAF (1 mL, 1 mmol) and acetic acid (0.028 mL, 0.504 mmol) in THF (3 mL). The solution was stirred for 72 h and concentrated. The crude product was purified by flash chromatography using 4% methanol (MeOH) in $CH_2Cl_2$ to yield 85 mg of 1001. LCMS (ESI) m/z 424 (M+H).

Synthesis of Imidazole 1002

To a solution of imidazole (70 mg, 1.0 mmol) in DMF (5 mL) was added sodium hydride (NaH, 60%, 41 mg, 1 mmol) at 0° C. and the mixture was stirred for 30 minutes before the addition of mesylate 64 (114 mg, 0.250 mmol). The resulting solution was heated to 80° C. for 3 h, concentrated and purified by flash chromatography (5% MeOH in $CH_2Cl_2$). After trituration with ether, the residue afforded 40 mg of 1002. LCMS (ESI) m/z 423 (M+H).

Example 3

Synthesis of Piperazines 1003-1006

Scheme 3 illustrates the synthesis of compounds 1003-1006. Mesylate 52 served as alkylating agent for piperazine intermediates 68, 69 and 70 to afford compounds 1003, 1004 and 1006 respectively. Mesylate 67 was employed to alkylate piperazine intermediate 69 to provide compound 1005.

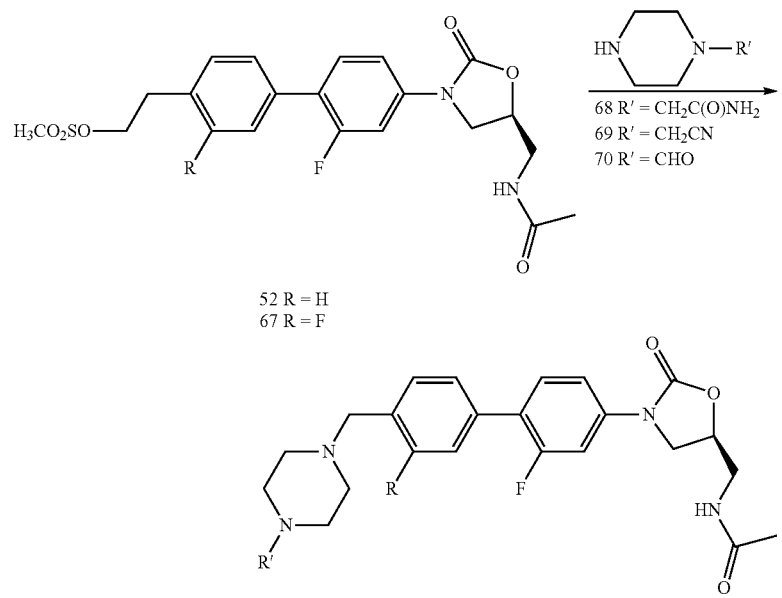

Scheme 3

Synthesis of Mesylate 67

Mesylate 67 was synthesized by coupling iodide 50 and 4-formyl-3-fluorophenylboronic acid following the procedure described above for the synthesis of N-[3-(2-fluoro-4'-hydroxymethyl-biphenyl-4-yl)-2-oxo-oxazolidin-5-ylmethyl]-acetamide (see Example 1). The biaryl aldehyde obtained (1.0 g, 2.67 mmol) was suspended in 40 mL methanol and the mixture was cooled to 0° C. Sodium borohydride (0.112 g, 2.943 mmol) was added, and the mixture was stirred for 50 min Water was added (20 mL), and after stirring another 20 min the mixture was partitioned between methylene chloride and brine. The aqueous phase was extracted twice with methylene chloride. The aqueous phase was acidified to pH 7, then extracted twice with methylene chloride. The combined organic phase was washed with brine, dried over $Na_2SO_4$, and concentrated. The crude material was azeotroped with toluene to afford the expected alcohol (900 mg).

The above alcohol (900 mg) was dissolved in methylene chloride (20 mL), DMF (13 mL) and Hunig's base (1.23 mL) and the mixture was cooled to 0° C. Methanesulfonyl chloride (557 uL, 7.20 mmol) was added and the mixture was stirred for 1.5 h at 0° C. LCMS indicated a mixture of desired mesylate and some of the corresponding benzyl chloride. The mixture was stirred for another 30 min and then concentrated. The residue was treated with 400 mL water, and the precipitate was filtered and washed with water. Drying under vacuum overnight yielded 750 mg crude mesylate 67 (as a mixture with some of the corresponding chloride).

Synthesis of Piperazine 68

A solution of tert-butyl-1-piperazine carboxylate (1 g, 5.4 mmol), bromoacetamide (820 mg, 5.94 mmol) and Hunig's base (1.2 mL, 7.2 mmol) in a mixture of $CH_2Cl_2$ (10 mL) and MeOH (10 mL) was heated to reflux for 4 h. The reaction mixture was concentrated and the crude product thus obtained was purified by flash chromatography (19:1: 0.01 $CH_2Cl_2$/MeOH/$NH_4OH$) to yield 1.3 g of pure BOC-protected piperazinyl acetamide. To a solution of the acetamide (250 mg, 1 mmol) in $CH_2Cl_2$ (10 mL) was added trifluoroacetic acid (TFA, 5 mL) at 0° C. and the mixture was stirred at that temperature for 2 h. The reaction mixture was concentrated to yield 68 which was used for subsequent reactions without further purification.

Synthesis of Piperazine 69

A solution of tert-butyl-1-piperazine carboxylate (1 g, 5.4 mmol), bromoacetonitrile (0.5 mL, 5.94 mmol) and Hunig's base (1.2 mL, 7.2 mmol) in a mixture of $CH_2Cl_2$ (10 mL) and MeOH (10 mL) was stirred at ambient temperature for 4 h. The reaction mixture was concentrated and the crude product thus obtained was purified by flash chromatography (19:1:0.01 $CH_2Cl_2$/MeOH/$NH_4OH$) to yield 1.3 g of pure BOC-protected piperazinyl acetonitrile. To a solution of the piperazinyl acetonitrile (300 mg, 1.3 mmol) in $CH_2Cl_2$ (10 mL) was added TFA (5 mL) at 0° C. and the mixture was stirred at that temperature for 2 h. The reaction mixture was concentrated to yield 69 which was used for subsequent reactions without further purification.

Synthesis of Compound 1003

A solution of mesylate of 52 (138 mg, 0.320 mmol) and 68 (~1 mmol) in Hunig's base (2 mL) and DMF (8 mL) was heated to 90° C. for 2 h. Then the solution was concentrated and purified by flash chromatography over silica gel (20:1: 0.01 $CH_2Cl_2$/MeOH/$NH_4OH$) to yield 1003. LCMS (ESI) m/z 484 $(M+H)^+$.

Synthesis of Compound 1004

Compound 1004 was synthesized from mesylate 52 and piperazine intermediate 69 in the same manner as described above for the synthesis of compound 1003. LCMS (ESI) m/z 466 $(M+H)^+$.

Synthesis of Compound 1005

Compound 1005 was synthesized from mesylate 67 and piperazine intermediate 69 in the same manner as described above for the synthesis of compound 1003. LCMS (ESI) m/z 484 $(M+H)^+$.

Synthesis of Compound 1006

Compound 1006 was synthesized from mesylate 52 and available piperazine intermediate 70 in the same manner as described above for the synthesis of compound 1003. LCMS (ESI) m/z 455 $(M+H)^+$.

Example 4

Synthesis of Compounds 1007-1010

Scheme 4 illustrates the synthesis of compounds 1007-1010. Mesylate 52 was converted to nitrile 71, which was subsequently transformed to tetrazole 1007. Mesylate 52 served as alkylating agent for the anion derived from imidazole to afford imidazole derivative 1008. Mesylate 67 was converted to azide 72, which was then subsequently converted to triazole 1009. Mesylate 67 served as alkylating agent for the anion derived from imidazole to afford imidazole derivative 1010.

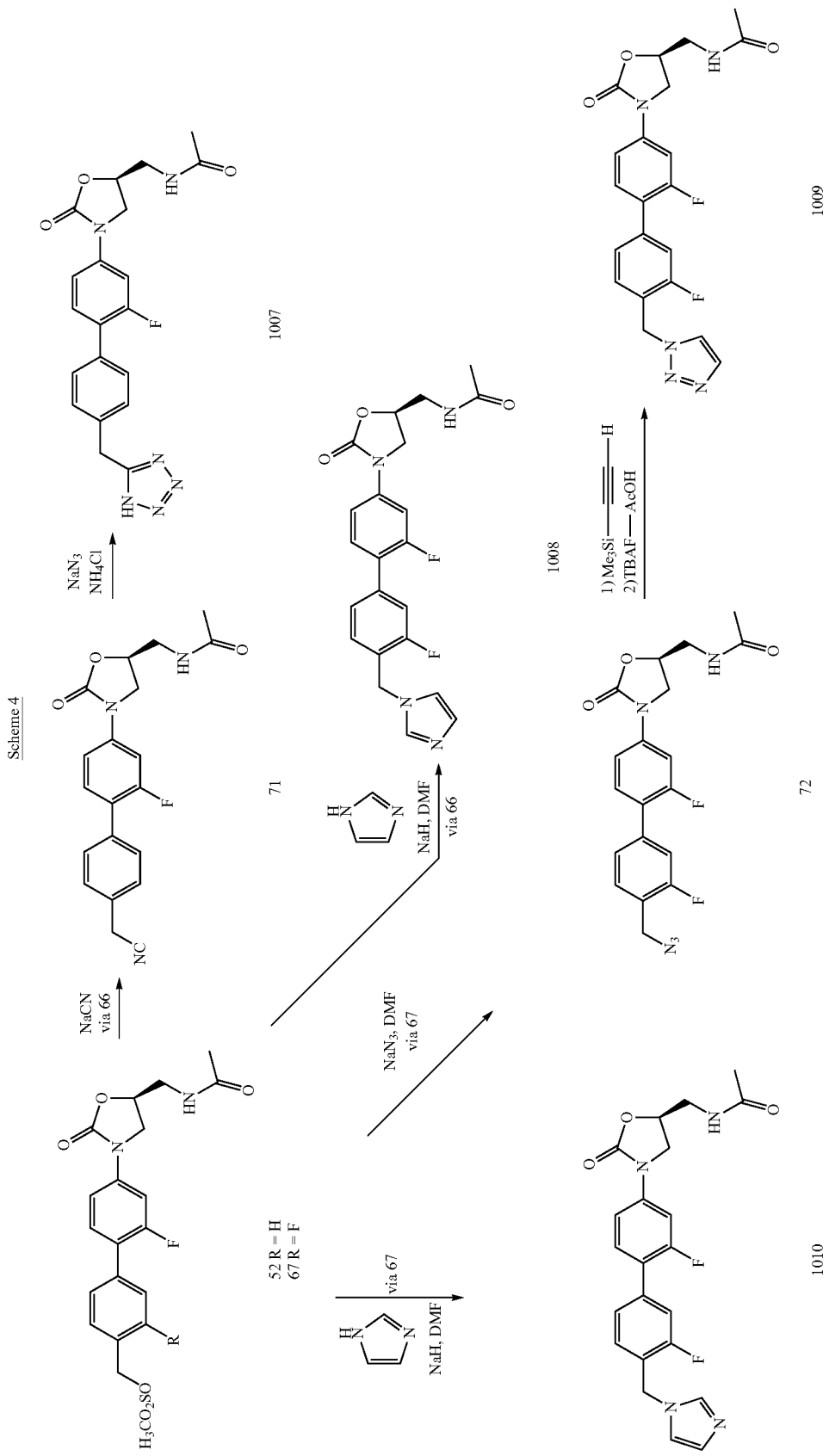

Synthesis of Tetrazole 1007

To a solution of mesylate 52 (2.0 g, 4.6 mmol) in DMF (30 mL) was added sodium cyanide (NaCN, 0.45 g, 9.2 mmol) and the mixture was heated to 70° C. for 3 h. The reaction mixture was cooled to ambient temperature and poured into water (800 mL). The solid thus obtained was filtered and passed through a small bed of silica gel ($CH_2Cl_2$:MeOH=12:1) to yield 1.8 g of nitrile 71. LCMS (ESI) m/z 368 $(M+H)^+$.

A mixture of 71 (100 mg, 0.272 mmol), $NaN_3$ (40 mg, 0.598 mmol) and ammonium chloride ($NH_4Cl$, 32 mg, 0.598 mmol) in DMF (2 mL) was heated to 90° C. for 3 days. The reaction mixture was concentrated and purified by flash chromatography (10% MeOH in $CH_2Cl_2$) to yield 35.6 mg of tetrazole 1007. LCMS (ESI) m/z 411 $(M+H)^+$.

Synthesis of Imidazole 1008

To a solution of imidazole (37.4 mg, 0.550 mmol) in DMF (5 mL) was added NaH (60%, 20 mg, 0.50 mmol) at 0° C. and the mixture was stirred for 30 minutes before the addition of mesylate 52 (200 mg, 0.459 mmol). The resulting solution was heated to 60° C. for 2 h and poured into water (75 mL). The aqueous suspension was extracted with 10% MeOH in $CH_2Cl_2$ (3×75 mL) and the combined organic layer was washed with saturated $NH_4Cl$ solution (2×100 mL). The organic layer was dried (anhydrous $Na_2SO_4$), concentrated and triturated with ether to yield 170 mg of imidazole 1008. LCMS (ESI) m/z 409 $(M+H)^+$.

Synthesis of Azide 72

Crude mesylate 67 (100 mg, 0.224 mmol; as a mixture with some corresponding benzyl chloride) was dissolved in DMF (10 mL) and sodium azide (114.6 mg, 1.762 mmol) was added. The mixture was stirred at room temperature for 14 h, and then partitioned between ethyl acetate and water. The organic phase was washed with water, dried over $Na_2SO_4$, and concentrated to provide azide 72 as a solid (190 mg).

Synthesis of Triazole 1009

Compound 1009 was synthesized from azide 72 and trimethylsilylacetylene in the same manner as described above for the synthesis of triazole 1001. LCMS (ESI) m/z 428 $(M+H)^+$.

Synthesis of Imidazole 1010

Compound 1010 was synthesized from mesylate 67 and imidazole in the same manner as described above for the synthesis of imidazole derivative 1008. LCMS (ESI) m/z 427 $(M+H)^+$.

Example 5

Synthesis of Compounds 1011-1015

Scheme 5 illustrates the synthesis of compounds 1011-1015. The cycloaddition of azide 53 with alkynes 74-76 afforded triazoles 1011-1013 respectively. The cycloaddition of azide 53 with alkyne 77 gave BOC-protected intermediate 78 which was subsequently cleaved to provide derivative 1014. The cycloaddition of azide 53 with trimethylsilylacetylene, followed by desilylation, yielded triazole 1015.

Scheme 5

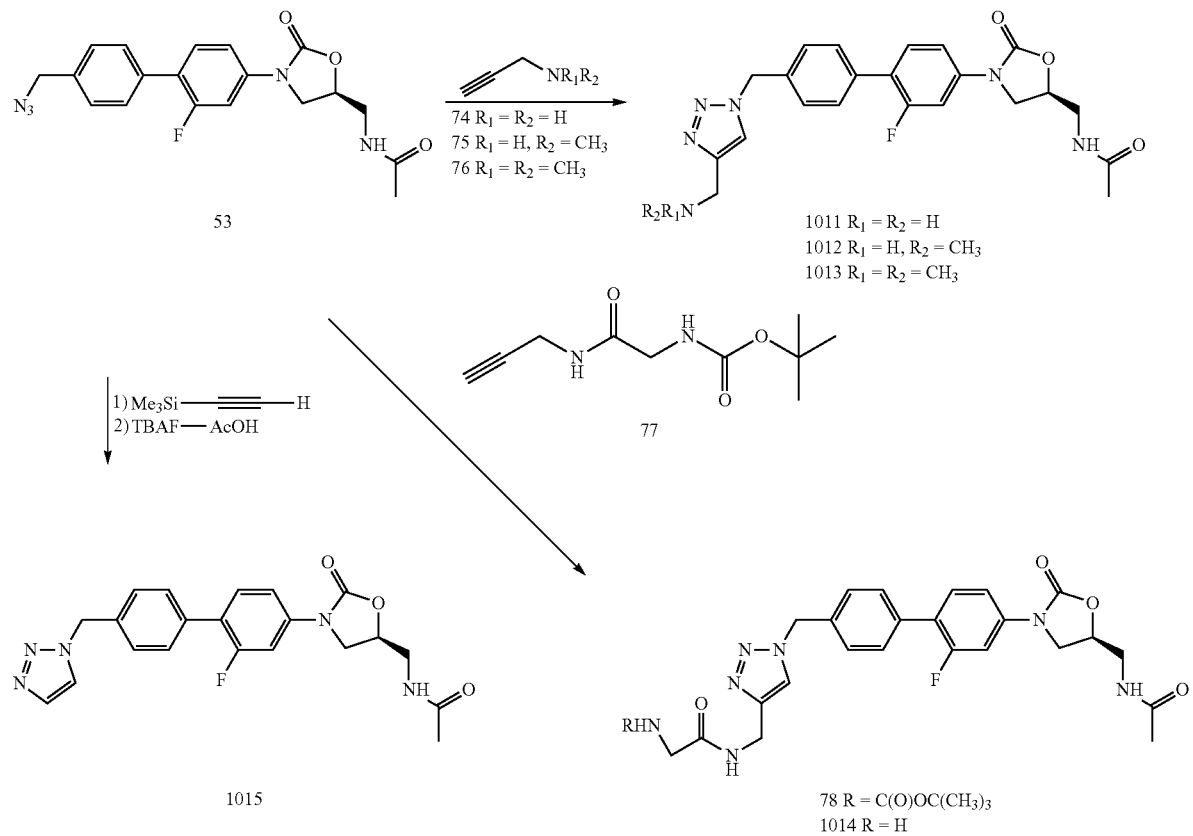

Synthesis of Triazole 1011

A solution of azide 53 (0.10 g, 0.26 mmol) in propargyl amine 74 (0.50 mL) was treated with copper iodide (0.05 g, 0.26 mmol) and was stirred at 23° C. for 0.5 h. The reaction mixture was diluted with $CH_2Cl_2$ and MeOH and purified by flash chromatography and preparative TLC to afford 1011 as a brown solid (0.027 g; 24%). LCMS (ESI) m/z 439 $(M+H)^+$.

Synthesis of Triazole 1012

A solution of azide 53 (0.10 g, 0.26 mmol) in N-methylpropargyl amine 75 (0.50 mL) was treated with copper iodide (5.00 mg, 0.026 mmol) and stirred at 23° C. for 12 h. The solvent was removed in vacuo, and the crude product was purified by preparative TLC to afford 1012 as a brown solid (0.038 g; 32%). LCMS (ESI) m/z 453 $(M+H)^+$.

Synthesis of Triazole 1013

A solution of azide 53 (0.10 g, 0.26 mmol) in N, N-dimethylpropargyl amine 76 (0.056 mL, 0.520 mmol) was treated with copper iodide (5.00 mg, 0.026 mmol) and stirred at 23° C. for 12 h. The solvent was removed in vacuo, and the crude product was purified by flash chromatography to afford 1013 as a yellow film (0.073 g; 60%). LCMS (ESI) m/z 467 $(M+H)^+$.

Synthesis of Alkyne 77

A solution of propargyl amine 74 (0.34 mL, 5.0 mmol) in methylene chloride (25 mL) was treated with BOC-glycine (0.96 g, 5.5 mmol) and EDCI (1.1 g, 5.5 mmol) and stirred at 23° C. for 0.5 h. The reaction mixture was diluted with $CH_2Cl_2$, washed with 1.0 M HCl (aqueous), washed with saturated aqueous sodium bicarbonate ($NaHCO_3$), dried over $Na_2SO_4$, and the solvent evaporated in vacuo to afford alkyne 77 (0.51 g; 48%).

Synthesis of Triazole 1014

A solution of azide 53 (0.15 g, 0.39 mmol) in THF (2 mL) was treated with alkyne 77 (0.17 g, 0.78 mmol) and copper iodide (7.00 mg, 0.039 mmol) and stirred at 23° C. for 16 h. The solvent was removed in vacuo, and the crude product was purified by flash chromatography to afford 78 as a white powder (0.16 g; 68%). LCMS (ESI) m/z 618 $(M+Na)^+$.

A solution of 78 (0.15 g, 0.25 mmol) was treated with HCl (1.3 mL of 4.0 M solution in dioxane) and was stirred at 23° C. for 2 h. The solvent was removed in vacuo, and the residue twice redissolved in methylene chloride and evaporated to afford 1014 as a white film (0.14 g, 100%). LCMS (ESI) m/z 496 $(M+H)^+$.

Synthesis of Triazole 1015

A solution of azide 53 (0.75 mg, 2.0 mmol) in DMF (10 mL) was treated with trimethylacetylene (2.3 mL, 20 mmol) and was stirred at 90° C. for 12 h. The reaction mixture was cooled to 23° C. and the solvent was removed in vacuo to afford the expected silyl-substituted triazole as a brown foam (0.24 mg; 25%). LCMS (ESI) m/z 482 $(M+H)^+$.

A solution of the above silyl-substituted triazole (0.050 g, 0.10 mmol) in THF (0.20 mL) was treated with acetic acid (6 μL, 0.10 mmol) and tetrabutylammonium fluoride (0.21 mL of 1.0 M solution in THF) and was stirred at 23° C. for 16 h. The reaction mixture was diluted with $CH_2Cl_2$, washed with water, dried ($Na_2SO_4$), and the solvent removed in vacuo. The crude product was purified to afford 1015 as a white powder (0.020 g; 47%). LCMS (ESI) m/z 432 $(M+Na)^+$.

Example 6

Synthesis of Compounds 1016-1017

Scheme 6 illustrates the synthesis of compounds 1016-1017. Hydroxyamidine 79 was converted to bromide 80 which was subsequently coupled to boronate 81 to afford compound 1016. Hydroxyamidine 79 was transformed to oxadiazole 82, which was coupled to boronate 81 to afford compound 1017.

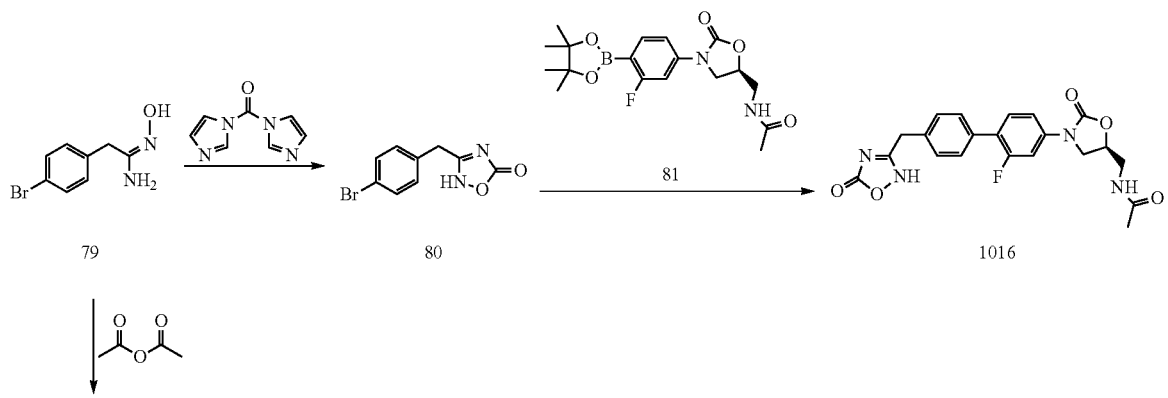

Scheme 6

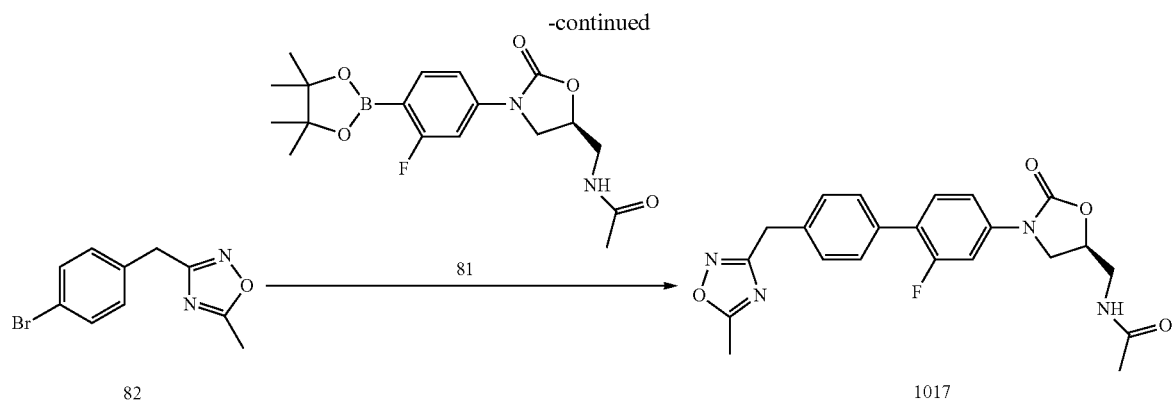

Synthesis of Hydroxyamidine 79

A solution of 4-bromophenylacetonitrile (10 g, 54 mmol) in methanol (100 mL) was treated with sodium bicarbonate (2.2 g, 57 mmol) and hydroxylamine hydrochloride (4.0 g, 57 mmol) and refluxed for 1.5 h. Additional sodium bicarbonate (0.21 g, 5.4 mmol) and hydroxylamine hydrochloride (0.38 g, 5.4 mmol) were added, and the reaction mixture was refluxed for 12 h. The reaction mixture was cooled to 23° C. and the solvent removed in vacuo to afford hydroxyamidine 79 as a blue powder (4.0 g; 34%).

Synthesis of Bromide 80

A solution of hydroxyamidine 79 (0.20 g, 0.91 mmol) in 1,4-dioxane (1 mL) was treated with 1,1'-carbonyldiimidazole (0.18 g, 1.1 mmol) and diazabicycloundecene (DBU, 0.15 mL, 0.97 mmol) and stirred at 105° C. for 1 h. The reaction mixture was diluted with water and extracted with ethyl acetate. The water layer was treated with 1.0 M HCl (aqueous) until the pH was 2, and then extracted with ethyl acetate. The organic layer was dried over $Na_2SO_4$, and the solvent removed in vacuo to afford bromide 80 as a yellow powder (0.11 g; 49%).

Synthesis of Boronate 81

A suspension of N-[3-(3-fluoro-4-iodo-phenyl)-2-oxo-oxazolidin-5-ylmethyl]acetamide 62 (20.0 g, 52.8 mmol) in anhydrous 1,4-dioxane (130 mL) was treated with 4,4,5,5-tetramethyl-[1,3,2]dioxaborolane (10.2 g, 11.6 mL, 80.0 mmol) and triethylamine (16.0 g, 22.4 mL, 158.4 mmol) at room temperature, and the resulting reaction mixture was degassed three times under a steady stream of argon before being treated with dichloro[1,1'-bis(diphenylphosphino)ferrocene]palladium (II) ($Pd(dppf)_2Cl_2$, 1.32 g, 1.6 mmol, 0.03 equiv) at room temperature. The reaction mixture was then degassed three times again under a steady stream of argon before being heated to reflux for 7 h. When TLC and LCMS showed that the reaction was complete, the reaction mixture was cooled down to room temperature before being treated with water (100 mL) and ethyl acetate (100 mL). The two layers were separated, and the aqueous layer was extracted with ethyl acetate (2×50 mL). The combined organic extracts were washed with water (2×50 mL) and saturated aqueous NaCl solution (50 mL), dried over magnesium sulfate ($MgSO_4$), and concentrated in vacuo. The residual brown oil was further dried in vacuo to afford the crude desired N-{3-[3-fluoro-4-(4,4,5,5-tetramethyl-[1,3,2]dioxaborolan-2-yl)-phenyl]-2-oxo-oxazolidin-5-ylmethyl} acetamide 81 (18.8 g, 20.0 g theoretical, 94%) as a brown solid which was of sufficient purity to be used in subsequent reactions.

Synthesis of Compound 1016

A solution of boronate ester 81 (0.085 g, 0.220 mmol), bromide 80 (0.055 g, 0.220 mmol), and potassium carbonate (0.12 g, 0.90 mmol) in dioxane (1.4 mL), ethanol (0.46 mL) and water (0.46 mL) was degassed and treated with Pd(dppf)$Cl_2$ (6.0 mg, 6.7 μmol), degassed again, and heated at 80° C. for 1.5 h. The reaction mixture was diluted with $CH_2Cl_2$ and water, and the precipitate in the water layer was recovered by vacuum filtration to afford 1016 as a grey powder (0.034 g; 36%). LCMS (ESI) m/z 427 $(M+H)^+$.

Synthesis of Bromide 82

A solution of hydroxyamidine 79 (0.25 g, 1.1 mmol) in pyridine (5 mL) was cooled to 0° C. and treated with a solution of acetic anhydride (0.11 mL, 1.1 mmol) in pyridine (5 mL) and then stirred at 120° C. for 1.5 h. The reaction mixture was diluted with ethyl acetate, washed with 1.0 M HCl (aqueous), washed with saturated aqueous sodium bicarbonate, dried over $Na_2SO_4$, and the solvent evaporated in vacuo. The crude product was purified by flash chromatography to afford bromide 82 as a clear film (0.10 g; 36%).

Synthesis of Compound 1017

A solution of boronate ester 81 (0.15 g, 0.40 mmol), bromide 82 (0.10 g, 0.40 mmol), and potassium carbonate (0.22 g, 1.6 mmol) in dioxane (2.5 mL), ethanol (0.83 mL) and water (0.83 mL) was degassed and treated with Pd(dppf)$Cl_2$ (10.0 mg, 0.012 mmol), degassed again, and stirred at 80° C. for 2 h. The reaction mixture was diluted with $CH_2Cl_2$ and washed with water. The water layer was extracted with 2×$CH_2Cl_2$, dried over $Na_2SO_4$, and the solvent evaporated in vacuo. The crude product was purified by flash chromatography and preparative TLC to afford 1017 as a white powder (0.054 g; 32%). LCMS (ESI) m/z 425 $(M+H)^+$.

Example 7

Synthesis of Compounds 1018-1019

Scheme 7 illustrates the synthesis of compounds 1018-1019. Known aryl iodide 83 was coupled to 4-hydroxymethylboronic acid to afford biaryl alcohol 84. Alcohol 84 was converted to azide 85, which was used in alkyne cycloaddition reactions to afford triazoles 1018 and 1019.

mmol) was added. The mixture was heated to 70° C. for 4 hours. The reaction mixture was partitioned with ethyl acetate and water, and the organic layer was washed with

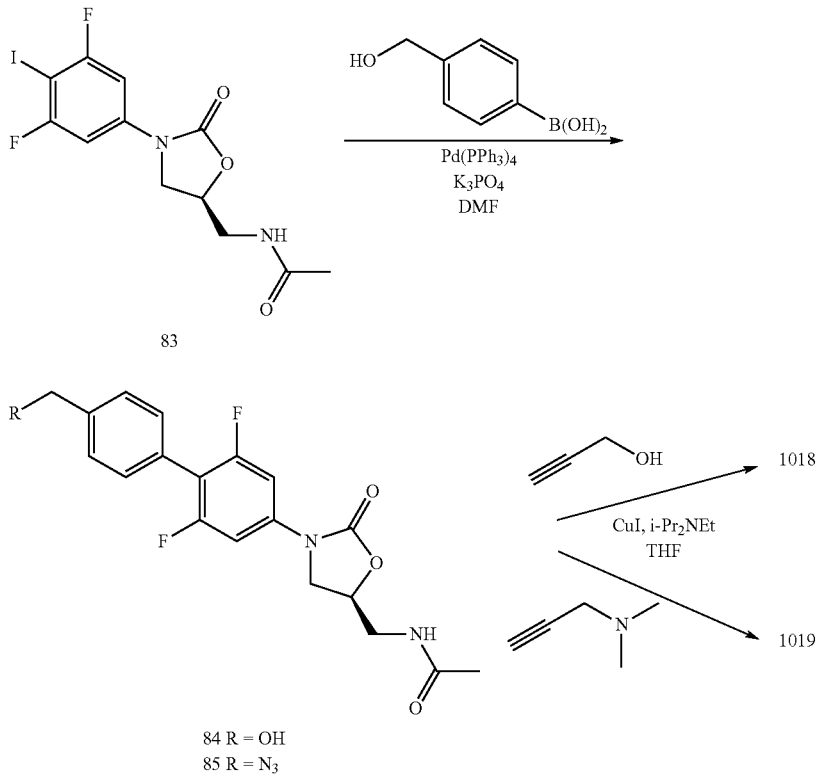

Synthesis of Azide 85

Known aryl iodide 83 (Gravestock, M. B., International Patent Application WO9910342) (1.00 g, 2.52 mmol) was dissolved in 6 mL DMF. 4-Hydroxymethyl-phenylboronic acid (0.461 g, 3.03 mmol) was added, followed by potassium phosphate ($K_3PO_4$, 0.804 g, 3.79 mmol) and $Pd(PPh_3)_4$ (0.292 g, 0.253 mmol). The mixture was degassed by evacuating the air from the flask, and refilling with argon (3 times), and then heated to 100° C. for 4 hours. The mixture was allowed to cool and was then partitioned between ethyl acetate and water. The aqueous phase was extracted with ethyl acetate, and the combined organic phase was washed with brine, dried over $MgSO_4$, and evaporated. The residue was chromatographed on silica using a gradient mixture of methanol/methylene chloride (1% to 8%) to afford alcohol 84 (0.315 g, 0.838 mmol; 33%) as an ivory solid. An analytical sample was obtained by recrystallizing the material from methanol/methylene chloride/pentane. LCMS (ESI) m/z 377.

Alcohol 84 (0.889 g, 2.36 mmol) was suspended in 0.3 mL methylene chloride and 0.3 mL DMF. Triethylamine (0.66 mL, 4.74 mmol) was added, and the mixture was cooled to 0° C. Methanesulfonyl chloride (0.260 mL, 3.36 mmol) was added dropwise, and the mixture was stirred for 25 minutes. The mixture was then partitioned with ethyl acetate and water, and the organic layer was washed with brine, dried over $MgSO_4$, and evaporated. The residue was dissolved in 3 mL DMF, and sodium azide (0.384 g, 5.91 brine, dried over $MgSO_4$, and evaporated. The residue was chromatographed on silica using a gradient mixture of methanol/methylene chloride (1% to 4%) to afford azide 85 (0.480 g, 1.20 mmol; 51%) as a tan solid. LCMS (ESI) m/z 402.

Synthesis of Triazole 1018

Azide 85 (0.084 g, 0.209 mmol) was dissolved in 0.7 mL THF and propargyl alcohol (25 µL, 0.400 mmol) was added, followed by Hunig's base (73 µL, 0.400 mmol) and copper (I) iodide (0.040 g, 0.210 mmol). The mixture was allowed to stir overnight at room temperature, and then was placed in a −20° C. freezer for 2 days. The mixture was then partitioned with ethyl acetate and water, and the aqueous layer was extracted with ethyl acetate and then 2% methanol/methylene chloride. The combined organic layer was washed with brine, dried over $MgSO_4$ and evaporated. The residue was chromatographed on silica using a gradient mixture of methanol/methylene chloride (1% to 8%) to afford triazole 1018 (0.060 g, 0.131 mmol; 63%) as an ivory solid. LCMS (ESI) m/z 458.

Synthesis of Triazole 1019

Azide 85 (0.135 g, 0.337 mmol) was dissolved in 1.5 mL THF and dimethyl-prop-2-ynyl-amine (72 µL, 0.674 mmol) was added, followed by i-$Pr_2NEt$ (117 µL, 0.674 mmol) and copper(I)iodide (0.064 g, 0.337 mmol). The mixture was allowed to stir overnight at room temperature (the solvents evaporated overnight with positive pressure from argon gas). The residue was suspended in ethyl acetate and methylene chloride and filtered through celite. The pad of celite was washed with ethyl acetate and methylene chloride, and the combined organic washes were evaporated. The residue was chromatographed on silica using a gradient mixture of methanol/methylene chloride (0% to 14%) and the product obtained was triturated with methylene chloride and pentane. The tan solid was collected to afford triazole 1019 (0.072 g, 0.149 mmol; 44%). LCMS (ESI) m/z 485.

Example 8

Synthesis of Compounds 1020-1021

Scheme 8 illustrates the synthesis of compounds 1020-1021. Bromoketone 86 was subjected to alkylation with thioureas 87a and 87b to afford thiazoles 88a and 88b respectively. Coupling of 88a and 88b with boronate 81 yielded thiazoles 1020 and 1021.

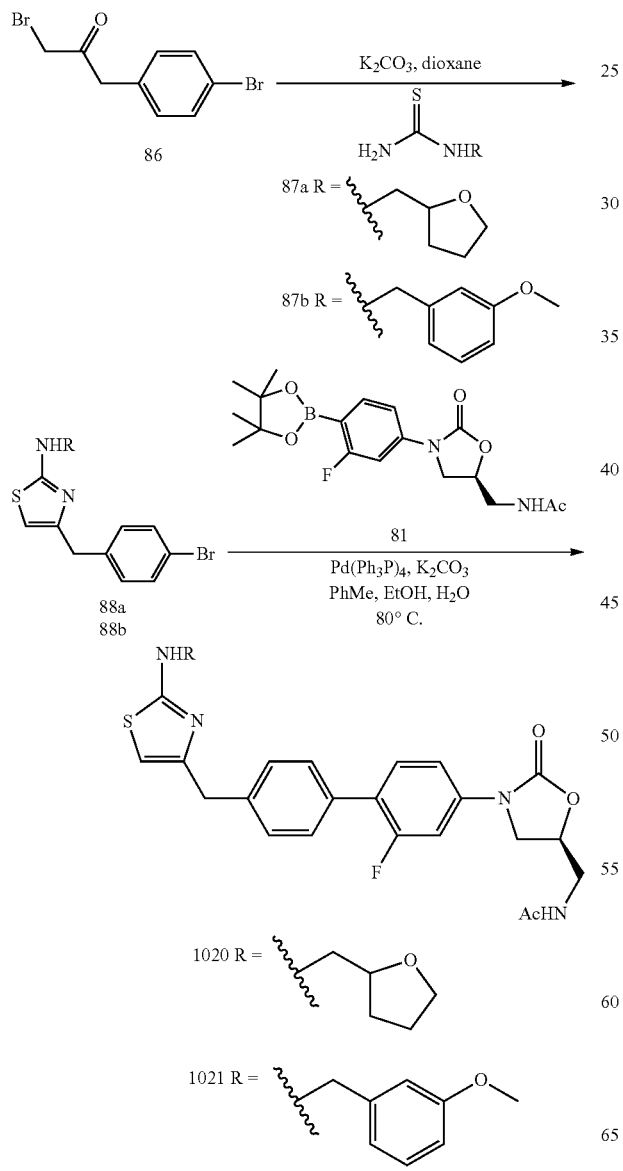

Synthesis of Thiazole 88a

Bromoketone 86 (0.29 g, 1.0 mmol) was dissolved in dioxane (10 mL). Thiourea 87a (0.19 g, 1.2 mmol) and potassium carbonate (0.28 g, 2 mmol) were added sequentially and the resulting slurry stirred at 50° C. for 4 h. The mixture was cooled to room temperature, diluted with 100 mL $CH_2Cl_2$, and washed with sat. aq. $NaHCO_3$, and brine. The aqueous washes were back-extracted with $CH_2Cl_2$ (2×50 mL). The combined organic extracts were dried over $K_2CO_3$, filtered and concentrated in vacuo to afford 88a as a yellow solid (0.32 g) which was used without further purification. LCMS (ESI) m/z 353 $(M+H)^+$.

Synthesis of Thiazole 1020

The crude aryl bromide 88a obtained above (0.20 g, 0.56 mmol), boronate ester 81 (0.25 g, 0.66 mmol), and $K_2CO_3$ (0.14 g, 1.0 mmol) were combined with a 1:1:1 mixture of toluene, ethanol and water (2 mL each). The slurry was degassed by alternately applying high vacuum to the reaction mixture and flushing with dry argon. The reaction vessel was then sealed and heated in an 80° C. oil bath for 14 h. The reaction mixture was cooled to room temperature, diluted with 100 mL 9:1 $CH_2Cl_2$/MeOH, and washed with water and brine (50 mL each). The aqueous washes were back-extracted once with 50 mL 9:1 $CH_2Cl_2$/MeOH. The combined organic extracts were dried on $K_2CO_3$, filtered, and concentrated in vacuo to afford 0.48 g of a brown solid which was purified by silica gel chromatography (25 mm×6" column eluted with 7:3 acetone/hexane) to yield 1020 as an off-white solid (0.17 g, 0.32 mmol). LCMS (ESI) m/z 525 $(M+H)^+$.

Synthesis of Thiazole 1021

Compound 21 was synthesized according to the procedure described above for 1020, using thiourea 88b in place of 88a. The reaction yielded 1021 as a white solid (0.12 g, 0.21 mmol). LCMS (ESI) m/z 561 $(M+H)^+$.

Example 9

Synthesis of Compounds 1022-1025

Scheme 9 illustrates the synthesis of compounds 1022-1025. Azetidine 89 was deprotected and alkylated with chloride 90 to afford amide 91. The amide of 91 was dehydrated with trifluoroacetic anhydride to produce nitrile 1022. The alkylation of 1,2,3-triazole with benzyl chloride 90 gave triazole 1023. Similarly, the alkylation of 5-amino-tetrazole with benzyl chloride 90 yielded a mixture of tetrazole 1024 and tetrazole 1025.

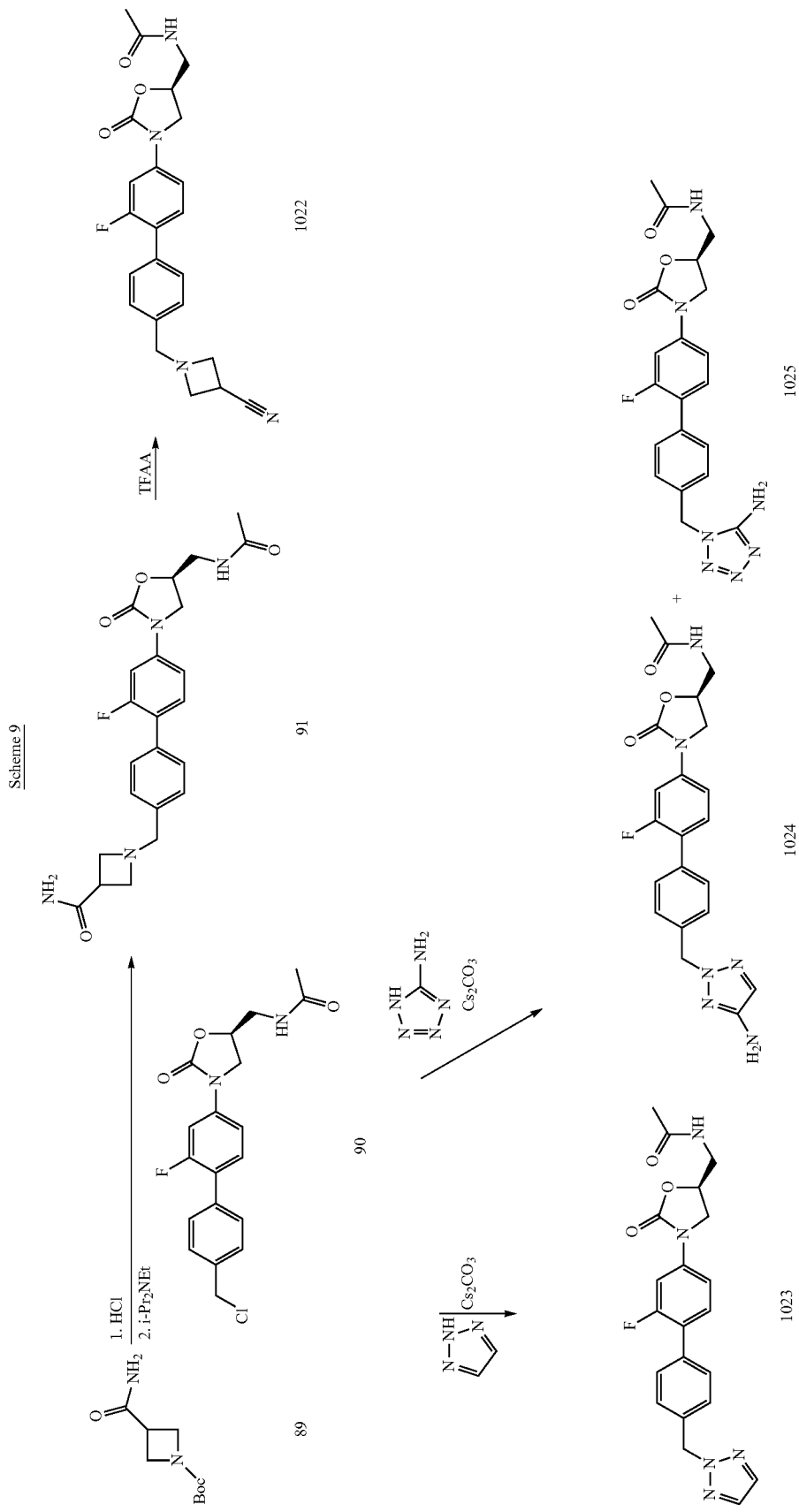
Scheme 9

Synthesis of Chloride 90

N-[3-(2-fluoro-4'-hydroxymethyl-biphenyl-4-yl)-2-oxo-oxazolidin-5-ylmethyl]-acetamide 51 (3.0 g, 8.4 mmol) 51 was dissolved in $CH_2Cl_2$ (20 mL) and Hunig's base (2 mL). Methanesulfonyl chloride (1.4 mL, 12.6 mmol) was added dropwise and the resulting solution stirred at room temperature for 4 h. The mixture was poured into 100 mL sat. aqueous $NaHCO_3$ and extracted with $CH_2Cl_2$ (3×50 mL). The combined organic extracts were washed with brine, dried over $MgSO_4$, filtered, and concentrated to give 3.9 g of an oily yellow solid. The crude material was purified by silica gel chromatography to give chloride 90 as an off-white solid (2.7 g, 7.2 mmol). LCMS (ESI) m/z 377 $(M+H)^+$, 418 $(M+CH_3CN+H)^+$, 440 $(M+CH_3CN+Na)^+$.

Synthesis of Amide 91

A solution of 89 (*J. Med. Chem.* 1993, 36, 801) (33 mg, 0.17 mmol) in $CH_2Cl_2$ (1.0 mL) was treated with 4.0 M HCl-dioxane (0.2 mL) and stirred at 23° C. for 2 h. The reaction mixture was evaporated and the residue dissolved in DMF (1.0 mL) and treated with benzyl chloride 90 (63 mg, 0.17 mmol) and Hunig's base (0.17 mL, 1.0 mmol) and stirred at 60° C. for 2 h. The reaction mixture was cooled to 23° C., diluted with $H_2O$ (10 mL) and extracted with $CH_2Cl_2$ (4×25 mL), dried $(Na_2SO_4)$ and evaporated. The crude residue was purified by preparative TLC (1% $NH_4OH$-10% MeOH-89% $CH_2Cl_2$) to afford 91 (36 mg; 50%) as a tan powder. LCMS (ESI) m/z 441.1 $(M+H)^+$.

Synthesis of Nitrile 1022

A solution of 91 (26 mg, 0.06 mmol) in $CH_2Cl_2$ (1.0 mL) was treated with pyridine (0.02 mL, 0.2 mmol) and trifluoroacetic anhydride (0.035 mL, 0.21 mmol) and stirred at 0° C. for 1 h. The reaction mixture was directly purified by preparative TLC (1% $NH_4OH$-10% MeOH-89% $CH_2Cl_2$) to afford 1022 (6.0 mg; 24%) as a tan powder. LCMS (ESI) m/z 423.1 $(M+H)^+$.

Synthesis of Triazole 1023

A solution of 90 (0.19 g, 0.50 mmol) in DMF (2.0 mL) was treated with 1,2,3-triazole (0.058 mL, 1.0 mmol) and cesium carbonate $(Cs_2CO_3, 0.33$ g, 1.0 mmol) and stirred at 23° C. for 16 h. The reaction mixture was diluted with $H_2O$ (100 mL) and the resulting precipitate was isolated by filtration and purified by preparative TLC (10% MeOH-45% $CH_2Cl_2$-45% EtOAc) to afford 1023 (39 mg; 19%) as a white powder. LCMS (ESI) m/z 473.2 $(M+CH_3CN+Na)^+$.

Synthesis of Tetrazoles 1024 and 1025

A solution of 90 (0.19 g, 0.50 mmol) in DMF (2.0 mL) was treated with 5-aminotetrazole (87 mg, 1.0 mmol) and $Cs_2CO_3$ (0.33 g, 1.0 mmol) and stirred at 23° C. for 12 h. The reaction mixture was diluted with $H_2O$ (100 mL) and the resulting precipitate was isolated by filtration and suspended in 50 mL of a 1:1 mixture of $CH_2Cl_2$ and MeOH. The insoluble material (55 mg; 26%) was isolated by filtration and assigned the structure of 1024. LCMS (ESI) m/z 426.1 $(M+H)^+$. The soluble material was isolated by evaporation and purified by preparative TLC (1% $NH_4OH$-10% MeOH-89% $CH_2Cl_2$) to afford a white powder assigned the structure of 1025 (39 mg; 19%). LCMS (ESI) m/z 489.2 $(M+CH_3CN+Na)^+$.

Example 10

Synthesis of Compounds 1026 and 1027

Scheme 10 illustrates the synthesis of compounds 1026 and 1027. Azide 53 was converted to triazole 1026, which was then subsequently cyclized to compound 1027.

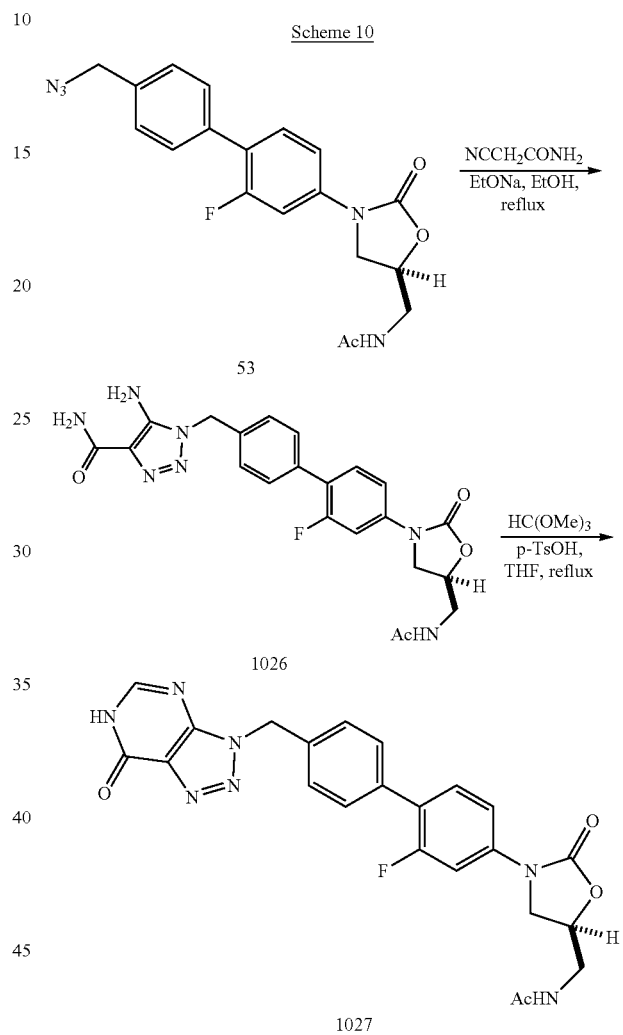

Scheme 10

Synthesis of Triazole 1026

A solution of azide 53 (383 mg, 1.0 mmol) in ethanol (4.0 mL) was treated with cyanoacetamide (101 mg, 1.2 mmol) and a solution of sodium ethoxide (21% wt solution in ethanol, 648 mg, 0.75 mL) at room temperature under $N_2$. The resulting reaction mixture was stirred for 10 min at room temperature before being warmed up to reflux for 2 h. When TLC showed that the reaction was complete, the reaction mixture was cooled down to room temperature before being treated with $H_2O$ (10 mL). The white precipitate was then collected by filtration, washed with $H_2O$ (2×10 mL), and dried in vacuo to afford the desired triazole 1026 (312 mg; 67%) as an off-white powder, which was of sufficient purity to be used directly in subsequent reactions. LCMS (ESI) m/z 468 $(M+H)^+$.

Synthesis of Compound 1027

A suspension of 1026 (165 mg, 0.353 mmol) in anhydrous THF (5 mL) was treated with p-toluenesulfonic acid monohydrate (34.2 mg, 0.18 mmol) and trimethyl orthoformate (374 mg, 0.386 mL, 3.53 mmol) at 25° C. under $N_2$, and the resulting mixture was warmed up to reflux for 2 h. The solvents were removed in vacuo, and the residue was directly purified by column chromatography (5-10% MeOH/ $CH_2Cl_2$ gradient elution) to afford the desired compound 1027 (42 mg; 25%) as a white powder. LCMS (ESI) m/z 478 $(M+H)^+$.

Example 11

Synthesis of Triazole 1028

A suspension of azide 53 (124 mg, 0.324 mmol) in anhydrous 1,4-dioxane (5.0 mL) was treated with propargyl alcohol (182 mg, 0.19 mL, 3.24 mmol) at 25° C., and the resulting reaction mixture was warmed up to reflux for 12 h. When TLC and LCMS showed the reaction was complete, the reaction mixture was concentrated in vacuo, and the residue was directly purified by column chromatography (0-5% MeOH/$CH_2Cl_2$ gradient elution) to afford triazole 1028 (93.9 mg; 66%) as a pale-yellow solid. LCMS (ESI) m/z 440 $(M+H)^+$.

Example 12

Synthesis of Piperazine 1029 and Piperidine 1030

Scheme 11 illustrates the reductive amination chemistry used to synthesize 1029 and 1030.

Synthesis of Piperazine 1029

A solution of aldehyde 92 (made from iodide 50 and 4-formylboronic acid in the same fashion as N-[3-(2-fluoro-4'-hydroxymethyl-biphenyl-4-yl)-2-oxo-oxazolidin-5-ylmethyl]-acetamide in Example 1) (180 mg, 0.5 mmol) and 2-piperidin-4-yl-ethanol (65 mg, 0.065 mL, 0.5 mmol) in anhydrous THF (4.0 mL) and anhydrous DMF (1.0 mL) was treated with sodium triacetoxyborohydride (160 mg, 0.75 mmol) at 25° C., and the resulting mixture was stirred at 25° C. for 12 h. When TLC and LCMS showed the reductive amination reaction was complete, the reaction mixture was concentrated in vacuo. The residue was directly purified by flash column chromatography (0-5% MeOH—$CH_2Cl_2$ gradient elution) to afford piperazine 1029 (306 mg; 65%) as a colorless oil, which solidified upon standing at room temperature in vacuo. LCMS (ESI) m/z 471 $(M+H)^+$.

Synthesis of Piperidine 1030

A solution of aldehyde 92 (356 mg, 1.0 mmol) and 2-piperazin-1-yl-ethanol (130 mg, 0.123 mL, 1.0 mmol) in anhydrous THF (8.0 mL) and anhydrous DMF (1.6 mL) was treated with sodium triacetoxyborohydride ($NaB(OAc)_3H$, 318 mg, 1.5 mmol) at 25° C., and the resulting mixture was stirred at 25° C. for 12 h. When TLC and LCMS showed the reductive amination reaction was complete, the reaction mixture was concentrated in vacuo. The residue was directly purified by flash column chromatography (0-5% MeOH—$CH_2Cl_2$ gradient elution) to afford piperidine 1030 (169 mg; 72%) as a colorless oil, which solidified upon standing at room temperature in vacuo. LCMS (ESI) m/z 470 $(M+H)^+$.

Scheme 11

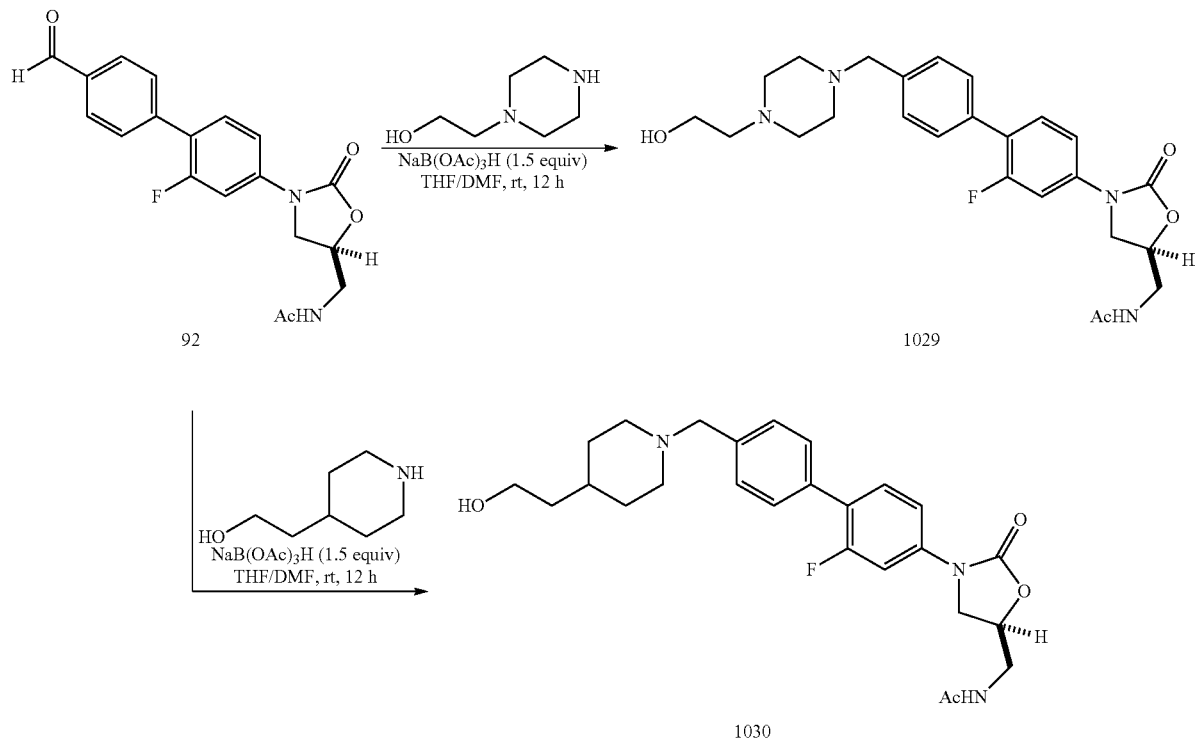

Example 13

Synthesis of Imidazole 1031

Scheme 12 depicts the synthesis of tetrazole derivative 1031. D-p-Hydroxyphenylglycine was converted to triflate 95, which was subsequently coupled to boronate 81 to afford alcohol 96. Mesylation of 96, followed by displacement with the anion of imidazole and deprotection of the BOC group yielded imidazole derivative 1031.

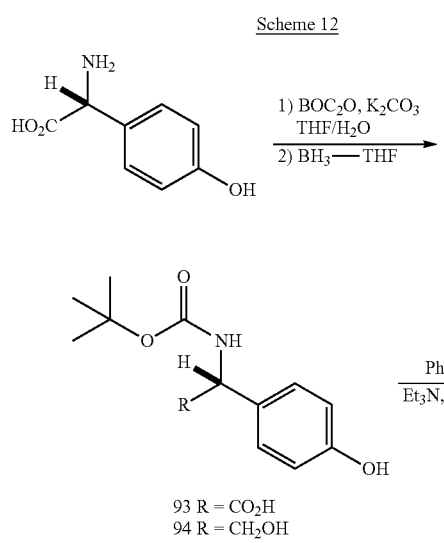

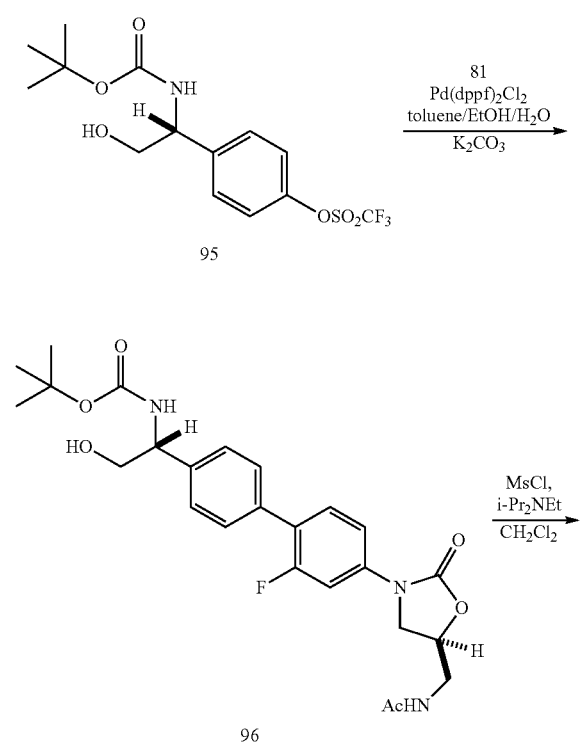

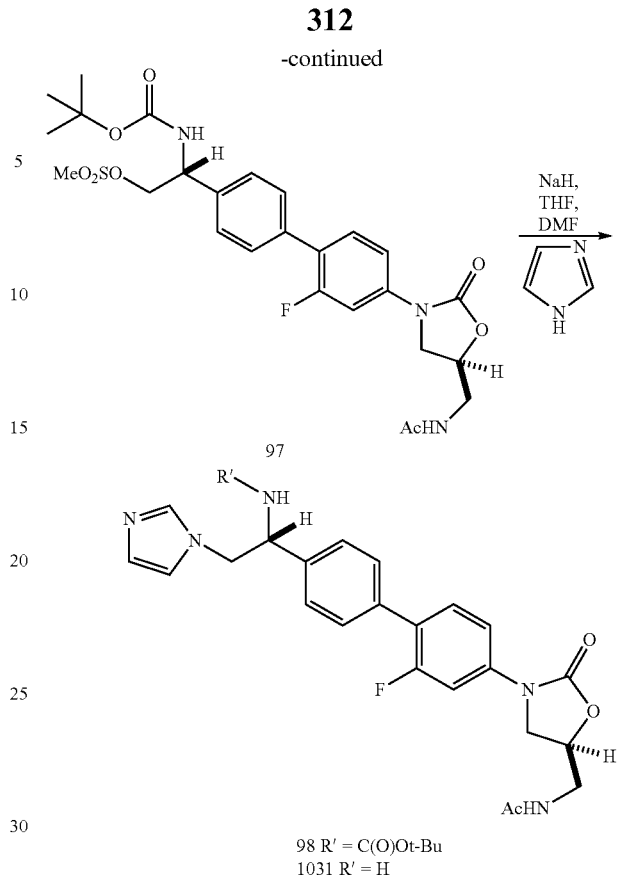

Synthesis of Triflate 95

A solution of D-p-hydroxyphenylglycine (23.8 g, 142.3 mmol) and potassium carbonate (39.3 g, 284.6 mmol) in THF (200 mL) and H$_2$O (200 mL) was treated with di-tert-butyl dicarbonate (BOC$_2$O, 34.14 g, 156.6 mmol) at 25° C., and the resulting reaction mixture was stirred at 25° C. for 2 h. When TLC and LCMS showed that the reaction was complete, the reaction mixture was treated with ethyl acetate (200 mL) and H$_2$O (200 mL). The two layers were separated, and the aqueous solution was extracted with ethyl acetate (200 mL), and the combined organic extracts were discarded. The aqueous layer was then acidified with a 2 N HCl aqueous solution to pH 4 before being extracted with ethyl acetate (2×200 mL). The combined organic extracts were then washed with water (2×100 mL) and saturated aqueous NaCl solution (100 mL), dried over MgSO$_4$, and concentrated in vacuo. The residual white solids were further dried in vacuo to afford the crude desired acid 93 (36.5 g; 96%), which was of suitable purity for use in subsequent reactions.

A solution of acid 93 (4.005 g, 15 mmol) in anhydrous THF (20 mL) was treated dropwise with a 1 M solution of BH$_3$-THF in THF (30 mL, 30 mmol) at 0-5° C., and the resulting reaction mixture was stirred at 0-5° C. for an additional 2 h. When TLC and LCMS showed that the reduction reaction was complete, the reaction mixture was treated with water (50 mL) and ethyl acetate (50 mL). The mixture was then stirred at 25° C. for 30 min before being separated, and the aqueous layer was extracted with ethyl acetate (2×50 mL). The combined organic extracts were washed with water (2×20 mL) and saturated aqueous NaCl solution (20 mL), dried over MgSO$_4$, and concentrated in vacuo. The residue was then directly purified by flash column chromatography (0-5% MeOH—CH$_2$Cl$_2$ gradient elution) to afford desired alcohol 94 (2.50 g; 66%) as a white powder which was of suitable purity for use in subsequent reactions.

A suspension alcohol 94 (670 mg, 2.65 mmol) in CH$_2$Cl$_2$ (10 mL) was treated with N-phenyltrifluoromethane sulfonamide (947 mg, 2.65 mmol) and triethylamine (535.3 mg, 0.74 mL, 5.3 mmol) at 25° C., and the resulting reaction mixture was stirred at 25° C. for an additional 2 h. When TLC and LCMS showed that the reaction was complete, the reaction mixture was quenched with water (10 mL) and CH$_2$Cl$_2$ (20 mL). The two layers were then separated, and the aqueous layer was extracted with CH$_2$Cl$_2$ (2×20 mL). The combined organic extracts were then washed with water (2×10 mL) and saturated aqueous NaCl solution (10 mL), dried over MgSO$_4$, and concentrated in vacuo. The residue was then directly purified by flash column chromatography (0-5% MeOH—CH$_2$Cl$_2$ gradient elution) to afford triflate 95 (945 mg; 93%) as a white powder which was of suitable purity for use in subsequent reactions.

Synthesis of Alcohol 96

A solution of boronate 81 (2.162 g, 5.72 mmol) and triflate 95 (1.70 g, 4.4 mmol) in toluene (24 mL) was treated with solid potassium carbonate (1.82 g, 13.2 mmol), ethanol (8.0 mL) and H$_2$O (8.0 mL) at room temperature, and the resulting reaction mixture was degassed three times under a steady stream of argon before being treated with Pd(dppf)$_2$Cl$_2$ (184 mg, 0.22 mmol) at room temperature. The reaction mixture was then degassed three times again under a steady stream of argon before being warmed up to reflux for 2 h. When TLC and LCMS showed that the reaction was complete, the reaction mixture was cooled down to room temperature before being treated with water (20 mL) and ethyl acetate (20 mL). The two layers were separated, and the aqueous layer was extracted with ethyl acetate (2×20 mL). The combined organic extracts were washed with water (2×20 mL) and saturated aqueous NaCl solution (20 mL), dried over MgSO$_4$, and concentrated in vacuo. The residue was then purified by flash column chromatography (0-5% MeOH—CH$_2$Cl$_2$ gradient elution) to afford (1-{4'-[5-(acetylamino-methyl)-2-oxo-oxazolidin-3-yl]-2'-fluoro-biphenyl-4-yl}-2-hydroxyethyl)carbamic acid tert-butyl ester 96 (1.543 g; 72%) as yellow oil, which solidified upon standing at room temperature in vacuo.

Synthesis of Mesylate 97

A suspension of alcohol 96 (694 mg, 1.43 mmol) in anhydrous CH$_2$Cl$_2$ (10 mL) was treated with diisopropylethylamine (388 mg, 0.522 mL, 2.85 mmol) and methanesulfonyl chloride (196 mg, 0.132 mL, 1.71 mmol) at 0-5° C., and the resulting reaction mixture was stirred at 0-5° C. for an additional 2 h. When TLC and LCMS showed that the reaction was complete, the reaction mixture was quenched with water (10 mL). The two layers were separated, and the aqueous layer was extracted with CH$_2$Cl$_2$ (2×10 mL). The combined organic extracts were washed with water (2×10 mL) and saturated aqueous NaCl solution (10 mL), dried over MgSO$_4$, and concentrated in vacuo. The residue was then purified by flash column chromatography (0-5% MeOH—CH$_2$Cl$_2$ gradient elution) to afford mesylate 97 (647 mg; 80%) as a pale-yellow solid, which was of suitable purity for use in subsequent reactions.

Synthesis of Imidazole 98

A solution of imidazole (41 mg, 0.6 mmol) in anhydrous THF (3 mL) was treated with NaH (60% oil dispersion, 29 mg, 0.72 mmol) at 0° C., and the resulting mixture was stirred at 0-5° C. for 30 min before a solution of mesylate 97 (170 mg, 0.3 mmol) in anhydrous DMF (3.0 mL) was added. The resulting reaction mixture was then stirred at 0-5° C. for 30 min before being gradually warmed up to room temperature for 12 h. When TLC and LCMS showed that the reaction was complete, the solvents were removed in vacuo, and the residue was directly purified by flash column chromatography (0-5% MeOH—CH$_2$Cl$_2$ gradient elution) to afford imidazole 98 (46 mg; 29%) as a yellow solid.

Synthesis of Imidazole 1031

A solution of imidazole 98 (23 mg, 0.043 mmol) in MeOH (1.0 mL) was treated with a solution of 4 N HCl in 1,4-dioxane (3.0 mL), and the resulting reaction mixture was stirred at room temperature for 30 min. When TLC and LCMS showed that the reaction was complete, the solvents were removed in vacuo, and the desired N-{3-[4'-(1-amino-2-imidazol-1-yl-ethyl)-2-fluoro-biphenyl-4-yl]-2-oxo-oxazolidin-5-ylmethyl}acetamide hydrochloride 1031 (18.8 mg; 100%) was obtained as a yellow solid. LCMS (ESI) m/z 438 (M+H)$^+$.

Example 14

Synthesis of Tetrazoles 1032-1034

Scheme 13 depicts the synthesis of tetrazole derivatives 1032-1034. Iodide 99 was converted to boronate 100 which served as the coupling partner for bromide 101 to afford tetrazole 102. Deprotection of 102 afforded tetrazole amine 1032, which was subsequently acylated to afford tetrazole 1033 and 1034.

Scheme 13

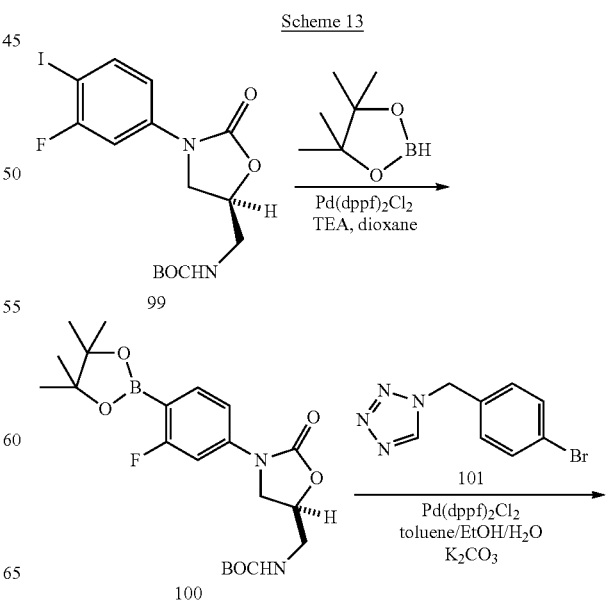

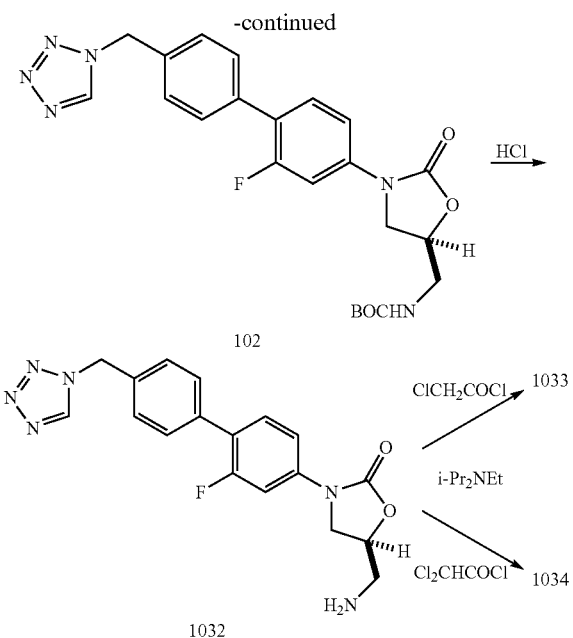

Synthesis of Iodide 99

A solution of known 5-aminomethyl-3-(3-fluoro-4-iodophenyl)-oxazolidin-2-one (2.02 g, 6.0 mmol; see U.S. Pat. Nos. 5,523,403 and 5,565,571) and potassium carbonate (1.66 g, 12.0 mmol) in THF (20 mL) and $H_2O$ (20 mL) was treated with $BOC_2O$ (1.334 g, 6.12 mmol) at 25° C., and the resulting reaction mixture was stirred at 25° C. for 2 h. When TLC and LCMS showed the reaction was complete, the reaction mixture was treated with ethyl acetate (20 mL) and $H_2O$ (20 mL). The two layers were separated, and the aqueous solution was extracted with ethyl acetate (20 mL), and the combined organic extracts were then washed with water (2×10 mL) and saturated aqueous NaCl solution (10 mL), dried over $MgSO_4$, and concentrated in vacuo. The residual white solids were further dried in vacuo to afford the crude, desired iodide 99 (2.40 g; 92%), which was of suitable purity for use in subsequent reactions.

Synthesis of Boronate 100

A solution of iodide 99 (1.11 g, 2.55 mmol) in 1,4-dioxane (25 mL) was treated with 4,4,5,5-tetramethyl-[1,3,2]dioxaborolane (489 mg, 0.56 mL, 3.82 mmol) and triethylamine (772 mg, 1.07 mL, 7.65 mmol) at room temperature, and the resulting reaction mixture was degassed three times under a steady stream of argon before being treated with $Pd(dppf)_2Cl_2$ (107 mg, 0.13 mmol) at room temperature. The reaction mixture was then degassed three times again under a steady stream of argon before being warmed up to reflux for 6 h. When TLC and LCMS showed that the reaction was complete, the reaction mixture was cooled down to room temperature before being treated with water (20 mL) and ethyl acetate (20 mL). The two layers were separated, and the aqueous layer was extracted with ethyl acetate (2×20 mL). The combined organic extracts were washed with water (2×20 mL) and saturated aqueous NaCl solution (20 mL), dried over $MgSO_4$, and concentrated in vacuo. The residual brown oil was then purified by flash column chromatography (10-30% EtOAc-hexanes gradient elution) to afford boronate 100 (646 mg; 58%) as a brown oil, which solidified upon standing at room temperature in vacuo and was of suitable purity for use in subsequent reactions.

Synthesis of Bromide 101

A solution of 4-bromobenzylamine hydrochloride (2.22 g, 10.0 mmol) in acetic acid (30 mL) was treated with triethyl orthoformate (2.964 g, 3.29 mL, 20.0 mmol) and sodium azide (2.30 g, 20.0 mmol) at room temperature, and the resulting reaction mixture was subsequently stirred at reflux for 12 h. When TLC and LCMS showed that the reaction was complete, the reaction mixture was cooled down to room temperature, and the cooled reaction mixture was poured into ice-water (100 mL). The precipitate was then collected by filtration, washed with water (2×20 mL), and dried in vacuo to afford crude bromide 101 (460 mg; 19%) as a white solid, which was of suitable purity for use in subsequent reactions.

Synthesis of Tetrazole 102

A solution of boronate 100 (658 mg, 1.5 mmol) and bromide 101 (300 mg, 1.25 mmol) in toluene (9.0 mL) was treated with solid potassium carbonate (621 mg, 4.5 mmol), ethanol (3.0 mL) and $H_2O$ (3.0 mL) at room temperature, and the resulting reaction mixture was degassed three times under a steady stream of argon before being treated with $Pd(dppf)_2Cl_2$ (52.3 mg, 0.063 mmol) at room temperature. The reaction mixture was then degassed three times again under a steady stream of argon before being warmed up to reflux for 3 h. When TLC and LCMS showed that the reaction was complete, the reaction mixture was cooled down to room temperature before being treated with water (10 mL) and ethyl acetate (20 mL). The two layers were separated, and the aqueous layer was extracted with ethyl acetate (2×10 mL). The combined organic extracts were washed with water (2×5 mL) and saturated aqueous NaCl solution (5 mL), dried over $MgSO_4$, and concentrated in vacuo. The residue was then purified by flash column chromatography (0-5% MeOH—$CH_2Cl_2$ gradient elution) to afford tetrazole 102 (357 mg; 61%) as a yellow oil, which solidified upon standing at room temperature in vacuo.

Synthesis of Tetrazole 1032

A solution of tetrazole 102 (350 mg, 0.748 mmol) in EtOAc (5.0 mL) was treated with a solution of 4 N HCl in 1,4-dioxane (5.0 mL), and the resulting reaction mixture was stirred at room temperature for 30 min. When TLC and LCMS showed that the reaction was complete, the solvents were removed in vacuo, and the residue was treated with an aqueous sodium bicarbonate solution (10 mL) and EtOAc (15 mL). The mixture was stirred at room temperature for 30 min before the two layers were separated. The aqueous layer was extracted with EtOAc (10 mL), and the combined organic extracts were washed with $H_2O$ (10 mL) and saturated aqueous NaCl solution (10 mL), dried over $MgSO_4$, and concentrated in vacuo to afford tetrazole amine 1032 (266 mg; 97%) as a pale-yellow solid. LCMS (ESI) m/z 369 $(M+H)^+$.

317
Synthesis of Tetrazole 1033

A suspension of tetrazole amine 1032 (74 mg, 0.2 mmol) in anhydrous $CH_2Cl_2$ (5.0 mL) was treated with diisopropylethylamine (52 mg, 0.07 mL, 0.4 mmol) and chloroacetyl chloride (34 mg, 0.024 mL, 0.3 mmol) at 0-5° C., and the resulting reaction mixture was stirred at 0-5° C. for 2 h. When TLC and LCMS showed the reaction was complete, the reaction mixture was concentrated in vacuo. The residue was directly purified by flash column chromatography (0-5% MeOH—$CH_2Cl_2$ gradient elution) to afford tetrazole 1033 (43 mg; 48% yield) as a white solid. LCMS (ESI) m/z 445 (M+H)$^+$.

318
Example 15

Synthesis of Compounds 1035 and 1036

Scheme 14 depicts the synthesis of tetrazole derivatives 1035 and 1036. Aldehyde 103 was reduced to 104 which was coupled to boronate 81 to yield alcohol 105. Mesylation of 105, followed by displacement with sodium azide, yielded azide 107. Reduction of 107 to amine 108 was followed by conversion to tetrazole 1035. Cycloaddition of azide 107 with trimethylsilylacetylene, followed by desilylation, afforded triazole 1036.

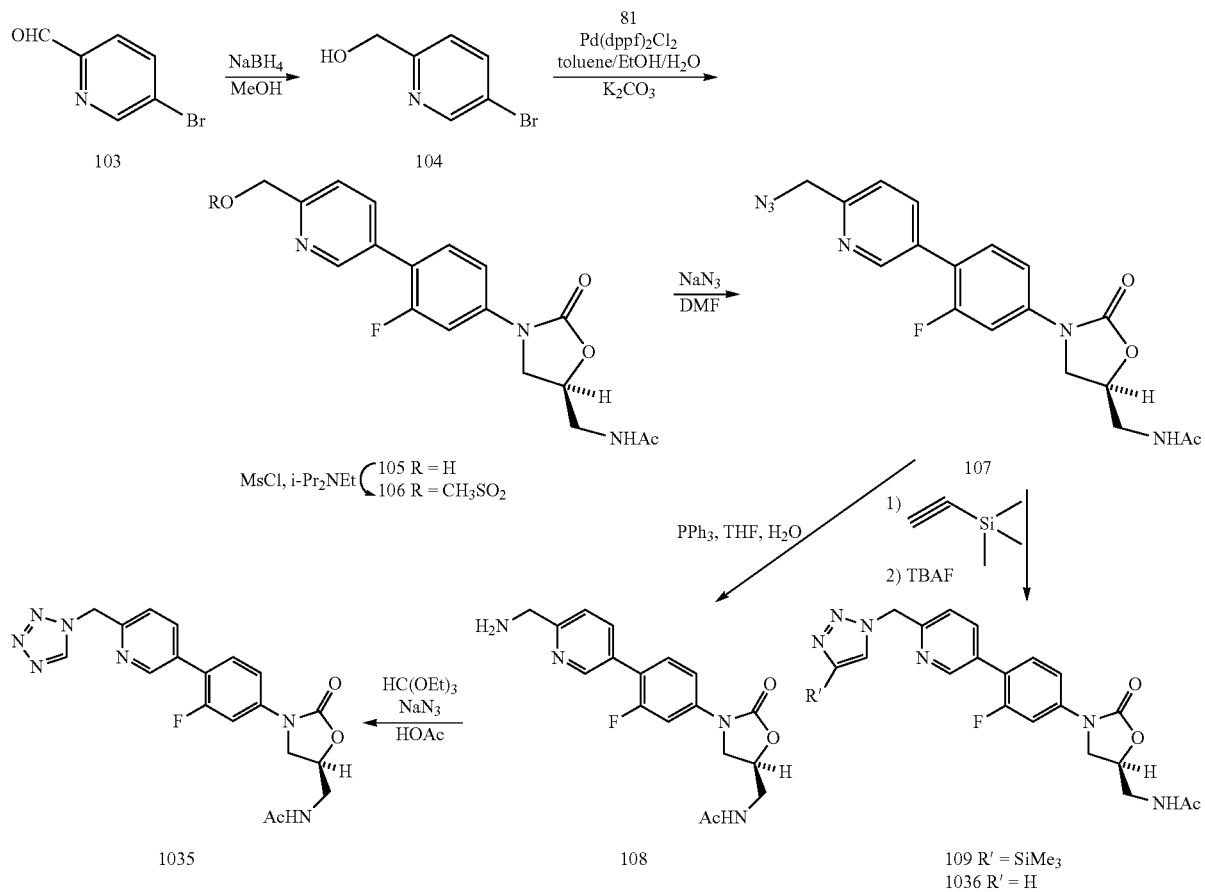

Scheme 14

Synthesis of Tetrazole 1034

A suspension of tetrazole amine 1032 (74 mg, 0.2 mmol) in anhydrous $CH_2Cl_2$ (5.0 mL) was treated with diisopropylethylamine (52 mg, 0.07 mL, 0.4 mmol) and dichloroacetyl chloride (44 mg, 0.029 mL, 0.3 mmol) at 0-5° C., and the resulting reaction mixture was stirred at 0-5° C. for 2 h. When TLC and LCMS showed the reaction was complete, the reaction mixture was concentrated in vacuo. The residue was directly purified by flash column chromatography (0-5% MeOH—$CH_2Cl_2$ gradient elution) to afford tetrazole 1034 (41 mg; 43% yield) as a white solid. LCMS (ESI) m/z 479 (M+H)$^+$.

Synthesis of Aldehyde 103

A solution of 2,5-dibromopyridine (25 g, 105.5 mmol) in toluene (1.24 L) was cooled down to −78° C. before being treated dropwise with a 2.5 M solution of n-BuLi in hexane (50.6 mL, 126.6 mmol) at −78° C. under $N_2$. The resulting reaction mixture was stirred at −78° C. for 1 h before being treated with anhydrous DMF (11.6 g, 12.2 mL, 158.0 mmol) at −78° C. The reaction mixture was stirred at −78° C. for an additional 1 h before being gradually warmed up to room temperature for 6 h. When TLC and LCMS showed that the reaction was complete, the reaction mixture was quenched with water (200 mL). The two layers were separated, and the aqueous layer was extracted with ethyl acetate (2×50 mL).

The combined organic extracts were then washed with $H_2O$ (2×200 mL), and saturated aqueous NaCl solution (100 mL), and dried over $MgSO_4$. The solvents were then removed in vacuo, and the residual pale-yellow oil was purified by flash column chromatography (0-15% EtOAc-hexane gradient elution) to afford aldehyde 103 (10.2 g; 52%) as a pale-yellow solid.

Synthesis of Bromide 104

A solution aldehyde 103 (4.91 g, 26.4 mmol) in methanol (120 mL) was treated with sodium borohydride (1.18 g, 31.7 mmol) at 0-5° C., and the resulting reaction mixture was stirred at 0-5° C. for an additional 1 h. When TLC and LCMS showed that the reaction was complete, the reaction mixture was quenched with water (20 mL). The solvents were then removed in vacuo, and the residue was directly purified by flash column chromatography (5-25% EtOAc-hexane gradient elution) to afford bromide 104 (4.23 g; 85%) as a white solid.

Synthesis of Alcohol 105

A solution of boronate 81 (11.05 g, 29.2 mmol) and bromide 104 (4.227 g, 22.5 mmol) in toluene (150 mL) was treated with solid potassium carbonate (9.315 g, 67.5 mmol), ethanol (50 mL) and $H_2O$ (50 mL) at room temperature, and the resulting reaction mixture was degassed three times under a steady stream of argon before being treated with $Pd(dppf)_2Cl_2$ (564 mg, 0.675) at room temperature. The reaction mixture was then degassed three times again under a steady stream of argon before being warmed up to reflux for 1 h. When LCMS showed that the reaction was complete, the reaction mixture was cooled down to room temperature before being treated with water (200 mL) and ethyl acetate (100 mL). The two layers were separated, and the aqueous layer was extracted with ethyl acetate (2×50 mL). The combined organic extracts were washed with water (2×50 mL) and saturated aqueous NaCl solution (50 mL), dried over $MgSO_4$, and concentrated in vacuo. The residue was then purified by flash column chromatography (0-5% MeOH—$CH_2Cl_2$ gradient elution) to afford alcohol 105 (6.16 g; 76%) as a grey solid.

Synthesis of Azide 107

A suspension of alcohol 105 (2.15 g, 6.0 mmol) in $CH_2Cl_2$ (25 mL) was treated with diisopropylethylamine (1.551 g, 2.10 mL, 12.0 mmol) and methanesulfonyl chloride (756 mg, 0.511 mL, 6.6 mmol) at 0-5° C., and the resulting reaction mixture was stirred at 0-5° C. for an additional 2 h. When TLC and LCMS showed that the reaction was complete, the reaction mixture was treated with water (20 mL) and $CH_2Cl_2$ (40 mL). The two layers were separated, and the aqueous layer was extracted with $CH_2Cl_2$ (20 mL). The combined organic extracts were washed with water (20 mL) and saturated aqueous NaCl solution (20 mL), dried over $MgSO_4$, and concentrated in vacuo. The residue was then purified by flash column chromatography (0-5% MeOH—$CH_2Cl_2$ gradient elution) to afford mesylate 106 (2.47 g; 94%) as a yellow solid.

A solution of mesylate 106 (874 mg, 2.0 mmol) in DMF (8.0 mL) was treated with sodium azide (260 mg, 4.0 mmol) at room temperature, and the resulting reaction mixture was warmed up to 40-45° C. for 3 h. When TLC and LCMS showed that the reaction was complete, the reaction mixture was treated with water (20 mL), and the precipitate was collected by filtration, washed with water (2×10 mL), and dried in vacuo to afford crude azide 107 (699 mg; 91%) as a grey solid, which was of suitable purity for use in subsequent reactions.

Synthesis of Amine 108

A suspension of azide 107 (2.611 g, 6.8 mmol) in THF (25 mL) was treated with water (0.13 mL, 68 mmol) and triphenylphosphine ($PPh_3$, 2.14 g, 8.2 mmol) at room temperature, and the resulting reaction mixture was subsequently stirred at room temperature for 12 h. When TLC and LCMS showed that the reaction was complete, the solvents were removed in vacuo, and the residue was directly purified by flash column chromatography (0-15% MeOH—$CH_2Cl_2$ gradient elution) to afford amine 108 (2.233 g; 92%) as a yellow solid.

Synthesis of Tetrazole 1035

A solution of amine 108 (90 mg, 0.25 mmol) in acetic acid (3.0 mL) was treated with triethyl orthoformate (0.1 mL) and sodium azide (40 mg) at room temperature, and the resulting reaction was subsequently stirred at reflux for 4 h. When TLC and LCMS showed that the reaction was complete, the reaction mixture was cooled down to room temperature and concentrated in vacuo. The residue was then directly purified by flash column chromatography (0-5% MeOH—$CH_2Cl_2$ gradient elution) to afford tetrazole 1035 (43 mg; 36%) as a white solid. LCMS (ESI) m/z 412 $(M+H)^+$.

Synthesis of Triazole 1036

A solution of azide 107 (142 mg, 0.37 mmol) in DMF (5 mL) was treated with thimethylsilyl acetylene (0.5 mL) at room temperature, and the resulting reaction mixture was subsequently stirred at 70-80° C. for 12 h. When TLC and LCMS showed that the reaction was complete, the reaction mixture was cooled down to room temperature before being concentrated in vacuo. The residue was then directly purified by flash column chromatography (0-5% MeOH—$CH_2Cl_2$ gradient elution) to afford triazole 109 (152 mg; 85%) as a pale-yellow oil, which was directly used in the subsequent reaction.

A solution of triazole 109 (152 mg, 0.315 mmol) in THF (10 mL) was treated with a 1N solution of tetrabutylammonium fluoride in THF (2.0 mL) at 0-5° C., and the resulting reaction mixture was stirred at 0-5° C. for 1 h before being gradually warmed up to room temperature for 10 h. When TLC and LCMS showed that the reaction was complete, the reaction mixture was cooled down to room temperature before being concentrated in vacuo. The residue was then directly purified by flash column chromatography (0-5% MeOH—$CH_2Cl_2$ gradient elution) to afford triazole 1036 (67 mg; 52%) as a pale-yellow oil, which solidified upon standing at room temperature in vacuo. LCMS (ESI) m/z 411 $(M+H)^+$.

Example 16

Synthesis of Triazole 1037

A solution of mesylate 52 (436 mg, 1.0 mmol) in anhydrous DMF (5 mL) was treated with 1,2,4-triazole sodium salt (182 mg, 2.0 mmol) at 0-5° C., and the resulting reaction mixture was stirred at 0-5° C. for 1 h before being gradually warmed up to room temperature for 10 h. When TLC and LCMS showed that the reaction was complete, the reaction mixture was concentrated in vacuo. The residue was then directly purified by flash column chromatography (0-5% MeOH—CH$_2$Cl$_2$ gradient elution) to afford triazole 1037 (388 mg; 95%) as a white solid. LCMS (ESI) m/z 410 (M+H)$^+$.

Example 17

Synthesis of Piperazine 1038

A suspension of the aldehyde 92 (142 mg, 0.4 mmol) in MeOH (4.0 mL) and THF (1.0 mL) was treated with 1-(3-chloro-5-trifluoromethyl-pyridin-2-yl)piperazine (106 mg, 0.4 mmol) and sodium triacetoxyborohydride (160 mg, 0.8 mmol) at 25° C., and the resulting reaction mixture was stirred at 25° C. for 6 h. When TLC and LCMS showed the reductive amination reaction was complete, the reaction mixture was concentrated in vacuo. The residue was directly purified by flash column chromatography (0-5% MeOH—CH$_2$Cl$_2$ gradient elution) to afford piperazine 1038 (38 mg; 16% yield) as a colorless oil, which solidified upon standing at room temperature in vacuo. LCMS (ESI) m/z 607 (M+H)$^+$.

Example 18

Synthesis of Tetrazoles 1039-1042

Scheme 15 shows the synthesis of compounds 1039-1042. Nitrile 110 is converted to tetrazole 1039, which was deprotected to afford tetrazole 1040. Tetrazole 1039 is methylated to afford 1041, which was subsequently deprotected to yield 1042.

Scheme 15

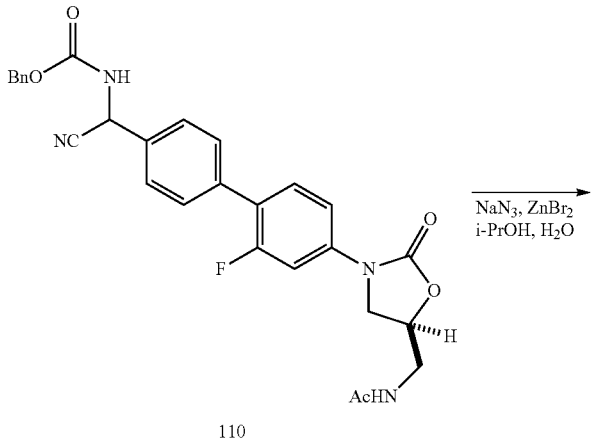

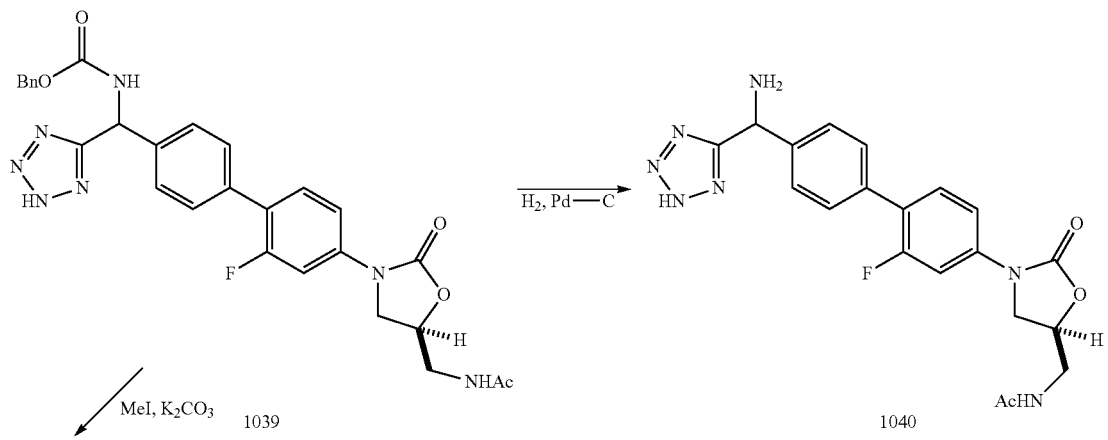

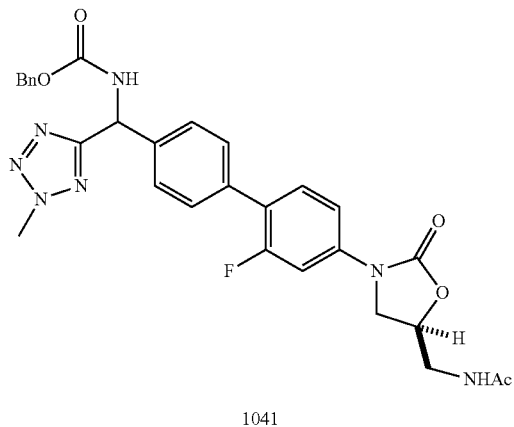

1041

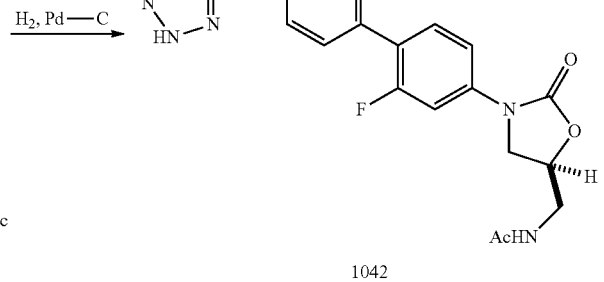

1042

Synthesis of Nitrile 110

A suspension of aldehyde 92 (1.884 g, 5.3 mmol) in MeOH (25 mL) was treated with a solution of NaCN (312 mg, 6.4 mmol) in H$_2$O (10 mL) and a solution of ammonium chloride (340 mg, 6.4 mmol) in H$_2$O (15 mL) at 25° C., and the resulting mixture was stirred at 25° C. for 30 min before being warmed up to 50° C. for 1 h. When TLC and LCMS showed that the reaction was complete, the reaction mixture was cooled down to room temperature before being treated with H$_2$O (25 mL) at 25° C., and the resulting mixture was cooled down to 0-5° C. for 1 h. The solid precipitates were collected by filtration, washed with H$_2$O (2×20 mL) and 20% EtOAc/hexane (2×20 mL), and dried in vacuo. The crude desired N-{3-[4'-(amino-cyano-methyl)-2-fluoro-biphenyl-4-yl]-2-oxo-oxazolidin-5-ylmethyl}-acetamide (1.801 g; 89% yield) was obtained as off-white solids, which by HPLC and $^1$H NMR was of sufficient purity to be used in subsequent reactions. LCMS (ESI) m/z 383 (M+H)$^+$.

A solution of N-{3-[4'-(amino-cyano-methyl)-2-fluoro-biphenyl-4-yl]-2-oxo-oxazolidin-5-ylmethyl}-acetamide obtained above (1.70 g, 4.45 mmol) in THF (40 mL) and H$_2$O (40 mL) was treated with benzyl chloroformate (940 mg, 5.34 mmol) and potassium carbonate (1.23 g, 8.9 mmol) at 25° C., and the resulting reaction mixture was stirred at 25° C. for 2 h. When TLC and LCMS showed the reaction was complete, the reaction mixture was quenched with H$_2$O (20 mL) and EtOAc (50 mL). The two layers were separated, and the aqueous layer was extracted with EtOAc (50 mL). The combined organic extracts were washed with water (2×20 mL), and saturated aqueous NaCl solution (20 mL), dried over MgSO$_4$, and concentrated in vacuo. The residue was then purified by column chromatography (0-5% MeOH—CH$_2$Cl$_2$ gradient elution) to afford the desired nitrile 110 (2.20 g; 96%) as a colorless oil, which solidified upon standing at room temperature in vacuo. This material by $^1$H NMR was found to be a mixture of two diastereomers. LCMS (ESI) m/z 517 (M+H)$^+$.

Synthesis of Tetrazole 1039

A solution of 0.130 g (2.52 mmol) of nitrile 110, 0.033 g (5.04 mmol) of NaN$_3$, and 0.028 g (1.26 mmol) of zinc bromide (ZnBr$_2$) in 9 ml of isopropanol/H$_2$O (1:2) was allowed to stir at reflux for 24 h. Once the reaction mixture cooled down, it was diluted with 1 N HCl, extracted with MeOH/CH$_2$Cl$_2$ (1:3) (40 ml×3), and the combined organic layers were washed with brine, dried over MgSO$_4$, and evaporated to give 0.050 g of tetrazole 1039 as a mixture of tautomers. LCMS (ESI) m/z 560 (M+H)$^+$.

Synthesis of Tetrazole 1040

A solution of 0.030 g of 1039 and 0.020 g of palladium on carbon (Pd/C) (10%) in 6 ml of (1:1 H$_2$O/THF) was allowed to stir at 25° C. under H$_2$ atmosphere (balloon) for 16 h. The reaction mixture was filtered through celite, and washed with MeOH/CH$_2$Cl$_2$. The filtrate was concentrated, washed with small amount of EtOAc, then dried via vacuum to give 0.010 g of tetrazole 1040. LCMS (ESI) m/z 426 (M+H)$^+$.

Synthesis of Methyl Tetrazole 1041

A solution of 0.218 g (0.39 mmol) of 1039, 0.080 g (0.58 mmol) of K$_2$CO$_3$, and 0.061 g (0.43 mmol) of methyl iodide (MeI) in 5 ml of DMF was allowed to stir at 25° C. for 16 h. The reaction solvent was removed by vacuum. The residue was dissolved in a mixture of MeOH/CH$_2$Cl$_2$ (1:1), filtered through a pipette column, and the filtrate was concentrated to give the crude product 1041 in the amount of about 0.220 g. A small amount was purified through preparative HPLC. LCMS (ESI) m/z 574 (M+H)$^+$.

Synthesis of Methyl Tetrazole 1042

A solution of 0.220 g of 1041 and 0.020 g of Pd (10% on carbon) in 3 ml of DMF was allowed to stir at 25° C. under H$_2$ atmosphere (balloon) for 24 h. The solvents were removed by rotary evaporation, the residue was then dissolved in a mixture of MeOH/CH$_2$Cl$_2$, and filtered through celite. The filtrate was concentrated and further purified by preparative HPLC to give 0.052 g of methyl tetrazole 1042. LCMS (ESI) m/z 440 (M+H)$^+$.

Example 19

Synthesis of Pyrazole 1043

To a suspension of 0.048 g (2.0 mmol) of NaH and 0.125 g (1.83 mmol) of pyrazole in 8 ml of DMF at 0° C. was added 0.400 g (0.92 mmol) of mesylate 52. Then, the reaction mixture was warmed up to 25° C., and was allowed to stir for 3 h. The DMF was removed and the residue was purified by preparative TLC to give 0.360 g of pyrazole 1043 (96% yield). LCMS (ESI) m/z 409 (M+H)+.

Example 20

Synthesis of Compounds 1044-1046

Scheme 16 depicts the synthesis of aryl bromides 112-114 required for the synthesis of compounds 1044-1046. Epoxide 111 was treated with 1-formyl piperazine to afford a mixture of 112 and 113. Epoxide ring-opening of 111 with imidazole afforded 114. These bromides were coupled with boronate 81 to deliver the target compounds 1044-1046.

General Procedure for the Synthesis of Compounds 1044-1046 from Bromides 112-114

A suspension of bromide intermediate (1 eq), boronate 81 (1 eq), PdCl$_2$(dppf)$_2$ (0.05 eq), and K$_2$CO$_3$ (4 eq) in a mixture of dioxane/EtOH/H$_2$O (ratio of 3:1:1) was degassed by a stream of argon. The mixture was stirred at 75° C. to 85° C. for 3 to 15 h. The solvent was removed by vacuum and the residue was purified by flash chromatography to afford the product.

Conditions for 1044: 80° C., 3.5 h, flash chromatography (4:100 MeOH/CH$_2$Cl$_2$); Yield 150 mg. LCMS (ESI) m/z 485 (M+H)+.

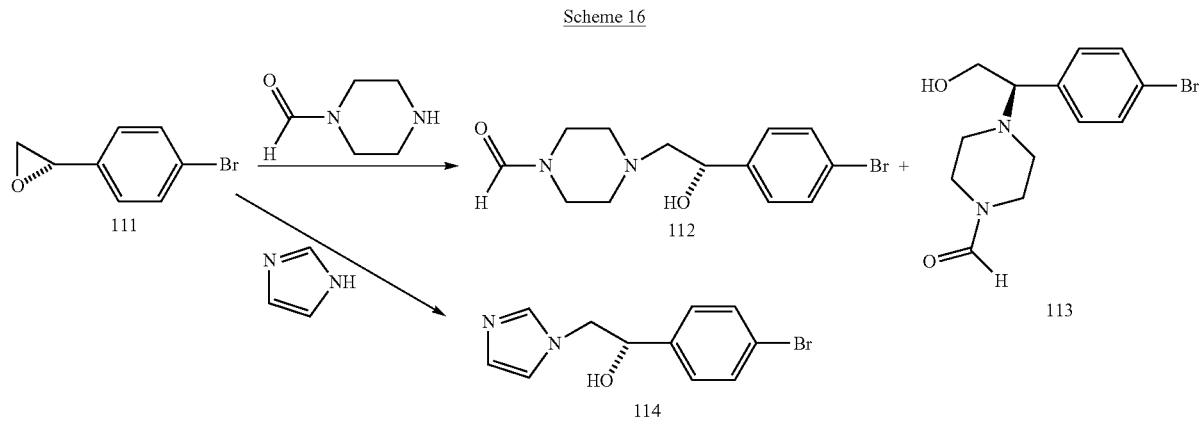

Scheme 16

Synthesis of Epoxide 111

To a solution of 4-bromostyrene (5.00 g, 26.8 mmol) in CH$_2$Cl$_2$ (130 mL) was added 4-methylmorpholine N-oxide (NMO, 12.90 g, 107.1 mmol, anhydrous) and Jacobsen catalyst ((1S,2S)-(+)-[1,2-(cyclohexanodiamino-N,N'-bis(3,5-di-t-butyl-salicylidene)]manganese(III) chloride, 850 mg, 1.34 mmol). The solution was cooled to −78° C., then m-chloroperbenzoic acid (m-CPBA, 7.40 g, 42.8 mmol) was added in four portions every 10 min. The mixture was stirred at −78° C. for 2 h. The reaction was quenched by addition of sodium thiosulfate (Na$_2$S$_2$O$_3$) solution (10.0 g in 30 mL water), then the cooling bath was removed, and water (70 mL), 1N sodium hydroxide (NaOH, 60 mL) was added. The aqueous phase was extracted with CH$_2$Cl$_2$ (30 mL×3), dried with Na$_2$SO$_4$, and evaporated. The residue was purified by flash chromatography (4:100 Et$_2$O/Hexane) to yield 5.20 g epoxide 111 (98% yield).

General Procedure for the Synthesis of Bromides 112-114 from Epoxide 111

To a suspension of epoxide 111 (1 mmol, 1 eq) in acetonitrile (3.0 mL) at room temperature was added lithium perchlorate (LiClO$_4$, 1.05 mmol, 1.05 eq). After the formation of a clear solution, the amine (1.5 mmol, 1.5 eq) was added. The mixture was stirred at room temperature or at 60° C. The solvent was removed under vacuum and the residue was purified by flash chromatography.
Conditions for 112 and 113: room temperature, 16 h, flash chromatography (3:100 MeOH/CH$_2$Cl$_2$). Yield of 112: 132 mg; Yield of 113: 42 mg.
Conditions for 114: 60° C., 4 h, flash chromatography (3:100 MeOH/CH$_2$Cl$_2$). Yield of 114: 103 mg.

Conditions for 1045: 80° C., 3.5 h, flash chromatography (5:100 MeOH/CH$_2$Cl$_2$); Yield 52 mg. LCMS (ESI) m/z 485 (M+H)+.

Conditions for 1046: 80° C., 2.5 h, flash chromatography (10:100 MeOH/CH$_2$Cl$_2$); Yield 155 mg. LCMS (ESI) m/z 439 (M+H)+.

Example 21

Synthesis of Compounds 1047 and 1048

Scheme 17 depicts the synthesis of tetrazoles 1047 and 1048. Azides 53 and 85 were reduced to amines 115 and 116 respectively. These amines were then converted to triazoles 1047 and 1048 by treatment with sodium azide and trimethylorthoformate in hot acetic acid.

Scheme 17

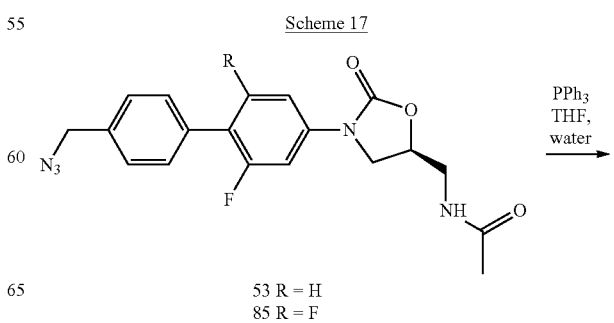

53 R = H
85 R = F

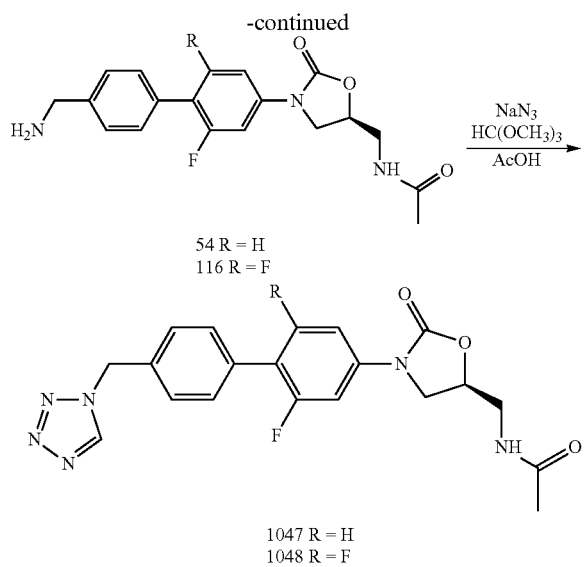

54 R = H
116 R = F

1047 R = H
1048 R = F

Synthesis of Amine 54

Amine 54 was prepared from azide 53 according to the method described in Example 1.

Synthesis of Amine 116

Azide 85 (1.10 g, 2.74 mmol) was dissolved in 17 mL THF and 0.6 mL water. Triphenylphosphine (1.30 g, 4.96 mmol) was added, and the mixture was heated to reflux for 4 h. The mixture was allowed to stir overnight at room temperature, and was partitioned between ethyl acetate and 20 mL 2N aqueous HCl. The organic layer was extracted with 20 mL 2N aqueous HCl, and then the aqueous layer was basified with 85 mL 1N aqueous NaOH. The cloudy aqueous phase was extracted with ethyl acetate (2×), and 5% methanol/methylene chloride (2×). The combined organic extracts were dried over $Na_2SO_4$, and evaporated. The residue was chromatographed on silica gel using a gradient elution of methylene chloride then methanol/methylene chloride (up to 10% methanol) to afford amine 116 (0.587 g, 1.57 mmol; 57%) as a tan solid. LCMS (ESI) m/z 376 $(M+H)^+$.

Synthesis of Tetrazole 1047

A solution of amine 54 (0.20 g, 0.56 mmol) in acetic acid (5 mL) was treated with sodium azide (0.05 g, 0.84 mmol) followed by triethylorthoformate (0.15 mL, 0.90 mmol). The reaction mixture was heated to reflux for 4 h. The mixture was cooled and added to ice water (10 mL). After standing at room temperature for 48 h, the precipitated product was collected by filtration and washed with cold $CH_3OH$ to yield tetrazole 1047 (101 mg; 50%) as a white solid. LCMS (ESI) m/z 474 $(M+H)^+$.

Synthesis of Tetrazole 1048

Tetrazole 1048 was made from amine 116 using the same procedure for the synthesis of 1047. LCMS (ESI) m/z 429.

Example 22

Synthesis of Compounds 1049-1054

Synthesis of 1049

A solution of mesylate 52 (0.10 g, 0.24 mmol) in dimethyl sulfoxide (DMSO, 2.0 mL) was treated with ethyl 4-pyrazole carboxylate (0.03 g, 0.24 mmol), $K_2CO_3$ (0.06 g, 0.46 mmol) and the mixture was heated to 90° C. for 16 h. The reaction mixture was cooled to room temperature, diluted with ethyl acetate (100 mL), and washed with brine (2×50 mL). The organic phase was dried and evaporated. The residue was purified by preparative thin layer chromatography (using 95% $CH_2Cl_2$, 5% MeOH as eluant) to provide 1049. LCMS (ESI) m/z 481 $(M+H)^+$.

Synthesis of 1050

This compound was made from mesylate 52 and 4-(hydroxymethyl)imidazole using the same procedure described for the synthesis of 1049. LCMS (ESI) m/z 439 $(M+H)^+$.

Synthesis of 1051

This compound was made from mesylate 52 and 4-pyrazolecarboxylic acid using the same procedure described for the synthesis of 1049. LCMS (ESI) m/z 453 $(M+H)^+$.

Synthesis of 1052

This compound was made from mesylate 52 and 4-methylpyrazole using the same procedure described for the synthesis of 1049. LCMS (ESI) m/z 423 $(M+H)^+$.

Synthesis of 1053

This compound was made from mesylate 52 and 3-aminopyrazole using the same procedure for the synthesis of 1049. LCMS (ESI) m/z 424 $(M+H)^+$.

Synthesis of 1054

This compound was made from mesylate 52 and pyrrole using the same procedure for the synthesis of 1049. LCMS (ESI) m/z 408 $(M+H)^+$.

Example 23

Synthesis of Aldehyde 1055

A solution of amine 54 (0.20 g, 0.56 mmol) in acetic acid (5 mL) was treated with 2,5-dimethoxy-3-tetrahydrofurancarboxaldehyde (0.12 g, 0.78 mmol). The reaction mixture was heated to reflux for 2 h. The mixture was cooled and the solvent removed under high vacuum. The residue was purified by preparative thin layer chromatography (using 95% $CH_2Cl_2$, 5% MeOH as eluant) to provide 1055. LCMS (ESI) m/z 436 $(M+H)^+$.

Example 24

Synthesis of Tetrazole 1056

A solution of mesylate 52 (0.50 g, 1.14 mmol) in acetonitrile ($CH_3CN$, 5 mL) was treated with tetrazole (12 mL, 5.73 mmol), and triethylamine (0.8 mL, 5.73 mmol), and the mixture was heated to reflux for 18 h. The reaction mixture was cooled to room temperature and diluted with ethyl acetate (100 mL), and washed with brine (2×50 mL). The organic phase was dried and evaporated. The residue was purified by preparative thin layer chromatography (using 95% $CH_2Cl_2$, 5% MeOH as eluant) to provide 1056. LCMS (ESI) m/z 411.

Example 25

Synthesis of Imidazole 1084

Scheme 18 depicts the synthesis of imidazole 1084.

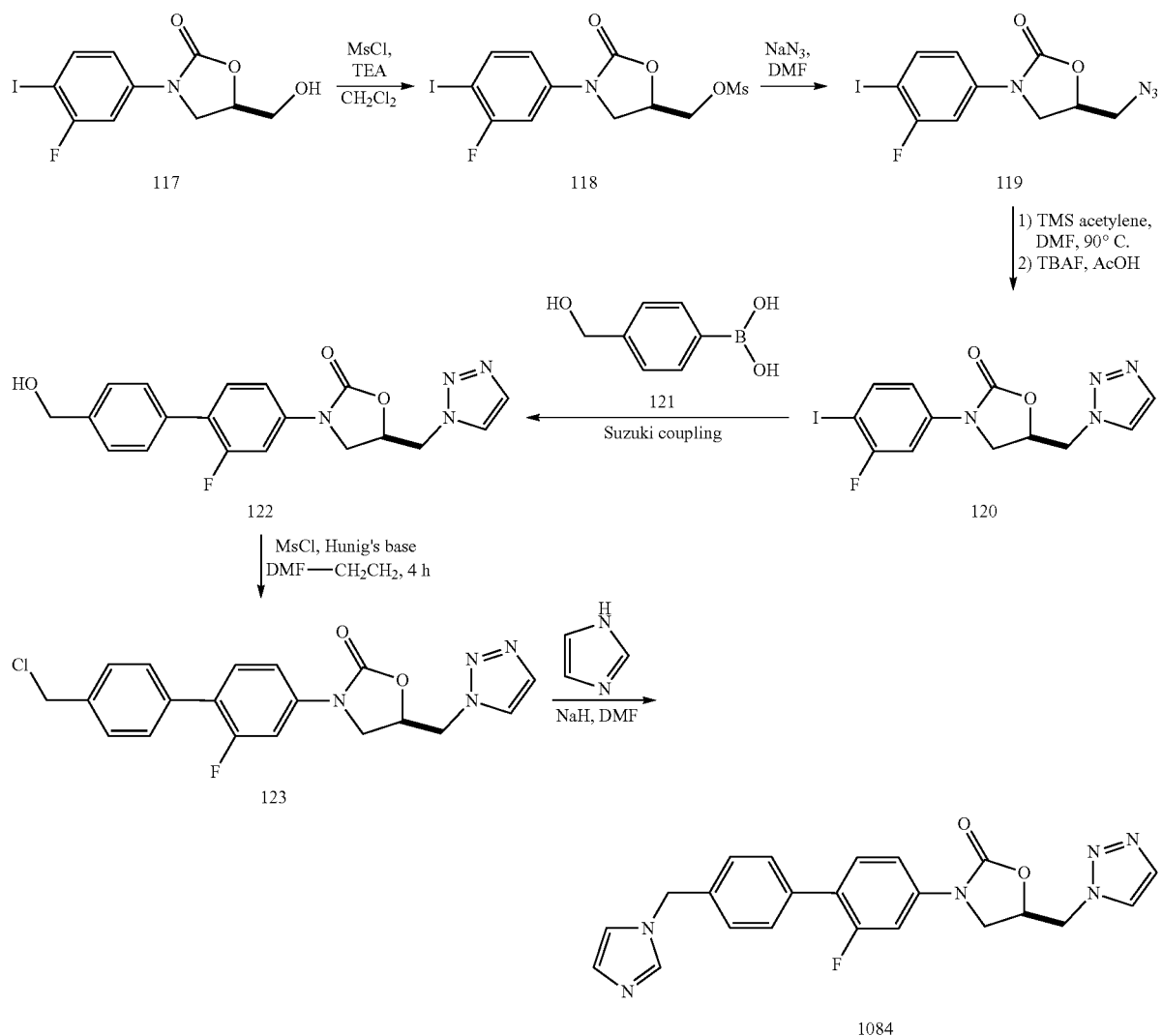

Scheme 18

Synthesis of Iodide 120

To a suspension of alcohol 117 (5 g, 14.84 mmol) in CH$_2$Cl$_2$ (80 mL) was added triethyl amine (2.5 mL, 17.8 mmol) and methanesulphonyl acid chloride (1.4 mL, 17.8 mmol) at 0° C. and stirred the clear solution for 1 h at the same temperature. The reaction mixture was poured into brine solution (100 mL) and extracted with CH$_2$Cl$_2$ (2×50 mL). The combined organic layer was washed with brine solution (3×100 mL), dried over anhydrous Na$_2$SO$_4$, and concentrated to yield mesylate 118. To this was added NaN$_3$ (2 g, 29.7 mmol) and DMF (50 mL) and the mixture was heated to 80° C. overnight. The solution was poured into a mixture of ethyl acetate (150 mL) and water (100 mL). The organic layer was separated and the aqueous portion was extracted with ethyl acetate (3×50 mL). The combined organic layer was washed with brine (1×150 mL), dried over anhydrous Na$_2$SO$_4$, and concentrated to yield 5.4 g of azide 119.

A solution of aizde 119 (5.4 g, 14.84 mmol) and trimethylsilyl acetylene (10.48 mL, 74.2 mmol) in DMF (20 mL) was heated to 90° C. for 12 h. The reaction mixture was concentrated and treated with TBAF (60 mL, 1M in THF) and acetic acid (2 mL, 29.7 mmol) and stirred at ambient temperature for 12 h. The solution was concentrated and poured into a mixture of saturated NH$_4$Cl (50 mL), ethyl acetate (150 mL) and brine solution (50 mL). The organic layer was separated and the aqueous portion was extracted with ethyl acetate (3×50 mL). The combined organic layer was dried over anhydrous Na$_2$SO$_4$, concentrated and the solid thus obtained was washed with water (5×200 mL) to yield 5.7 g of tetrazole derivative 120. LCMS (ESI) m/e 389 (M+H$^+$).

Synthesis of Alcohol 122

To a mixture of tetrazole 120 (5.7 g, 14.84 mmol), boronic acid 121 (2.9 g, 19.29 mmol), K$_2$CO$_3$ (6.0 g, 44.52 mmol)

and Pd(PPh$_3$)$_4$ (857 mg, 5 mol %) was added toluene (120 mL), ethyl alcohol (40 mL) and water (40 mL). The reaction mixture was degassed, flushed with argon, and refluxed for 4 h. The solvent was concentrated under reduced pressure and the residue thus obtained was poured into water (2000 mL). The pale yellow solid was filtered, and dried at 40° C. under vacuum to yield 4.76 g of alcohol 122. LCMS (ESI) m/e 369 (M+H$^+$).

Synthesis of Chloride 123

To a solution of alcohol 122 (4.6 g, 12.5 mmol) and Hunig's base (6.4 mL, 38.75 mmol) in DMF (40 mL) and CH$_2$Cl$_2$ (30 mL) was added methanesulphonyl chloride (2.9 mL, 37.5 mmol) at 0° C., and the resulting solution was stirred at ambient temperature for 3 h. The solution was concentrated to remove the CH$_2$Cl$_2$ and poured into water (1000 mL). The pale yellow solid was filtered and successively washed with water (5×200 mL), 10% ethyl acetate in hexanes (5×100 mL) and 50% ether in hexanes (5×100 mL). The resulting solid was dried at 40° C. under vacuum to yield 4.5 g of chloride 123. LCMS (ESI) m/e 387 (M+H$^+$).

Synthesis of 1084

To a solution of imidazole (31 mg, 0.224 mmol) in DMF (3 mL) was added NaH (17 mg, 0.448 mmol) at 0° C., and the solution was stirred for 20 min at 0° C. Chloride 123 was added and the reaction was stirred at ambient temperature for 90 min. The reaction mixture was concentrated and purified by flash chromatography over silica gel (96:4 CH$_2$Cl$_2$/MeOH) to yield 65 mg of 1084. LCMS (ESI) m/e 419 (M+H$^+$).

Example 26

Synthesis of Imidazole 1086

Scheme 19 depicts the synthesis of imidazole 1086.

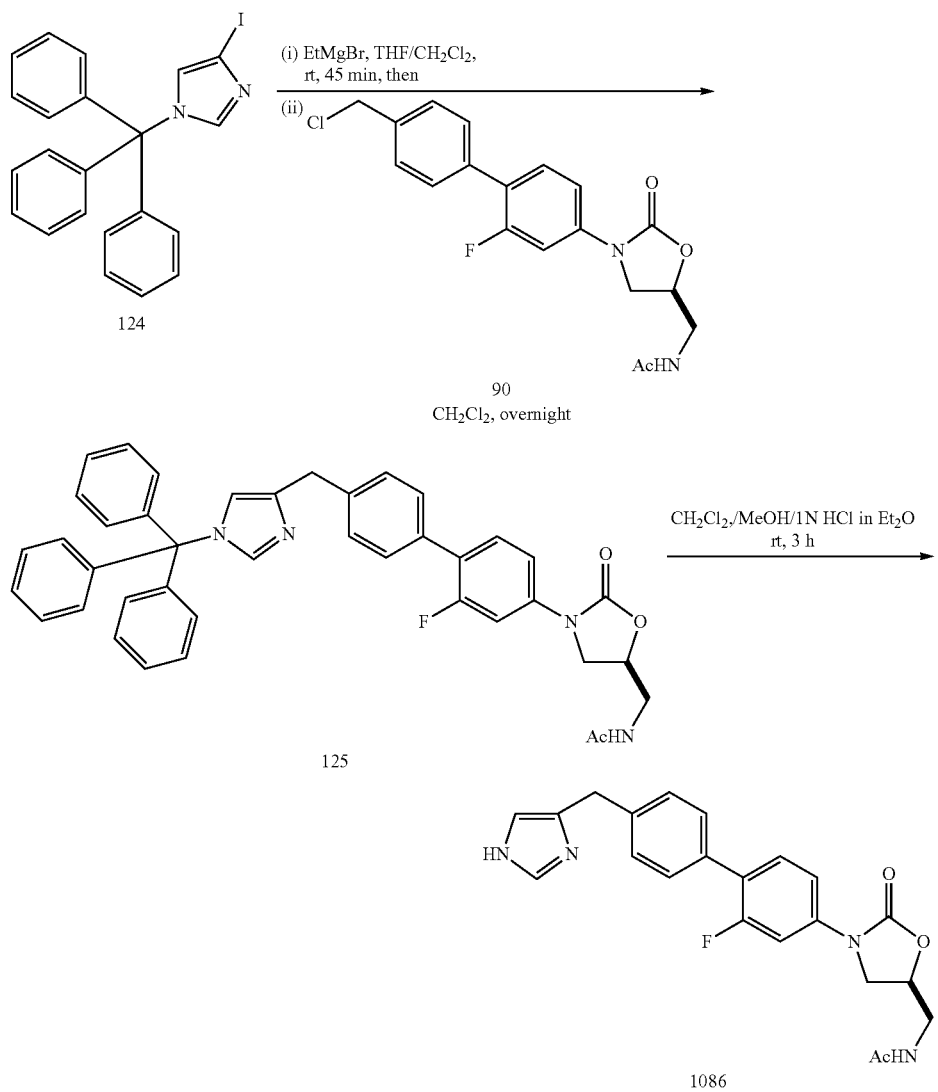

To a solution of imidazole 124 (0.25 g, 0.56 mmol) in dry CH$_2$Cl$_2$ (3 mL) was added 1M ethyl magnesium bromide (EtMgBr) in THF (0.62 mL, 0.62 mmol) at room temperature. After stirring for 45 min, oxazolidinone 90 (0.233 g, 0.62 mmol) was added to the mixture and stirring continued overnight. The reaction was quenched with aqueous NH$_4$Cl (20 mL), extracted with CH$_2$Cl$_2$ (25 mL) and dried over Na$_2$SO$_4$. The solvent was evaporated to yield 125 as a solid residue. The crude was dissolved in 10% MeOH in CH$_2$Cl$_2$ (10 mL), and 1N HCl in diethyl ether (2 mL, 2 mmol) was added, followed by stirring for 3 h. The solvent was evaporated and the residue was partitioned between dilute NH$_4$OH (30 mL) and CH$_2$Cl$_2$ (30 mL). The layers were separated, the aqueous layer was back extracted with CH$_2$Cl$_2$ (2×30 mL), and the combined organic layer was dried over Na$_2$SO$_4$. The solvent was evaporated and the crude product was purified on silica gel column, eluting with 1-8% MeOH in CH$_2$Cl$_2$ to yield imidazole 1086 as a thick oil which precipitated to white solid in diethyl ether (0.051 g, 22%). LCMS (ESI) m/e 409.0 (M+H)$^+$.

Example 27

Synthesis of Compound 1101

Scheme 20 depicts the synthesis of compound 1101.

Synthesis of Alcohol 126

To a stirred solution of 0.050 g (0.14 mmol) of aldehyde 92 and 0.010 g (0.17 mmol) of aminoethanol in 5 ml of DMF was added 0.059 g (0.28 mmol) of NaB(OAc)$_3$H. The reaction mixture was stirred for 2 h. DMF was removed in vacuo, and the residue was purified by preparative TLC to give 0.055 g of alcohol 126. MS (M+1): 438.

Synthesis of Alcohol 127

A solution of 0.050 g (0.11 mmol) of 126, 0.030 g (0.14 mmol) of (BOC)$_2$O, 0.038 g (0.46 mmol) of NaHCO$_3$ in 10 ml of THF:H$_2$O (4:1) was stirred at 25° C. for 6 h. The reaction mixture was diluted with water (30 ml) and extracted with CH$_2$Cl$_2$ (50 ml×3). The combined organic layers were washed with brine (40 ml), dried over MgSO$_4$, and concentrated to give 0.040 g of alcohol 127. MS (M+1): 501.

Synthesis of Compound 1101

A solution of 0.126 g (0.25 mmol) of alcohol 127 and 0.11 ml (0.75 mmol) of Et$_3$N in 5 ml of DMF was heated to 60° C. for 24 h. The reaction mixture was cooled and the solvent was removed in vacuo. The residue was purified via preparative TLC to yield 0.033 g of compound 1101. MS (M+1): 428.

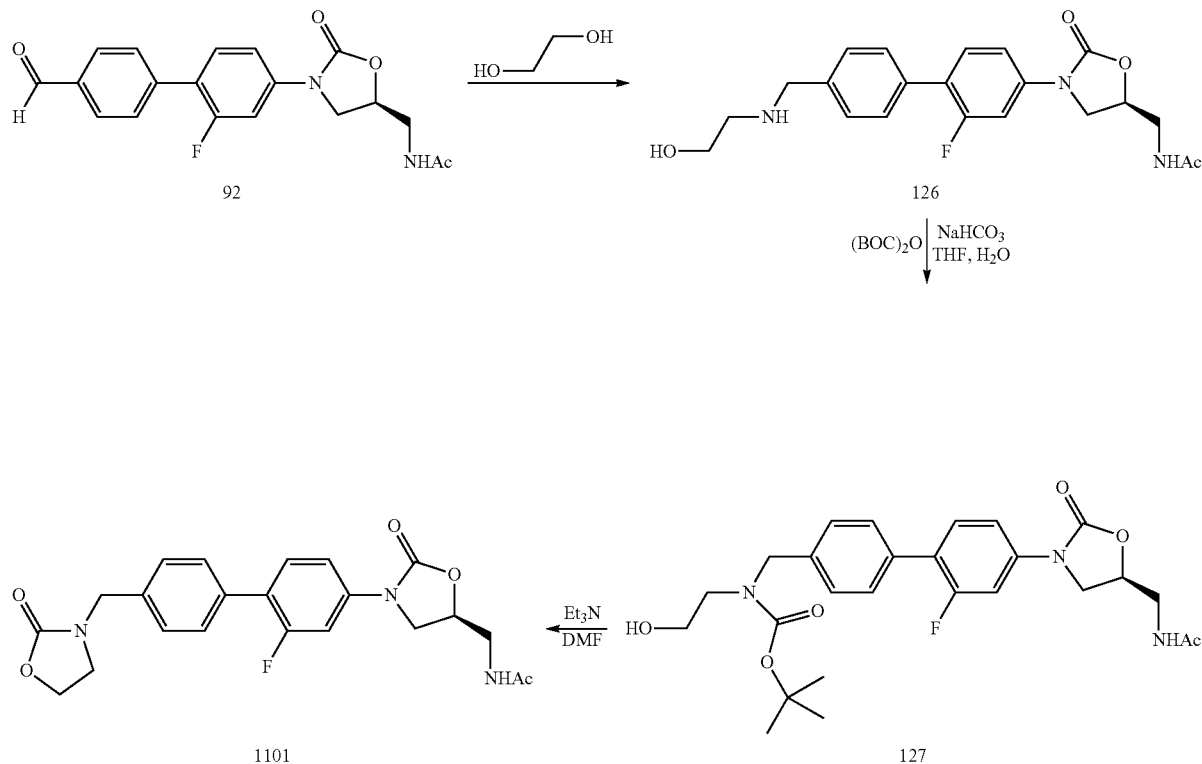

Example 28

Synthesis of Imidazole 1113

Scheme 21 depicts the synthesis of imidazole 1113.

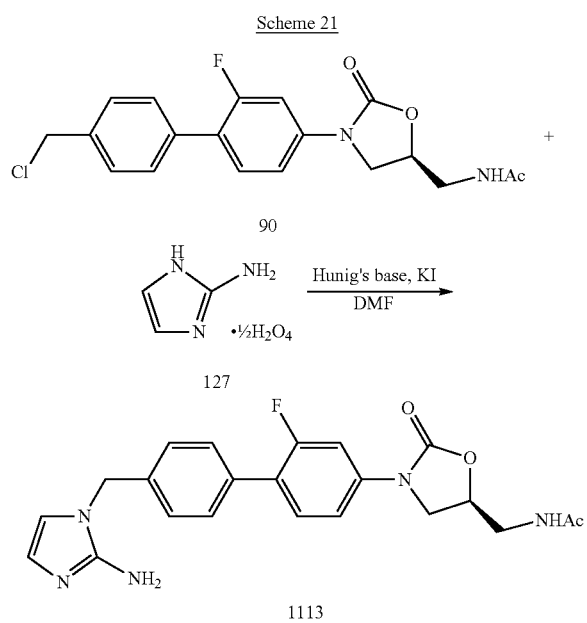

Scheme 22

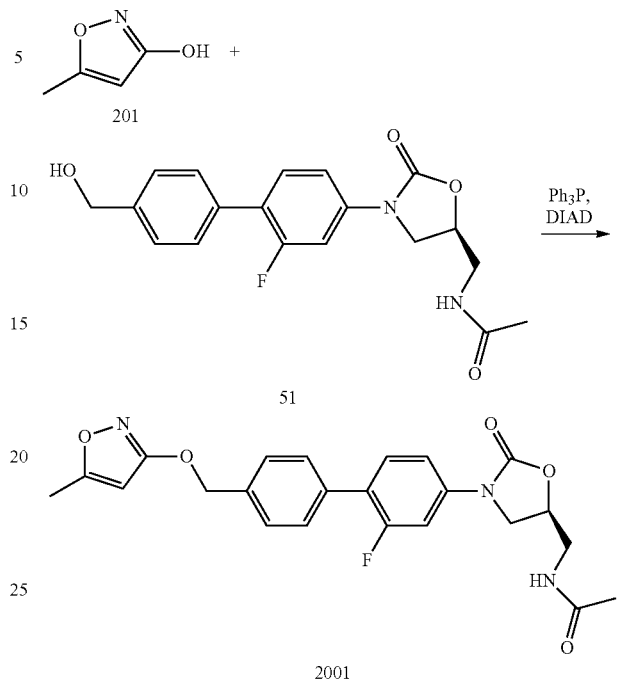

Synthesis of Isoxazole 2001

A mixture of chloride 90 (113 mg, 0.3 mmol), 2-aminoimidazole sulfate 127 (119 mg, 0.9 mmol), N,N-diisopropylethylamine (0.26 mL, 1.5 mmol) and KI (17 mg, 0.1 mmol) in DMF (5 mL) was stirred at room temperature for 12 h. The reaction was concentrated in vacuo, and the crude product was purified by preparative thin layer chromatography (10:1:0.1 $CH_2Cl_2$:MeOH:$NH_3$.$H_2O$) to afford 90 mg of 1113 in a yield of 71%. MS (ESI): 424.0 (100%, (M+H)$^+$).

Example 29

Synthesis of Isoxazole 2001

Scheme 22 depicts the reaction leading to isoxazole 2001. Hydroxyisoxazole 201 was coupled to alcohol 51 using the Mitsunobu reaction to yield isoxazole 2001.

The known isoxazole 201 was synthesized from methyl tetrolate as reported in literature (Iwai, I. et al. *Chem. Pharm. Bull.* 1966, 14, 1277-1286). To a suspension of isoxazole 201 (33 mg, 0.279 mmol), alcohol 51 (100 mg, 0.335 mmol) and triphenyl phosphine (95 mg, 0.363 mmol) was added diisopropyl azodicarboxylate (DIAD, 0.072 mL, 0.363 mmol) at −20° C. The reaction mixture was warmed to ambient temperature and stirred for 3 h. The solution was concentrated and purified by flash chromatography (4% MeOH in 1:1 $CH_2Cl_2$/EtOAc) to yield 64 mg of 2001. LCMS (ESI) m/z 440 (M+H)$^+$.

Example 30

Synthesis of Compounds 2002-2006

Scheme 23 illustrates the reductive amination chemistry leading to compounds 2002-2006. Aldehyde 92 is treated with various amines in the presence of a reducing agent to yield the desired targets.

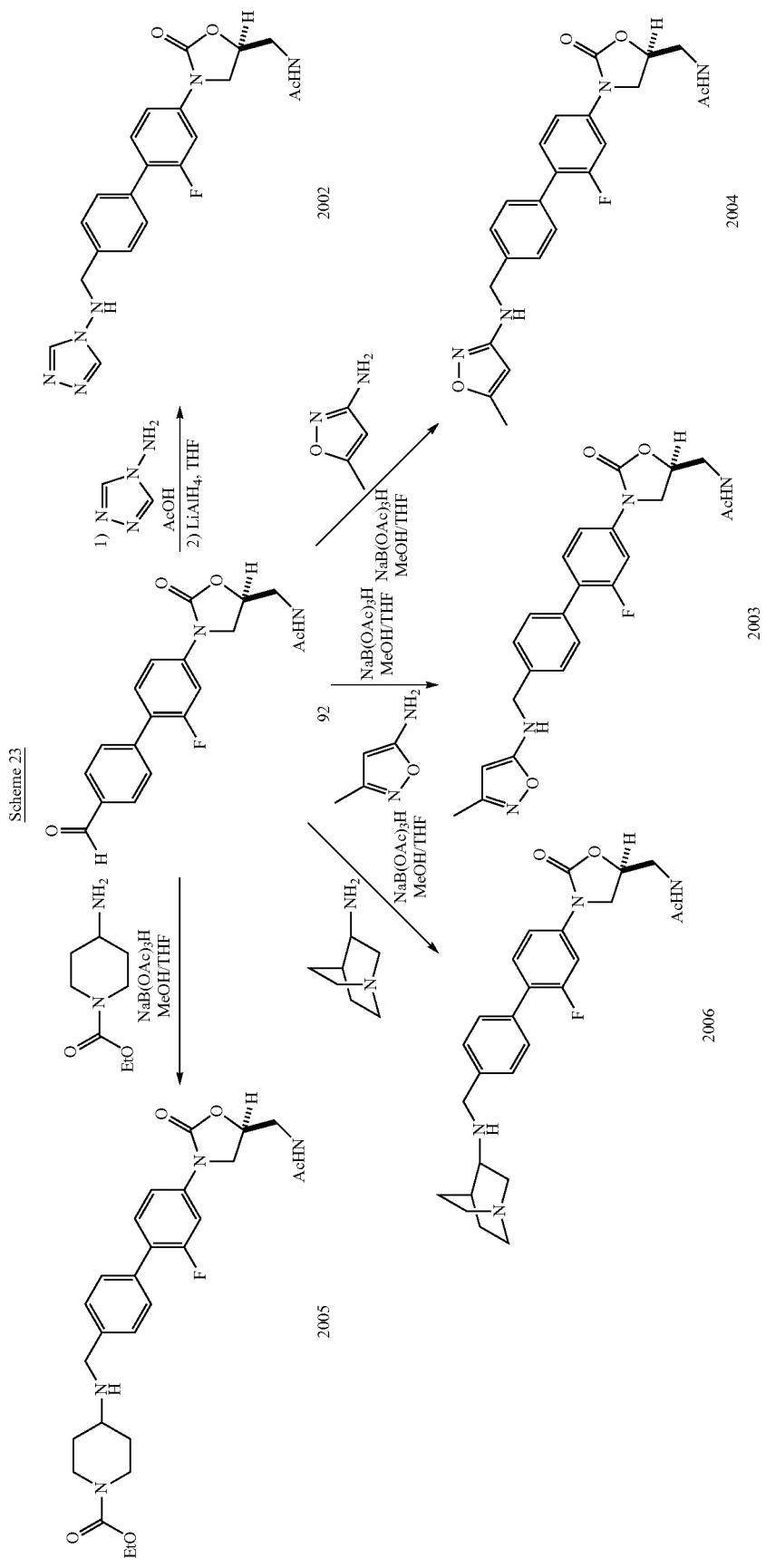

Synthesis of Triazole 2002

A suspension of the aldehyde 92 (178 mg, 0.5 mmol) in THF (4.0 mL) was treated with [1,2,4]triazol-4-ylamine (84 mg, 1.0 mmol) and acetic acid (0.02 mL) at room temperature, and the resulting reaction mixture was stirred at room temperature for 1 h before lithium aluminumhydride (38 mg, 1.0 mmol) was added at room temperature. The resulting reaction mixture was stirred at room temperature for an additional 1 h. When TLC and LCMS showed the reaction was complete, the reaction mixture was concentrated in vacuo, and the residue was directly purified by column chromatography (0-5% MeOH/CH$_2$Cl$_2$ gradient elution) to afford the desired triazole 2002 (40 mg; 19%) as a yellow solid. LCMS (ESI) m/z 425 (M+H)$^+$.

Synthesis of Isoxazole 2003

A suspension of aldehyde 92 (107 mg, 0.3 mmol) in MeOH (4.0 mL) and THF (1.0 mL) was treated with 3-methyl-isoxazol-5-ylamine (59 mg, 0.6 mmol) and sodium triacetoxyborohydride (127 mg, 0.6 mmol) at 25° C., and the resulting reaction mixture was stirred at 25° C. for 6 h. When TLC and LCMS showed the reductive amination reaction was complete, the reaction mixture was concentrated in vacuo. The residue was directly purified by flash column chromatography (0-5% MeOH—CH$_2$Cl$_2$ gradient elution) to afford the desired isoxazole 2003 (12 mg; 9% yield) as a colorless oil, which solidified upon standing at room temperature in vacuo. LCMS (ESI) m/z 439 (M+H)$^+$.

Synthesis of Isoxazole 2004

A solution of aldehyde 92 (107 mg, 0.3 mmol) in MeOH (3.0 mL) and THF (3.0 mL) was treated with 5-methyl-isoxazol-3-ylamine (59 mg, 0.6 mmol) and sodium triacetoxyborohydride (127 mg, 0.6 mmol) at 25° C., and the resulting reaction mixture was stirred at 25° C. for 6 h. When TLC and LCMS showed the reductive amination reaction was complete, the reaction mixture was concentrated in vacuo. The residue was directly purified by flash column chromatography (0-5% MeOH—CH$_2$Cl$_2$ gradient elution) to afford isoxazole 2004 (41 mg; 31%) as a colorless oil, which solidified upon standing at room temperature in vacuo. LCMS (ESI) m/z 439 (M+H)$^+$.

Synthesis of Carbamate 2005

A suspension of aldehyde 92 (142 mg, 0.4 mmol) in MeOH (4.0 mL) and THF (1.0 mL) was treated with 4-amino-piperidine-1-carboxylic acid ethyl ester (69 mg, 0.4 mmol) and sodium triacetoxyborohydride (160 mg, 0.8 mmol) at 25° C., and the resulting reaction mixture was stirred at 25° C. for 6 h. When TLC and LCMS showed the reductive amination reaction was complete, the reaction mixture was concentrated in vacuo. The residue was directly purified by flash column chromatography (0-5% MeOH—CH$_2$Cl$_2$ gradient elution) to afford carbamate 2005 (98 mg; 48% yield) as a colorless oil, which solidified upon standing at room temperature in vacuo. LCMS (ESI) m/z 513 (M+H)$^+$.

Synthesis of Bicyclic Diamine 2006

A suspension of aldehyde 92 (142 mg, 0.4 mmol) in MeOH (4.0 mL) and THF (1.0 mL) was treated with 1-aza-bicyclo[2.2.2]oct-3-ylamine (80 mg, 0.4 mmol) and sodium triacetoxyborohydride (160 mg, 0.8 mmol) at 25° C., and the resulting reaction mixture was stirred at 25° C. for 6 h. When TLC and LCMS showed the reductive amination reaction was complete, the reaction mixture was concentrated in vacuo. The residue was directly purified by flash column chromatography (0-5% MeOH—CH$_2$Cl$_2$ gradient elution) to afford diamine 2006 (71 mg; 38% yield) as a colorless oil, which solidified upon standing at room temperature in vacuo. LCMS (ESI) m/z 467 (M+H)$^+$.

Example 31

Synthesis of Compounds 2007 and 2008

Synthesis of Amide 2007

To a solution of anthranilamide (74 mg, 0.532 mmol) and mesylate 52 (100 mg, 0.229 mmol) in DMF (2.0 mL) was added Hunig's base (185 µL, 1.06 mmol). The mixture was stirred at 80° C. for 16 h, then the mixture was concentrated by vacuum. The residue was directly isolated by reverse-phase preparative HPLC, to give 112 mg of 2007 as a white powder in 88% yield. LCMS (ESI) m/z 477 (M+H)$^+$.

Synthesis of Amide 2008

To a solution of 3-aminothiophene-2-carboxamide (67 mg, 0.459 mmol) and mesylate 52 (100 mg, 0.229 mmol) in DMF (2.0 mL) was added Hunig's base (160 µL, 0.916 mmol). The mixture was stirred at 80° C. for 16 h, then the mixture was concentrated under vacuum. The residue was directly isolated by flash chromatography on silica gel (5:100 MeOH/CH$_2$Cl$_2$ as eluant), to afford 51 mg of 2008 as a white powder in 46% yield. LCMS (ESI) m/z 482 (M+Na)$^+$.

Example 32

Synthesis of Compounds 2009 and 2010

Scheme 24 depicts the synthesis of 2009 and 2010 from D- and L-cycloserine respectively via alkylation with mesylate 52.

Scheme 24

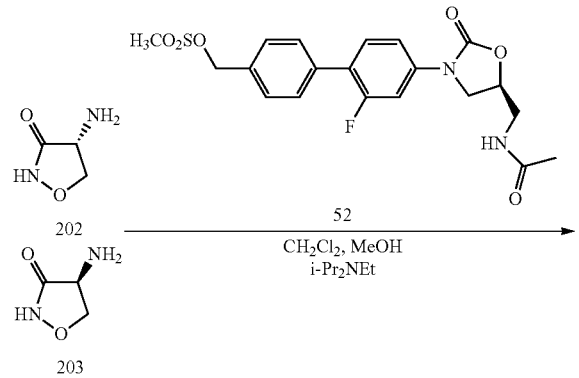

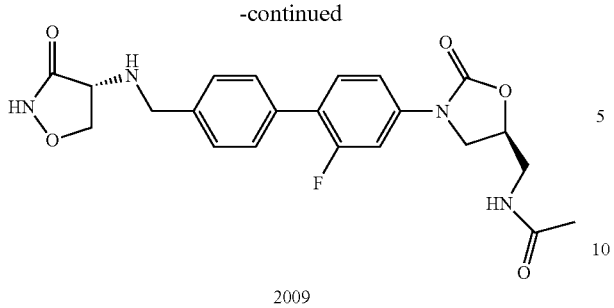

2009

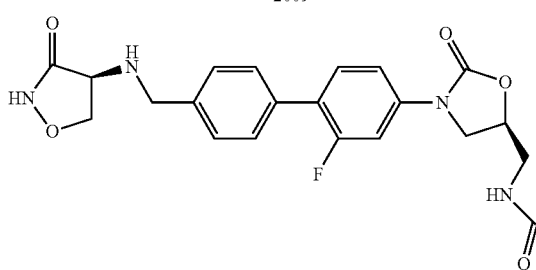

2010

Synthesis of Cycloserine Derivative 2009

A mixture of D-cycloserine 202 (0.22 g, 2.04 mmol) and mesylate 52 (0.30 g, 0.68 mmol) in anhydrous $CH_2Cl_2$ (5 mL), MeOH (5 mL) and Hunig's base (2 mL) was heated to reflux for 3 h. The solvent was evaporated and the crude was purified on silica gel column, eluting with $CH_2Cl_2$/MeOH 20:1 then with $CH_2Cl_2$/MeOH/$NH_4OH$ 20:1:0.04 to 16:1: 0.04 to give a white solid. The isolated solid was titurated with $Et_2O$/$CH_3CN$ 1:1 (15 mL) and the suspension filtered to give analytically pure 2009 as a white solid (0.072 g, 24%). LCMS (ESI) m/z 443 (M+H)$^+$.

Synthesis of Cycloserine Derivative 2010

Compound 2010 was synthesized from L-cycloserine 203 and mesylate 52 as described above for the synthesis of 2009. LCMS (ESI) m/z 443 (M+H)$^+$.

Example 33

Synthesis of Azetidine 2011

A mixture of aldehyde 92 (100 mg, 0.28 mmol) and tert-butyl 3-amino-azetidine-1-carboxylate (58 mg, 0.34 mmol) in THF (2 mL) and DMF (0.5 mL) was stirred at room temperature for 1 h. Sodium triacetoxyborohydride (120 mg, 0.56 mmol) was added. After stirring at room temperature for 2 h, the reaction was concentrated, and the residue was dissolved in $CH_2Cl_2$, washed with water, and dried over $MgSO_4$. The $CH_2Cl_2$ solution was treated with trifluoroacetic acid (0.5 mL) at room temperature. After stirring for 1 h, the mixture was concentrated and purified by preparative thin layer chromatography (10:1:0.05 $CH_2Cl_2$/MeOH/$NH_3.H_2O$) to afford 45 mg of 2011 in a yield of 39%. LCMS (ESI) m/z 413.1 (M+H)$^+$.

Example 34

Synthesis of Thiadiazoles 2012-2013

As Scheme 25 illustrates, thiadiazole 2012 was synthesized from chlorothiadiazole 205 by substitution with amine 54 followed by BOC deprotection. Acylation of 2012 with aminoacid fragments afforded thiadiazoles 2013 and 2014.

Scheme 25

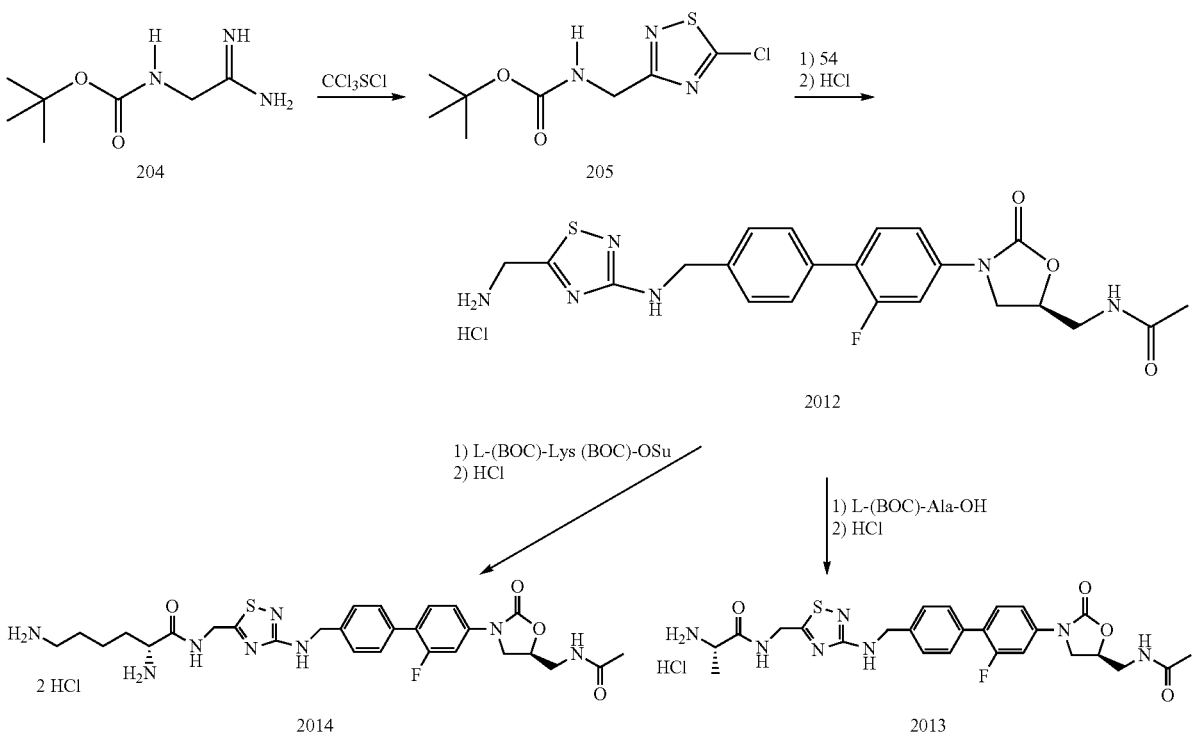

Synthesis of Chlorothiadiazole 205

To a solution of BOC-aminoacetoamidine 204 (3.11 g, 18 mmol) in $CH_2Cl_2$ (60 mL) was added 3M NaOH (12.6 mL, 37.7 mmol) at −10° C. Under strong stirring, half of a solution of trichloromethanesulfenyl chloride ($Cl_3CSCl$, 1.96 mL, 18 mmol) in $CH_2Cl_2$ (30 mL) was slowly added. Then an additional 3M NaOH (12.6 mL, 37.7 mmol) was added, followed by the remaining $Cl_3CSCl$ solution. The mixture was stirred at −10° C. for 30 min and then at 0° C. for 15 min before being diluted with ice-water (50 mL) and extracted with in $CH_2Cl_2$ (2×80 mL). The combined organic layer was washed with brine (1×20 mL), dried over $Na_2SO_4$ and the solvent was evaporated. The crude residue was purified on silica gel eluting with hexanes/ethyl acetate 6:1, yielding 205 as a yellow oil (2.9 g; 65%). $^1$H-NMR (300 MHz, $CDCl_3$) δ 5.12 (s 1H), 4.42-4.40 (m, 2H), 1.29 (s, 9H).

Synthesis of Thiadiazole 2012

To a solution of the amine 54 (1.0 g, 2.8 mmol) in MeOH (15 mL) and DMF (3 mL) was added chlorothiadiazole 205 (800 mg, 3.1 mmol) and Hunig's base (1 mL, 5.6 mmol). The mixture was stirred at 50° C. overnight and then poured into 5% $Na_2CO_3$/ice (20 mL) and extracted with 9:1 $CH_2Cl_2$-isopropanol (2×100 mL). The combined organic layer was dried over $Na_2SO_4$ and the solvent evaporated. The crude residue was purified on silica gel eluting with 10:1 ethyl acetate/$CH_2Cl$ followed by 95:5 ethyl acetate/MeOH, yielding white crystals, which were dissolved in 4M HCl in dioxane (20 mL). The mixture was stirred at room temperature for 2 h. The suspension was filtered and washed with ether (2×10 mL), and dried at high vacuum, yielding 2012 (830 mg; 93%). LCMS (ESI) m/z 471 $(M+H)^+$.

Synthesis of Thiadiazole 2013

To a solution of thiadiazole 2012 (150 mg, 0.30 mmol) in $CH_2Cl_2$ (4 mL) and DMF (3 mL) was added Hunig's base (0.16 mL, 0.90 mmol), (L)-BOC-Ala-OH (67 mg, 0.36 mmol) and 1-(3-dimethylaminopropyl)-3-ethylcarbodiimide hydrochloride (EDCI, 79 mg, 0.42 mmol). The mixture was stirred overnight at room temperature, then additional amounts of (L)-BOC-Ala-OH (34 mg, 0.18 mmol), EDCI (40 mg, 0.21 mmol) and Hunig's base (0.08 mL, 0.44 mmol) were added. The mixture was stirred at room temperature overnight, poured into 1N HCl-ice (20 mL), and extracted with $CH_2Cl_2$-isopropanol 95:5 (2×50 mL). The combined organic layer was washed with water (15 mL), 5% sodium carbonate ($Na_2CO_3$, 15 mL), water (15 mL), brine (15 mL), and then dried over $Na_2SO_4$ and the solvent evaporated. The crude residue was purified on silica gel eluting with ethyl acetate/MeOH 95:5. The residue was dissolved in 4M HCl in dioxane (7 mL). The mixture was stirred at room temperature for 2 h and then evaporated. The residue was diluted with ether (3 mL), filtered, and the solid washed with ether (2×5 mL), then dried at high vacuum, yielding 2013 (122 mg; 91%). LCMS (ESI) m/z 542 $(M+H)^+$.

Synthesis of Thiadiazole 2014

To a solution of thiadiazole 2012 (150 mg, 0.30 mmol) in $CH_2Cl_2$ (3 mL) and DMF (3 mL) was added Hunig's base (0.08 mL, 0.45 mmol) and (L)-BOC-Lys (BOC)-OSu (157 mg, 0.36 mmol). The mixture was stirred overnight at room temperature, poured into 5% $Na_2CO_3$-ice (20 mL), extracted with $CH_2Cl_2$-isopropanol 95:5 (3×50 mL), dried over $Na_2SO_4$ and the solvent evaporated. The crude residue was purified on silica gel eluting with ethyl acetate followed by 5:1 ethyl acetate/MeOH. The BOC-protected material obtained was dissolved in 4M HCl in dioxane (6 mL) and MeOH (2 mL), stirred at room temperature for 3 h and then evaporated. The residue was diluted with ether (6 mL), filtered, washed with ether (2×5 mL) and dried at high vacuum, yielding 2014 (100 mg; 50%). LCMS (ESI) m/z 599 $(M+H)^+$.

Example 35

Synthesis of Compounds 2015-2019

As Scheme 26 illustrates, benzyl chloride 90 served as alkylating agent for thiolates or thiols to afford compounds 2015-2019.

Scheme 26

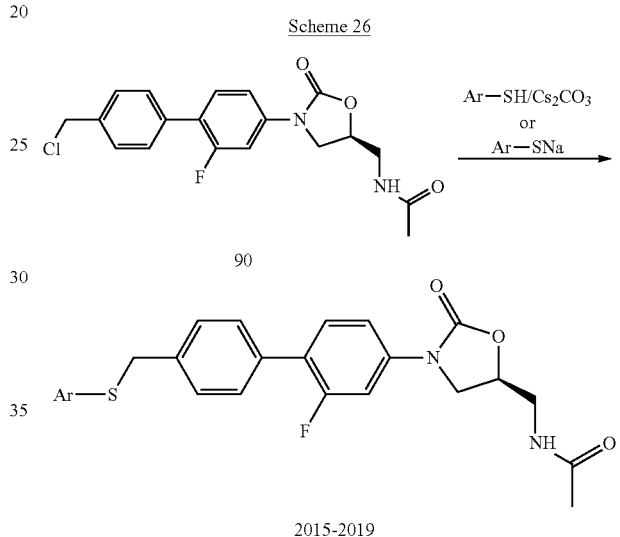

2015-2019

Synthesis of Tetrazole 2015

A solution of chloride 90 (0.15 g, 0.40 mmol) in DMF (2 mL) was treated with 5-mercapto-4-methyltetrazole, sodium salt, dihydrate (0.14 g, 0.80 mmol) and stirred at 23° C. for 0.5 h. The reaction mixture was diluted with water and the precipitate was recovered by vacuum filtration to afford tetrazole 2015 as a white powder (63%). LCMS (ESI) m/z 456 $(M+H)^+$.

Synthesis of Triazole 2016

Tetrazole 2016 was prepared with chloride 90 (0.30 g, 0.80 mmol) and 4-mercapto-1,2,3-triazole, sodium salt, (0.20 g, 1.6 mmol) according to the procedure above used to synthesize tetrazole 2015 to afford 2016 as a yellow powder (0.29 g, 0.66 mmol, 82%). LCMS (ESI) m/z 442 $(M+Na)^+$.

Synthesis of Compound 2017

Compound 2017 was prepared with chloride 90 (0.20 g, 0.53 mmol) and 2-thiobarbituric acid, sodium salt, (0.18 g, 1.1 mmol) according to the procedure above used to synthesize tetrazole 2015 to afford 2017 as a white powder (0.078 g, 0.16 mmol; 30%). LCMS (ESI) m/z 507 $(M+Na)^+$.

Synthesis of Mercaptopyridine 2018

A solution of chloride 90 (0.20 g, 0.53 mmol) in DMF (2.7 mL) was treated with cesium carbonate (0.21 g, 0.64 mmol) and 2-mercaptopyridine (0.071 g, 0.64 mmol) and was stirred at 23° C. for 0.5 h. The reaction mixture was diluted with water and the precipitate was recovered by vacuum filtration to afford 2018 as a yellow powder (91%). LCMS (ESI) m/z 452 (M+H)$^+$.

Synthesis of Mercaptopyridine 2019

Mercaptopyridine 2019 was prepared with chloride 90 (0.20 g, 0.53 mmol), cesium carbonate (0.21 g, 0.64 mmol), and 4-mercaptopyridine (0.071 g, 0.64 mmol) according to the procedure above used to synthesize 2018 to afford a yellow powder (0.078 g, 0.16 mmol; 30%). LCMS (ESI) m/z 452 (M+H)$^+$.

Example 36

Synthesis of Sulfoxides 2020-2023

As Scheme 27 illustrates, sulfides 2015, 2016, 2019, and 2018 were oxidized under controlled conditions to afford sulfoxides 2020-2023 respectively.

Scheme 27

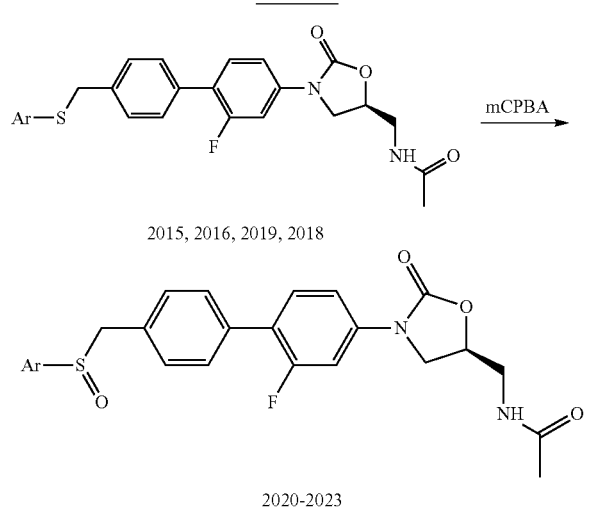

2015, 2016, 2019, 2018

2020-2023

Synthesis of Sulfoxide 2020

A solution of 2015 (0.020 g, 0.044 mmol) in chloroform (0.44 mL) and methanol (0.050 mL) was treated with 3-chloroperoxybenzoic acid (77%, 0.010 g, 0.044 mmol) and stirred at 23° C. for 12 h. The reaction mixture was diluted with methylene chloride, washed with saturated aqueous sodium bicarbonate, dried over Na$_2$SO$_4$, and the solvent removed in vacuo. The crude product was purified with preparative TLC (1:4.5:4.5 MeOH/ethyl acetate/CH$_2$Cl$_2$) to afford 2020 as a white powder (3.6 mg, 0.008 mmol; 19%). LCMS (ESI) m/z 495 (M+Na)$^+$.

Synthesis of Sulfoxide 2021

Sulfoxide 2021 was prepared from sulfide 2016 (0.030 g, 0.068 mmol) and 3-chloroperoxybenzoic acid (77%, 0.015 g, 0.068 mmol) according to the procedure described above for the synthesis of sulfoxide 2020 to afford a white powder (0.021 g, 0.046 mmol; 68%). LCMS (ESI) m/z 480 (M+Na)$^+$.

Synthesis of Sulfoxide 2022

Sulfoxide 2022 was prepared from sulfide 2019 (0.080 g, 0.18 mmol) and 3-chloroperoxybenzoic acid (77%, 0.040 g, 0.18 mmol) according to the procedure described above for the synthesis of sulfoxide 2020 to afford a white powder (0.021 g, 0.094 mmol; 52%). LCMS (ESI) m/z 468 (M+H)$^+$.

Synthesis of Sulfoxide 2023

Sulfoxide 2023 was prepared from sulfide 2018 (0.10 g, 0.22 mmol) and 3-chloroperoxybenzoic acid (77%, 0.050 g, 0.22 mmol) according to the procedure described above for the synthesis of sulfoxide 2020 to afford a white powder (0.068 g, 0.15 mmol; 66%). LCMS (ESI) m/z 466.

Example 37

Synthesis of Sulfones 2024 and 2025

As Scheme 28 illustrates, sulfides 2015 and 2016 were oxidized with excess 3-chloroperoxybenzoic acid to afford sulfones 2024 and 2025.

Scheme 28

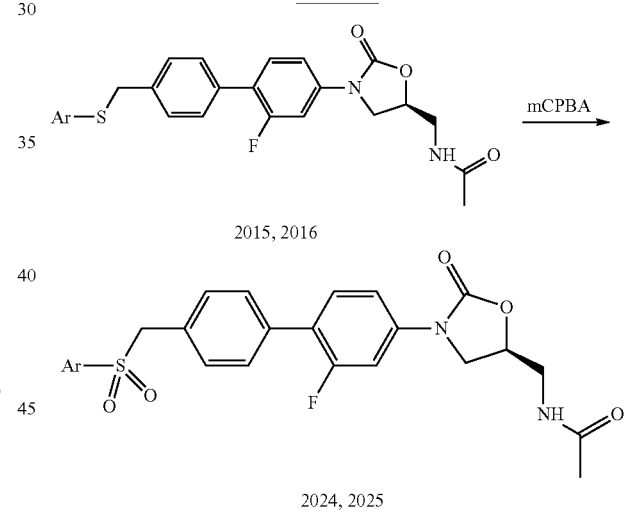

2015, 2016

2024, 2025

Synthesis of Sulfone 2024

A solution of sulfide 2015 (0.020 g, 0.044 mmol) in chloroform (0.44 mL) and methanol (0.050 mL) was treated with 3-chloroperoxybenzoic acid (77%, 0.030 g, 0.13 mmol) and stirred at 23° C. for 1 h and then heated to 50° C. for 12 h. The reaction mixture was cooled to 23° C., diluted with methylene chloride, washed with saturated aqueous sodium bicarbonate, dried (Na$_2$SO$_4$), and the solvent removed in vacuo. The crude product was purified by preparative TLC (5% MeOH in CH$_2$Cl$_2$) to afford sulfone 2024 as a white powder (3.6 mg; 17%). LCMS (ESI) m/z 489 (M+H)$^+$.

Synthesis of Sulfone 2025

A solution of sulfide 2016 (0.050 g, 0.11 mmol) in chloroform (1.1 mL) and methanol (0.1 mL) was treated with 3-chloroperoxybenzoic acid (77%, 0.076 g, 0.34 mmol) and stirred at 23° C. for 2 h. The precipitate was recovered through vacuum filtration to yield sulfone 2025 as a white solid (0.020 g; 37%). LCMS (ESI) m/z 474 (M+H)+.

Example 38

Synthesis of Mercaptotriazole 2026

A solution of mesylate 64 (0.012 g, 0.027 mmol) in DMF (0.14 mL) was treated with 4-mercapto-1,2,3-triazole, sodium salt (7 mg, 0.054 mmol) and was stirred at 45° C. for 2 h. The solvent was removed in vacuo and the crude product was purified by preparative TLC (5% MeOH in $CH_2Cl_2$) to afford mercaptotriazole 2026 as a white solid (3.1 mg; 24%). LCMS (ESI) m/z 456 (M+H)+.

Example 39

Synthesis of Compounds 2027-2033

As Scheme 29 illustrates, benzyl chloride 90 was used to alkylate thiols 207a-g to provide compounds 2027-2033 respectively.

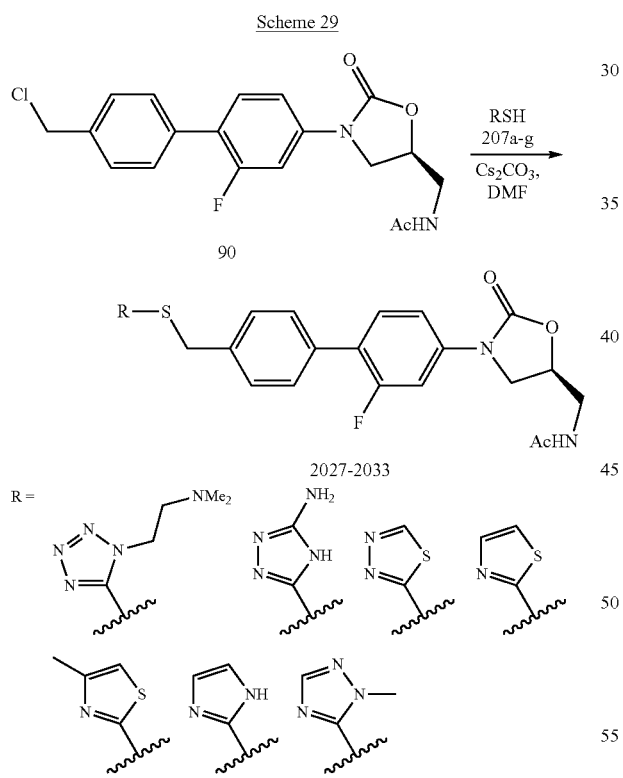

Synthesis of Tetrazole 2027

Benzyl chloride 90 (0.20 g, 0.53 mmol) was dissolved in DMF (5 mL). Thiol 207a (62 mg, 0.53 mmol) and cesium carbonate (0.20 g, 0.64 mmol) were added sequentially and the resulting slurry stirred at room temperature for 4 h. The mixture was poured into 70 mL $H_2O$ and stirred for 1 h. The solids were filtered, rinsed with ether and dried under vacuum to afford tetrazole 2027 as a brown solid (187 mg, 0.36 mmol). LCMS (ESI) m/z 514 (M+H)+.

Synthesis of Triazole 2028

Triazole 2028 was synthesized by the process described for 2027 above using thiol 207b in place of 207a to yield 138 mg of triazole 2028 as a yellow solid (0.30 mmol). LCMS (ESI) m/z 457 (M+H)+.

Synthesis of Thiadiazole 2029

Thiadiazole 2029 was synthesized by the process described for 2027 above using thiol 207c in place of 207a to yield 147 mg of thiadiazole 2029 as a white solid (0.32 mmol). LCMS (ESI) m/z 481 (M+Na)+, 522 (M+Na+$CH_3CN$)+.

Synthesis of Thiazole 2030

Thiazole 2030 was synthesized by the process described for 2027 above using thiol 207d in place of 207a to yield 129 mg of thiazole 2030 as a white solid (0.28 mmol). LCMS (ESI) m/z 458 (M+H)+, 521 (M+Na+$CH_3CN$)+.

Synthesis of Thiazole 2031

Thiazole 2031 was synthesized by the process described for 2027 above using thiol 207e in place of 207a to yield 155 mg of thiazole 2031 as an off-white solid (0.33 mmol). LCMS (ESI) m/z 472 (M+H)+.

Synthesis of Imidazole 2032

Imidazole 2032 was synthesized by the process described for 2027 above using thiol 207f in place of 207a to yield 91 mg of imidazole 2032 as a white solid (0.21 mmol). LCMS (ESI) m/z 441 (M+H)+.

Synthesis of Triazole 2033

Triazole 2033 was synthesized by the process described for 2027 above using thiol 207g in place of 207a to yield 91 mg of triazole 2033 as a white solid (0.21 mmol). LCMS (ESI) m/z 456 (M+H)+, 478 (M+Na)+, 519 (M+Na+$CH_3CN$)+.

Example 40

Synthesis of Compounds 2034-2039

As Scheme 30 illustrates, compounds 2027 and 2029-2033 were oxidized to afford sulfoxides 2034-2039 respectively.

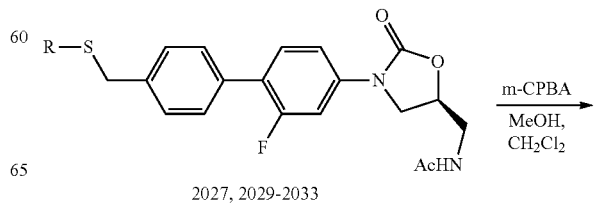

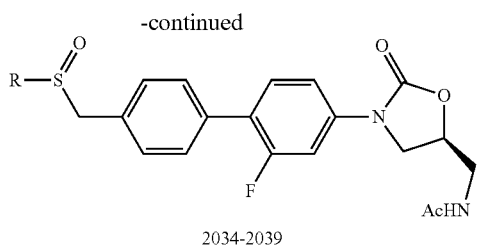

2034-2039

Synthesis of Sulfoxide 2034

Tetrazole 2027 (80 mg, 0.16 mmol) was dissolved in 3:1 $CH_2Cl_2$/MeOH (3 mL) m-CPBA was added (75% pure; 39 mg, 0.17 mmol) and the mixture was stirred at room temperature for 6 h. The reaction mixture was poured into 50 mL ether and stirred for 1 h. The solids were filtered and dried in vacuo to give sulfoxide 2034 as an off-white solid (55 mg, 0.10 mmol). LCMS (ESI) m/z 530 $(M+H)^+$.

Synthesis of Sulfoxide 2035

Sulfoxide 2035 was synthesized by the process described above for 2034 starting with thiadiazole 2029 in place of tetrazole 2027 to yield 39 mg of 2035 as a white solid (0.08 mmol). LCMS (ESI) m/z 497 $(M+Na)^+$, 538 $(M+Na+CH_3CN)^+$.

Synthesis of Sulfoxide 2036

Sulfoxide 2036 was synthesized by the process described above for 2034 starting with thiazole 2030 in place of tetrazole 2027 to yield 48 mg of 2036 as an off-white solid (0.10 mmol). LCMS (ESI) m/z 496 $(M+Na)^+$, 537 $(M+Na+CH_3CN)^+$.

Synthesis of Sulfoxide 2037

Sulfoxide 2037 was synthesized by the process described above for 2034 starting with thiazole 2031 in place of tetrazole 2027 to yield 44 mg of 2037 as an off-white solid (0.09 mmol). LCMS (ESI) m/z 488 $(M+H)^+$, 510 $(M+Na)^+$, 551 $(M+Na+CH_3CN)^+$.

Synthesis of Sulfoxide 2038

Sulfoxide 2038 was synthesized by the process described above for 2034 starting with imidazole 2032 in place of tetrazole 2027 to yield 51 mg of 2038 as a white solid (0.11 mmol). LCMS (ESI) m/z 457 $(M+H)^+$.

Synthesis of Sulfoxide 2039

Sulfoxide 2039 was synthesized by the process described above for 2034 starting with triazole 2033 in place of tetrazole 2027 to yield 48 mg of 2039 as a white solid (0.10 mmol). LCMS (ESI) m/z 472 $(M+H)^+$ 494 $(M+Na)^+$, 535 $(M+Na+CH_3CN)^+$.

Example 41

Synthesis of Compound 2040

A solution of mesylate 106 (43.7 mg, 1.0 mmol) in anhydrous DMF (4.0 mL) was treated with 1H-5-mercapto-1,2,3-triazole sodium salt (24.6 mg, 2.0 mmol) at room temperature, and the resulting reaction mixture was stirred at room temperature overnight. When TLC and LCMS showed that the reaction was complete, the reaction mixture was concentrated in vacuo, and the residue was directly purified by flash column chromatography (0-5% MeOH—$CH_2Cl_2$ gradient elution) to afford mercaptotriazole 2040 (29.0 mg; 66%) as a pale-yellow solid. LCMS (ESI) m/z 443 $(M+H)^+$.

Example 42

Synthesis of Compounds 2043 and 2044

Synthesis of Compound 2043

A solution of amine 54 (0.070 g, 0.20 mmol) in DMF (1.0 mL) was treated with triethylamine (0.055 mL, 0.40 mmol) and 1-methyl-1H-imidazole-4-sulfonyl chloride (0.039 mg, 0.22 mmol) and stirred at 23° C. for 30 minutes. The solvent was removed in vacuo, and the crude product was purified by flash chromatography (4.5:4.5:1 methylene chloride/ethyl acetate/methanol) to afford compound 2043 (0.054 g, 0.11 mmol, 55%). MS (ESI): 502 $(M+H)^+$.

Synthesis of Compound 2044

A solution of amine 54 (0.070 g, 0.20 mmol) in DMF (1.0 mL) was treated with triethylamine (0.055 mL, 0.40 mmol) and 6-morpholin-4-yl-pyridine-3-sulfonyl chloride (0.057 g, 0.22 mmol) and stirred at 23° C. for 30 minutes. The solvent was removed in vacuo, and the crude product was purified by flash chromatography (0-10% methanol in 1:1 ethyl acetate/methylene chloride) to afford compound 2044 (0.052 g, 0.09 mmol, 45%). MS (ESI): 584 $(M+H)^+$.

Example 43

Synthesis of Compound 2047

A solution of chloride 90 (0.19 g, 0.50 mmol) in DMF (5 mL) was treated with 3-mercapto-1,2,4-triazole (0.20 g, 1.0 mmol) and $Cs_2CO_3$ (0.33 g, 1.0 mmol), and stirred at 23° C. for 1 h. The reaction mixture was diluted with $H_2O$ (45 mL), and the resulting precipitate filtered, washed with $H_2O$ and dried under vacuum to afford compound 2047 (0.139 g, 0.315 mmol, 63%) as a white powder. MS (ESI): 442 $(M+H)^+$.

Example 44

Synthesis of Compound 2050

Scheme 31 depicts the synthesis of compound 2050.

Scheme 31

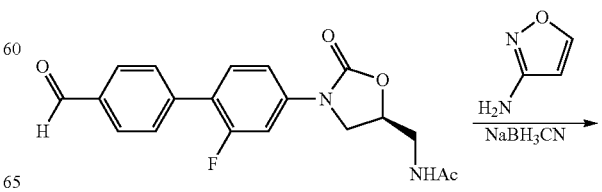

92

-continued

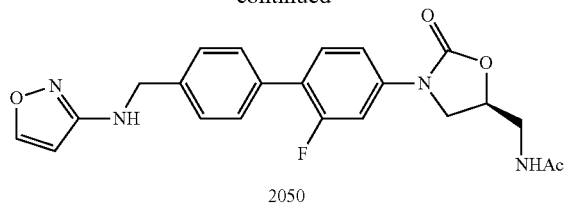

2050

To a solution of 0.050 g (0.15 mmol) of aldehyde 92 and 0.026 g (0.30 mmol) of aminoisoxazole in 2 ml of TFA at 25° C. was added 0.018 g (0.30 mmol) of sodium cyanoborohydride (NaBH$_3$CN). The reaction mixture was stirred at 25° C. for 4 h. The TFA was removed, and the residue was purified by preparative TLC to give 0.040 g of compound 2050. MS (M+1): 425.

Example 45

Synthesis of Compounds 3001-3004

As Scheme 32 illustrates, bromide 301 was coupled to boronate 81 to yield pyridyl derivative 3001. Successive oxidations provided sulfoxide 3002, sulfone 3003, and the pyridyl N-oxide 3004.

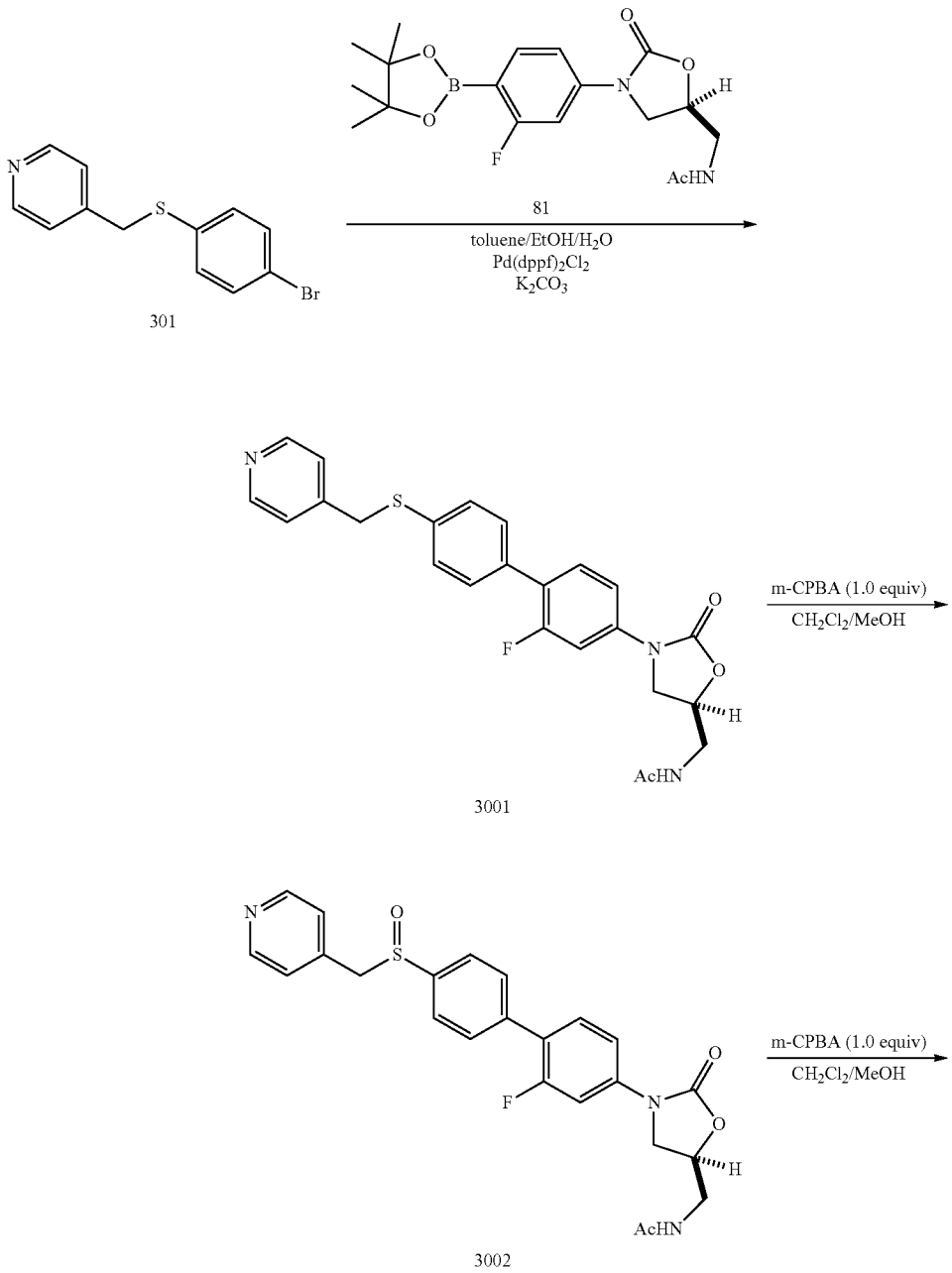

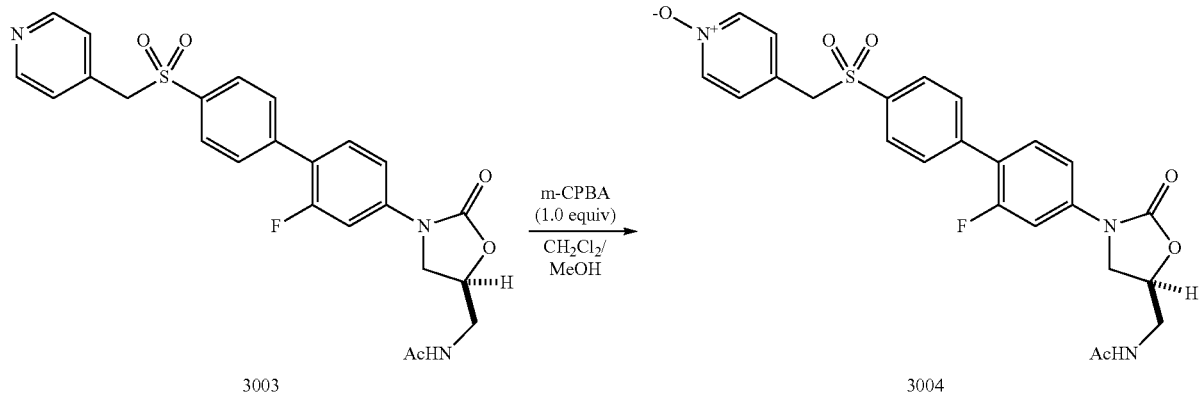

Synthesis of Bromide 301

A suspension of 4-bromomethylpyridine hydrochloride (1.59 g, 6.3 mmol) in THF (10 mL) was treated dropwise with a solution of potassium carbonate (3.33 g, 24.0 mmol) in H₂O (6 mL) at 0-5° C., and the resulting mixture was stirred at 0-5° C. for 10 min before being treated dropwise with a solution of 4-bromo-benzenethiol (1.14 g, 6.0 mmol) in THF (5.0 mL) at 0-5° C. under N₂. The resulting reaction mixture was subsequently stirred at 0-5° C. for an additional 20 min. When TLC and LCMS showed that the reaction was complete, the reaction mixture was treated with water (15 mL) and ethyl acetate (25 mL). The two layers were separated, and the aqueous layer was extracted with ethyl acetate (2×20 mL). The combined organic extracts were washed with water (2×15 mL) and saturated aqueous NaCl solution (10 mL), dried over MgSO₄, and concentrated in vacuo. The residue was purified by flash column chromatography (5-25% EtOAc-hexane gradient elution) to afford the desired 4-(4-bromo-phenylsulfanylmethyl) pyridine 301 (1.374 g; 82%) as a pale-yellow solid, which was directly used in subsequent reactions.

Synthesis of Compound 3001

A solution of boronate 81 (200 mg, 0.53 mmol) and bromide 301 (150 mg, 0.53 mmol) in toluene (9 mL) was treated with solid potassium carbonate (220 mg, 1.6 mmol), ethanol (3.0 mL) and H₂O (3.0 mL) at room temperature, and the resulting reaction mixture was degassed three times under a steady stream of argon before being treated with Pd(dppf)₂Cl₂ (16 mg, 0.013 mmol) at room temperature. The reaction mixture was then degassed three times again under a steady stream of argon before being warmed up to reflux for 2 h. When LCMS showed that the reaction was complete, the reaction mixture was cooled down to room temperature before being treated with water (10 mL) and ethyl acetate (20 mL). The two layers were separated, and the aqueous layer was extracted with ethyl acetate (2×10 mL). The combined organic extracts were washed with water (2×10 mL) and saturated aqueous NaCl solution (10 mL), dried over MgSO₄, and concentrated in vacuo. The residue was then purified by flash column chromatography (0-5% MeOH—CH₂Cl₂ gradient elution) to afford compound 3001 (177 mg; 74%) as a yellow oil, which solidified upon standing at room temperature in vacuo. LCMS (ESI) m/z 452 (M+H)⁺.

Synthesis of Sulfoxide 3002

A solution of compound 3001 (58 mg, 0.13 mmol) in CH₂Cl₂ (2.0 mL) and MeOH (0.5 mL) was treated with m-CPBA (22 mg, 0.13 mmol) at room temperature, and the resulting reaction mixture was stirred at room temperature for 2 h. The solvents were removed, and the residue was directly purified by flash column chromatography (0-5% MeOH—CH₂Cl₂ gradient elution) to afford sulfoxide 3002 (43 mg; 71%) as a colorless oil, which solidified upon standing at room temperature in vacuo. LCMS (ESI) m/z 468 (M+H)⁺.

Synthesis of Sulfone 3003

A solution of sulfoxide 2002 (22 mg, 0.047 mmol) in CH₂Cl₂ (2.0 mL) and MeOH (0.5 mL) was treated with m-CPBA (9.0 mg, 0.047 mmol) at room temperature, and the resulting reaction mixture was stirred at room temperature for 2 h. The solvents were removed, and the residue was directly purified by flash column chromatography (0-5% MeOH—CH₂Cl₂ gradient elution) to afford sulfone 3003 (16 mg; 71%) as a colorless oil, which solidified upon standing at room temperature in vacuo. LCMS (ESI) m/z 484 (M+H)⁺.

Synthesis of Pyridyl N-Oxide 3004

A solution of sulfone 3003 (16 mg, 0.033 mmol) in CH₂Cl₂ (1.0 mL) and MeOH (0.5 mL) was treated with m-CPBA (6.0 mg, 0.033 mmol) at room temperature, and the resulting reaction mixture was stirred at room temperature for 2 h. The solvents were removed, and the residue was directly purified by flash column chromatography (0-5% MeOH—CH₂Cl₂ gradient elution) to afford the pyridyl N-oxide 3004 (11 mg; 67% yield) as colorless oil, which solidified upon standing at room temperature in vacuo. LCMS (ESI) m/z 500 (M+H)⁺.

Example 46

Synthesis of Compound 3005

Scheme 33 illustrates the synthesis of compound 3005.

Scheme 33

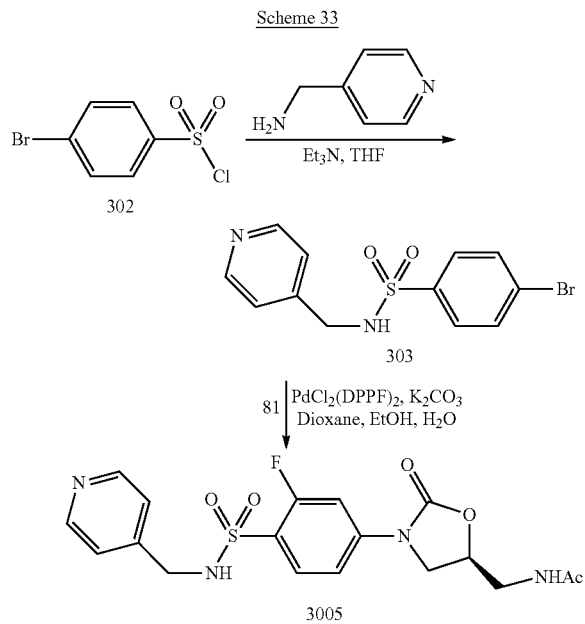

Synthesis of Bromide 303

4-bromobenzenesulfonyl chloride 302 (2.56 g, 10 mmol) was added to a solution of 4-aminomethylpyridine (1.08 g, 10 mmol) and triethylamine (2 mL, 14.3 mmol) in THF (20 mL) at 0° C. After stirring at same temperature for 1 h, 50 mL of cool water was added. A white solid was collected by filtration, washing with EtOAc and dried in vacuum to give 3.10 g of bromide 303 in a yield of 95%.

Synthesis of Compound 3005

Bromide 303 (327 mg, 1 mmol), boronate 81 (378 mg, 1 mmol), Pd(dppf)$_2$Cl$_2$ (40 mg, 0.05 mmol) and K$_2$CO$_3$ (414 mg, 3 mmol) were dissolved 8 mL of a mixture of dioxane:EtOH:H$_2$O (3:1:1) under argon atmosphere. After heating at 100° C. for 12 hours, the reaction was added to 20 mL of cool water. The organic solvent was removed in vacuo and the crude product was collected by filtration. The crude product was treated with active charcoal and recrystallized in a mixed solvent system (1:2:2 MeOH:CH$_2$Cl$_2$:acetone) to give 155 mg of 3005 in a yield of 31%. MS (ESI): 499.1 (100%, (M+H)$^+$).

Example 47

Synthesis of Amide 4008

A solution of amine 54 (36 mg, 0.1 mmol) in DMF was treated with quinoline-4-carboxylic acid (26 mg, 0.15 mmol, 1.5 equiv) at 25° C. under N$_2$, and the resulting mixture was treated with EDCI (28.5 mg, 0.15 mmol, 1.5 equiv) at 25° C. under N$_2$. The reaction mixture was subsequently stirred at 25° C. for 12 h. When TLC and HPLC showed the coupling reaction was complete, the reaction mixture was concentrated in vacuo. The residue was then directly purified by flash column chromatography (0-7% MeOH—CH$_2$Cl$_2$ gradient elution) to afford the desired amide 4008 (36.4 mg, 71% yield) as an off-white powder. LCMS (ESI) m/e 513 (M$^+$+H).

Example 48

General Synthesis of Carboxylic Acid-Loaded Tfp Resins and Synthesis of Amide 4011

A suspension of polymeric 4-hydroxy-2,3,5,6-tetrafluorophenol (TFP, *J. Comb. Chem.* 2000, 2, 691) amide resin (1.00 g, 1.27 mmol) in DMF (10 mL) was shaken for 10 minutes in a 70 mL polypropylene cartridge and then treated with indole-6-carboxylic acid (1.02 g, 6.35 mmol), 3-hydroxybenzotriazole (18 mg, 0.13 mmol), and diisopropylcarbodiimide (1.2 mL, 7.6 mmol). The reaction mixture was shaken for 18 h at 23° C., and then the resin was washed with DMF (10×50 mL), THF (10×50 mL), and methylene chloride (10×50 mL) and dried in vacuo.

A suspension of the above TFP ester (35 mg) in 1 mL of DMF was treated with amine 54 (10 mg, 0.027 mmol) and shaken for 18 h in a 10 mL polypropylene cartridge. The filtrate was collected and dried to give amide 4011 (11 mg, 0.022 mmol, 81%) as a yellow solid. $^1$HNMR (300 MHz, 10:1 CDCl$_3$:CD$_3$OD): δ 7.89 (s, 1H), 7.75-7.71 (m, 1H), 7.55-7.52 (m, 1H), 7.46-7.30 (m, 6H), 7.16 (dd, J=8, 2 Hz, 1H), 6.45-6.44 (m, 1H), 4.70-4.68 (m, 1H), 4.60-4.59 (m, 2H), 4.03-3.97 (m, 1H), 3.73-3.71 (m, 4H), 3.58-3.42 (m, 2H), 3.27-3.25 (m, 1H), 1.90 (s, 3H). LCMS (ESI) m/e 501.0 (M+H)$^+$.

Example 49

Synthesis of Amides 4010 and 4012-4105

Synthesis of Amide 4010

Amide 4010 was prepared from the TFP ester of N-methylpyrrole-2-carboxylic acid (477 mg, 3.81 mmol), which was prepared according to the general method of Example 48. The TFP ester was reacted with amine 54 using the acylation procedure of Example 48 to synthesize amide 4011. The desired amide 4010 was obtained as a solid (10 mg, 0.022 mmol, 81%). $^1$HNMR (300 MHz, 10:1 CDCl$_3$:CD$_3$OD): δ 7.71-7.56 (m, 6H), 7.33 (dd, J=9, 2 Hz, 1H), 6.93-6.92 (m, 1H), 6.77 (dd, J=4, 2 Hz, 1H), 6.55 (dd, J=12, 6 Hz, 2H), 6.27 (dd, J=4, 3 Hz, 1H), 4.77-4.69 (m, 1H), 4.54-4.52 (m, 2H), 4.02-3.96 (m, 1H), 3.90 (s, 3H), 3.73 (dd, J=9, 7 Hz, 1H), 3.62-3.58 (m, 2H), 1.96 (s, 3H). LCMS (ESI) m/e 465.0 (M+H)$^+$.

Synthesis of Amide 4012

Amide 4012 was prepared from the TFP ester of 3-methylsulfonylbenzoic acid (1.27 g, 6.35 mmol), which was prepared according to the general method of Example 48. The TFP ester was reacted with amine 54 using the acylation procedure of Example 48 to synthesize amide 4011. The desired amide 4012 was obtained as a solid (13 mg, 0.024 mmol, 89%). $^1$HNMR (300 MHz, 10:1 CDCl$_3$: CD$_3$OD): δ 8.31-8.30 (m, 1H), 8.14-8.11 (m, 1H), 8.00-7.97 (m, 1H), 7.64-7.58 (m, 2H), 7.45-7.29 (m, 6H), 7.12 (dd, J=9, 2 Hz, 1H), 4.73-4.71 (m, 1H), 4.59-4.58 (m, 2H), 4.05-3.99 (m, 1H), 3.73 (dd, J=9, 7 Hz, 1H), 3.61-3.44 (m, 6H), 3.30-3.27 (m, 1H), 3.03 (s, 3H). LCMS (ESI) m/e 540.1 (M+H)+.

Synthesis of Amide 4013

Amide 4013 was prepared from the TFP ester of 4-fluorobenzoic acid (890 mg, 6.35 mmol), which was prepared according to the general method of Example 48. The TFP ester was reacted with amine 54 using the acylation procedure of Example 48 to synthesize amide 4011. The desired amide 4013 was obtained as a solid (12 mg, 0.025 mmol, 93%). LCMS (ESI) m/e 480.0 (M+H)+.

Synthesis of Amide 4014

Amide 4014 was prepared from the TFP ester of piperonylic acid (1.05 g, 6.35 mmol), which was prepared according to the general method of Example 48. The TFP ester was reacted with amine 54 using the acylation procedure of Example 48 to synthesize amide 4011. The desired amide 4014 was obtained as a solid (13 mg, 0.026 mmol, 96%). $^1$HNMR (300 MHz, CDCl$_3$): δ 7.72-7.70 (m, 1H), 7.54-7.28 (m, 8H), 7.24-7.23 (m, 1H), 7.17 (dd, J=9, 2 Hz, 1H), 5.93 (s, 2H), 4.65-4.79 (m, 1H), 4.54-4.52 (m, 2H), 4.05-3.99 (m, 1H), 3.72 (dd, J=9, 7 Hz, 1H), 3.55-3.48 (m, 2H), 3.28-3.26 (m, 2H), 1.92 (s, 3H). LCMS (ESI) m/e 506.0 (M+H)+.

Synthesis of Amide 4015

Amide 4015 was prepared from the TFP ester of 5-methoxyindole-2-carboxylic acid (486 mg, 2.54 mmol), which was prepared according to the general method of Example 48. The TFP ester was reacted with amine 54 using the acylation procedure of Example 48 to synthesize amide 4011. The desired amide 4015 was obtained as a solid (10 mg, 0.019 mmol, 70%). $^1$HNMR (300 MHz, 10:1 CDCl$_3$: CD$_3$OD): δ 7.87-7.79 (m, 1H), 7.48-7.14 (m, 7H), 6.94 (s, 1H), 6.89-6.81 (m, 2H), 4.67-4.61 (m, 1H), 4.54-4.52 (m, 2H), 4.02-3.93 (m, 2H), 3.71-3.61 (s, 3H), 1.89 (s, 3H). LCMS (ESI) m/e 531.1 (M+H)+.

Example 50

Synthesis of Amine 4016

A solution of amine 54 (36 mg, 0.1 mmol) in a mixture of THF and DMF (3:1, v/v) was treated with quinoline-4-carboxaldehyde (16 mg, 0.1 mmol, 1.0 equiv) at 25° C. under argon, and the resulting reaction mixture was stirred at 25° C. for 30 min before being treated with sodium triacetoxyborohydride (NaB(OAc)$_3$H, 33 mg, 0.15 mmol, 1.5 equiv) at 25° C. The reaction mixture was subsequently stirred at 25° C. for 6 h. When TLC and HPLC showed the reductive amination reaction was complete, the reaction mixture was concentrated in vacuo. The residue was then directly purified by flash column chromatography (0-7% MeOH—CH$_2$Cl$_2$ gradient elution) to produce the desired N-[3-(2-fluoro-4'-{[(quinolin-4-ylmethyl)-amino]-methyl}-biphenyl-4-yl)-2-oxo-oxazolidin-5-ylmethyl]-acetamide 4016 (32.9 mg, 66% yield) as pale-yellow oil, which solidified upon standing at room temperature in vacuo. $^1$H NMR (300 MHz, DMSO-d$_6$) δ 1.85 (s, 3H, COCH$_3$), 3.44 (t, 2H, J=5.4 Hz), 3.79 (dd, 1H, J=6.4, 9.2 Hz), 3.88 (s, 2H), 4.17 (t, 1H, J=9.1 Hz), 4.30 (s, 2H), 4.77 (m, 1H), 7.41 (dd, 1H, J=2.0, 8.0 Hz), 7.51-7.63 (m, 8H, aromatic-H), 7.74 (t, 1H, J=8.0 Hz), 8.04 (d, 1H, J=8.0 Hz), 8.18 (d, 1H, J=8.0 Hz), 8.27 (t, 1H, J=5.8 Hz, NHCOCH$_3$), 8.87 (d, 1H, J=8.0 Hz). LCMS (ESI) m/e 499 (M+H)+.

Example 51

Synthesis of Amines 4018-4026

Synthesis of Amine 4018

To a solution of 0.032 g (0.089 mmol) of amine 54 in 3 mL of MeOH/THF (2:1, with 1% acetic acid) were added 0.009 g (0.080 mmol) of 4-pyridylcarboxaldehyde and 0.027 g (0.12 mmol) of sodium triacetoxyborohydride at room temperature. The reaction mixture was allowed to stir at 25° C. until the aldehyde was consumed based on TLC analysis. The solvents of the reaction were removed via rotary evaporation and the residue was then purified on a preparative TLC plate to give 7.0 mg of 4018. $^1$H NMR (300 MHz, CD$_3$OD): δ 8.57 (s, 1H), 8.48 (d, J=4.2 Hz, 1H), 7.91-7.33 (a series of multiplet peaks, 9H), 2.05 (s, 3H). LCMS (ESI) m/e 449 (M+H)+.

Synthesis of Amine 4019

To a solution of 0.080 g (0.22 mmol) of amine 54 in 3 mL of MeOH/THF (2:1, with 1% acetic acid) were added 0.032 g (0.20 mmol) of 2-quinolinecarboxaldehyde and 0.094 g (0.44 mmol) of sodium triacetoxyborohydride at room temperature. The reaction mixture was allowed to stir at 25° C. until the aldehyde was consumed based on TLC analysis. The solvents of the reaction were removed via rotary evaporation, and the residue was then purified on a preparative TLC plate to give 44 mg of 4019. $^1$H NMR (300 MHz, CD$_3$OD+CDCl$_3$): δ 8.32 (d, J=5.4 Hz, 1H), 8.06 (d, J=5.4 Hz, 1H), 7.94 (d, J=6 Hz, 1H), 7.79-7.36 (a series of multiplet peaks, 10H), 4.83 (m, 1H), 3.97 (s, 1H), 2.05 (s, 3H). LCMS (ESI) m/e 499 (M+H)+.

Synthesis of 4020

To a solution of 0.080 g (0.22 mmol) of amine 54 in 3 mL of MeOH/THF (2:1, with 1% acetic acid) was added 0.030 g (0.20 mmol) of 2-benzofurancarboxaldehyde and 0.094 g (0.44 mmol) of sodium triacetoxyborohydride at room temperature. The reaction mixture was allowed to stir at 25° C. until the aldehyde was consumed based on TLC analysis. The solvents of the reaction were removed via rotary evaporation, and the residue was then purified on a preparative TLC plate to give 49 mg of 4020. $^1$H NMR (300 MHz, CD$_3$OD+CDCl$_3$): δ 7.44-7.01 (a series of multiplet peaks, 11H), 6.62 (s, 1H), 3.92 (s, 2H), 3.82 (s, 2H), 3.75-3.60 (m, 1H). LCMS (ESI) m/e 488 (M+H)+.

Synthesis of Amine 4021

To a solution of 0.080 g (0.22 mmol) of amine 54 in 3 mL of MeOH/THF (2:1, with 1% acetic acid) were added 0.032 g (0.20 mmol) of 3-quinolinecarboxaldehyde and 0.094 g (0.44 mmol) of sodium triacetoxyborohydride at room temperature. The reaction mixture was allowed to stir at 25° C. until the aldehyde was consumed based on TLC analysis. The solvents of the reaction was removed via rotary evaporation, and the residue was then purified on a preparative TLC plate to give 49 mg of 4021. $^1$H NMR (300 MHz, CD$_3$OD+CDCl$_3$): δ 8.89 (s, 1H), 8.33 (s, 1H), 8.03 (d, J=5.4

Hz, 1H), 7.95 (d, J=5.4 Hz, 1H), 7.80~7.34 (a series of multiple peaks, 9H), 1.98 (s, 3H). LCMS (ESI) m/e 499 (M+H)$^+$.

Synthesis of Amine 4022

To a solution of 0.100 g (0.28 mmol) of amine 54 in 3 mL of MeOH/THF (2:1, with 1% acetic acid) were added 0.042 g (0.27 mmol) of 1-naphthaldehyde and 0.119 g (0.56 mmol) of sodium triacetoxyborohydride at room temperature. The reaction mixture was allowed to stir at 25° C. until the aldehyde was consumed based on TLC analysis. The solvents of the reaction were removed via rotary evaporation, and the residue was then purified on a preparative TLC plate to give 49 mg of 4022. $^1$H NMR (300 MHz, CD$_3$OD+CDCl$_3$): δ 7.98~7.24 (a series of multiple peaks, 14H), 2.00 (s, 3H). LCMS (ESI) m/e 498 (M+H)$^+$.

Synthesis of Amine 4023

To a solution of 0.100 g (0.28 mmol) of amine 54 in 3 mL of MeOH/THF (2:1, with 1% acetic acid) were added 0.024 g (0.25 mmol) of 3-furaldehyde and 0.119 g (0.56 mmol) of sodium triacetoxyborohydride at room temperature. The reaction mixture was allowed to stir at 25° C. until the aldehyde was consumed based on TLC analysis. The solvents of the reaction were removed via rotary evaporation, and the residue was then purified on a preparative TLC plate to give 32 mg of 4023. $^1$H NMR (300 MHz, CD$_3$OD+CDCl$_3$): δ 7.50~7.22 (a series of multiple peaks, 9H), 6.39 (s, 1H), 1.90 (s, 3H). LCMS (ESI) m/e 438 (M+H)$^+$.

Synthesis of Amine 4024

To a solution of 0.100 g (0.28 mmol) of amine 54 in 3 mL of MeOH/THF (2:1, with 1% acetic acid) were added 0.027 g (0.25 mmol) of 2-pyridylcarboxaldehyde and 0.089 g (0.42 mmol) of sodium triacetoxyborohydride at room temperature. The reaction mixture was allowed to stir at 25° C. until the aldehyde was consumed based on TLC analysis. The solvents of the reaction was removed via rotary evaporation, and the residue was then purified on a preparative TLC plate to give 30.0 mg of 4024. $^1$H NMR (300 MHz, CD$_3$OD): δ 8.39 (s, 1H), 8.30 (d, J=2.1 Hz, 1H), 7.70~7.21 (a series of multiplet peaks, 9H), 1.86 (s, 3H). LCMS (ESI) m/e 449 (M+H)$^+$.

Synthesis of Amine 4025

To a solution of 0.100 g (0.28 mmol) of amine 54 in 3 mL of MeOH/THF (2:1, with 1% acetic acid) were added 0.027 g (0.25 mmol) of 3-pyridylcarboxaldehyde and 0.089 g (0.42 mmol) of sodium triacetoxyborohydride at room temperature. The reaction mixture was allowed to stir at 25° C. until the aldehyde was consumed based on TLC analysis. The solvents of the reaction were removed via rotary evaporation, and the residue was then purified on a preparative TLC plate to give 30.0 mg of 4025. $^1$H NMR (300 MHz, CD$_3$OD): δ 8.57 (s, 1H), 8.48 (d, J=4.2 Hz, 1H), 7.91~7.33 (a series of multiplet peaks, 9H), 2.05 (s, 3H). LCMS (ESI) m/e 449 (M+H)$^+$.

Synthesis of Amine 4026

To a solution of 0.100 g (0.28 mmol) of amine 54 in 3 mL of MeOH/THF (2:1, with 1% acetic acid) were added 0.024 g (0.25 mmol) of 2-furaldehyde and 0.089 g (0.42 mmol) of sodium triacetoxyborohydride at room temperature. The reaction mixture was allowed to stir at 25° C. until the aldehyde was consumed based on TLC analysis. The solvents of the reaction were removed via rotary evaporation, and the residue was then purified on a preparative TLC plate to give 26.6 mg of 4026. $^1$H NMR (300 MHz, CD$_3$OD): δ 7.52~7.26 (a series of multiplet peaks, 10H), 1.87 (s, 3H). LCMS (ESI) m/e 438 (M+H)$^+$.

Example 52

Synthesis of Amine 4038

Method A

A solution of 8.00 g (115.9 mmol) of isoxazole and 31.30 g (139.1 mmol) of N-iodosuccinimide in 60 ml of trifluoroacetic acid was heated to 50° C. for 6 h. The reaction mixture was cooled and evaporated at 0° C. to remove the majority of trifluoroacetic acid. The residue was then dissolved in 200 ml of diethyl ether, washed sequentially with saturated NaHCO$_3$ (40 ml×4), 10% sodium thiosulfate (40 ml×2), and brine (40 ml), dried over MgSO$_4$, filtered and concentrated to give 16.50 g of the desired 4-iodoisoxazole product. $^1$H NMR (300 MHz, CDCl$_3$): δ 8.44 (s, 1H), 8.29 (s, 1H).

To a solution of 6.80 g (34.8 mmol) of 4-iodoisoxazole in 200 ml of THF at −100° C. was added dropwise 22.9 ml (36.6 mmol) of n-BuLi (1.6 M in hexanes). The reaction mixture was allowed to stir for 30 min. Ethyl formate (3.08 ml, 38.4 mmol) was added to the mixture, and the mixture was stirred further for 30 min at −100° C. Hydrochloric acid (36.60 ml of 1N HCl in ether) was added at −100° C., and the reaction mixture was allowed to warm gradually to 25° C. The mixture was diluted with ether (200 ml), washed sequentially with saturated NaHCO$_3$ (100 ml) and brine (100 ml), dried over MgSO$_4$, filtered and concentrated (at 0° C.) to give ~2.00 g of the desired isoxazole-4-carbaldehyde (based on estimation from $^1$H NMR; contaminated with residual EtOH) of suitable purity for use in subsequent reactions. $^1$H NMR (300 MHz, CDCl$_3$): δ 10.01 (s, 1H), 9.05 (s, 1H), 8.68 (s, 1H).

A solution of 4.00 g (11.2 mmol) of amine 54, 1.03 g (10.6 mmol) of isoxazole-4-carbaldehyde, and 4.750 g (22.4 mmol) of NaB(OAc)$_3$H in 30 ml of DMF with 1.0 ml of acetic acid was stirred at 25° C. for 4 h. The reaction solvents were removed by rotary evaporation. The residue was purified by silica gel column chromatography using 5% MeOH in CH$_2$Cl$_2$ as eluent to give 1.57 g of amine 4038 plus 1.58 g of the imine intermediate. LCMS (ESI) m/e 439 (M+H)$^+$.

Method B

A solution of 1.00 g (5.05 mmol) of isoxazol-4-ylmethyl-carbamic acid tert-butyl ester in 10 ml of 4.0 N HCl in dioxane was stirred at 25° C. for 6 h. The reaction mixture was then diluted with 30 ml of diethyl ether and filtered. The solid was washed with diethyl ether and dried to give 0.65 g of C-isoxazol-4-yl-methylamine hydrochloride salt of suitable purity for use in subsequent reactions. $^1$H NMR (300 MHz, DMSO): δ 9.02 (s, 1H), 8.68 (s, 1H), 3.94 (q, J=6, 1H).

A solution of aldehyde 92 (0.150 g, 0.42 mmol), C-isoxazol-4-yl-methylamine hydrochloride salt (0.068 g, 0.51 mmol) obtained above, and NaB(OAc)$_3$H (0.268 g, 1.26 mmol) in 5 ml of DMF was stirred at 25° C. for 2 h. The reaction solvent was removed by rotary evaporation, and the residue was purified by preparative thin-layer chromatography to give 0.160 g of amine 4038. LCMS (ESI) m/e 439 (M+H)+.

Example 53

Synthesis of Amine 4215

Scheme 34 depicts the synthesis of amine 401 used in the synthesis of compound 4215.

Scheme 34

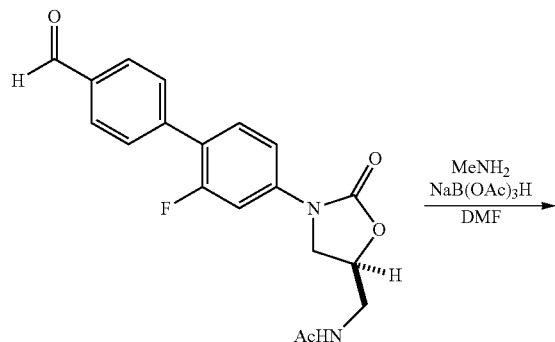

Synthesis of Amine 401

A solution of aldehyde 92 (3.56 g, 10.0 mmol) in anhydrous DMF (20 mL) was treated with a 2 N solution of methylamine in THF (25 mL, 50.0 mmol) and sodium triacetoxyborohydride (3.20 g, 15.0 mmol) at room temperature, and the resulting reaction mixture was stirred at room temperature for 6 h. When TLC and LCMS showed that the reaction was complete, the reaction mixture was quenched with H$_2$O (40 mL), and the resulting mixture was stirred at room temperature for 30 min. The solid precipitate was then collected by filtration, washed with H$_2$O (2×50 mL), and dried in vacuo. This crude material was subsequently purified by flash column chromatography (5-15% MeOH—CH$_2$Cl$_2$ gradient elution) to afford amine 401 (2.26 g; 61%) as an off-white solid. $^1$H NMR (300 MHz, DMSO-d$_6$) δ 2.03 (s, 3H, COCH$_3$), 2.46 (s, 3H, NMe), 3.62 (t, 2H, J=5.4 Hz), 3.86 (s, 2H, Ar—CH$_2$)), 3.96 (dd, 1H, J=6.4, 9.2 Hz), 4.35 (t, 1H, J=9.2 Hz), 4.90~4.99 (m, 1H), 7.58-7.80 (m, 7H, aromatic-H), 8.45 (t, 1H, J=5.8 Hz, NHCOCH$_3$); LCMS (ESI) m/z 372 (M+H)+.

Synthesis of Amine 4215

A solution of amine 401 (0.070 g, 0.19 mmol) in methanol (2 mL) and acetic acid (0.020 mL) was treated with quinoline-3-carboxaldehyde (0.033 g, 0.21 mmol) and sodium triacetoxyborohydride (0.080 g, 0.38 mmol) and stirred at 23° C. for 2 h. Additional sodium triacetoxyborohydride (0.080 g, 0.38 mmol) and acetic acid (0.020 mL) were added, and the reaction mixture was stirred for 16 h. The solvent was removed in vacuo, and the residue was dissolved in THF (3 mL) and acetic acid (0.020 mL) and treated with quinoline-3-carboxaldehyde (0.015 g, 0.095 mmol) and sodium triacetoxyborohydride (0.080 g, 0.38 mmol) and stirred for 9 h. Additional sodium triacetoxyborohydride (0.080 g, 0.38 mmol) was added, and the reaction mixture was stirred for 60 h. The reaction mixture was diluted with methylene chloride (30 mL) and washed with saturated aqueous sodium bicarbonate (25 mL). Drying over Na$_2$SO$_4$ and evaporation of solvent yielded crude product, which was purified by flash chromatography (18:1:0.1 methylene chloride:methanol:ammonium hydroxide, 5-10% methanol in 1:1 methylene chloride:ethyl acetate) to afford amine 4215 as a solid (0.030 g, 0.059 mmol; 31%). LCMS (ESI) m/z 513 (M+H)+.

Example 54

Synthesis of Sulfide 4216 and Sulfoxide 4217

Scheme 35 depicts the synthesis of compounds 4216 and 4217. Benzyl chloride 90 is displaced with thiolacetic acid to afford thioacetate 402. Hydrolysis of 402 afforded thiol 403 which was alkylated with 2-bromomethyl pyridine to yield sulfide 4216. Oxidation of 4216 then provided sulfoxide 4217.

Scheme 35

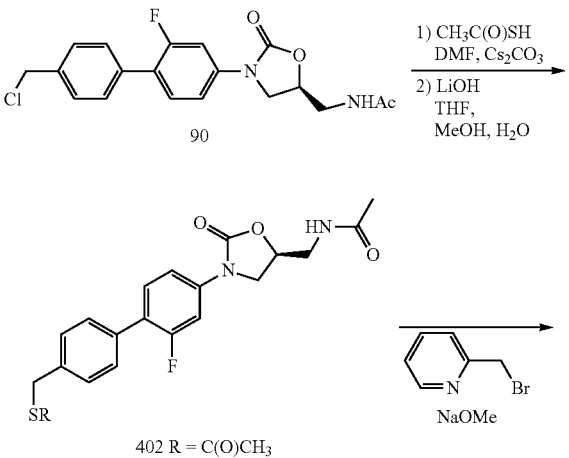

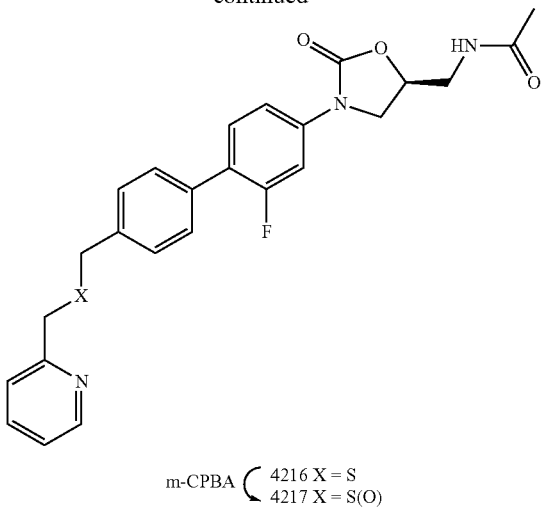

m-CPBA  4216 X = S
        4217 X = S(O)

Synthesis of Chloride 90

Alcohol 51 (3.0 g, 8.4 mmol) was dissolved in $CH_2Cl_2$ (20 mL) and Hunig's base (2 mL). Methanesulfonyl chloride (1.4 mL, 12.6 mmol) was added dropwise and the resulting solution stirred at rt for 4 h. The mixture was poured into 100 mL sat. aqueous $NaHCO_3$ and extracted with $CH_2Cl_2$ (3×50 mL). The combined organic extracts were washed with brine, dried over $MgSO_4$, filtered, and concentrated to give 3.9 g of an oily yellow solid. The crude material was purified by silica gel chromatography to give chloride 90 as an off-white solid (2.7 g, 7.2 mmol). LCMS (ESI) m/z 377 $(M+H)^+$, 418 $(M+CH_3CN+H)^+$, 440 $(M+CH_3CN+Na)^+$.

Synthesis of Thioester 402

Under an argon atmosphere, thiolacetic acid (1.55 mL, 21.7 mmol) was added to a mixture of chloride 90 (4.08 g, 10.8 mmol) and $Cs_2CO_3$ (3.52 g, 10.8 mmol) in DMF (25 mL). The reaction was stirred at room temperature for 2 hours. Then 50 mL of water was added. The off-white product 402 (4.3 g) was collected by filtration in a yield of 96%. LCMS (ESI) m/z 417 $(M+H)^+$.

Synthesis of Thiol 403

LiOH (360 mg, 15 mmol) was added to a solution of 402 (4.3 g, 10.3 mmol) in a mixture of THF (50 mL), MeOH (50 mL) and water (20 mL). After stirring for 30 minutes at room temperature under argon atmosphere, the insoluble solid was removed by filtration. The filtrate was diluted with water (50 mL), concentrated to remove organic solvents, then neutralized with 10% HCl. The off-white product 403 (3.5 g) was collected by filtration in a yield of 91%. LCMS (ESI) m/z 375 $(M+H)^+$.

Synthesis of Sulfide 4216

A solution of sulfide 403 (0.20 g, 0.54 mmol) in tetrahydrofuran (1.3 mL), methanol (1.3 mL), and dimethylformamide (1.3 mL) was treated with sodium methoxide (25% in methanol, 0.24 mL, 1.1 mmol) and 2-(bromomethyl)pyridine and stirred at 23° C. for 0.5 h. The reaction mixture was diluted with methylene chloride (25 mL), washed with water (25 mL), and the water layer was extracted with methylene chloride (25 mL). The combined organic fractions were dried over $Na_2SO_4$, and evaporated in vacuo to yield crude product, which was purified by preparative thin-layer chromatography (5% methanol/methylene chloride) to afford 4216 as a white powder (0.12 g, 0.26 mmol; 48%). LCMS (ESI) m/z 466 $(M+H)^+$.

Synthesis of Sulfoxide 4217

A solution of 4216 (0.11 g, 0.23 mmol) in methylene chloride (2.3 mL) was treated with 3-chloroperoxybenzoic acid (0.051 g, 0.23 mmol) and stirred at 23° C. for 15 minutes. The solvent was evaporated in vacuo and the crude product was purified by flash chromatography (5% methanol/methylene chloride) to afford 4217 as a white powder (0.093 g, 0.19 mmol; 83%). LCMS (ESI) m/z 482 $(M+H)^+$.

Example 55

Synthesis of Compounds 4218-4220

Synthesis of Amine 4218

A solution of amine 54 (0.600 g, 1.68 mmol), 1-methylindole-3-carboxaldehyde (0.254 g, 1.60 mmol), and $NaB(OAc)_3H$ (0.712 g, 3.36 mmol) in 30 ml of MeOH with a few drops of acetic acid was stirred at 25° C. for 24 h. The reaction solvents were removed by rotary evaporation. The residue was purified by preparative TLC plate to give 0.070 g of amine 4218. LCMS (ESI) m/z 501 $(M+H)^+$.

Synthesis of Amine 4219

A solution of amine 54 (0.060 g (0.17 mmol), tetrahydrofuran-3-carboxaldehyde (0.016 g, 0.16 mmol), and $NaB(OAc)_3H$ (0.071 g, 0.34 mmol) in 5 ml of MeOH with a few drops of acetic acid was stirred at 25° C. for 6 h. The reaction solvents were removed by rotary evaporation. The residue was purified by preparative TLC plate to give 0.057 g of amine 4219. LCMS (ESI) m/z 442 $(M+H)^+$.

Synthesis of Amine 4220

A solution of amine 54 (0.500 g, 1.40 mmol), 1,2,3-thiadiazole-4-carboxaldehyde (0.152 g, 1.33 mmol), and $NaB(OAc)_3H$ (0.594 g, 2.80 mmol) in 8 ml of DMF with a few drops of acetic acid was stirred at 25° C. for 2 h. The reaction solvents were removed by rotary evaporation. The residue was purified by preparative TLC to give 0.484 g of amine 4220. LCMS (ESI) m/z 492 $(M+H)^+$.

Example 56

Synthesis of Compound 4221

A solution of amine 54 (79.0 mg, 0.22 mmol) in anhydrous DMF (3 mL) was treated with 3-(2-oxo-1,2-dihydropyridin-3-yl)-acrylic acid (36.3 mg, 0.22 mmol) and 1-(3-dimethylaminopropyl)-3-ethylcarbodiimide hydrochloride (62.7 mg, 0.33 mmol) at room temperature, and the resulting reaction mixture was stirred at 25° C. for 12 h. When TLC and LCMS showed that the reaction was complete, the reaction mixture was concentrated in vacuo. The residue was directly purified by flash column chromatography (0-7% MeOH—$CH_2Cl_2$ gradient elution) to afford amide 4221 (45.5 mg; 41%) as a white solid. LCMS (ESI) m/z 505 $(M+H)^+$.

Example 57

Synthesis of Amidine 4222

Scheme 36 illustrates the synthesis of amidine 4222. Nitrile 404 and furfurylamine were heated together in the presence of copper chloride to yield amidine 4222.

Synthesis of Amidine 4222

Under an argon atmosphere, a mixture of nitrile 404 (98 mg, 0.28 mmol), furfurylamine (27 mg, 0.28 mmol) and copper (I) chloride (CuCl, 28 mg, 0.28 mmol) in DMSO (2 mL) was heated at 80° C. for 48 h. The reaction was diluted with $CH_2Cl_2$, washed with saturated $Na_2CO_3$ and dried under vacuum. The crude product was purified by chromatography (5:1:0.05 $CH_2Cl_2$/MeOH/$NH_3.H_2O$) to afford 4222 (14 mg; 11%). LCMS (ESI) m/z 451 (M+H)$^+$.

Example 58

Synthesis of Amide 4223

Scheme 37 illustrates the synthesis of amide 4223. 2,5-Dibromopyridine is converted to activated pyridyl ester 405 which is then treated with histamine to provide amide 406. The Suzuki coupling of 406 and boronate 81 gave the final target amide 4223.

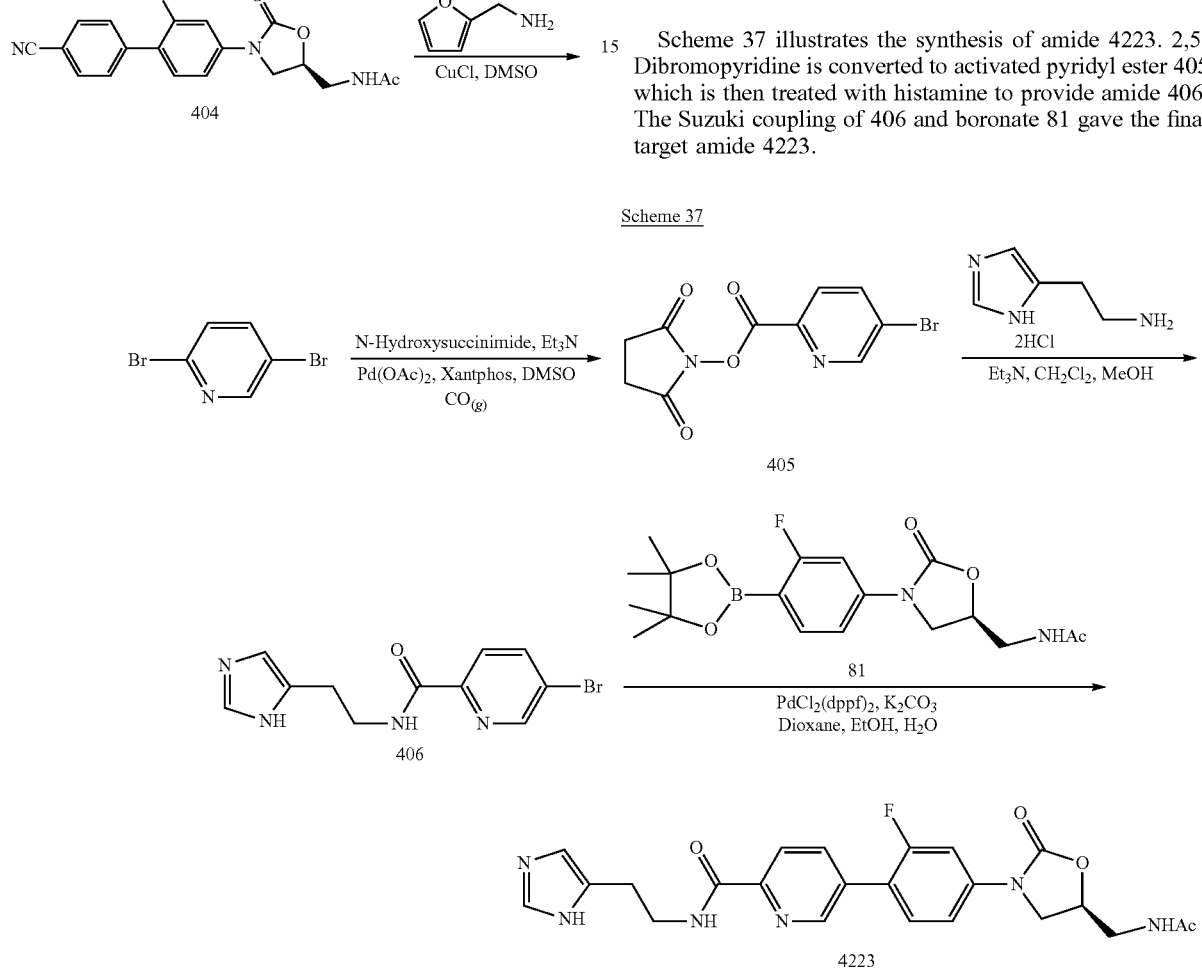

Synthesis of Nitrile 404

This compound was made from 4-cyanophenylboronic acid and iodide 50 as described above for the synthesis of alcohol 51.

Synthesis of Ester 405

Under an argon atmosphere, triethylamine (0.31 mL, 2.25 mmol) was added to a mixture of 2,5-dibromopyridine (355 mg, 1.5 mmol), palladium acetate (16.8 mg. 0.075 mmol), Xantphos (4,5-bis(diphenylphosphino)-9,9-dimethylxanthene, 43.4 mg, 0.075 mmol) and N-hydroxysuccinimide (241.5 mg, 2.1 mmol) in DMSO (2 mL). The solution was purged with carbon monoxide for 15 min and stirred under a carbon monoxide balloon at 80° C. for 16 h. The reaction mixture was then cooled to room temperature, diluted with 20 mL of ethyl acetate and washed with saturated sodium bicarbonate solution and water. The organic phase was dried over sodium sulfate and evaporated to give crude product. Chromatography on silica gel using hexane:acetone (3:1) provided ester 405 (75 mg; 17%). $^1$HNMR (300 MHz, CDCl$_3$) δ 8.85 (m, 1H), 8.06 (m, 2H), 2.90 (s, 4H).

Synthesis of Amide 406

A mixture of active ester 405 (350 mg, 1.17 mmol), histamine dihydrochloride (216 mg, 1.17 mmol) and Et$_3$N (0.33 mL, 2.34 mmol) in CH$_2$Cl$_2$ (5 mL) was stirred at room temperature for 1 h. The reaction was washed with brine and dried under vacuum. The crude product was purified by chromatography (15:1:0.05 CH$_2$Cl$_2$/MeOH/NH$_3$.H$_2$O) to afford 406 (280 mg; 81%). LCMS (ESI) m/z 295 (M+H)$^+$.

Synthesis of Amide 4223

Under an argon atmosphere, a mixture of 406 (230 mg, 0.78 mmol), boronate 81 (295 mg, 0.78 mmol), Pd(dppf)$_2$Cl$_2$ (19 mg, 0.023 mmol) and K$_2$CO$_3$ (323 mg, 2.34 mmol) in 5 mL of a mixture of dioxane/EtOH/H$_2$O (3:1:1) was heated at 100° C. for 12 h. The reaction was concentrated and the residue was dissolved in MeOH (2 mL) and CH$_2$Cl$_2$ (10 mL). Inorganic salts were removed by filtration. The filtrate was concentrated and purified by chromatography (15:1:0.05 CH$_2$Cl$_2$/MeOH/NH$_3$.H$_2$O) to afford amide 4223 (106 mg; 29%). LCMS (ESI) m/z 467 (M+H)$^+$.

Example 59

Synthesis of Amides 4224 and 4225

Scheme 38 illustrates the synthesis of amides 4224 and 4225. Aryl bromides 407 and 408 were coupled to boronate 81 to afford 4224 and 4225 respectively.

Synthesis of Amide 4224

A mixture of 4-bromobenzoyl chloride (110 mg, 0.5 mmol), 1,2,4-oxadiazol-3-yl-methylamine hydrochloride (68 mg, 0.5 mmol), DMF (1 drop) and Et$_3$N (0.33 mL, 2.34 mmol) in CH$_2$Cl$_2$ (5 mL) was stirred at room temperature for 4 h. The reaction was washed with brine and dried under vacuum to afford crude amide 407. The amide 407 obtained was added to a mixture of boronate 81 (189 mg, 0.5 mmol), Pd(dppf)$_2$Cl$_2$ (20 mg, 0.025 mmol) and K$_2$CO$_3$ (207 mg, 1.5 mmol) in 5 mL of dioxane/EtOH/H$_2$O (3:1:1) under an argon atmosphere. After being heated at 100° C. for 12 h, the reaction was diluted with water and MeOH, and then filtered through celite. The filtrate was concentrated to remove organic solvent. The crude product was collected by filtration and further purified by chromatography (25:1:0.05 CH$_2$Cl$_2$/MeOH/NH$_3$.H$_2$O) to afford 4224 (45 mg; 32%). LCMS (ESI) m/z 452 (M−H)$^+$.

Synthesis of Amide 4225

A mixture of 4-bromobenzoyl chloride (29 mg, 0.132 mmol), 1,2,4-thiadiazol-3-yl-methylamine hydrochloride (20 mg, 0.132 mmol), DMF (1 drop) and Et$_3$N (27 mg, 0.264 mmol) in THF (4 mL) was stirred at room temperature for 2 h. The reaction was concentrated, dissolved in CH$_2$Cl$_2$, washed with brine and dried under vacuum to afford crude amide 408. The resultant amide 408 obtained above was added to a mixture of boronate 81 (50 mg, 0.132 mmol), Pd(dppf)$_2$Cl$_2$ (6 mg, 0.0066 mmol) and K$_2$CO$_3$ (55 mg, 0.396 mmol) in 2 mL of dioxane/EtOH/H$_2$O (3:1:1) under an argon atmosphere. After being heated at 100° C. for 12 h, the reaction was concentrated, dissolved in EtOAc, washed with brine and dried under vacuum. The crude product was purified by chromatography on silica gel (25:1:0.05 CH$_2$Cl$_2$/MeOH/NH$_3$.H$_2$O) to afford amide 4225 (30 mg; 48%). LCMS (ESI) m/z 470 (M+H)$^+$.

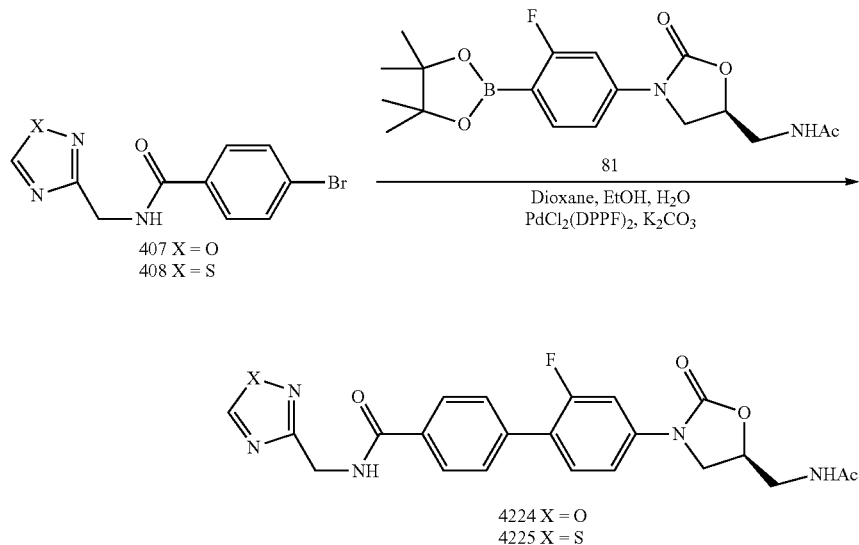

Scheme 38

Example 60

Synthesis of Sulfide 4226

Under an argon atmosphere, sodium methoxide (NaOMe, 25% by wt. in MeOH, 95 mg, 0.44 mmol) was added to a solution of thiol 403 (75 mg, 0.2 mmol) and epibromohydrin (30 mg, 0.22 mmol) in MeOH (3 mL) and THF (3 mL). After stirring at room temperature for 2 h, the reaction was concentrated. The residue was dissolved CH$_2$Cl$_2$, washed with brine, dried over MgSO$_4$ and concentrated under vacuum. The crude product was purified by chromatography on silica gel (25:1:0.05 CH$_2$Cl$_2$/MeOH/NH$_3$.H$_2$O) to afford sulfide 4226 (55 mg; 61% as a mix of diastereomers). LCMS (ESI) m/z 453 (M+Na)$^+$.

Example 61

Synthesis of Amines 4227-4229

Synthesis of Amine 4227

A suspension of aldehyde 92 (107 mg, 0.3 mmol) in anhydrous THF (2 mL) and anhydrous methanol (MeOH, 2 mL) was treated with 2-(1H-imidazol-4-yl)-ethylamine (110.0 mg, 0.6) and sodium triacetoxyborohydride (127 mg, 0.6 mmol) at room temperature, and the resulting reaction mixture was stirred at room temperature for 6 h. When TLC and LCMS showed that the reaction was complete, the reaction mixture was concentrated in vacuo. This residue was directly purified by flash column chromatography (0-10% MeOH—CH$_2$Cl$_2$ gradient elution) to afford amine 4227 (24 mg, 135.3 mg; 18%) as an off-white solid. LCMS (ESI) m/z 452 (M+H)$^+$.

Synthesis of Amine 4228

A suspension of aldehyde 92 (107 mg, 0.3 mmol) in anhydrous THF (2 mL) and anhydrous methanol (MeOH, 2 mL) was treated with 2-(5-methyl-1H-indol-3-yl)-ethylamine hydrochloride (126.0 mg, 0.6 mmol) and sodium triacetoxyborohydride (127 mg, 0.6 mmol) at room temperature, and the resulting reaction mixture was stirred at room temperature for 12 h. When TLC and LCMS showed that the reaction was complete, the reaction mixture was concentrated in vacuo. This residue was directly purified by flash column chromatography (0-10% MeOH—CH$_2$Cl$_2$ gradient elution) to afford amine 4228 (32 mg; 21%) as off-white solids. LCMS (ESI) m/z 515 (M+H)$^+$.

Synthesis of Amine 4229

A suspension of aldehyde 92 (107 mg, 0.3 mmol) in anhydrous THF (2 mL) and anhydrous methanol (2 mL) was treated with (5-methyl-isoxazol-3-yl)-methylamine (67.0 mg, 0.6 mmol) and sodium triacetoxyborohydride (127 mg, 0.6 mmol) at room temperature, and the resulting reaction mixture was stirred at room temperature for 12 h. When TLC and LCMS showed that the reaction was complete, the reaction mixture was concentrated in vacuo. This residue was directly purified by flash column chromatography (0-5% MeOH—CH$_2$Cl$_2$ gradient elution) to afford amine 4229 (34 mg; 25%) as an off-white solid. LCMS (ESI) m/z 453 (M+H)$^+$.

Example 62

Synthesis of Amines 4230 and 4231

Scheme 39 shows the synthesis of amines 4230 and 4231. Known alcohol 409 (see U.S. Pat. Nos. 5,523,403 and 5,565,571) is coupled to 4-formylphenylboronic acid to afford alcohol 410 which is then converted to mesylate 411. Alkylation of mesylate 411 with the appropriate nucleophiles affords biaryl aldehydes 412 and 413 which are transformed to amines 4230 and 4231 respectively by reductive amination chemistry.

Scheme 39

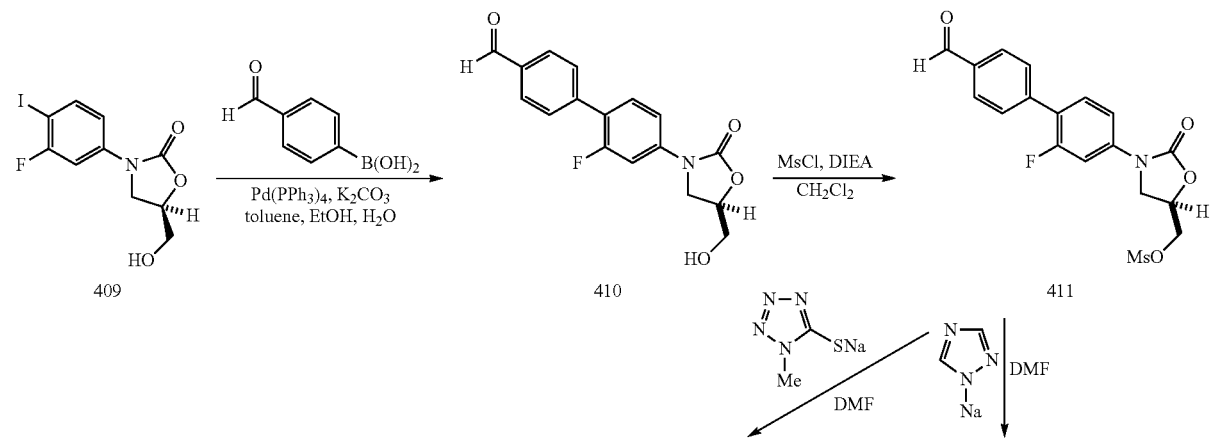

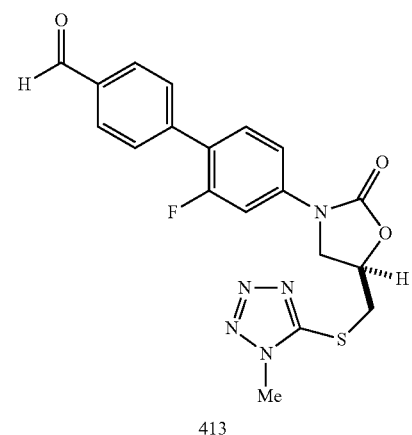

413

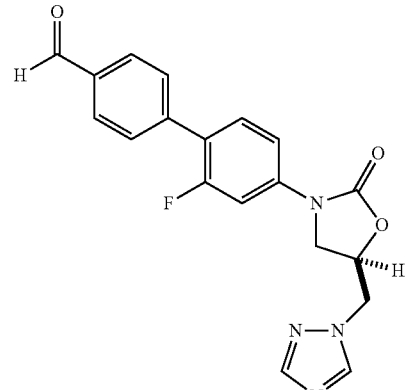

412

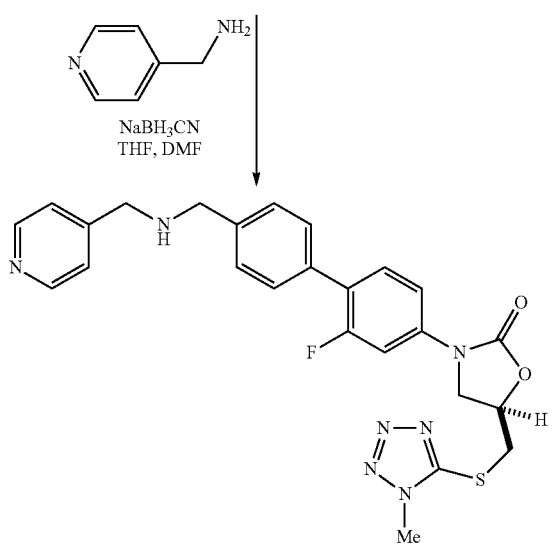

4231

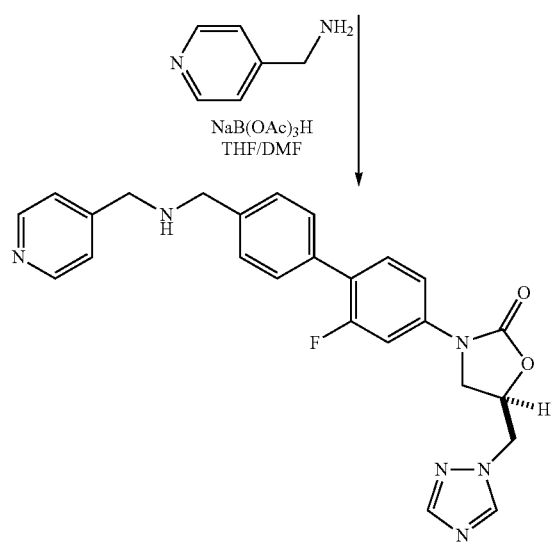

4230

Synthesis of Alcohol 410

A suspension of alcohol 409 (5.07 g, 15.0 mmol) in toluene (30 mL) was treated with 4-formylphenylboronic acid (3.15 g, 21.0 mmol), $K_2CO_3$ (6.22 g, 45.0 mmol), EtOH (10 mL), and $H_2O$ (10 mL) at 25° C., and the resulting mixture was degassed three times under a steady stream of argon at 25° C. $Pd(dppf)_2Cl_2$ (370 mg, 0.45 mmol) was subsequently added to the reaction mixture, and the resulting reaction mixture was degassed three times again before being warmed to gentle reflux for 2 h. When TLC and LCMS showed the coupling reaction was complete, the reaction mixture was cooled to room temperature before being treated with $H_2O$ (100 mL). The resulting mixture was then stirred at room temperature for 10 min before being cooled to 0-5° C. for 1 h. The solid precipitate was collected by filtration, washed with $H_2O$ (2×40 mL) and 20% EtOAc/hexane (2×40 mL), and dried in vacuo. The crude alcohol 410 (4.62 g; 98%) was obtained as a brown solid, which by HPLC and $^1H$ NMR was found to be of suitable purity to be used in subsequent reactions. LCMS (ESI) m/z 316 (M+H)$^+$.

Synthesis of Mesylate 411

A solution of the crude alcohol 410 (4.2 g, 13.3 mmol) in $CH_2Cl_2$ (50 mL) was treated with diisopropylethylamine (2.6 g, 3.5 mL, 20.0 mmol) at 25° C., and the resulting mixture was cooled to 0-5° C. before being treated dropwise with methanesulfonyl chloride (1.83 g, 1.25 mL, 16.0 mmol) at 0-5° C. The resulting reaction mixture was subsequently stirred at 0-5° C. for 2 h. When TLC and LCMS showed the reaction was complete, the reaction mixture was treated with $H_2O$ (50 mL) at 0-5° C. The mixture was then concentrated in vacuo to remove most of the $CH_2Cl_2$, and the resulting slurry was treated with $H_2O$ (50 mL). The mixture was stirred at room temperature for 10 min before being cooled to 0-5° C. for 30 min. The solid precipitate was collected by filtration, washed with $H_2O$ (2×40 mL) and 20% EtOAc/hexane (2×20 mL), and dried in vacuo. The crude mesylate 411 (4.60 g; 88%) was obtained as a brown solid, which by $^1H$ NMR and HPLC was found to be of suitable purity to be used in subsequent reactions. LCMS (ESI) m/z 394 (M+H)$^+$.

Synthesis of Aldehyde 412

A solution of mesylate 411 (393 mg, 0.1 mmol) in anhydrous DMF (4 mL) was treated with 1H-1,2,4-triazole sodium salt (100 mg, 1.1 mmol) at room temperature, and the resulting reaction mixture was warmed to 40° C. and stirred at 40° C. for 4 h. When TLC and LCMS showed that the reaction was complete, the reaction mixture was concentrated in vacuo. This residue was directly purified by flash column chromatography (0-5% MeOH—CH$_2$Cl$_2$ gradient elution) to afford aldehyde 412 (318.4 mg; 87%) as an off-white solid. LCMS (ESI) m/z 367 (M+H)$^+$.

Synthesis of Amine 4230

A suspension of aldehyde 412 (90.0 mg, 0.25 mmol) in anhydrous THF (2 mL) and anhydrous DMF (2 mL) was treated with C-pyridin-4-yl-methylamine (29.0 mg, 0.27 mmol) and sodium triacetoxyborohydride (106.0 mg, 0.5 mmol) at room temperature, and the resulting reaction mixture was stirred at room temperature for 6 h. When TLC and LCMS showed that the reaction was complete, the reaction mixture was concentrated in vacuo. This residue was directly purified by flash column chromatography (0-5% MeOH—CH$_2$Cl$_2$ gradient elution) to afford amine 4230 (47.0 mg; 41%) as an off-white solid. LCMS (ESI) m/z 459 (M+H)$^+$.

Synthesis of Aldehyde 413

A solution of 1-methyl-1H-tetrazole-5-thiol sodium salt (174.0 mg, 1.5 mmol) in anhydrous THF (5 mL) was treated with NaH (60% oil dispersion in mineral oil, 60.0 mg, 1.5 mmol) at 0-5° C., and the resulting reaction mixture was stirred at 0-5° C. for 1 h. The mixture was then treated with mesylate 411 (393.0 mg, 1.0 mmol) and anhydrous DMF (5 mL) at 0-5° C., and the resulting reaction mixture was gradually warmed to room temperature before being warmed to 40° C. for 4 h. When TLC and LCMS showed that the reaction was complete, the reaction mixture was concentrated in vacuo. This residue was directly purified by flash column chromatography (0-5% MeOH—CH$_2$Cl$_2$ gradient elution) to afford aldehyde 413 (272.6 mg; 66%) as an off-white solid. LCMS (ESI) m/z 414 (M+H)$^+$.

Synthesis of Amine 4231

A suspension of aldehyde 413 (100.0 mg, 0.24 mmol) in anhydrous THF (2 mL) and anhydrous DMF (2 mL) was treated with C-pyridin-4-yl-methylamine (29.0 mg, 0.27 mmol) and sodiumborohydride (15.0 mg, 0.24 mmol) at room temperature, and the resulting reaction mixture was stirred at room temperature for 12 h. When TLC and LCMS showed that the reaction was complete, the reaction mixture was concentrated in vacuo. This residue was directly purified by flash column chromatography (0-5% MeOH—CH$_2$Cl$_2$ gradient elution) to afford amine 4231 (44.0 mg; 36%) as an off-white solid. LCMS (ESI) m/z 506 (M+H)$^+$.

Example 63

Synthesis of Amine 4233

Scheme 40 shows the synthesis of isoxadiazole 4233. BOC-Aminoacetonitrile was converted to hydroxyamidine 414 which was then cyclized to isoxadiazole 415. Reductive amination of 415 with aldehyde 92 afforded amine 4233.

Scheme 40

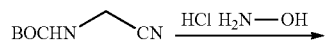

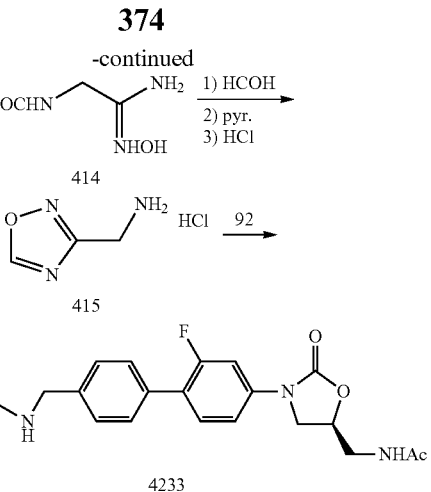

Synthesis of Hydroxyamidine 414

To a solution of BOC-aminoacetonitrile (6.0 g, 38 mmol) in EtOH (60 mL) was added 50% aq. hydroxylamine (4.5 mL, 77 mmol) and the mixture was refluxed for 5 h. The solvents were evaporated and the residue redissolved in CH$_2$Cl$_2$ (100 mL), dried over Na$_2$SO$_4$ and again evaporated, yielding hydroxyamidine 414 (7 g; 96%). $^1$H-NMR, (300 MHz, CDCl$_3$) δ 5.43-5.39 (m 1H), 5.12-5.03 (m, 3H), 3.75 (d, J=5 Hz, 2H), 1.46 (s, 9H).

Synthesis of Isoxadiazole 415

To a solution of 414 (2.8 g, 14.7 mmol) in CH$_2$Cl$_2$ (45 mL) was added Et$_3$N (4.1 mL, 29.5 mmol), formic acid (0.72 mL, 19.2 mmol), EDCI (4.24 g, 22 mmol), and DMAP (89 mg, 0.7 mmol). The mixture was stirred at room temperature for 3 h, evaporated to ca. 15 mL, diluted with ethyl acetate (50 mL), washed with 1M citric acid (20 mL), water (2×20 mL), brine (1×20 mL), dried over Na$_2$SO$_4$ and the solvent evaporated. The crude residue was dissolved in pyridine (11 mL) and stirred at 105° C. for 4.5 h, poured into 1M citric acid-ice (100 mL) and extracted with ethyl acetate (2×50 mL). The combined organic layer was washed with water (2×15 mL), brine (1×15 mL), dried over Na$_2$SO$_4$ and the solvent evaporated. The residue was dissolved in 4M HCl in dioxane (7 mL). The mixture was stirred at room temperature for 2 h and then evaporated and diluted with ether (3 mL). The solution was filtered and the solid was washed with ether (2×5 mL) and dried under high vacuum to yield 415 (855 mg; 83%). $^1$H-NMR, (300 MHz, d$_6$-DMSO) δ 9.6 (s, 1H), 8.77 (br s, 3H), 4.09 (m, 2H).

Synthesis of Amine 4233

Amine 4233 was synthesized from 415 and aldehyde 92 using the same conditions described in Example 53 for the synthesis of amine 401 from aldehyde 92. LCMS (ESI) m/z 441 (M+H)$^+$.

Example 64

Synthesis of Amine 4234

Scheme 41 depicts the synthesis of amine 4234. Known ester 416 (*Liebigs Annalen der Chemie* 1979, 1370) was reduced to alcohol 417 which was manipulated to amine salt 418 via standard chemistry. Reductive amination of 418 with aldehyde 19 yielded amine 4234.

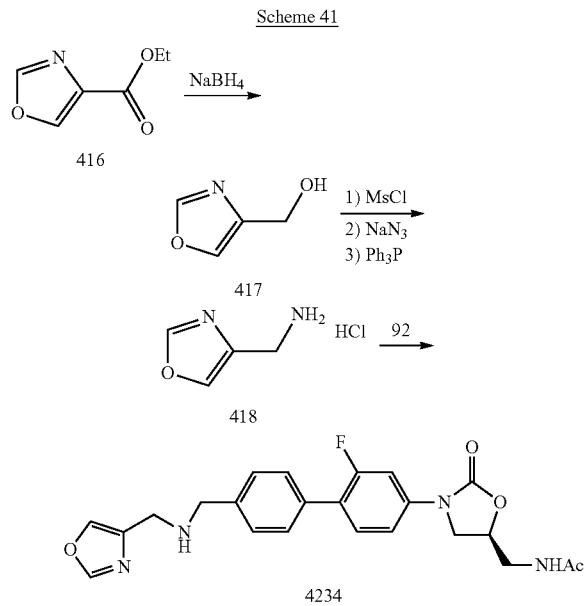

Synthesis of Alcohol 417

To a solution of the oxazole 416 (500 mg, 4.4 mmol) in MeOH (20 mL) was added sodium borohydride (NaBH$_4$, 540 mg, 17.5 mmol). The mixture was stirred at room temperature for 2 h, then NaBH$_4$ (540 mg, 17.5 mmol) was added. After 1 h an additional amount of NaBH$_4$ (270 mg, 9.0 mmol) was added. After stirring for 2 h, the mixture was quenched with 5% Na$_2$CO$_3$ (2 mL) and evaporated. The crude residue was purified on silica gel eluting with ether, yielding 417 as a clear oil (300 mg; 86%). $^1$H-NMR, (300 MHz, CDCl$_3$) δ 7.82 (s, 1H), 7.57 (s, 1H), 4.57 (s, 2H).

Synthesis of Amine Hydrochloride 418

Alcohol 417 was converted to amine salt 418 following the procedure described above to make amine 54 from alcohol 51. The crude material was taken up HCl in dioxane and then triturated with ether to isolate the salt as was described above for amine salt 415.

Synthesis of Amine 4234

This amine was synthesized from 418 and aldehyde 92 using the same conditions described above for the synthesis of amine 401 from aldehyde 92. LCMS (ESI) m/z 439 (M+H)$^+$.

Example 65

Synthesis of Amine 4235

Scheme 42 depicts the synthesis of amine 4235 from aldehyde 419 and amine salt 418.

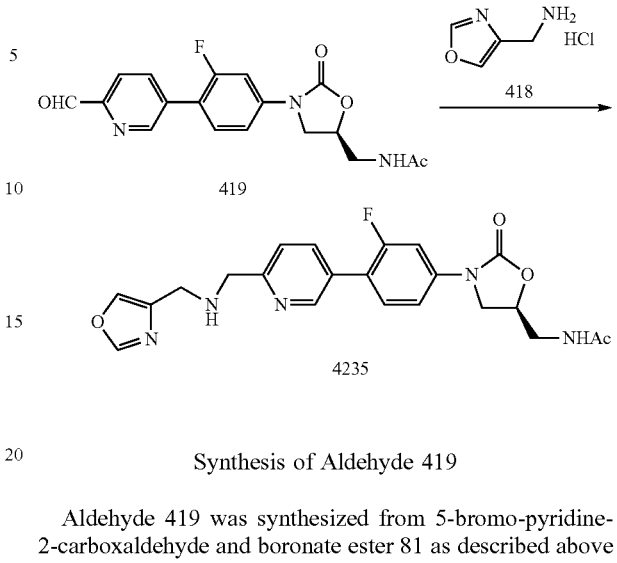

Synthesis of Aldehyde 419

Aldehyde 419 was synthesized from 5-bromo-pyridine-2-carboxaldehyde and boronate ester 81 as described above for the synthesis of amide 4223.

Synthesis of Amine 4235

Amine 4235 was synthesized from aldehyde 419 and amine salt 418 using the same conditions described in Example 53 for the synthesis of amine 401 from aldehyde 92. LCMS (ESI) m/z 440 (M+H)$^+$.

Example 66

Synthesis of Compound 4208

Scheme 43 depicts the synthesis of compound 4208.

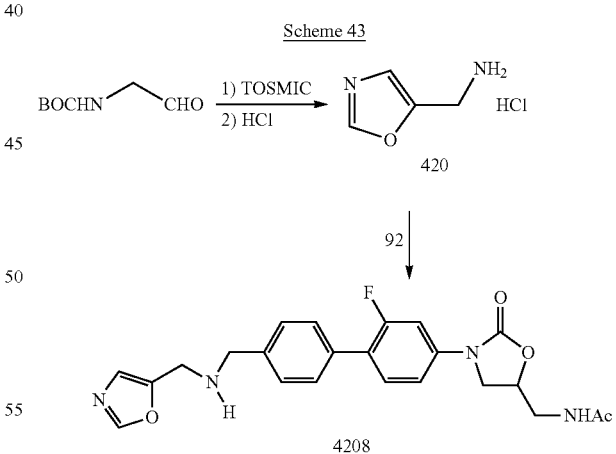

To a solution of tert-Butyl N-(2-oxoethyl)carbamate (4.0 g, 25.1 mmol) in MeOH (80 mL) was added K$_2$CO$_3$ (10.4 g, 75.4 mmol) followed by tosylmethylisocyanide (TOSMIC, 4.91 g, 25.1 mmol). The suspension was refluxed for 1 h and then evaporated. The residue was poured into ice-water (100 mL) and extracted with ethyl acetate (2×50 mL). The combined organic extracts were washed with water (2×20 mL), brine (1×20 mL), dried over Na$_2$SO$_4$ and evaporated. The residue was purified on silica gel eluting with hexanes/ ethyl acetate 1:1, yielding a faint yellow oil which was directly dissolved in 4 M HCl in dioxane (15 mL), stirred for 45 min., and evaporated. The residue was crystallized with ether (10 mL) and filtered, yielding amine 420 (1.50 g, 42%). ¹H-NMR, (300 MHz, d-DMSO δ 8.73 (br.s 3H), 8.48 (s, 1H), 7.28 (s, 1H), 4.20-4.12 (m, 2H).

Compound 4208 was synthezised from amine 420 and aldehyde 92 using the same conditions described in Example 53 for the synthesis of amine 401 from aldehyde 92. LCMS (ESI): 439.1 (M+H)⁺.

Example 67

Synthesis of Compound 4136

A solution of amine 54 (0.070 g, 0.20 mmol) in DMF (1.0 ml) was treated with triethylamine (0.055 ml, 0.40 mmol) and 2-phthalimidoethanesulfonyl chloride (0.059 mg, 0.22 mmol) and stirred at 23° C. for 3.5 h. Additional 2-phthalimidoethanesulfonyl chloride (0.081 mg, 0.30 mmol) and triethylamine (0.087 ml, 0.63 mmol) were added, and the reaction mixture was stirred for 16 h. The reaction mixture was diluted with methylene chloride (20 ml), washed with 1 M hydrochloric acid (20 ml), and washed with saturated aqueous sodium bicarbonate (20 ml). Drying over Na₂SO₄ and evaporation of solvent yielded crude product, which was purified by flash chromatography (2.5-5% methanol in 1:1 methylene chloride/ethyl acetate) to afford compound 4136 (0.082 g, 0.14 mmol, 70%). MS (ESI): 617 (M+Na)⁺.

Example 68

Synthesis of Compound 4239

Scheme 44 depicts the synthesis of compound 4208.

Scheme 44

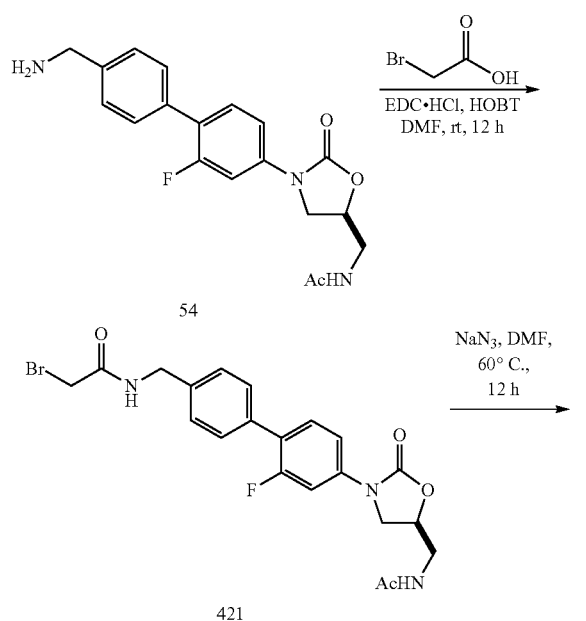

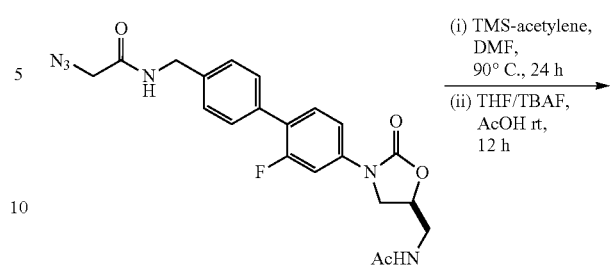
422

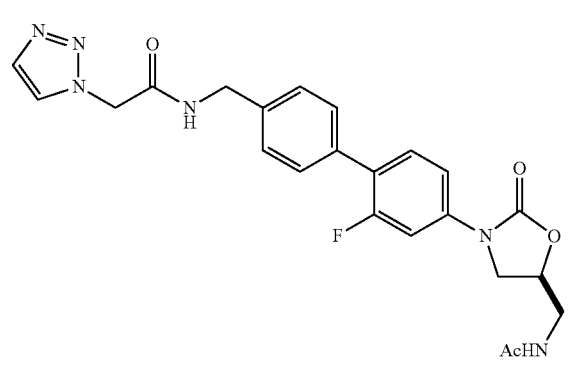
4239

Synthesis of Azide 422

To a solution of bromoacetic acid (1.0 g, 2.8 mmol) and 1-hydroxybenzotriazole hydrate (HOBT, 0.44 g, 3.4 mmol) in DMF (15 mL) was added 1-(3-dimethylaminopropyl)-3-ethylcarbodiimide hydrochloride (EDC.HCl, 0.66 g, 3.4 mmol) and amine 54 (0.45 g, 3.2 mmol) in a rapid succession. The resulting mixture was stirred at room temperature overnight. The solvent was evaporated and the crude product was suspended in water (about 40 mL). The suspension was filtered and the residue was washed with water, diethyl ether (about 50 mL) and dried in vacuo to give analytically pure compound 421 as white solid in quantitative yield.

Compound 421 was dissolved in DMF (10 mL) and NaN₃ (0.55 g, 8.0 mmol) was added. The mixture was heated at 60° C. overnight and solvent evaporated off. The crude was suspended in water (about 40 mL), filtered, and the residue was washed with water, diethyl ether (about 50 mL) and dried in vacuo to give analytically pure azide 422 as white solid (0.97 g, 69.3%). LCMS (ESI): 441 (M+H)⁺.

Synthesis of Triazole 4239

Azide 422 (0.25 g, 0.57 mmol) and TMS-acetylene (0.28 g, 2.84 mmol) were dissolved in DMF (5 mL) and the mixture was heated at 90° C. for 24 h under an argon atmosphere. The solvent was evaporated off, leaving a solid residue. The residue was suspended in water, filtered and dried in vacuo. To the solution of this residue in THF (5 mL) was added 1M TBAF in THF (1.14 mL) and acetic acid (0.04 mL, 0.57 mmol), and the mixture was stirred at room temperature overnight, after which time TLC showed a complete consumption of the starting material. The solvent was evaporated off and the crude was suspended in diethyl ether (about 40 mL). The suspension was filtered, and the residue was washed in succession with $CH_2Cl_2$ (about 50 mL), 10% $CH_3CN$ in diethyl ether (about 50 mL), diethyl ether (about 20 mL). The residue was air dried to give analytically pure triazole 4239 as white solid (0.238 g, 89.6%). LCMS (ESI): 467.1 $(M+H)^+$.

Example 69

Synthesis of Compound 4252

A solution of the methanesulfonic acid 5-{4-[5-(acety-lamino-methyl)-2-oxo-oxazolidin-3-yl]-2-fluoro-phenyl}-pyridin-2-ylmethyl ester 106 (220 mg, 0.5 mmol) in DMF (4.0 mL) was treated with C-isoxazol-4-yl-methylamine (68 mg, 0.5 mmol, 1.0 equiv) at room temperature, and the resulting reaction mixture was warmed to 60° C. and stirred for 6 hours. When TLC and MS showed the reaction to be complete, the reaction mixture was concentrated in vacuo, and the residue was directly purified by column chromatography (0-5% MeOH/$CH_2Cl_2$ gradient elution) to afford the desired N-{3-[3-Fluoro-4-(6-{[(isoxazol-4-ylmethyl)-amino]-methyl}-pyridin-3-yl)-phenyl]-2-oxo-oxazolidin-5-ylmethyl}-acetamide 4252 (22 mg, 10%) as off-white solids. LCMS (EI): 440 $(M^++H)$.

Example 70

Synthesis of Compound 4262

Scheme 45 depicts the synthesis of compound 4262.

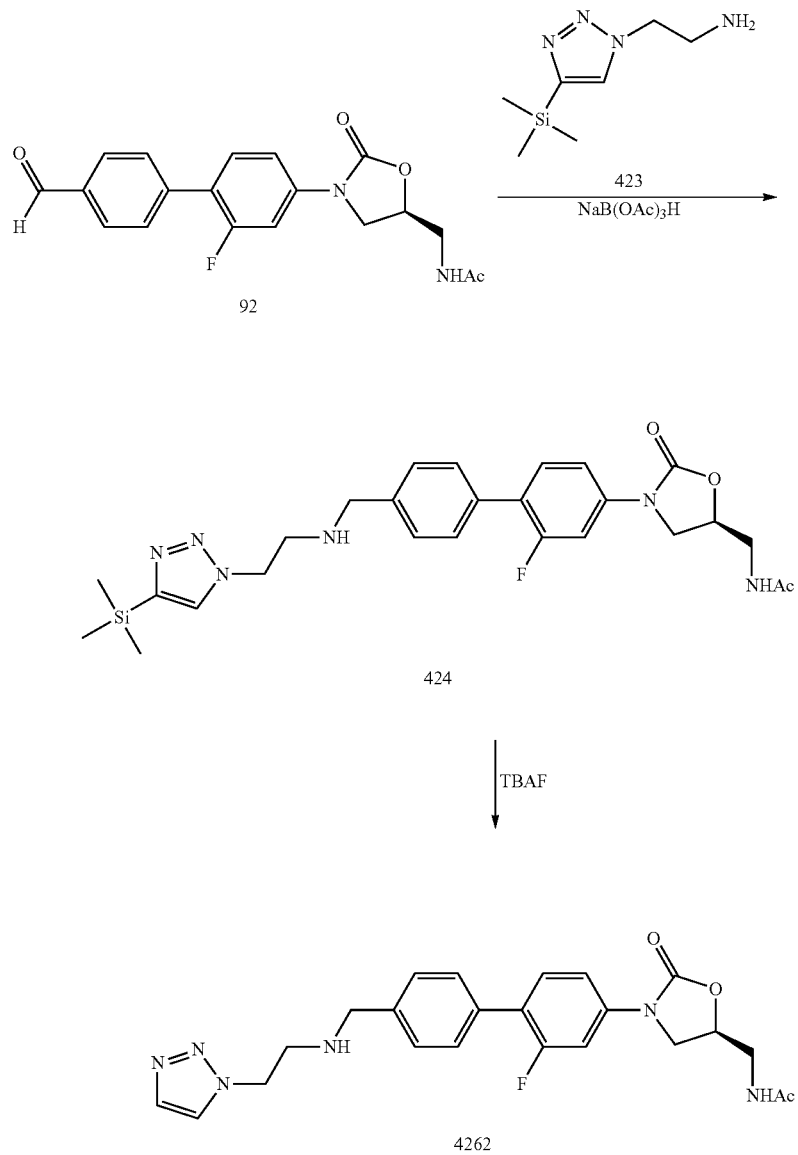

To a solution of 0.060 g (0.17 mmol) of aldehyde 92 and 0.056 g (0.25 mmol) of the HCl salt of amine 423 in 3 ml of DMF was added 0.071 g (0.34 mmol) of NaB(OAc)$_3$H. The reaction mixture was stirred at 25° C. for 2 h. The DMF was removed, and the residue was purified by preparative TLC to give 0.041 g of compound 424. MS (M+1): 525.

To a solution of 0.012 g (0.023 mmol) of 424 and 0.03 ml (0.027 mmol) of TBAF (1 M in THF) in 4 ml of CH$_2$Cl$_2$ was added a few drops of acetic acid, and the mixture was stirred at 0° C. for 4 h. The reaction solvents were removed by rotary evaporation, and the residue was purified by preparative TLC to give 0.008 g of compound 4262. MS (M+1): 489.

Example 71

Synthesis of Triazole 4276

Scheme 46 depicts the synthesis of triazole 4276.

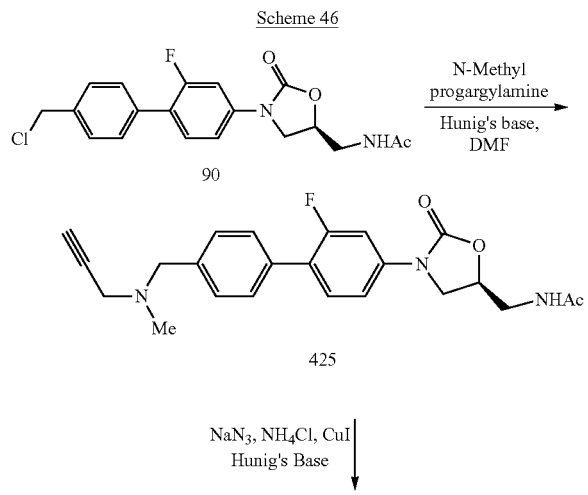

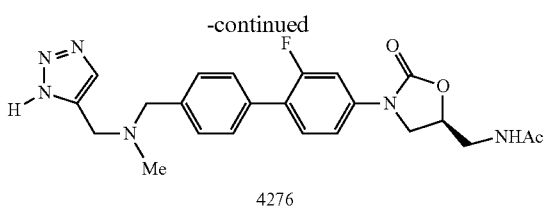

Synthesis of Alkyne 425

To a solution of chloride 90 (2 g, 5.3 mmol) and Hunig's base (diisopropylethylamine, 1.7 mL, 10 mmol) in DMF (15 mL) was added a solution of N-methyl propargylamine (0.55 g mg, 8.0 mmol) in DMF (1 mL). After stirring at room temperature for 16 h, the DMF was removed in vacuo. The crude product was purified by preparative thin layer chromatography (10:1:0.05 CH$_2$Cl$_2$/MeOH/NH$_3$.H$_2$O) to afford 2.05 g of alkyne 425 in a yield of 95%. MS (ESI): 410.1 (100%) (M+Na)$^+$.

Synthesis of Compound 4276

A mixture of alkyne 425 (1.8 g, 4.4 mmol), sodium azide (0.43 g, 6.6 mmol), ammonium chloride (0.35 g, 6.6 mmol), copper(I) iodide (84 mg, 0.44 mmol) and Hunig's base (3.5 mL, 20 mmol) in DMF (10 mL) was heated under argon atmosphere at 80° C. for 48 h. The DMF was removed in vacuo, and the residue was dissolved in MeOH (5 mL), CH$_2$Cl$_2$ (50 mL), conc. ammonium hydroxide (20 mL) and saturated ammonium chloride solution (20 mL). After stirring at room temperature for 2 h, the organic phase was separated, washed with saturated NH$_4$Cl solution and water, dried over MgSO$_4$, and concentrated. The crude product was purified by preparative thin layer chromatography (10:1:0.05 CH$_2$Cl$_2$/MeOH/NH$_3$.H$_2$O) to afford 1.75 mg of triazole 4276 in a yield of 88%. MS (ESI): 453.1 (100%) (M+H)$^+$, 475.2 (M+Na)$^+$.

Example 72

Synthesis of Triazole 4278

Scheme 47 depicts the synthesis of triazole 4278.

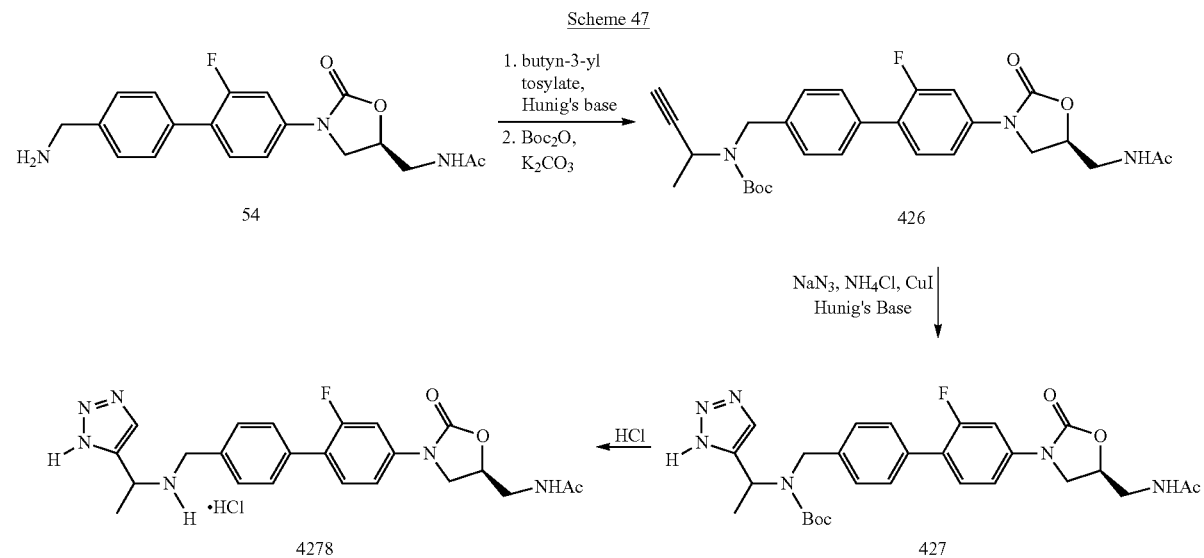

Synthesis of Alkyne 426

A mixture of amine 54 (422 mg, 1.18 mmol), butyn-3-yl tosylate (265 mg, 1.18 mmol), Hunig's base (diisopropylethylamine, 0.2 mL, 1.15 mmol) and potassium iodide (17 mg, 0.1 mmol) in DMF (5 mL) was heated at 70° C. 15 h. The DMF was removed in vacuo. The residue was dissolved in a mixed solvent of THF (10 mL) and water (2 mL), $K_2CO_3$ (276 mg, 2 mmol), and then di-tert-butyl dicarbonate (218 mg, 1 mmol) was added. The reaction was stirred at room temperature for 12 h, and the THF was removed in vacuo. 40 mL of EtOAc was added and the solution was washed with water, dried over $MgSO_4$ and concentrated. The crude product was purified by preparative thin layer chromatography (15:1:0.05 $CH_2Cl_2$/MeOH/$NH_3.H_2O$) to afford 210 mg of alkyne 426 in a yield of 22%. MS (ESI): 410.1, 532.1 (M+Na)$^+$, 573.1 (100%).

Synthesis of Triazole 427

A mixture of alkyne 426 (150 mg, 0.29 mmol), sodium azide (29 mg, 0.44 mmol), ammonium chloride (24 mg, 0.44 mmol), copper(I) iodide (56 mg, 0.29 mmol) and Hunig's base (0.26 mL, 1.5 mmol) in DMF (3 mL) was heated under argon atmosphere at 80° C. for 24 h. The DMF was removed in vacuo, and the residue was dissolved in $CH_2Cl_2$ and conc. ammonium hydroxide solution. The organic phase was separated, washed with saturated $NH_4Cl$ solution and water, dried over $MgSO_4$, and concentrated. The crude product was purified by preparative thin layer chromatography (15:1: 0.05 $CH_2Cl_2$/MeOH/$NH_3.H_2O$) to afford 155 mg of triazole 427 in a yield of 95%. MS (ESI): 453.1 (100%), 575.1 (M+Na)$^+$.

Synthesis of Compound 4278

To a solution of triazole 427 (155 mg, 0.28 mmol) in $CH_2Cl_2$ (5 mL) and MeOH (1 mL) was added 2 mL of HCl solution (4.0 M in dioxane). After stirring at room temperature for 15 h, the reaction was concentrated and washed with EtOAc/MeOH to give 130 mg of compound 4278 in a yield of 95%. MS (ESI): 453.1.1 (100%) (M+H)$^+$.

Example 73

Synthesis of Compounds 4316 and 4314

Synthesis of Morpholine 4316

Scheme 48 depicts the synthesis of morpholine 4316.

Scheme 48

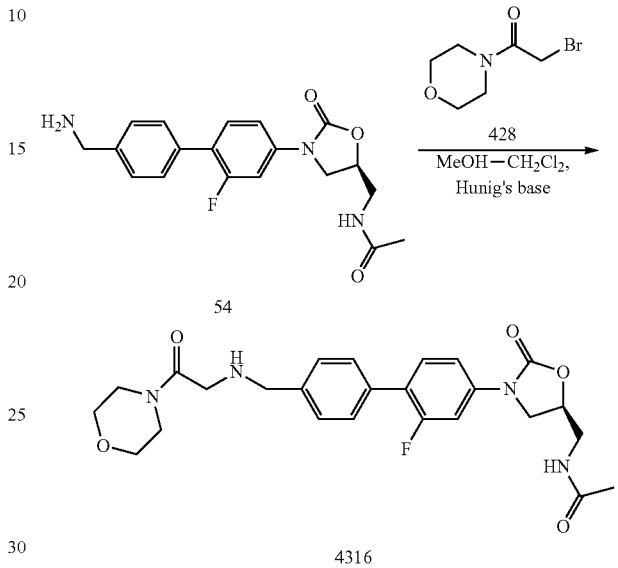

Known bromide 428 was synthesized from morpholine and bromoacetyl bromide as reported in the literature (Thompson, W. J. et al. *J. Med. Chem.* 1992, 35, 1685). To a solution of amine 54 (86 mg, 0.23 mmol) in a mixture of methyl alcohol (2 mL), methylene chloride (2 mL) and Hunig's base (2 mL) was added bromide 428 (32 mg, 0.23 mmol) at 0° C. The reaction mixture was warmed to room temperature and heated over an oil bath at 80° C. for 18 h. The solution was concentrated and purified by flash chromatography over silica gel (14:1:0.05 $CH_2Cl_2$/MeOH: $NH_4OH$) to yield 66 mg of compound 4316. $^1$HNMR (300 MHz, $CD_3OD$): δ 7.50-7.22 (m, 7H), 4.77-4.69 (m, 1H), 4.06 (t, J=9 Hz, 1H), 3.77 (dd, J=6, 3 Hz, 1H), 3.70 (s, 1H), 3.55-3.46 (m, 8H), 3.39-3.36 (m, 3H), 3.34-3.30 (m, 2H), 1.86 (s, 3H). LCMS (ESI) m/e 485 (M+H)$^+$.

Synthesis of Piperazine 4314

Scheme 49 depicts the synthesis of piperazine 4314.

Scheme 49

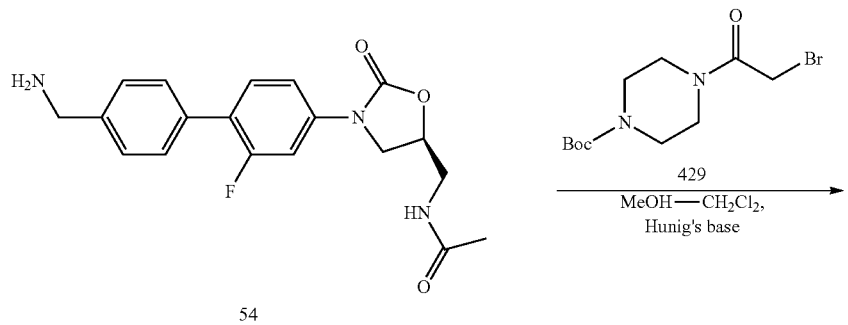

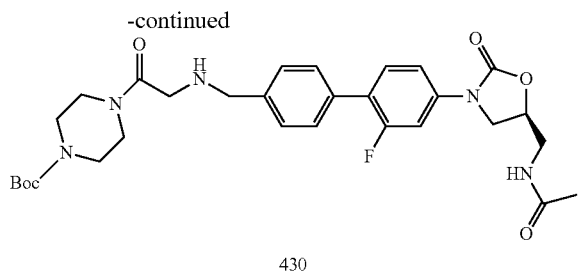

430

↓ 50% TFA in CH₂Cl₂

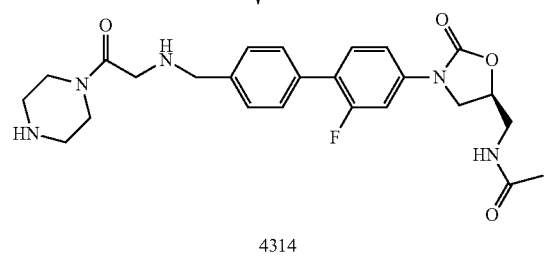

4314

Bromide 429 was synthesized from tert-Butyl 1-piperazine carboxylate and bromoacetyl bromide following literature procedures (Thompson, W. J. et al. *J. Med. Chem.* 1992, 35, 1685). ¹HNMR (300 MHz, CDCl₃): δ 3.86 (s, 2H), 3.61-3.41 (m, 8H), 1.46 (s, 9H). Compound 430 was synthesized from amine 54 and bromide 429 using the same procedure as described for compound 4316. LCMS (ESI) m/e 584 (M+H)⁺. A solution of 430 (50 mg, 0.085 mmol) in CH₂Cl₂—CF₃COOH (1:1, 4 mL) was stirred at 0° C. for 1 h. The reaction mixture was concentrated and the crude product after purification (7:1:0.05 CH₂Cl₂/MeOH/NH₄OH) afforded 35 mg of compound 4314. ¹HNMR (300 MHz, CD₃OD): δ 7.51-7.23 (m, 7H), 4.73-4.67 (m, 1H), 4.07 (t, J=9 Hz, 1H), 3.75 (dd, J=8, 3 Hz, 1H), 3.73 (s. 2H), 3.48-3.41 (m, 6H), 3.24 (s, 2H), 3.21-3.19 (m, 2H), 2.75-2.65 (m, 4H), 1.87 (s, 3H). LCMS (ESI) m/e 484 (M+H)⁺.

Example 74

Synthesis of Triazole 5001

Scheme 50 depicts the synthesis of triazole 5001.

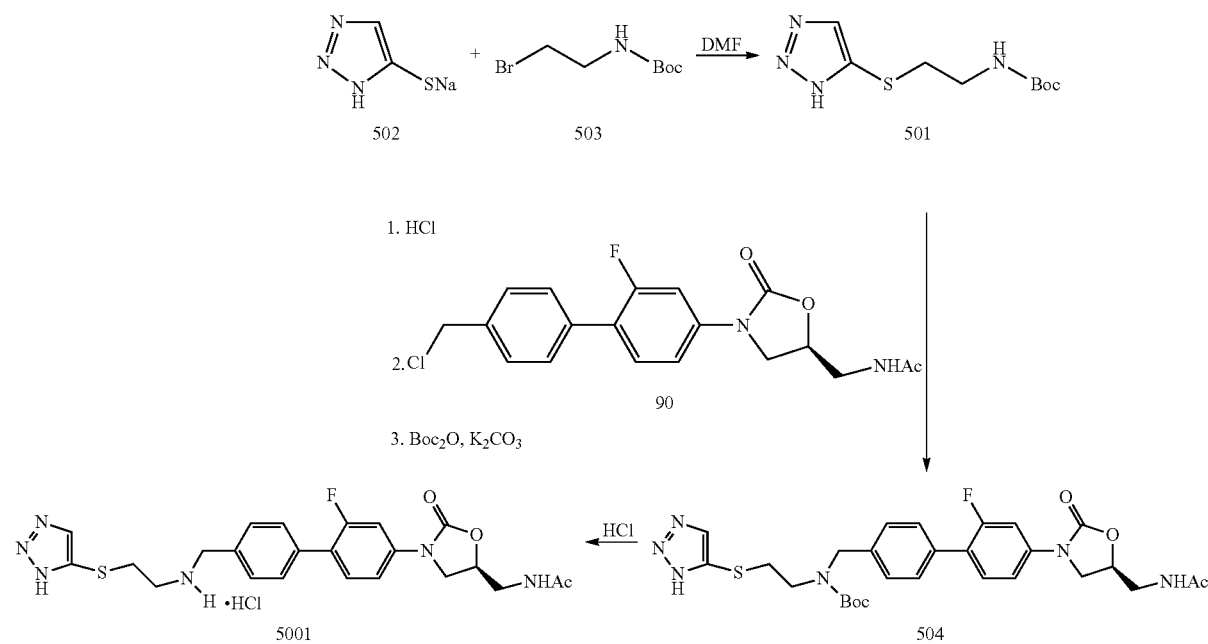

Synthesis of Triazole 501

A mixture of 1H-1,2,3-triazole-5-thiol sodium salt 502 (246 mg, 2 mmol) and 2-(Boc-amino)ethyl bromide 503 (448 mg, 2 mmol) in DMF (2 mL) was stirred at room temperature for 2 h. 50 mL of EtOAc was added and the solution was washed with water, dried over $MgSO_4$ and concentrated to afford 458 mg of triazole 501 as colorless oil in a yield of 94%. MS (ESI): 267.0 (100%) $(M+Na)^+$.

Synthesis of Triazole 504

To a solution of triazole 501 (458 mg, 1.88 mmol) in $CH_2Cl_2$ (10 mL) and MeOH (2 mL) was added 4 mL of HCl solution (4.0 M in dioxane). After stirring at room temperature for 2 h, the reaction was concentrated to dryness. The residue was dissolved in DMF (7 mL) and then chloride 90 (377 mg, 1 mmol) and Hunig's base (diisopropylethylamine, 0.8 mL, 4.6 mmol) were added. The solution was heated at 70° C. for 3 h. The DMF was removed in vacuo, and the residue was dissolved in a mixed solvent of THF (10 mL) and water (2 mL) $K_2CO_3$ (414 mg, 3 mmol) and di-tert-butyl dicarbonate (545 mg, 2.5 mmol) were then added, and the reaction was stirred at room temperature for 12 h. The THF was removed in vacuo, 50 mL of EtOAc was added, and the solution was washed with water, dried over $MgSO_4$ and concentrated. The crude product was purified by preparative thin layer chromatography (15:1:0.1 $CH_2Cl_2$/MeOH/$NH_3.H_2O$) to afford 192 mg of triazole 504 in a yield of 33%. MS (ESI): 485.1 (100%), 607.2 $(M+Na)^+$.

Synthesis of Compound 5001

To a solution of triazole 504 (192 mg, 0.33 mmol) in $CH_2Cl_2$ (10 mL) and MeOH (2 mL) was added 4 mL of HCl solution (4.0 M in dioxane). After stirring at room temperature for 12 h, the reaction was concentrated and washed with EtOAc/MeOH to give 150 mg of triazole 5001 in a yield of 94%. MS (ESI): 485.1 (100%) $(M+H)^+$, 507.2 $(M+Na)^+$.

Example 75

Synthesis of Triazole 5002

Scheme 51 depicts the synthesis of triazole 5002.

Synthesis of Triazole 505

A mixture of 1H-1,2,3-triazole-5-thiol sodium salt 502 (246 mg, 2 mmol) and 2-(BOC-amino)propyl bromide 506 (476 mg, 2 mmol) in DMF (2 mL) was stirred at room temperature for 1 h. 50 mL of EtOAc was added and the solution was washed with water, dried over $MgSO_4$ and concentrated to afford 508 mg of triazole 505 as colorless oil in a yield of 98%. MS (ESI): 281.1 (100%, $(M+Na)^+$).

Synthesis of Triazole 507

To a solution of triazole 505 (365 mg, 1.36 mmol) in $CH_2Cl_2$ (10 mL) and MeOH (2 mL) was added 4 mL of HCl solution (4.0 M in dioxane). After stirring at room temperature for 2 h, the reaction was concentrated to dryness. The residue was dissolved in DMF (5 mL) and then chloride 90 (377 mg, 1 mmol) and Hunig's base (diisopropylethylamine, 0.52 mL, 3 mmol) were added. The solution was heated at 50° C. for 10 h. The DMF was removed in vacuo and the residue was purified by preparative thin layer chromatography (10:1:0.1 $CH_2Cl_2$/MeOH/$NH_3.H_2O$) to afford 230 mg of crude triazole 5002 (90% pure, MS (ESI): 499.1 (100%) (M+H)).

The free base of 5002 was dissolved in a mixed solvent of THF (10 mL) and water (2 mL), and $K_2CO_3$ (138 mg, 1 mmol) and di-tert-butyl dicarbonate (207 mg, 0.95 mmol) were then added. The reaction was stirred at room temperature for 12 h. The THF was removed in vacuo. 50 mL of EtOAc was added and the solution was washed with water, dried over $MgSO_4$ and concentrated. The crude product was purified by preparative thin layer chromatography (15:1:0.05 $CH_2Cl_2$/MeOH/$NH_3.H_2O$) to afford 220 mg of triazole 507 in a yield of 37%. MS (ESI): 499.3 (100%), 621.1 $(M+Na)^+$.

Synthesis of Compound 5002

To a solution of 507 (98 mg, 0.16 mmol) in $CH_2Cl_2$ (5 mL) and MeOH (1 mL) was added 2 mL of HCl solution (4.0 M in dioxane). After stirring at room temperature for 12 h, the reaction was concentrated and washed with EtOAc/MeOH to give 78 mg of compound 5002 in a yield of 95%. MS (ESI): 499.1 (100%, $(M+H)^+$).

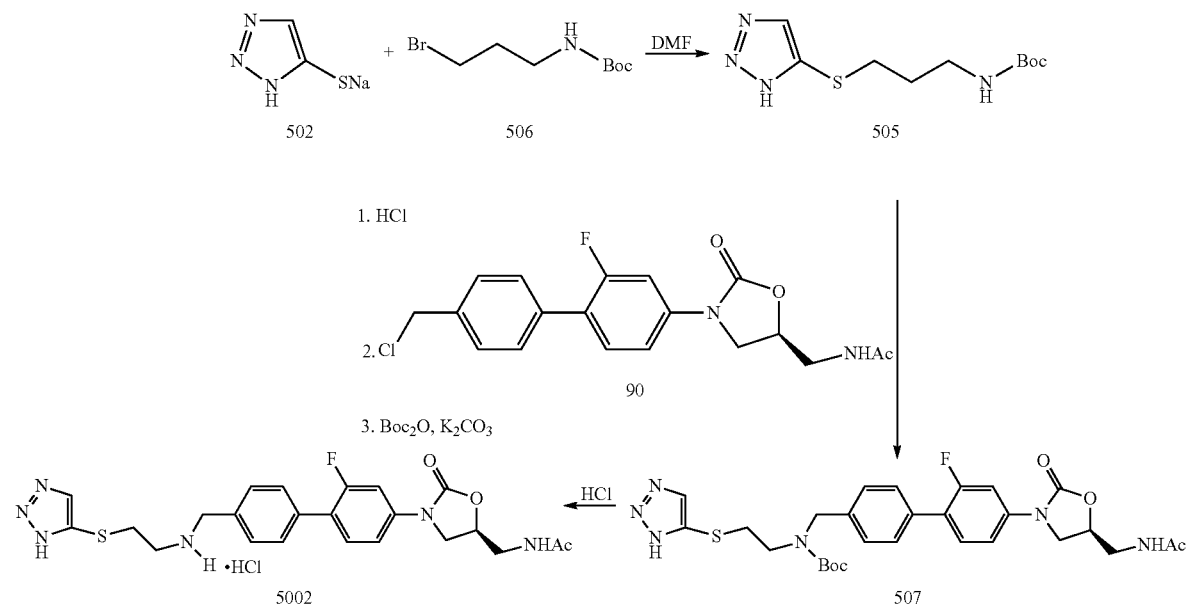

Scheme 51

Example 76

Synthesis of Triazole 5007

Scheme 52 depicts the synthesis of triazole 5007.

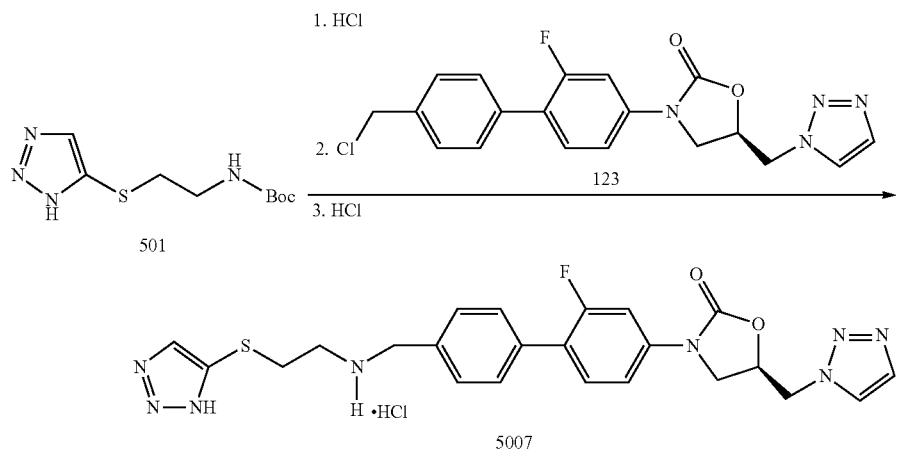

Scheme 52

To a solution of triazole 501 (488 mg, 2 mmol) in CH$_2$Cl$_2$ (10 mL) and MeOH (2 mL) was added 4 mL of HCl solution (4.0 M in dioxane). After stirring at room temperature for 2 h, the reaction was concentrated to dryness. The residue was dissolved in DMF (5 mL) and then chloride 123 (541 mg, 1.4 mmol) and diisopropylethylamine (0.7 mL, 4 mmol) were added. The solution was heated at 50° C. for 18 h. The DMF was removed in vacuo and the residue was purified by preparative thin layer chromatography (10:1:0.15 CH$_2$Cl$_2$/MeOH/NH$_3$.H$_2$O) to afford 250 mg of compound 5007 in a yield of 36%. MS (ESI): 495.0 (100%) (M+H)$^+$.

The free base of compound 5007 was dissolved in CH$_2$Cl$_2$ (5 mL) and MeOH (5 mL) 2 mL of HCl solution (4.0 M in dioxane) was added at 0° C. After stirring at room temperature for 1 h, the reaction was concentrated, washed with EtOAc/MeOH to give 260 mg of the HCl salt compound 5007 in a yield of 97%. MS (ESI): 495.1 (100%) (M+H)$^+$.

Example 77

Synthesis of Triazole 5005

Scheme 53 depicts the synthesis of triazole 5005.

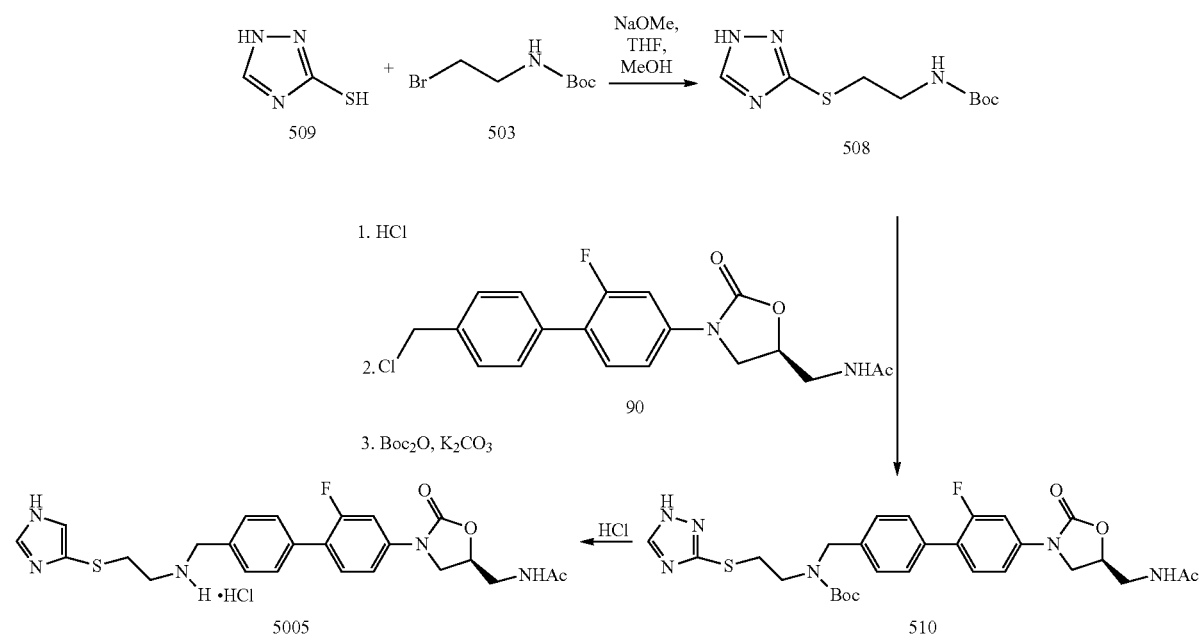

Scheme 53

Synthesis of Triazole 508

To a solution of 1H-1,2,4-triazole-3-thiol 509 (202 mg, 2 mmol) and 2-(BOC-amino)ethyl bromide 503 (448 mg, 2 mmol) in THF (5 mL) and MeOH (2 mL) was added a solution of NaOMe in MeOH (25% wt., 432 mg, 2 mmol). After stirring at room temperature for 2 h, 50 mL of EtOAc was added, and the solution was washed with water, dried over MgSO$_4$ and concentrated to afford 464 mg of triazole 508 as colorless oil in a yield of 95%. MS (ESI): 266.8 (100%) (M+Na)$^+$.

Synthesis of Triazole 510

To a solution of triazole 508 (366 mg, 1.5 mmol) in CH$_2$Cl$_2$ (10 mL) and MeOH (2 mL) was added 4 mL of HCl solution (4.0 M in dioxane). After stirring at room temperature for 3 h, the reaction was concentrated to dryness. The residue was dissolved in DMF (5 mL) and then chloride 90 (377 mg, 1 mmol) and Hunig's base (diisopropylethylamine, 0.7 mL, 4 mmol) were added. The solution was heated at 50° C. for 12 h. The DMF was removed in vacuo and the residue was purified by preparative thin layer chromatography (10:1:0.15 CH$_2$Cl$_2$/MeOH/NH$_3$.H$_2$O) to afford 250 mg of crude compound 5005 (85% pure, MS (ESI): 485.1 (100%) (M+H)$^+$)).

h. The THF was removed in vacuo. 50 mL of EtOAc was added and the solution was washed with water, dried over MgSO$_4$ and concentrated. The crude product was purified by preparative thin layer chromatography (15:1:0.1 CH$_2$Cl$_2$/MeOH/NH$_3$.H$_2$O) to afford 150 mg of 510 in a yield of 26%. MS (ESI): 485.1 (100%), 607.1 (M+Na)$^+$.

Synthesis of Compound 5005

To a solution of triazole 510 (150 mg, 0.26 mmol) in CH$_2$Cl$_2$ (10 mL) and MeOH (2 mL) was added 2 mL of HCl solution (4.0 M in dioxane). After stirring at room temperature for 12 h, the reaction was concentrated and washed with EtOAc/MeOH to give 120 mg of compound 5005 in a yield of 89%. MS (ESI): 485.1 (100%, (M+H)$^+$), 507.0 (M+Na)$^+$.

Example 78

Synthesis of 5011

Scheme 54 depicts the synthesis of triazole 5011.

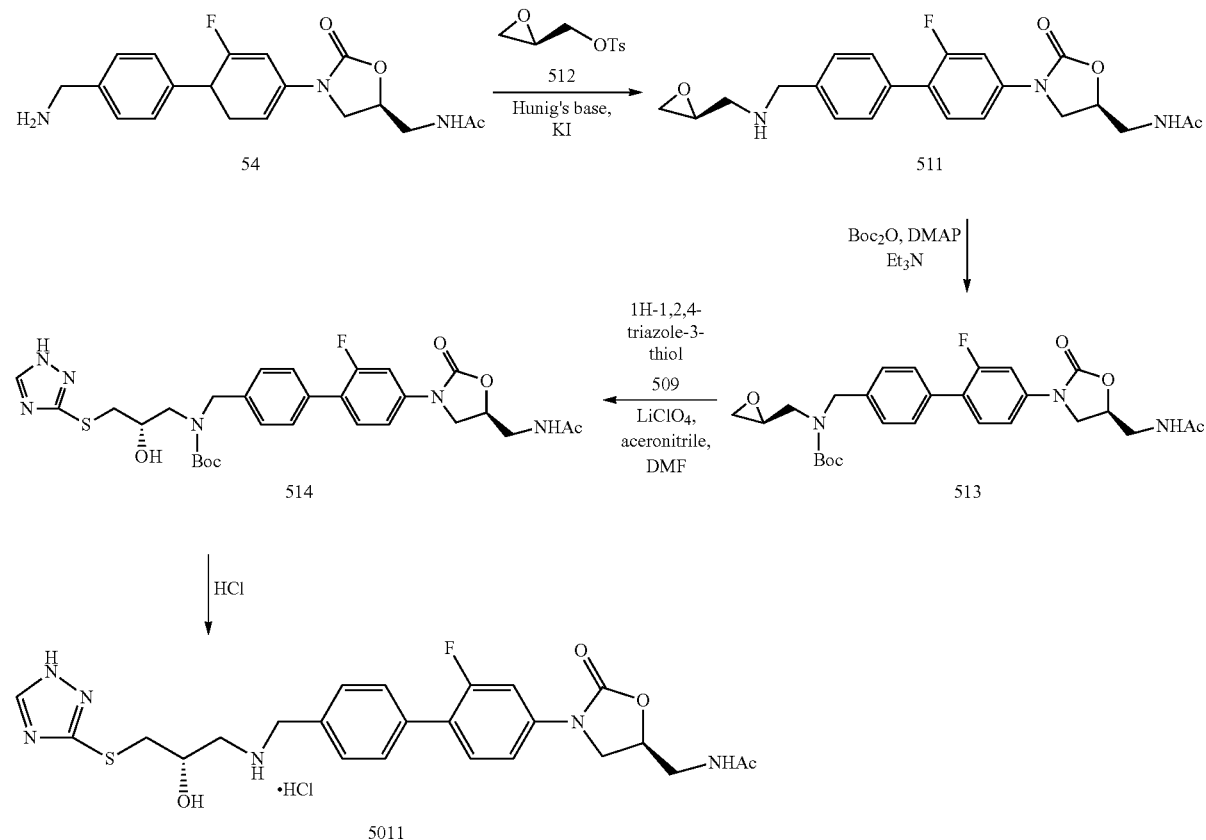

The crude 5005 was dissolved in a mixed solvent of THF (10 mL) and water (2 mL), and then K$_2$CO$_3$ (276 mg, 2 mmol) and di-tert-butyl dicarbonate (218 mg, 1 mmol) were added. The reaction was stirred at room temperature for 12

Synthesis of Compound 511

A mixture of amine 54 (714 mg, 2 mmol), 2R-(−)-glycidyl tosylate 512 (456 mg, 2 mmol), N,N-diisopropylethylamine (0.44 mL, 2.5 mmol) and potassium iodide (33 mg, 0.2 mmol) in DMF (5 mL) was heated at 70° C. for 1 h. The reaction was diluted with 50 mL of EtOAc. The solution was washed with water, dried over MgSO₄ and concentrated. The crude product was purified by preparative thin layer chromatography (10:1:0.1 CH₂Cl₂/MeOH/NH₃.H₂O) to afford 350 mg of compound 511 in a yield of 42%. MS (ESI): 414.1 (100%), 436.0 (M+Na)⁺.

Synthesis of Compound 513

To a solution of compound 511 (160 mg, 0.39 mmol) in THF (10 mL) and DMF (1 mL) was added di-tert-butyl dicarbonate (138 mg, 0.63 mmol), triethylamine (0.2 mL, 1.4 mmol) and N,N-dimethylaminopyridine. The reaction was stirred at room temperature for 1 h, and THF was removed in vacuo. 40 mL of EtOAc was added and the solution was washed with water, dried over MgSO₄ and concentrated. The crude product was purified by preparative thin layer chromatography (15:1:0.1 CH₂Cl₂/MeOH/NH₃.H₂O) to afford 138 mg of compound 513 in a yield of 70%. MS (ESI): 514.1 (100%) (M+H)⁺, 536.1 (M+Na)⁺.

Synthesis of Compound 514

To a solution of compound 513 (120 mg, 0.23 mmol) and LiClO₄ (27 mg, 0.25 mmol) in acetonitrile (2 mL) was added 1H-1,2,4-triazole-3-thiol 509 (24 mg, 0.23 mmol). The reaction was heated at 100° C. for 6 days and concentrated to dryness. The crude product was purified by preparative thin layer chromatography (15:1:0.1 CH₂Cl₂/MeOH/NH₃.H₂O) to afford 75 mg of compound 514 in a yield of 53%. MS (ESI): 515.1 (100%), 615.1 (M+H)⁺.

Synthesis of Compound 5011

To a solution of compound 514 (75 mg, 0.12 mmol) in CH₂Cl₂ (5 mL) and MeOH (1 mL) was added 1 mL of HCl solution (4.0 M in dioxane). After stirring at room temperature for 24 h, the reaction was concentrated and washed with EtOAc/MeOH to give 62 mg of 5011 in a yield of 94%. MS (ESI): 515.1 (100%) (M+H)⁺.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A topical formulation comprising one or more dermatologically acceptable carriers and one or more compounds having the formula:

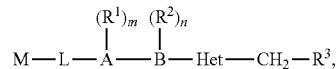

or a pharmaceutically acceptable salt, ester, tautomer or prodrug thereof, wherein:
A is selected from the group consisting of:
phenyl, pyridyl, pyrazinyl, pyrimidinyl, and pyridazinyl;
B is selected from the group consisting of:
phenyl, pyridyl, pyrazinyl, pyrimidinyl, and pyridazinyl;
Het-CH₂—R³ is selected from the group consisting of:

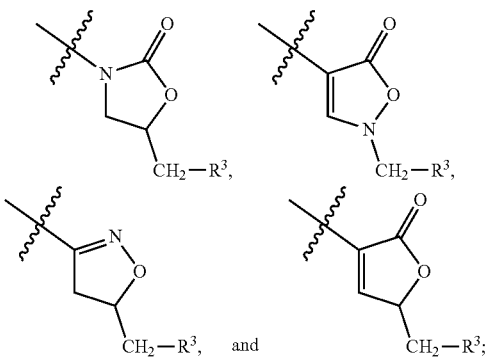

M is selected from the group consisting of:
a) saturated, unsaturated, or aromatic $C_{3-14}$ carbocycle, and b) saturated, unsaturated, or aromatic 3-14 membered heterocycle containing one or more heteroatoms selected from the group consisting of nitrogen, oxygen, and sulfur,
wherein a) or b) optionally is substituted with one or more R⁵ groups;
M-L is selected from the group consisting of:
a) M-X, b) M-L¹, c) M-L¹-X, d) M-X-L², e) M-L¹-X-L², f) M-X-L², g) M-L¹-X-L²-X, h) M-X—X—, i) M-L¹-X—X—, j) M-X—X-L², and k) M-L¹-X—X-L²,
wherein
X, at each occurrence, independently is selected from the group consisting of:
a) —O—, b) —NR⁴—, c) —N(O)—, d) —N(OR⁴)—, e) —S(O)ₚ—, f) —SO₂NR⁴—, g) —NR⁴SO₂—, h) —NR⁴—N=, i) =N—NR⁴—, j) —O—N=, k) =N—O—, l) —N=, m) =N—, n) —NR⁴—NR⁴—, o) —NR⁴C(O)O—, p) —OC(O)NR⁴—, q) —NR⁴C(O)NR⁴— r) —NR⁴C(NR⁴)NR⁴—, and s)

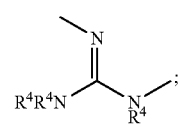

L¹ is selected from the group consisting of:
a) $C_{1-6}$ alkyl, b) $C_{2-6}$ alkenyl, and c) $C_{2-6}$ alkynyl, wherein any of a)-c) optionally is substituted with one or more $R^5$ groups; and $L^2$ is selected from the group consisting of:
a) $C_{1-6}$ alkyl, b) $C_{2-6}$ alkenyl, and c) $C_{2-6}$ alkynyl,
wherein any of a)-c) optionally is substituted with one or more $R^5$ groups;

$R^1$, at each occurrence, independently is selected from the group consisting of:
a) F, b) Cl, c) Br, d) I, e) —$CF_3$, f) —$OR^4$, g) —CN, h) —$NO_2$, i) —$NR^4R^4$, j) —$C(O)R^4$, k) —$C(O)OR^4$, l) —$OC(O)R^4$, m) —$C(O)NR^4R^4$, n) —$NR^4C(O)R^4$, o) —$OC(O)NR^4R^4$, p) —$NR^4C(O)OR^4$, q) —$NR^4C(O)NR^4R^4$, r) —$C(S)R^4$, s) —$C(S)OR^4$, t) —$OC(S)R^4$, u) —$C(S)NR^4R^4$, v) —$NR^4C(S)R^4$, w) —$OC(S)NR^4R^4$, x) —$NR^4C(S)OR^4$, y) —$NR^4C(S)NR^4R^4$, z) —$NR^4C(NR^4)NR^4R^4$, aa) —$S(O)_pR^4$, bb) —$SO_2NR^4R^4$, and cc) $R^4$;

$R^2$, at each occurrence, independently is selected from the group consisting of:
a) F, b) Cl, c) Br, d) I, e) —$CF_3$, f) —$OR^4$, g) —CN, h) —$NO_2$, i) —$NR^4R^4$, j) —$C(O)R^4$, k) —$C(O)OR^4$, l) —$OC(O)R^4$, m) —$C(O)NR^4R^4$, n) —$NR^4C(O)R^4$, o) —$OC(O)NR^4R^4$, p) —$NR^4C(O)OR^4$, q) —$NR^4C(O)NR^4R^4$, r) —$C(S)R^4$, s) —$C(S)OR^4$, t) —$OC(S)R^4$, u) —$C(S)NR^4R^4$, v) —$NR^4C(S)R^4$, w) —$OC(S)NR^4R^4$, x) —$NR^4C(S)OR^4$, y) —$NR^4C(S)NR^4R^4$, z) —$NR^4C(NR^4)NR^4R^4$, aa) —$S(O)_pR^4$, bb) —$SO_2NR^4R^4$, and cc) $R^4$;

$R^3$ is selected from the group consisting of:
a) —$OR^4$, b) —$NR^4R^4$, c) —$C(O)R^4$, d) —$C(O)OR^4$, e) —$OC(O)R^4$, f) —$C(O)NR^4R^4$, g) —$NR^4C(O)R^4$, h) —$OC(O)NR^4R^4$, i) —$NR^4C(O)OR^4$, j) —$NR^4C(O)NR^4R^4$, k) —$C(S)R^4$, l) —$C(S)OR^4$, m) —$OC(S)R^4$, n) —$C(S)NR^4R^4$, o) —$NR^4C(S)R^4$, p) —$OC(S)NR^4R^4$, q) —$NR^4C(S)OR^4$, r) —$NR^4C(S)NR^4R^4$, s) —$NR^4C(NR^4)NR^4R^4$, t) —$S(O)_pR^4$, u) —$SO_2NR^4R^4$, and v) $R^4$;

$R^4$, at each occurrence, independently is selected from the group consisting of:
a) H, b) $C_{1-6}$ alkyl, c) $C_{2-6}$ alkenyl, d) $C_{2-6}$ alkynyl, e) $C_{3-14}$ saturated, unsaturated, or aromatic carbocycle, f) 3-14 membered saturated, unsaturated, or aromatic heterocycle comprising one or more heteroatoms selected from the group consisting of nitrogen, oxygen, and sulfur, g) —C(O)—$C_{1-6}$ alkyl, h) —C(O)—$C_{2-6}$ alkenyl, i) —C(O)—$C_{2-6}$ alkynyl, j) —C(O)—$C_{3-14}$ saturated, unsaturated, or aromatic carbocycle, k) —C(O)-3-14 membered saturated, unsaturated, or aromatic heterocycle comprising one or more heteroatoms selected from the group consisting of nitrogen, oxygen, and sulfur, l) —C(O)O—$C_{1-6}$ alkyl, m) —C(O)O—$C_{2-6}$ alkenyl, n) —C(O)O—$C_{2-6}$ alkynyl, o) —C(O)O—$C_{3-14}$ saturated, unsaturated, or aromatic carbocycle, and p) —C(O)O-3-14 membered saturated, unsaturated, or aromatic heterocycle comprising one or more heteroatoms selected from the group consisting of nitrogen, oxygen, and sulfur,
wherein any of b)-p) optionally is substituted with one or more $R^5$ groups;

$R^5$, at each occurrence, is independently selected from the group consisting of:
a) F, b) Cl, c) Br, d) I, e) =O, f) =S, g) =$NR^6$, h) =$NOR^6$, i) =N—$NR^6R^6$, j) —$CF_3$, k) —$OR^6$, l) —CN, m) —$NO_2$, n) —$NR^6R^6$, o) —$C(O)R^6$, p) —$C(O)OR^6$, q) —$OC(O)R^6$, r) —$C(O)NR^6R^6$, s) —$NR^6C(O)R^6$, t) —$OC(O)NR^6R^6$, u) —$NR^6C(O)OR^6$, v) —$NR^6C(O)NR^6R^6$, w) —$C(S)R^6$, x) —$C(S)OR^6$, y) —$OC(S)R^6$, z) —$C(S)NR^6R^6$, aa) —$NR^6C(S)R^6$, bb) —$OC(S)NR^6R^6$, cc) —$NR^6C(S)OR^6$, dd) —$NR^6C(S)NR^6R^6$, ee) —$NR^6C(NR^6)NR^6R^6$, ff) —$S(O)_pR^6$, gg) —$SO_2NR^6R^6$, and hh) $R^6$;

$R^6$, at each occurrence, independently is selected from the group consisting of:
a) H, b) $C_{1-6}$ alkyl, c) $C_{2-6}$ alkenyl, d) $C_{2-6}$ alkynyl, e) $C_{3-14}$ saturated, unsaturated, or aromatic carbocycle, f) 3-14 membered saturated, unsaturated, or aromatic heterocycle comprising one or more heteroatoms selected from the group consisting of nitrogen, oxygen, and sulfur, g) —C(O)—$C_{1-6}$ alkyl, h) —C(O)—$C_{2-6}$ alkenyl, i) —C(O)—$C_{2-6}$ alkynyl, j) —C(O)—$C_{3-14}$ saturated, unsaturated, or aromatic carbocycle, k) —C(O)-3-14 membered saturated, unsaturated, or aromatic heterocycle comprising one or more heteroatoms selected from the group consisting of nitrogen, oxygen, and sulfur, l) —C(O)O—$C_{1-6}$ alkyl, m) —C(O)O—$C_{2-6}$ alkenyl, n) —C(O)O—$C_{2-6}$ alkynyl, o) —C(O)O—$C_{3-14}$ saturated, unsaturated, or aromatic carbocycle, and p) —C(O)O-3-14 membered saturated, unsaturated, or aromatic heterocycle comprising one or more heteroatoms selected from the group consisting of nitrogen, oxygen, and sulfur,
wherein any of b)-p) optionally is substituted with one or more $R^7$ groups;

$R^7$, at each occurrence, independently is selected from the group consisting of:
a) F, b) Cl, c) Br, d) I, e) =O, f) =S, g) =$NR^8$, h) =$NOR^8$, i) =N—$NR^8R^8$, j) —$CF_3$, k) —$OR^8$, l) —CN, m) —$NO_2$, n) —$NR^8R^8$, o) —$C(O)R^8$, p) —$C(O)OR^8$, q) —$OC(O)R^8$, r) —$C(O)NR^8R^8$, s) —$NR^8C(O)R^8$, t) —$OC(O)NR^8R^8$, u) —$NR^8C(O)OR^8$, v) —$NR^8C(O)NR^8R^8$, w) —$C(S)R^8$, x) —$C(S)OR^8$, y) —$OC(S)R^8$, z) —$C(S)NR^8R^8$, aa) —$NR^8C(S)R^8$, bb) —$OC(S)NR^8R^8$, cc) —$NR^8C(S)OR^8$, dd) —$NR^8C(S)NR^8R^8$, ee) —$NR^8C(NR^8)NR^8R^8$, ff) —$S(O)_pR^8$, gg) —$SO_2NR^8R^8$, hh) $C_{1-6}$ alkyl, ii) $C_{2-6}$ alkenyl, jj) $C_{2-6}$ alkynyl, kk) $C_{3-14}$ saturated, unsaturated, or aromatic carbocycle, and ll) 3-14 membered saturated, unsaturated, or aromatic heterocycle comprising one or more heteroatoms selected from the group consisting of nitrogen, oxygen, and sulfur,
wherein any of hh)-ll) optionally is substituted with one or more moieties selected from the group consisting of $R^8$, F, Cl, Br, I, —$CF_3$, —$OR^8$, —$SR^8$, —CN, —$NO_2$, —$NR^8R^8$, —$C(O)R^8$, —$C(O)OR^8$, —$OC(O)R^8$, —$C(O)NR^8R^8$, —$NR^8C(O)R^8$, —$OC(O)NR^8R^8$, —$NR^8C(O)OR^8$, —$NR^8C(O)NR^8R^8$, —$C(S)R^8$, —$C(S)OR^8$, —$OC(S)R^8$, —$C(S)NR^8R^8$, —$NR^8C(S)R^8$, —$OC(S)NR^8R^8$, —$NR^8C(S)OR^8$, —$NR^8C(S)NR^8R^8$, —$NR^8C(NR^8)NR^8R^8$, —$SO_2NR^8R^8$, and —$S(O)_pR^8$;

$R^8$, at each occurrence, independently is selected from the group consisting of:
a) H, b) $C_{1-6}$ alkyl, c) $C_{2-6}$ alkenyl, d) $C_{2-6}$ alkynyl, e) $C_{3-14}$ saturated, unsaturated, or aromatic carbocycle, f) 3-14 membered saturated, unsaturated, or aromatic heterocycle comprising one or more heteroatoms selected from the group consisting of nitrogen, oxygen, and sulfur, g) —C(O)—$C_{1-6}$ alkyl, h) —C(O)—$C_{2-6}$ alkenyl, i) —C(O)—$C_{2-6}$ alkynyl, j) —C(O)—$C_{3-14}$ saturated, unsaturated, or aromatic carbocycle, k) —C(O)-3-14 membered saturated, unsaturated, or aromatic heterocycle comprising one or more heteroatoms selected from the group consisting of nitrogen, oxygen, and sulfur, 1) —C(O)O—$C_{1-6}$ alkyl, m) —C(O)O—$C_{2-6}$ alkenyl, n) —C(O)O—$C_{2-6}$ alkynyl, o) —C(O)O—$C_{3-14}$ saturated, unsaturated, or aromatic carbocycle, and p) —C(O)O-3-14 membered saturated, unsaturated, or aromatic heterocycle comprising one or more heteroatoms selected from the group consisting of nitrogen, oxygen, and sulfur, wherein any of b)-p) optionally is substituted with one or more moieties selected from the group consisting of F, Cl, Br, I, —$CF_3$, —OH, —$OCH_3$, —SH, —$SCH_3$, —CN, —$NO_2$, —$NH_2$, —$NHCH_3$, —$N(CH_3)_2$, —$C(O)CH_3$, —$C(O)OCH_3$, —$C(O)NH_2$, —$NHC(O)CH_3$, —$SO_2NH_2$, —$SO_2NHCH_3$, —$SO_2N(CH_3)_2$, and —$S(O)_pCH_3$;

m is 0, 1, 2, 3, or 4;
n is 0, 1, 2, 3, or 4; and
p, at each occurrence, independently is 0, 1, or 2.

2. The formulation according to claim 1, wherein:
A is a phenyl;
B is a phenyl;
Het-$CH_2$—$R^3$ is:

M is a 5-membered unsaturated heterocycle containing one or more nitrogen heteroatoms optionally substituted with one or more $R^5$ groups, wherein the heterocycle contains only nitrogen atoms;

M-L is M-$L^1$-X-$L^2$, wherein
X, at each occurrence, independently is selected from the group consisting of:
a) —$NR^4$—, b) —$SO_2NR^4$—
$L^1$ is selected from the group consisting of:
a) $C_{1-6}$ alkyl, b) $C_{2-6}$ alkenyl, and c) $C_{2-6}$ alkynyl, wherein any of a)-c) optionally is substituted with one or more $R^5$ groups; and
$L^2$ is selected from the group consisting of:
a) $C_{1-6}$ alkyl, b) $C_{2-6}$ alkenyl, and c) $C_{2-6}$ alkynyl, wherein any of a)-c) optionally is substituted with one or more $R^5$ groups;
$R^1$, at each occurrence, independently is selected from the group consisting of:
a) F, b) Cl, c) Br, d) I;
$R^2$, at each occurrence, independently is selected from the group consisting of:
a) F, b) Cl, c) Br, d) I;
$R^3$ is —$NR^4C(O)R^4$;
$R^4$, at each occurrence, independently is selected from the group consisting of:
a) H, b) $C_{1-6}$ alkyl;
$R^5$, at each occurrence, is independently selected from the group consisting of:
a) F, b) Cl, c) Br, d) I, e) =O, f) =S, g) —$CF_3$, h) —CN, i) —$NO_2$, j) —$NR^6R^6$, k) —$C(O)R^6$, l) —$C(O)NR^6R^6$, m) —$S(O)_pR^6$, and n) $R^6$;
$R^6$, at each occurrence, independently is selected from the group consisting of:

a) H, b) $C_{1-6}$ alkyl, c) $C_{2-6}$ alkenyl, d) $C_{2-6}$ alkynyl, wherein any of b)-d) optionally is substituted with one or more $R^7$ groups;
$R^7$, at each occurrence, independently is selected from the group consisting of:
a) F, b) Cl, c) Br, d) I, e) =$NR^8$, f) —$CF_3$, g) —$OR^8$, h) —CN, i) —$NO_2$, j) —$NR^8R^8$, k) —$C(O)R^8$, and l) —$C(O)OR^8$;
$R^8$, at each occurrence, independently is selected from the group consisting of:
a) H, b) $C_{1-6}$ alkyl, c) $C_{2-6}$ alkenyl, d) $C_{2-6}$ alkynyl, wherein any of b)-d) optionally is substituted with one or more moieties selected from the group consisting of F, Cl, Br, I, —$CF_3$, and —OH;
m is 0, 1, 2, 3, or 4;
n is 0, 1, 2, 3, or 4; and
p, at each occurrence, independently is 0, 1, or 2.

3. The formulation according to claim 2, wherein said compound has the formula:

or a pharmaceutically acceptable salt, ester, tautomer or prodrug thereof.

4. A method of treating, preventing, or reducing the risk of a skin infection in a patient comprising administering an effective amount of the topical formulation of claim 1.

5. The method according to claim 4, wherein said compound has the formula:

or a pharmaceutically acceptable salt, ester, tautomer or prodrug thereof.

6. The method according to claim 5, wherein said compound has the formula:

or a pharmaceutically acceptable salt, ester, tautomer or prodrug thereof.

7. The method according to claim 4, wherein
A is selected from the group consisting of phenyl and pyridyl;
B is selected from the group consisting of phenyl and pyridyl;

m is 0, 1, or 2; and
n is 0, 1, or 2.

8. The method according to claim 4, wherein A-B is:

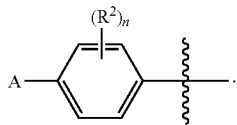

9. The method according to claim 8, wherein A-B is:

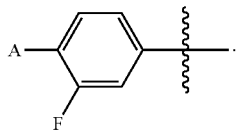

10. The method according to claim 4, wherein A-B is:

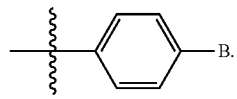

11. The method according to claim 4, wherein $R^3$ is —NHC(O)$R^4$.

12. The method according to claim 11, wherein $R^4$ is —CH$_3$.

13. The method according to claim 1, wherein $R^3$ is:

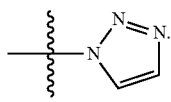

14. The method according to claim 4, wherein said compound has the formula:

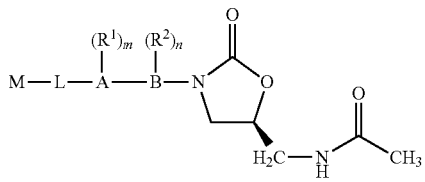

or a pharmaceutically acceptable salt, ester, tautomer or prodrug thereof.

15. The method according to claim 4, wherein said compound has the formula:

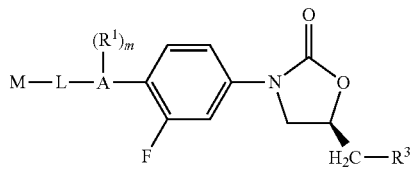

or a pharmaceutically acceptable salt, ester, tautomer or prodrug thereof.

16. The method of claim 4, wherein:
A is a phenyl;
B is a phenyl;
Het-CH$_2$—$R^3$ is:

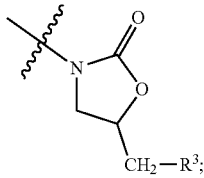

M is a 5-membered unsaturated heterocycle containing one or more nitrogen heteroatoms optionally substituted with one or more $R^5$ groups, wherein the heterocycle contains only nitrogen atoms;

M-L is M-$L^1$-X-$L^2$, wherein
X, at each occurrence, independently is selected from the group consisting of:
a) —N$R^4$—, b) —SO$_2$N$R^4$—
$L^1$ is selected from the group consisting of:
a) $C_{1-6}$ alkyl, b) $C_{2-6}$ alkenyl, and c) $C_{2-6}$ alkynyl, wherein any of a)-c) optionally is substituted with one or more $R^5$ groups; and
$L^2$ is selected from the group consisting of:
a) $C_{1-6}$ alkyl, b) $C_{2-6}$ alkenyl, and c) $C_{2-6}$ alkynyl wherein any of a)-c) optionally is substituted with one or more $R^5$ groups;
$R^1$, at each occurrence, independently is selected from the group consisting of:
a) F, b) Cl, c) Br, d) I;
$R^2$, at each occurrence, independently is selected from the group consisting of:
a) F, b) Cl, c) Br, d) I;
$R^3$ is —N$R^4$C(O)$R^4$;
$R^4$, at each occurrence, independently is selected from the group consisting of:
a) H, b) $C_{1-6}$ alkyl;
$R^5$, at each occurrence, is independently selected from the group consisting of:
a) F, b) Cl, c) Br, d) I, e) =O, f) =S, g) —CF$_3$, h) —CN, i) —NO$_2$, j) —N$R^6R^6$, k) —C(O)$R^6$, l) —C(O)N$R^6R^6$, m) —S(O)$_p R^6$, and n) $R^6$;
$R^6$, at each occurrence, independently is selected from the group consisting of:
a) H, b) $C_{1-6}$ alkyl, c) $C_{2-6}$ alkenyl, d) $C_{2-6}$ alkynyl, wherein any of b)-d) optionally is substituted with one or more $R^7$ groups;
$R^7$, at each occurrence, independently is selected from the group consisting of:
a) F, b) Cl, c) Br, d) I, e) =N$R^8$, f) —CF$_3$, g) —O$R^8$, h) —CN, i) —NO$_2$, j) —N$R^8R^8$, k) —C(O)$R^8$, and l) —C(O)O$R^8$;
$R^8$, at each occurrence, independently is selected from the group consisting of:
a) H, b) $C_{1-6}$ alkyl, c) $C_{2-6}$ alkenyl, d) $C_{2-6}$ alkynyl, wherein any of b)-d) optionally is substituted with one or more moieties selected from the group consisting of F, Cl, Br, I, —CF$_3$, and —OH;
m is 0, 1, 2, 3, or 4;
n is 0, 1, 2, 3, or 4; and
p, at each occurrence, independently is 0, 1, or 2.

17. A method of treating, preventing, or reducing the risk of a skin infection in a patient comprising administering an effective amount of the topical formulation of claim 1, wherein the compound has the formula:
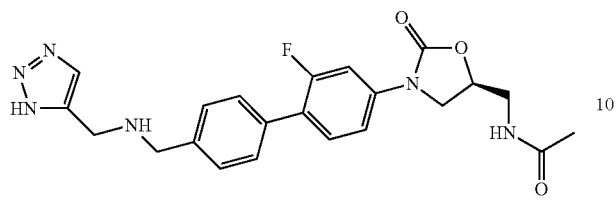
or a pharmaceutically acceptable salt, ester, tautomer or prodrug thereof.
* * * * *